(12) United States Patent
Watkins et al.

(10) Patent No.: US 7,981,895 B2
(45) Date of Patent: Jul. 19, 2011

(54) CARBAMIC ACID COMPOUNDS COMPRISING A PIPERAZINE LINKAGE AS HDAC INHIBITORS

(75) Inventors: Clare J. Watkins, Oxfordshire (GB); Maria-Rosario Romero-Martin, Didcot (GB); James Ritchie, Abingdon (GB); Paul W. Finn, Abingdon (GB); Ivars Kalvinsh, Riga (GB); Einars Loza, Riga (GB); Klara Dikovska, Riga (GB); Igor Starchenkov, Riga (GB); Daina Lolya, Riga (GB); Vija Gailite, Riga (GB)

(73) Assignee: Topotarget UK Limited, Oxford (GB)

( * ) Notice: Subject to any disclaimer, the term of this patent is extended or adjusted under 35 U.S.C. 154(b) by 0 days.

(21) Appl. No.: 12/165,686

(22) Filed: Jul. 1, 2008

(65) Prior Publication Data

US 2008/0269237 A1    Oct. 30, 2008

Related U.S. Application Data

(63) Continuation of application No. 10/509,732, filed as application No. PCT/GB03/01463 on Apr. 3, 2003.

(60) Provisional application No. 60/369,337, filed on Apr. 3, 2002.

(51) Int. Cl.
*A61K 31/497*     (2006.01)
*A61K 31/4965*    (2006.01)

(52) U.S. Cl. .............. 514/252.12; 514/255.01
(58) Field of Classification Search .......... 544/331, 544/359
See application file for complete search history.

(56) References Cited

U.S. PATENT DOCUMENTS

| | | | |
|---|---|---|---|
| 5,834,249 | A | 11/1998 | Furukawa et al. |
| 6,380,258 | B2 | 4/2002 | Bedell |
| 6,492,394 | B1 | 12/2002 | Billledeau et al. |
| 6,683,078 | B2 | 1/2004 | Barta et al. |
| 6,696,449 | B2 | 2/2004 | Bedell |
| 7,115,632 | B1 | 10/2006 | Bedell |
| 2005/0143385 | A1* | 6/2005 | Watkins et al. .......... 514/252.12 |

FOREIGN PATENT DOCUMENTS

| | | |
|---|---|---|
| EP | 0574758 | 12/1993 |
| EP | 0684240 | 11/1995 |
| EP | 0827742 | 3/1998 |
| JP | 10-114681 | 5/1998 |
| WO | WO 99/02510 | 1/1999 |
| WO | WO 99/24399 | 5/1999 |
| WO | WO 00/12477 | 3/2000 |
| WO | WO 00/12478 | 3/2000 |
| WO | WO/00/37436 | * 6/2000 |
| WO | WO 00/37436 | 6/2000 |
| WO | WO 00/46221 | 8/2000 |
| WO | WO 00/56704 | 9/2000 |
| WO | WO 00/69819 | 11/2000 |
| WO | WO 00/69839 | 11/2000 |
| WO | WO 01/10834 | 2/2001 |
| WO | WO 01/38322 | 5/2001 |
| WO | WO 01/44189 | 6/2001 |
| WO | WO 01/62751 | 8/2001 |
| WO | WO 01/85680 | 11/2001 |
| WO | WO 01/87870 | 11/2001 |
| WO | WO 02/22577 | 3/2002 |
| WO | WO 02/26696 | 4/2002 |
| WO | WO 02/26703 | 4/2002 |
| WO | WO 02/28829 | 4/2002 |
| WO | WO 02/30879 | 4/2002 |

OTHER PUBLICATIONS

Kwon Ho Jeong, et al., Histone deacetylase inhibitor FK228 inhibits tumor Angiogenesis, Int'l J. of Cancer, vol. 97, No. 3, pp. 290-296 (Jan. 20, 2002).*
Cancer Drug Design and Discovery Neidle, Stephen, ed. (Elsevier/Academic Press, 2008) pp. 427-431.*
Gura, Science Nov. 7, 1997: vol. 278. No. 5340, pp. 1041-1042.*
Roberts, Jr et al., JAMA 292(17): 2130-2140 (2004).*
Kamb, Nature Reviews Drug Discovery 4, 161-165 (Feb. 2005).*
Kola, Nature Reviews Drug Discovery 3, 711-715 (2004).*
Leaf, Clifton, Health Administrator vol. XVIII, No. 1: 172-183, 2005.*
"Expert Scientific Group on Phase One Clinical Trials Final Report" Nov. 30, 2006, pp. C1, C35-C38.*
Andrews et al., 2000 "Anti-malarial effect of histone deacetylation inhibitors and mammalian tumour cytodifferentiating agents," *Int. J. Parasitol.*, vol. 30, No. 6, pp. 761-768.
Barta et al., 2000, "Synthesis and activity of selective MMP inhibitors with an aryl backbone," *Bioorg. Med. Chem. Lett.*, vol. 10, No. 24, pp. 2815-2817.
Bernhard, D. et al., 1999, "Apoptosis induced by the histone deacetylase inhibitor sodium butyrate in human leukemic lymphoblasts," *FASEB J.*, vol. 13, No. 14, pp. 1991-2001.
Bernstein et al., 2000, "Genomewide studies of histone deacetylase function in yeast," *Proc. Natl. Acad. Sci. USA*, vol. 97, No. 25, pp. 13708-13713.
Brehm, A., et al., 1998, "Retinoblastoma protein recruits histone deacetylase to repress transcription," *Nature*, 1998, vol. 391, pp. 597-601.
Chang et al., 2000, "Activation of the BRLF1 promoter and lytic cycle of Epstein-Barr virus by histone acetylation," *Nucleic Acids Res.*, vol. 28, No. 20, pp. 3918-3925.
Dangond et al., 1998, Differential Display Cloning of a Novel Human Histone Deacetylase (HDAC3) cDNA from PHA-Activated Immune Cells, *Biochem. Biophys. Res. Commun.*, vol. 242, No. 3, pp. 648-652.

(Continued)

*Primary Examiner* — James O Wilson
*Assistant Examiner* — Erich A Leeser
(74) *Attorney, Agent, or Firm* — Nixon & Vanderhye P.C.

(57) ABSTRACT

This invention pertains to certain carbamic acid compounds which inhibit HDAC (histone deacetylase) activity of the following formula:

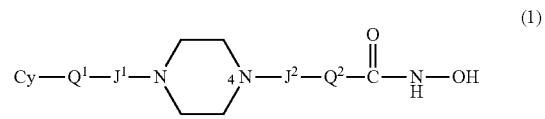

(1)

The present invention also pertains to pharmaceutical compositions comprising such compounds, and the use of such compounds and compositions, both in vitro and in vivo, to inhibit HDAC, and in the treatment of conditions mediated by HDAC, cancer, proliferative conditions, psoriasis, etc.

64 Claims, No Drawings

OTHER PUBLICATIONS

David, G., et al., 1998, "Histone deacetylase associated with mSin3A mediates repression by the acute promyelocytic leukemia-associated PLZF protein," *Oncogene*, vol. 16(19), pp. 2549-2556.

Davie, J.R., 1998, "Covalent modifications of histones: expression from chromatic templates," *Curr. Opin. Genet. Dev.*, vol. 8, pp. 173-178.

Desai, D., et al., 1999, "Chemopreventive efficacy of suberanilohydroxamic acid (SAHA), a cytodifferentiating agent, against tobacco-specific nitrosamine 4-(methylnitros-amino)-1-(3-pyridyI)-1-butanone (NNK)-induced lung tumorigenesis in female A/J mice," *Proceedings of the American Association for Cancer Research*, Pevention/Basic Science and Clinical Studies 4, vol. 40, p. 362, Abstract No. 2396.

Desmarits, C., et al., 2001, Nickel-catalysed sequential amination of aryl- and heteroaryl di- and trichlorides, *Tetrahedron*, vol. 57, p. 7657-7664.

Emiliani, S., et al., 1998, "Characterization of a human RPD3 ortholog, HDAC3," *Proc. Natl. Acad. Sci. USA*, vol. 95, p. 2795-2800.

Finnin et al., 1999, "Structures of a histone deacetylase homologue bound to the TSA and SAHA inhibitors," *Nature*, vol. 401, pp. 188-193.

Grozinger et al., 1999, "Three proteins define a class of human histone deacetylases related to yeast Hdalp," *Proc. Natl. Acad. Sci. USA*, vol. 96, pp. 4868-4873.

Hartwig, J.F., et al., 1999, "Room-Temperature Palladium-Catalyzed Amination of Aryl Bromides and Chlorides and Extended Scope of Aromatic C-N Bond Formation with a Commercial Ligand," *J. Org. Chem.*, vol. 64, pp. 5575-5580.

Hoshikawa, Y., et al., 1994, "Trichostatin A Induces Morphological Changes and Gelsolin Expression by Inhibiting Histone Deacetylase in Human Carcinoma Cell Lines," *Exp. Cell. Res.*, vol. 214(1), pp. 189-197.

Hou et al., 2001, "Binding affinities for a series of selective inhibitors of gelatinase-A using molecular dynamics with a linear interaction energy approach," *J. Phys. Chem. B*, vol. 105, No. 22, pp. 5304-5315.

Howe, L., et al., 1999, "Histone Acetyltransferase Complexes and Their Link to Transcription," *Crit. Rev. Eukaryot. Gene Expr.*, vol. 9(3-4), pp. 231-243.

Iavarone et al., 1999, "E2F and Histone Deacetylase Mediate Transforming Growth Factor β Repression of *cdc25A* during Keratinocyte Cell Cycle Arrest," *Mol. Cell Biol.*, vol. 19, No. 1, pp. 916-922.

Jung, M., et al., 1999, *Journal of Medicinal Chemistry* (ACS, Washington, USA), vol. 42, No. 22, pp. 4669-4679.

Kao et al., 2000, "Isolation of a novel histone deacetylase reveals that class I and class II deacetylases promote SMRT-mediated repression," *Genes & Dev.*, vol. 14, p. 55-66.

Kijima et al., 1993, "Trapoxin, an Antitumor Cyclic Tetrapeptide, Is an Irreversible Inhibitor of Mammalian Histone Deacetylase*," *J. Biol. Chem.*, vol. 268, pp. 22429-22435.

Kim et al., 1999, "Oxamflatin is a novel antitumor compound that inhibits mammalian histone deacetylase," *Oncogene*, vol. 18(15), pp. 2461-2470.

Kim, M.S., et al., 2001 " Histone deacetylases induce angiogenesis by negative regulation of tumour suppressor genes," *Nature Medicine*, vol. 7, No. 4, pp. 437-443.

Kimura et al., 1994, "Dual Modes of Action of Platelet-Derived Growth Factor and Its Inhibition by Trichostatin-A for DNA Synthesis in Primary Cultured Smooth Muscle Cells of Rat Aorta," *Biol. Pharm. Bull.*, vol. 17, No. 3, pp. 399-402.

Kitamura, K., et al., 2000, "Histone deacetylase inhibitor but not arsenic trioxide differentiates acute promyelocytic leukaemia cells with t(11;17) in combination with all-trans retinonic acid," *Br. J. Haematol.*, vol. 108(4), pp. 696-702.

Kouzarides, T., 1999, "Histone acetylases and deacetylases in cell proliferation," *Curr. Opin. Genet. Dev.*, vol. 9, No. 1, pp. 40-48.

Kuusisto et al., 2001, "Ubiquitin-Binding Protein p62 Expression is Induced during Apoptosis and Proteasomal Inhibition in Neuronal Cells," *Biochem. Biophys. Res. Commun.*, vol. 280, No. 1, pp. 223-228.

Kwon et al., 1998, "Depudecin induces morphological reversion of transformed fibroblasts via the inhibition of histone deacetylase," *Proc. Natl. Acad. Sci. USA*, vol. 95, pp. 3356-3361.

Laherty, C.D., et al., 1997, "Histone Deacetylases Associated with the mSin3 Corepressor Mediate Mad Transcriptional Repression," *Cell*, vol. 89(3), pp. 349-356.

Lea and Tulsyan, 1995, "Discordant Effects of Butyrate Analogues on Erythroleukemia Cell Proliferation, Differentiation and Histone Deacetylase," *Anticancer Res.*, vol. 15, pp. 879-883.

Lea et al., 1999, "Increased acetylation of histones induced by diallyl disulfide and structurally related molecules," *Int. J. Oncol.*, vol. 2, pp. 347-352.

Lin, R.J., et al., 1998, "Role of the histone deacetylase complex in acute promyelocytic leukaemia," *Nature*, vol. 391(6669), pp. 811-814.

McCaffrey et al., 1997, "Induction of γGlobin by Histone Deacetylase Inhibitors," *Blood*, vol. 90, No. 5, pp. 2075-2083.

Mielnicki, L.M., et al., 1999, "Epigenetic Regulation of Gelsolin Expression in Human Breast Cancer Cells," *Exp. Cell. Res.*, vol. 249(1), pp. 161-176.

Nakajima et al., 1998, "FR901228, a Potent Antitumor Antibiotic, Is a Novel Histone Deacetylase Inhibitor," *Exp. Cell Res.*, vol. 241, pp. 126-133.

Ng, N.H. and Bird, A., 2000, "Histone deacetylases: silencers for hire," *Trends Biochem. Sci.*, vol. 25(3), pp. 121-126.

Niki et al., 1999, "A Histone Deacetylase Inhibitor, Trichostatin A, Suppresses Myofibroblastic Differentiation of Rat Hepatic Stellate Cells in Primary Culture," *Hepatology*, vol. 29, No. 3, pp. 858-867.

Onishi et al., 1996, "Antibacterial Agents That Inhibit Lipid A Biosynthesis," *Science*, vol. 274, pp. 939-940.

Parrish, C.A., et al., 2001, "Use of Polymer-Supported Dialkylphosphinobiphenyl Ligands for Palladium-Catalyzed Amination and Suzuki Reactions," *J. Org. Chem.*, vol. 66, pp. 3820-3827.

Pazin, M.J., et al., 1997, "What's up and down with histone deacetylation and transcription?," *Cell*, vol. 89, No. 3, pp. 325-328.

Richon et al, 1996, "Second generation hybrid polar compounds are potent inducers of transformed cell differentiation," *Proc. Natl. Acad. Sci. USA*, vol. 93, pp. 5705-5708.

Richon et al., 1998, "A class of hybrid poler inducers of transformed cell differentiation inhibits histone deacetylases," *Proc. Natl. Acad. Sci. USA*, vol. 95, pp. 3003-3007.

Saito et al., 1999, "A synthetic inhibitor of histone deacetylase, MS-27-275, with marked in vivo antitumor activity against human tumors," *Proc. Natl. Acad. Sci. USA*, vol. 96, pp. 4592-4597.

Saunders, N. et al, 1999 "Histone deacetylase inhibitors as potential anti-skin cancer agents," *Cancer Res.*, vol. 59, No. 2 pp. 399-404.

Sonoda, H. et al., 1996, "Oxamflatin: a novel compound which reverses malignant phenotype to normal one via induction of JunD," *Oncogene*, vol. 13, pp. 143-149.

Spencer, V.A. and Davie, J.R., 1999, "Role of covalent modifications of histones in regulating gene expression," *Gene*, vol. 240(1), pp. 1-12.

Suzuki et al., 1999, "Synthesis and histone deactylase inhibitory activity of new benzamide derivatives," *J. Med. Chem.*, vol. 42, pp. 3001-3003.

Takahashi, I., et al, 1996, "Selective inhibition of IL-2 gene expression by trichostatin A, a potent inhibitor of mammalian histone deacetylase," *J. Antibiot.* (Tokyo), vol. 49, No. 5, pp. 453-457.

Taunton, J., et al., 1996, "A mammalian histone deacetylase related to the yeast transcriptional regulator Rpd3p," *Science*, vol. 272, pp. 408-411.

Tsuji et al., 1976, "A New Antifungal Antibiotic, Trichostatin*," *J. Antibiot.* (Tokyo), vol. 29, No. 1, pp. 1-6.

Ueda, H., et al., 1994, "FR901228, a novel antitumor bicyclic depsipeptide produced by *Chromobacterium violaceum* No. 968," *J. Antibiot.* (Tokyo), vol. 47(3), pp. 315-323.

Van den Wyngaert et al., "Cloning and characterization of human histone deacetylase 8," 2000, *FEBS*, vol. 478, pp. 77-83.

Vigushin et al., 2001, "Trichostatin A Is a Histone Deacetylase Inhibitor with Potent Antitumor Activity against Breast Cancer in vivo'," *Clin. Cancer Res.*, vol. 7, No. 4, pp. 971-976.

Warrell et al., 1998, "Therapeutic Targeting of Transcription in Acute Promyelocytic Leukemia by Use of an Inhibitor of Histone Deacetylase," *J. Natl. Cancer Inst.*, vol. 90, pp. 1621-1625.

Wolfe, J.P., et al., 2000a, "Scope and Limitations of the Pd/BINAP-Catalyzed Amination of Aryl Bromides," *J. Org. Chem.*, vol. 65, pp. 1144-1157.

Wolfe, J.P., et al., 2000b, "Simple, Efficient Catalyst System for the Palladium-Catalyzed Amination of Aryl Chlorides, Bromides, and Triflates," *J. Orq. Chem.*, vol. 65, pp. 1158-1174.

Wong, J., et al., 1998, "Distinct requirements for chromatin assembly in transcriptional repression by thyroid hormone receptor and histone deacetylase," *EMBO J.*, vol. 17(2), pp. 520-534.

Yang, W.M., et al., 1996, "Transcriptional repression of YY1 is mediated by interaction with a mammalian homolog of the yeast global regulator RPD3," *Proc. Natl. Acad. Sci. USA*, vol. 93, pp. 12845-12850.

Yang, W.M., et al., 1997, "Isolation and characterization of cDNAs corresponding to an additional member of the human histone deacetylase gene family," *J. Biol. Chem.*, vol. 272, pp. 28001-28007.

Yoshida et al., 1995, "Trichostatin A and trapoxin: novel chemical probes for the role of histone acetylation in chromatin structure and function," *Bioessays*, vol. 17, pp. 423-430.

Yoshida, M. and Horinouchi, S., 1999, "Inhibition of Histone Deacetylation and Signal-Dependent Nuclear Export," *Ann. N. Y. Acad. Sci.*, vol. 886, pp. 23-36.

Yoshida, M., Beppu, T., 1988, "Reversible arrest of proliferation of rat 3Y1 fibroblasts in both G1 and G2 phases by trichostatin A," *Exp. Cell. Res.*, vol. 177, pp. 122-131.

Yoshida, M., et al., 1990a, "Potent and Specific Inhibition of Mammalian Histone Deacetylase Both in Vivo and in Vitro by Trichostatin A*," *J. Biol. Chem.*, vol. 265(28), pp. 17174-17179.

Yoshida, M., et al., 1990b, "Structural specificity for biological activity of trichostatin A, a specific inhibitor of mammalian cell cycle with potent differentiation-inducing activity in friend leukemia cells," *J. Antibiot.* (Tokyo), vol. 43(9), pp. 1101-1106.

Bouchain, et al., Novel Hydroxamate and Anilide Derivatives as Potent Histone Deacetylase Inhibitors: Synthesis and Antiproliferative Evaluation, Curr. Med. Chem., 2003, 10, 2359-72.

Vippagunta et al, "Crystalline solids", Advanced Drug Delivery Reviews 48 (2001) 3-26.

Guillory et al, "Generation of Polymorphs, Hydrates, Solvates, and Amorphous Solids," in: *Polymorphism in Pharmaceutical Solids*, ed. Harry G. Brittan, vol. 95, Marcel Dekker, Inc., New York, 1999.

Banker, G., et al., 1996, "Modern Pharmaceuticals", Third Edition, Marcel Dekker, New York, pp. 596 and 451.

La Thangue, N. B., 2004, "Histone deacetylase inhibitors and cancer therapy", J. Chemo., vol. 16, Suppl. 4, pp. 64-67.

West, A. R., 1988, "Solid State Chemistry and Its Applications", Wiley, New York, pp. 358 and 365.

Wolff, M. E., 1995, "Burger's Medicinal Chemistry and Drug Discovery", Fifth Ed., vol. 1: Principles and Practice, John Wiley & Sons, pp. 975-957.

Claims filed May 8, 2009 in U.S. Appl. No. 10/509,732.

Vigushin et al., "Trichostatin A Is a Histone Deacetylase Inhibitor with Potent Antitumor Activity against Breast Cancer in Vivo" 2001, Clin. Cancer Res., vol. 7, No. 4, pp. 971-976.

Iavarone et al., "E2F and Histone Deacetylase Mediate Transforming Growth Factor β Repression of cdc25A during Keratinocyte Cell Cycle Arrest" 1999, Mol. Cell Biol., vol. 19, No. 1, pp. 916-922.

Niki et al., "A Histone Deacetylase Inhibitor, Trichostatin A, Suppresses Myofibroblastic Differentiation of Rat Hepatic Stellate Cells in Primary Culture" 1999, Hepatology, vol. 29, No. 3, pp. 858-867.

JP 10114681 A2 (with English abstract and machine translation) "Anti-Fibroosis Agent"; Jun. 1998.

Kimura et al., "Dual Modes of Action of Platelet-Derived Growth Factor and Its Inhibition by Trichostatin-A for DNA Synthesis in Primary Cultured Smooth Muscle Cells of Rat Aorta" 1994, Biol. Pharm. Bull., vol. 17, No. 3, pp. 399-402.

Kuusisto et al., "Ubiquitin-Binding Protein p62 Expression Is Induced During Apoptosis and Proteasomal Inhibition in Neuronal Cells" 2001, Biochem. Biophys. Res. Commun., vol. 280, No. 1, pp. 223-228.

Dangond et al., "Differential Display Cloning of a Novel Human Histone Deacetylase (HDAC3) cDNA from PHA-Activated Immune Cells" 1998, Biochem. Biophys. Res. Commun., vol. 242, No. 3, pp. 648-652.

Takahashi et al., "Selective Inhibition of IL-2 Gene Expression by Trichostatin A, a Potent Inhibitor of Mammalian Histone Deacetylase" 1996, J. Antibiot. (Tokyo), vol. 49, No. 5, pp. 453-457.

Kim et al., "Histone deacetylase Induce Angiogenesis by Negative Regulation of Tumor Suppressor Genes" 2001, Nature Medicine, vol. 7, No. 4, pp. 437-443.

McCaffrey et al., "Induction of γ-Globin by Histone Deacetylase Inhibitors" 1997, Blood, vol. 90, No. 5, pp. 2075-2083.

Bernstein et al., "Genomewide Studies of Histone Deacetylase Function in Yeast" 2000, Proc. Natl. Acad. Sci. USA, vol. 97, No. 25, pp. 13708-13713.

Tsuji et al., "A New Antifungal Antibiotic, Trichostatin" 1976, J. Antibiot. (Tokyo), vol. 29, No. 1, pp. 1-6.

Andrews et al., "Anti-malarial Effect of Histone Deacetylation Inhibitors and Mammalian Tumour Cytodifferentiating Agents" 2000, Int. J. Parasitol., vol. 30, No. 6, pp. 761-768.

Onishi et al., "Antibacterial Agents That Inhibit Lipid A Biosynthesis" 1996, Science, vol. 274, pp. 939-940.

Chang et al., "Activation of the BRLF1 Promoter and Lytic Cycle of Epstein-Barr Virus by Histone Acetylation" 2000, Nucleic Acids Res., vol. 28, No. 20, pp. 3918-3925.

Abel et al., "Epigenetic targets of HDAC inhibition in neurodegenerative and psychiatric disorders", 2008, Curr. Opin. Pharmacol., vol. 8, No. 1, pp. 57 64.

Tan et al., "Novel histone deacetylase inhibitors in clinical trials as anti-cancer agents", 2010, J. Hematology & Oncology, 3:5.

Bots et al., "Rational Combinations Using HDAC Inhibitors", 2009, Clin. Cancer Res., vol. 15, No. 12, pp. 3970 3977.

Gray et al., "Rationale for the Use of Histone Deacetylase Inhibitors as a Dual Therapeutic Modality in Multiple Sclerosis", 2006, Epigenetics, vol. 1, No. 2, pp. 67-75.

Hauke et al., "Survival motor neuron gene 2 silencing by DNA methylation correlates with spinal muscular atrophy disease severity and can be bypassed by histone deacetylase inhibition", 2008, Human Molecular Genetics, vol. 18, No. 2, pp. 304 317.

Kazantsev et al., "Therapeutic application of histone deacetylase inhibitors for central nervous system disorders", 2008, Nature Reviews, vol. 7, pp. 854 868.

\* cited by examiner

CARBAMIC ACID COMPOUNDS COMPRISING A PIPERAZINE LINKAGE AS HDAC INHIBITORS

This application is a continuation of application Ser. No. 10/509,732, filed Sep. 30, 2004 (pending), which is the U.S. national phase of international application PCT/GB03/01463 filed Apr. 3, 2003 which designated the US, and which claims the benefit of U.S. Provisional Application No. 60/369,337 filed Apr. 3, 2002, the entire contents of each of which is hereby incorporated by reference.

TECHNICAL FIELD

This invention pertains generally to the field of biologically active compounds, and more specifically to certain carbamic acid compounds which inhibit HDAC (histone deacetylase) activity. The present invention also pertains to pharmaceutical compositions comprising such compounds, and the use of such compounds and compositions, both in vitro and in vivo, to inhibit HDAC, and in the treatment of conditions mediated by HDAC, cancer, proliferative conditions, psoriasis, etc.

BACKGROUND

Throughout this specification, including any claims which follow, unless the context requires otherwise, the word "comprise," and variations such as "comprises" and "comprising," will be understood to imply the inclusion of a stated integer or step or group of integers or steps, but not the exclusion of any other integer or step or group of integers or steps.

It must be noted that, as used in the specification and any appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

DNA in eukaryotic cells is tightly complexed with proteins (histones) to form chromatin. Histones are small, positively charged proteins which are rich in basic amino acids (positively charged at physiological pH), which contact the phosphate groups (negatively charged at physiological pH) of DNA. There are five main classes of histones, H1, H2A, H2B, H3, and H4. The amino acid sequences of histones H2A, H2B, H3, and H4 show remarkable conservation between species, whereas H1 varies somewhat, and in some cases is replaced by another histone, e.g., H5. Four pairs of each of H2A, H2B, H3, and H4 together form a disk-shaped octomeric protein core, around which DNA (about 140 base pairs) is wound to form a nucleosome. Individual nucleosomes are connected by short stretches of linker DNA associated with another histone molecule (e.g., H1, or in certain cases, H5) to form a structure resembling a beaded string, which is itself arranged in a helical stack, known as a solenoid.

The majority of histones are synthesised during the S phase of the cell cycle, and newly synthesised histones quickly enter the nucleus to become associated with DNA. Within minutes of its synthesis, new DNA becomes associated with histones in nucleosomal structures.

A small fraction of histones, more specifically, the amino side chains thereof, are enzymatically modified by post-translational addition of methyl, acetyl, or phosphate groups, neutralising the positive charge of the side chain, or converting it to a negative charge. For example, lysine and arginine groups may be methylated, lysine groups may be acetylated, and serine groups may be phosphorylated. For lysine, the —(CH$_2$)$_4$—NH$_2$ sidechain may be acetylated, for example by an acetyltransferase enzyme, to give the amide —(CH$_2$)$_4$—NHC(=O)CH$_3$. Methylation, acetylation, and phosphorylation of amino termini of histones which extend from the nucleosomal core affects chromatin structure and gene expression. (See, for example, Spencer and Davie, 1999).

Acetylation and deacetylation of histones is associated with transcriptional events leading to cell proliferation and/or differentiation. Regulation of the function of transcription factors is also mediated through acetylation. Recent reviews of histone deacetylation include Kouzarides, 1999 and Pazin et al., 1997.

The correlation between the acetylation status of histones and the transcription of genes has been known for over 30 years (see, for example, Howe et al., 1999). Certain enzymes, specifically acetylases (e.g., histone acetyltransferase, HAT) and deacetylases (e.g., histone deacetylase, HDAC), which regulate the acetylation state of histones have been identified in many organisms and have been implicated in the regulation of numerous genes, confirming the link between acetylation and transcription. See, for example, Davie, 1998. In general, histone acetylation correlates with transcriptional activation, whereas histone deacetylation is associated with gene repression.

A growing number of histone deacetylases (HDACs) have been identified (see, for example, Ng and Bird, 2000). The first deacetylase, HDAC1, was identified in 1996 (see, for example, Tauton et al., 1996). Subsequently, two other nuclear mammalian deacetylases were found, HDAC2 and HDAC3 (see, for example, Yang et al., 1996, 1997, and Emiliani et al., 1998). See also, Grozinger et al., 1999; Kao et al., 2000; and Van den Wyngaert et al., 2000.

Eleven (11) human HDACs have been cloned so far:
 HDAC1 (Genbank Accession No. NP_004955)
 HDAC2 (Genbank Accession No. NP_001518)
 HDAC3 (Genbank Accession No. O15379)
 HDAC4 (Genbank Accession No. AAD29046)
 HDAC5 (Genbank Accession No. NP_005465)
 HDAC6 (Genbank Accession No. NP_006035)
 HDAC7 (Genbank Accession No. AAF63491)
 HDAC8 (Genbank Accession No. AAF73428)
 HDAC9 (Genbank Accession No. AAK66821)
 HDAC10 (Genbank Accession No. AAK84023)
 HDAC11 (Genbank Accession No. NM_024827

These eleven human HDACs fall in two distinct classes: HDACs 1, 2, 3 and 8 are in class I, and HDACs 4, 5, 6, 7, 9, 10 and 11 are in class II.

There are a number of histone deacetylases in yeast, including the following:
 RPD3 (Genbank Accession No. NP_014069)
 HDA1 (Genbank Accession No. P53973)
 HOS1 (Genbank Accession No. Q12214)
 HOS2 (Genbank Accession No. P53096)
 HOS3 (Genbank Accession No. Q02959)

There are also numerous plant deacetylases, for example, HD2, in *Zea mays* (Genbank Accession No. AF254073_1).

HDACs function as part of large multiprotein complexes, which are tethered to the promoter and repress transcription. Well characterised transcriptional repressors such as Mad (Laherty et al., 1997), pRb (Brehm et al., 1998), nuclear receptors (Wong et al., 1998) and YY1 (Yang et al., 1997) associate with HDAC complexes to exert their repressor function.

The study of inhibitors of histone deacetylases indicates that these enzymes play an important role in cell proliferation and differentiation. The inhibitor Trichostatin A (TSA) (Yoshida et al., 1990a) causes cell cycle arrest at both G1 and G2 phases (Yoshida and Beppu, 1988), reverts the transformed phenotype of different cell lines, and induces differentiation of Friend leukaemia cells and others (Yoshida et al., 1990b). TSA (and SAHA) have been reported to inhibit cell growth, induce terminal differentiation, and prevent the formation of tumours in mice (Finnin et al., 1999).

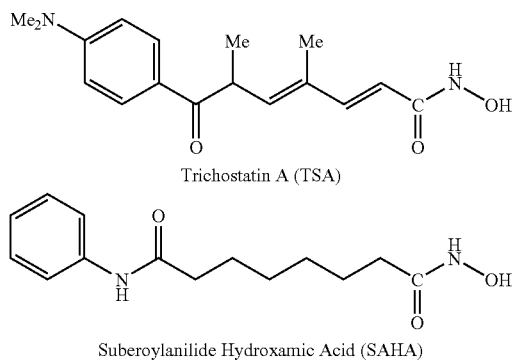

Cell cycle arrest by TSA correlates with an increased expression of gelsolin (Hoshikawa et al., 1994), an actin regulatory protein that is down regulated in malignant breast cancer (Mielnicki et al., 1999). Similar effects on cell cycle and differentiation have been observed with a number of deacetylase inhibitors (Kim et al., 1999).

Trichostatin A has also been reported to be useful in the treatment of fibrosis, e.g., liver fibrosis and liver cirrhosis. See, e.g., Geerts et al., 1998.

Recently, certain compounds that induce differentiation have been reported to inhibit histone deacetylases. Several experimental antitumour compounds, such as trichostatin A (TSA), trapoxin, suberoylanilide hydroxamic acid (SAHA), and phenylbutyrate have been reported to act, at least in part, by inhibiting histone deacetylase (see, e.g., Yoshida et al., 1990; Richon et al., 1998; Kijima et al., 1993). Additionally, diallyl sulfide and related molecules (see, e.g., Lea et al., 1999), oxamflatin (see, e.g., Kim et al., 1999; Sonoda et al., 1996), MS-27-275, a synthetic benzamide derivative (see, e.g., Saito et al., 1999; Suzuki et al., 1999; note that MS-27-275 was later re-named as MS-275), butyrate derivatives (see, e.g., Lea and Tulsyan, 1995), FR901228 (see, e.g., Nokajima et al., 1998), depudecin (see, e.g., Kwon et al., 1998), and m-carboxycinnamic acid bishydroxamide (see, e.g., Richon et al., 1998) have been reported to inhibit histone deacetylases. In vitro, some of these compounds are reported to inhibit the growth of fibroblast cells by causing cell cycle arrest in the G1 and G2 phases, and can lead to the terminal differentiation and loss of transforming potential of a variety of transformed cell lines (see, e.g., Richon et al., 1996; Kim et al., 1999; Yoshida et al., 1995; Yoshida & Beppu, 1988). In vivo, phenybutyrate is reported to be effective in the treatment of acute promyelocytic leukemia in conjunction with retinoic acid (see, e.g., Warrell et al., 1998). SAHA is reported to be effective in preventing the formation of mammary tumours in rats, and lung tumours in mice (see, e.g., Desai et al., 1999).

The clear involvement of HDACs in the control of cell proliferation and differentiation suggests that aberrant HDAC activity may play a role in cancer. The most direct demonstration that deacetylases contribute to cancer development comes from the analysis of different acute promyelocytic leukemias (APL). In most APL patients, a translocation of chromosomes 15 and 17 (t(15;17)) results in the expression of a fusion protein containing the N-terminal portion of PML gene product linked to most of RARα (retinoic acid receptor). In some cases, a different translocation (t(11;17)) causes the fusion between the zinc finger protein PLZF and RARα. In the absence of ligand, the wild type RARα represses target genes by tethering HDAC repressor complexes to the promoter DNA. During normal hematopoiesis, retinoic acid (RA) binds RARα and displaces the repressor complex, allowing expression of genes implicated in myeloid differentiation. The RARα fusion proteins occurring in APL patients are no longer responsive to physiological levels of RA and they interfere with the expression of the RA-inducible genes that promote myeloid differentiation. This results in a clonal expansion of promyelocytic cells and development of leukaemia. In vitro experiments have shown that TSA is capable of restoring RA-responsiveness to the fusion RARα proteins and of allowing myeloid differentiation. These results establish a link between HDACs and oncogenesis and suggest that HDACs are potential targets for pharmaceutical intervention in APL patients. (See, for example, Kitamura et al., 2000; David et al., 1998; Lin et al., 1998).

Furthermore, different lines of evidence suggest that HDACs may be important therapeutic targets in other types of cancer. Cell lines derived from many different cancers (prostate, colorectal, breast, neuronal, hepatic) are induced to differentiate by HDAC inhibitors (Yoshida and Horinouchi, 1999). A number of HDAC inhibitors have been studied in animal models of cancer. They reduce tumour growth and prolong the lifespan of mice bearing different types of transplanted tumours, including melanoma, leukaemia, colon, lung and gastric carcinomas, etc. (Ueda et al., 1994; Kim et al., 1999).

Psoriasis is a common chronic disfiguring skin disease which is characterised by well-demarcated, red, hardened scaly plaques: these may be limited or widespread. The prevalence rate of psoriasis is approximately 2%, i.e., 12.5 million sufferers in the triad countries (US/Europe/Japan). While the disease is rarely fatal, it clearly has serious detrimental effects upon the quality of life of the patient: this is further compounded by the lack of effective therapies. Present treatments are either ineffective, cosmetically unacceptable, or possess undesired side effects. There is therefore a large unmet clinical need for effective and safe drugs for this condition.

Psoriasis is a disease of complex etiology. Whilst there is clearly a genetic component, with a number of gene loci being involved, there are also undefined environmental triggers. Whatever the ultimate cause of psoriasis, at the cellular level, it is characterised by local T-cell mediated inflammation, by keratinocyte hyperproliferation, and by localised angiogenesis. These are all processes in which histone deacetylases have been implicated (see, e.g., Saunders et al., 1999; Bernhard et al., 1999; Takahashi et al., 1996; Kim et al, 2001). Therefore HDAC inhibitors may be of use in therapy for psoriasis. Candidate drugs may be screened, for example, using proliferation assays with T-cells and/or keratinocytes.

Thus, one aim of the present invention is the provision of compounds which are potent inhibitors of histone deacetylases (HDACs). There is a pressing need for such compounds, particularly for use as antiproliferatives, for example, anticancer agents, agents for the treatment of psoriasis, etc.

Such molecules desirably have one or more of the following properties and/or effects:

(a) easily gain access to and act upon tumour cells;
(b) down-regulate HDAC activity;
(c) inhibit the formation of HDAC complexes;
(d) inhibit the interactions of HDAC complexes;
(e) inhibit tumour cell proliferation;
(e) promote tumour cell apoptosis;
(f) inhibit tumour growth; and,
(g) complement the activity of traditional chemotherapeutic agents.

A number of carbamic acid compounds have been described.

Certain classes of carbamic acid compounds which inhibit HDAC are described in Watkins et al., 2002a, 2002b, and 2002c.

Piperazino Amides

Alpegiani et al., 1999, describe compounds of the following type ($Q^2$ has backbone=2; is alkylene; is α-substituted) which are proposed to be useful in the treatment of diseases involving matrix metalloproteases (MMPs) and/or tumor necrosis factor α (TNF-α).

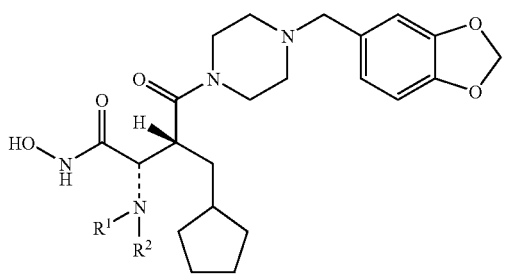

Alpegiani et al., 1999, also describes the following compound ($Q^2$ has backbone=2; is alkylene; is α-substituted):

Example 42 (page 15)

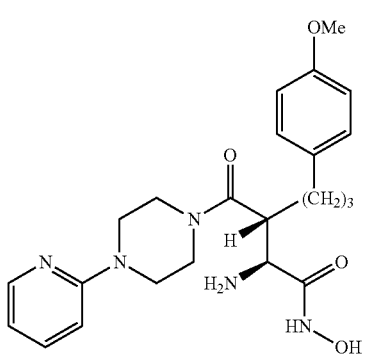

Billedeau et al., 2000, describe compounds of the following type (wherein $R^1$ is, e.g., phenyl) ($Q^2$ has backbone=3; is alkylene; is α-substituted), which apparently inhibit procollagen C-proteinase, and are proposed for use in the treatment of fibrotic diseases.

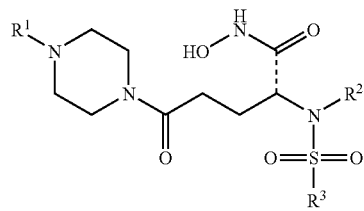

Broadhurst et al., 1993, describe the following compound ($Q^2$ has backbone=2; is alkylene; is α-substituted), which apparently inhibits collagenase.

Compound F (page 9)

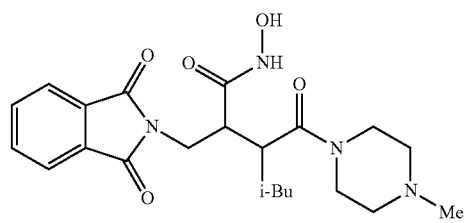

Broadhurst et al., 1995, describe the following compound ($Q^2$ has backbone=2; is alkylene; is α-substituted), which apparently inhibits collagenase, and is proposed for use in the treatment of cancer, arteriosclerosis and inflammation.

Example 18 (page 15)

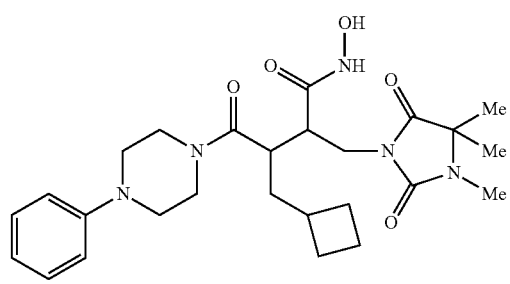

Hou et al., 2001, describe the following compound ($Q^2$ has backbone=2; is alkylene; is α-substituted), which apparently inhibits the proteinase gelatinase-A.

Compound a15 (page 5314)

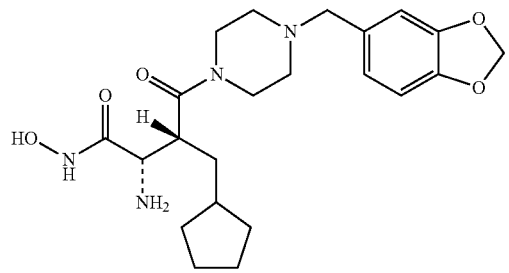

Owen et al., 2001, describe the following compound ($Q^2$ has backbone=2; is alkylene), which apparently inhibits certain MMPs, and is proposed for use in the treatment of inflammation.

Example 4 (page 20)

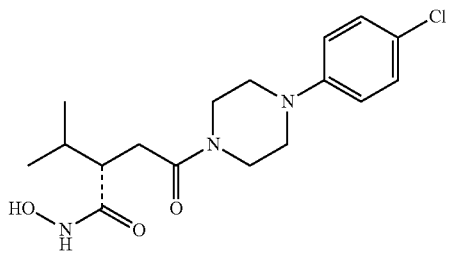

Pratt et al., 2001, describe the following compounds ($Q^2$ has backbone=2; is alkylene), which apparently have antibacterial activity.

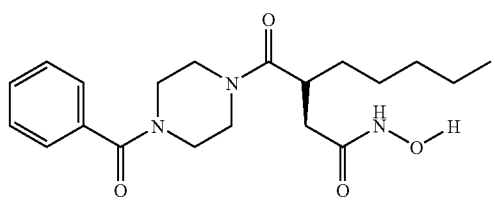

CAS No. 409129-96-0P

Billedeau et al., 2000 describe the following two compounds ($Q^2$ has backbone=3; is alkylene; is α-substituted) as inhibitors of procollagen C-proteinase for use in the treatment of fibrosis, sclerosis, arthritis and acute respiratory distress syndrome.

Example 41 (page 47)

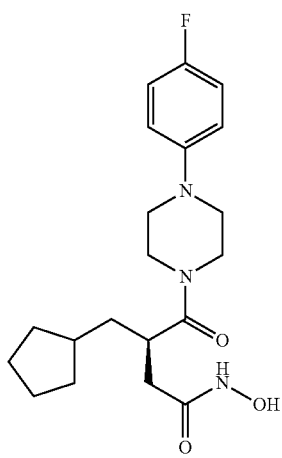

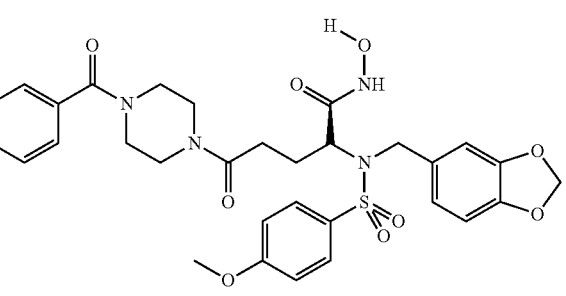

CAS No. 279255-56-0P

Example 42 (page 49)

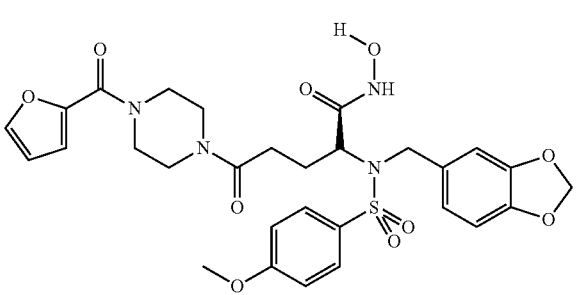

CAS No. 279255-58-2P

Piperazino Sulfonamides

Barlaam et al., 2000, describe compounds of the following type (wherein $R^3$ may be, e.g., phenyl) ($Q^2$ has backbone=2; is alkylene; is optionally β-substituted), which apparently inhibit MMP-13.

Piperazino Bisamides

A number of hydroxamic acids comprising a piperazine moiety with carbonyl groups adjacent to each nitrogen atom of the piperazine moiety are known.

Chong et al., 2002 describe the following compound ($Q^2$ has backbone=2; is alkylene) as an inhibitor of peptide deformylase for use as an antibiotic.

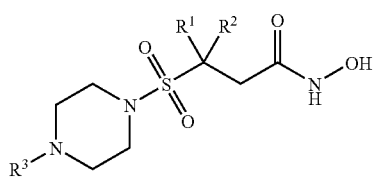

Two examples of such compounds ($Q^2$ has backbone=2; is alkylene) include the following.

Example 3 (page 29)

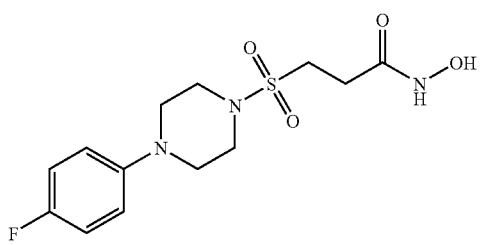

Example 35 (page 29)

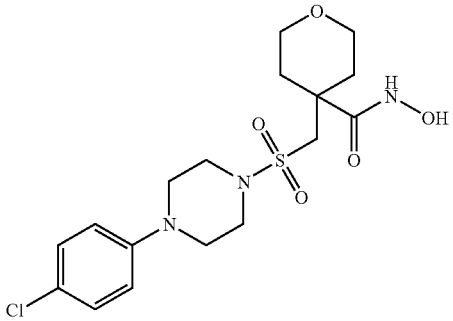

Example 4 (page 31)

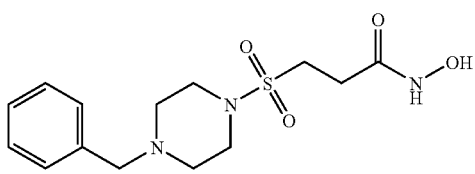

Baxter et al., 2000, (Darwin Discovery, UK) describe compounds of the following type ($Q^2$ has backbone=2; is alkylene), which apparently inhibitor certain MMPs.

Barlaam et al., 2001, describe compounds of the following type ($Q^2$ has backbone=2; is alkylene) which apparently inhibit MMP-13 and collagenase 3.

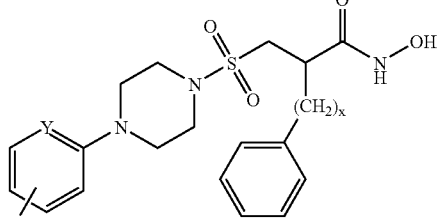

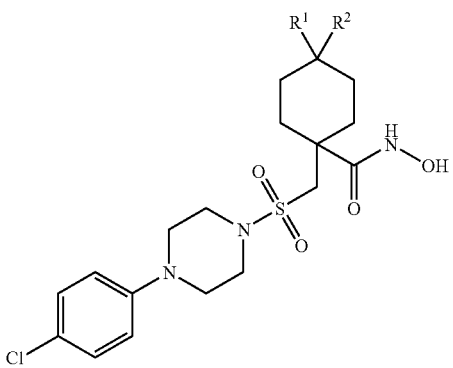

Barta et al., 2000, describe the following compound ($Q^2$ has backbone=2; is phenylene), which apparently inhibits MMP-2 and MMP-13.

Bedell et al., 2000, and Bedell et al., 2001, describe compounds of the following type ($Q^2$ has backbone=2; is phenylene), which apparently inhibit certain MMPs.

Compound 6k (page 2816)

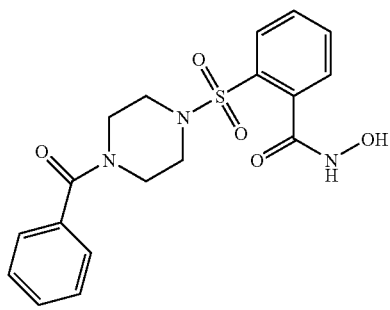

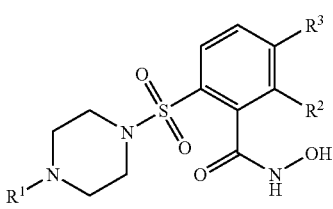

De Crescenzo et al., 2000, describe compounds of the following type ($Q^2$ has backbone=2; is alkylene), which apparently inhibit certain MMPs.

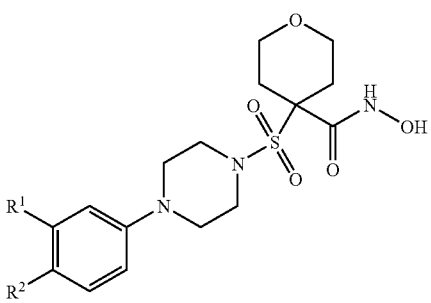

Baxter et al., 1999, (Darwin Discovery, UK) describe the following compound ($Q^2$ has backbone=2; is alkylene), which apparently inhibits certain MMPs.

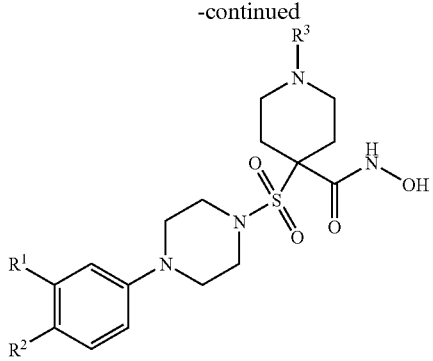

Hannah et al., 2001, (Darwin Discovery, UK) describe compounds of the following type (Q² has backbone=2; is alkylene; is optionally α-substituted), which apparently inhibit certain MMPs.

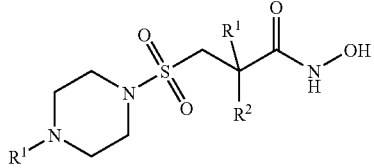

Martin et al., 2000, describes the following compound (Q² has backbone=2; is alkylene), which apparently inhibits certain MMPs.

Example 8 (page 23)

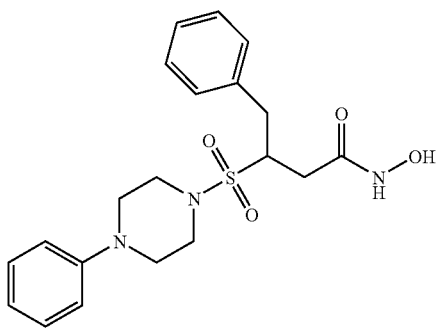

Owen et al., 2000, (Darwin Discovery, UK) describe compounds of the following type (Q² has backbone=2; is phenylene), which are apparently inhibit certain MMPs.

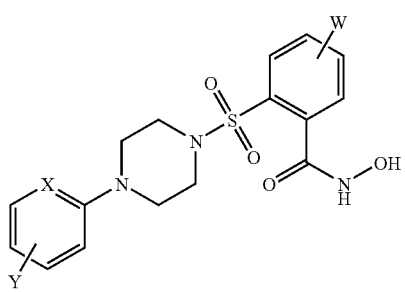

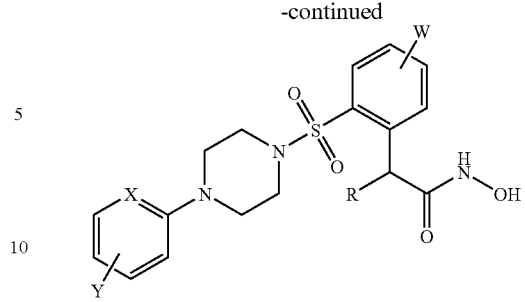

Owen et al., 2000, (Darwin Discovery, UK) also describes the following compound (Q² has backbone=3; is phenylene):

Example 64 (page 32)

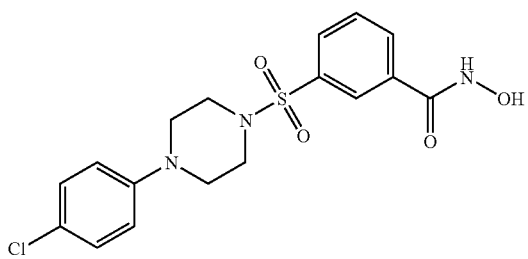

SUMMARY OF THE INVENTION

One aspect of the invention pertains to active carbamic acid compounds, as described herein.

Another aspect of the invention pertains to active compounds, as described herein, which inhibit HDAC activity.

Another aspect of the invention pertains to active compounds, as described herein, which treat conditions which are known to be mediated by HDAC, or which are known to be treated by HDAC inhibitors (such as, e.g., trichostatin A).

Another aspect of the invention pertains to active compounds, as described herein, which (a) regulate (e.g., inhibit) cell proliferation; (b) inhibit cell cycle progression; (c) promote apoptosis; or (d) a combination of one or more of these.

Another aspect of the invention pertains to active compounds, as described herein, which are anti-HDAC agents, and which treat a condition mediated by HDAC.

Another aspect of the invention pertains to active compounds, as described herein, which are anticancer agents, and which treat cancer.

Another aspect of the invention pertains to active compounds, as described herein, which are antiproliferative agents, and which treat a proliferative condition.

Another aspect of the invention pertains to active compounds, as described herein, which are antipsoriasis agents, and which treat psoriasis.

Another aspect of the present invention pertains to a composition comprising a compound, as described herein, and a carrier.

Another aspect of the present invention pertains to a composition comprising a compound, as described herein, and a pharmaceutically acceptable carrier.

Another aspect of the present invention pertains to methods of inhibiting HDAC in a cell, comprising contacting said cell with an effective amount of an active compound, as described herein, whether in vitro or in vivo.

Another aspect of the present invention pertains to methods of (a) regulating (e.g., inhibiting) cell proliferation; (b) inhibiting cell cycle progression; (c) promoting apoptosis; or (d) a combination of one or more of these, comprising contacting a cell with an effective amount of an active compound, as described herein, whether in vitro or in vivo.

Another aspect of the present invention pertains to methods of treating a condition which is known to be mediated by HDAC, or which is known to be treated by HDAC inhibitors (such as, e.g., trichostatin A), comprising administering to a subject in need of treatment a therapeutically-effective amount of an active compound, as described herein.

Another aspect of the present invention pertains to methods of treating cancer, comprising administering to a subject in need of treatment a therapeutically-effective amount of an active compound, as described herein.

Another aspect of the present invention pertains to methods of treating a proliferative condition comprising administering to a subject in need of treatment a therapeutically-effective amount of an active compound, as described herein.

Another aspect of the present invention pertains to methods of treating psoriasis comprising administering to a subject in need of treatment a therapeutically-effective amount of an active compound, as described herein.

Another aspect of the present invention pertains to an active compound, as described herein, for use in a method of treatment of the human or animal body by therapy.

Another aspect of the present invention pertains to use of an active compound, as described herein, for the manufacture of a medicament for use in the treatment of a condition mediated by HDAC, a condition known to be treated by HDAC inhibitors (such as, e.g., trichostatin A), cancer, a proliferative condition, psoriasis, or other condition as described herein.

Another aspect of the present invention pertains to a kit comprising (a) the active compound, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

In one aspect, the present invention pertains to carbamic acid compounds of the formula:

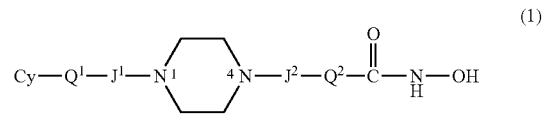

wherein:
Cy is independently a cyclyl group;
$Q^1$ is independently a covalent bond or cyclyl leader group;
the piperazin-1,4-diyl group is optionally substituted;
$J^1$ is independently a covalent bond or —C(═O)—;
$J^2$ is independently —C(═O)f or —S(═O)$_2$—;
$Q^2$ is independently an acid leader group;
wherein:
Cy is independently:
  $C_{3-20}$carbocyclyl,
  $C_{3-20}$heterocyclyl, or
  $C_{5-20}$aryl;
  and is optionally substituted;
$Q^1$ is independently:
  a covalent bond;
  $C_{1-7}$alkylene; or
  $C_{1-7}$alkylene-X—$C_{1-7}$alkylene, —X—$C_{1-7}$alkylene, or $C_{1-7}$alkylene-X—,
  wherein X is —O— or —S—;
  and is optionally substituted;
$Q^2$ is independently:
  $C_{4-6}$alkylene;
  and is optionally substituted;
  and has a backbone length of at least 4 atoms;
or:
$Q^2$ is independently:
  $C_{5-20}$arylene;
  $C_{5-20}$arylene-$C_{1-7}$alkylene;
  $C_{1-7}$alkylene-$C_{1-20}$arylene; or,
  $C_{1-7}$alkylene-$C_{5-20}$arylene-$C_{1-7}$alkylene;
  and is optionally substituted;
  and has a backbone length of at least 4 atoms;
and pharmaceutically acceptable salts, solvates, amides, esters, ethers, chemically protected forms, and prodrugs thereof.

In preferred embodiments, the carbamic acid group, —C(═O)NHOH, is unmodified (e.g., is not an ester).

Note that each of the groups -$J^1$-$Q^1$-Cy and -$J^2$-$Q^2$-C(═O)NHOH is a monovalent and monodentate species; and that is it not intended that these groups be linked, other than via the N-1 and N-4 atoms, respectively, of the piperazin-1,4-diyl group.

The Piperazin-1,4-diyl Group

The piperazin-1,4-diyl group is optionally substituted, i.e., unsubstituted or substituted.

In one embodiment, the piperazin-1,4-diyl group is unsubstituted (i.e., unsubstituted at the 2-, 3-, 5-, and 6-positions).

In one embodiment, the piperazin-1,4-diyl group is substituted (i.e., substituted at one or more the 2-, 3-, 5-, and 6-positions.

For example, in one embodiment, the piperazin-1,4-diyl group is substituted (i.e., substituted at one or more the 2-, 3-, 5-, and 6-positions with $C_{1-4}$alkyl, for example, -Me or -Et.

For example, in one embodiment, the piperazin-1,4-diyl group is: unsubstituted piperazin-1,4-diyl or 2-methyl-piperazin-1,4-diyl.

The piperazin-1,4-diyl group may be in any conformation, including, but not limited to, chair-, boat-, or twist-forms.

The Linkers, $J^1$ and $J^2$

In one embodiment, $J^1$ is independently a covalent bond.

In one embodiment, $J^1$ is independently —C(=O)—.
In one embodiment, $J^2$ is independently —C(=O)—.
In one embodiment, $J^2$ is independently —S(=O)$_2$—.
In one embodiment:
$J^1$ is a covalent bond and $J^2$ is —C(=O); or:
$J^1$ is —C(=O)— and $J^2$ is —C(=O)—; or:
$J^1$ is a covalent bond and $J^2$ is —S(=O)$_2$—.
In one embodiment:
$J^1$ is a covalent bond and $J^2$ is —C(=O)—; or:
$J^1$ is —C(=O)— and $J^2$ is —C(=O)—.
In one embodiment, $J^1$ is a covalent bond and $J^2$ is —C(=O)— (and the compounds may be referred to as "piperazino-amides"):

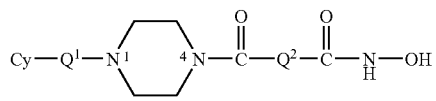
(2)

In one embodiment, $J^1$ is —C(=O)— and $J^2$ is —C(=O)— (and the compounds may be referred to as "piperazino-bisamides"):

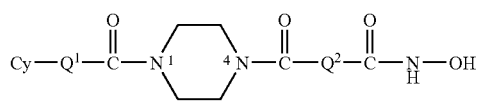
(3)

In one embodiment, $J^1$ is a covalent bond and $J^2$ is —S(=O)$_2$— (and the compounds may be referred to as "piperazino-sulfonamides"):

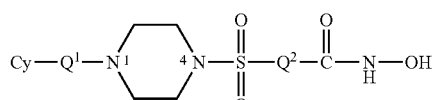
(4)

In one embodiment, $J^1$ is —C(=O)— and $J^2$ is —S(=O)$_2$— (and the compounds may be referred to as "piperazino-amide-sulfonamides"):

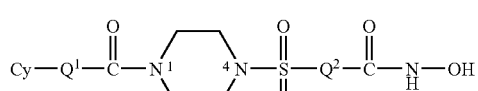
(5)

For the avoidance of doubt, it is intended that, if there is a —C(=O)— group immediately adjacent to the N-1 atom of the piperazin-1-4-diyl group, then that —C(=O)— group must be assigned as $J^1$ (that is, $J^1$ is —(C=O)—) and not as part of $Q^1$ (e.g., as part of an oxo-substituted $Q^1$ group). For example, if the Cy-$Q^1$-$J^1$- group is Ph-CH$_2$—C(=O)—, then Cy is Ph-, $Q^1$ is —CH$_2$—, and $J^1$ is —C(=O)—.

Assigning the Cyclyl Group, Cy

If, within the group -$J^1$-$Q^1$-Cy, there is a plurality of candidate groups satisfying the definition of Cy (referred to as candidate Cy groups), then the candidate Cy group which is furthest from the N-1 atom of the piperazin-1,4-diyl group is identified as Cy (and referred to as "the relevant Cy group").

In this context, distance (e.g., further, furthest) is measured as the number of chain atoms in the shortest continuous chain linking the groups (i.e., the N-1 atom and Cy).

If there is a plurality of furthest candidate Cy groups, then the one (including any substituents) with the largest molecular weight is the relevant one.

If there is a plurality of furthest heaviest candidate Cy groups, then the one (excluding any substituents) with the most annular heteroatoms is the relevant one.

If there is a plurality of furthest heaviest candidate Cy groups with the most annular heteroatoms, then the one with an IUPAC name which alphabetically precedes the other(s), is the relevant one.

Some illustrative examples are shown below.

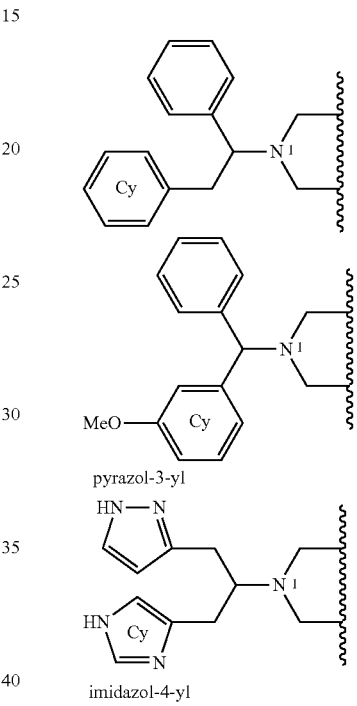

pyrazol-3-yl imidazol-4-yl

If the group, $Q^1$, is a cyclyl leader group (i.e., not a covalent bond) and/or J1 is —C(=O)—, the group -$Q^1$-$J^1$- has a backbone length, as determined by the number of chain atoms in the shortest continuous chain of atoms linking the relevant cyclyl group, Cy, and the N-1 atom of the piperazin-1,4-diyl group. In the following example, -$Q^1$-$J^1$- has a backbone length of 2.

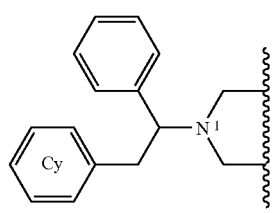

The Cyclyl Group, Cy

Cy is independently: $C_{3-20}$carbocyclyl, $C_{3-20}$heterocyclyl, or $C_{5-20}$aryl; and is optionally substituted.

In one embodiment, Cy is independently $C_{3-20}$carbocyclyl; and is optionally substituted.

In one embodiment, Cy is independently monocyclic $C_{3-7}$carbocyclyl, and is optionally substituted.

In one embodiment, Cy is independently monocyclic C$_{5-6}$carbocyclyl, and is optionally substituted.

In one embodiment, Cy is independently C$_{3-20}$carbocyclyl derived from one of the following: cyclopropane, cyclobutane, cyclopentane, cyclohexane, cyclopentene, cyclohexene, norbornane, adamantane, cyclopentanone, and cyclohexanone; and is optionally substituted.

In one embodiment, Cy is independently C$_{3-20}$heterocyclyl; and is optionally substituted.

In one embodiment, Cy is independently monocyclic C$_{3-7}$heterocyclyl, and is optionally substituted.

In one embodiment, Cy is independently monocyclic C$_{5-6}$heterocyclyl, and is optionally substituted.

In one embodiment, Cy is independently C$_{3-20}$heterocyclyl derived from one of the following: piperidine, azepine, tetrahydropyran, morpholine, azetidine, piperazine, imidazoline, piperazinedione, and oxazolinone; and is optionally substituted.

In one embodiment, Cy is independently C$_{5-20}$aryl; and is optionally substituted.

In one embodiment, Cy is independently C$_{5-20}$carboaryl or C$_{5-20}$heteroaryl; and is optionally substituted.

In one embodiment, Cy is independently C$_{5-20}$heteroaryl; and is optionally substituted. In one embodiment, Cy is monocyclic C$_{5-20}$heteroaryl; and is optionally substituted. In one embodiment, Cy is monocyclic C$_{5-6}$heteroaryl; and is optionally substituted.

In one embodiment, Cy is independently C$_{5-20}$carboaryl; and is optionally substituted. In one embodiment, Cy is monocyclic C$_{5-20}$carboaryl; and is optionally substituted. In one embodiment, Cy is monocyclic C$_{5-6}$carboaryl; and is optionally substituted. In one embodiment, Cy is phenyl; and is optionally substituted.

In one embodiment, Cy is independently C$_{5-20}$aryl derived from one of the following: benzene, pyridine, furan, indole, pyrrole, imidazole, pyrimidine, pyrazine, pyridizine, naphthalene, quinoline, indole, benzimidazole, benzothiofuran, fluorene, acridine, and carbazole; and is optionally substituted.

Examples of substituents on Cy include, but are not limited to, those described under the heading "Substituents" below.

In one embodiment, the optional substituents on Cy are as defined under the heading "The Cyclyl Group, Cy: Optionally Substituted Phenyl: Substituents."

The Cyclyl Group, Cy: Optionally Substituted Phenyl

In one embodiment, Cy is independently an optionally substituted phenyl group.

In one embodiment, Cy is independently an optionally substituted phenyl group of the formula:

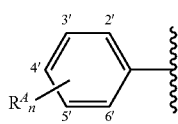

wherein n is independently an integer from 0 to 5, and each R$^A$ is independently a substituent as defined herein.

In one embodiment, Cy is an optionally substituted phenyl group, Q$^1$ is a covalent bond or a cyclyl leader group, J$^1$ is a covalent bond, and the compounds have the following formula:

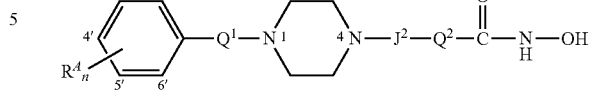

(6)

In one embodiment, Cy is an optionally substituted phenyl group, Q$^1$ is a cyclyl leader group, J$^1$ is a covalent bond, and the compounds have the following formula:

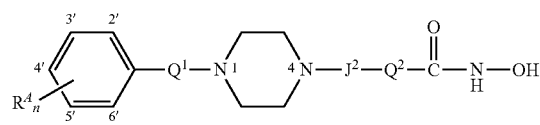

(7)

In one embodiment, Cy is an optionally substituted phenyl group, Q$^1$ is a covalent bond, J$^1$ is a covalent bond, and the compounds have the following formula:

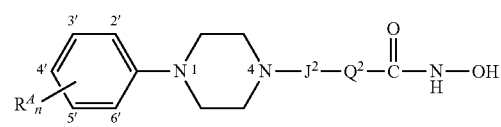

(8)

In one embodiment, n is an integer from 0 to 5.
In one embodiment, n is an integer from 0 to 4.
In one embodiment, n is an integer from 0 to 3.
In one embodiment, n is an integer from 0 to 2.
In one embodiment, n is 0 or 1.
In one embodiment, n is an integer from 1 to 5.
In one embodiment, n is an integer from 1 to 4.
In one embodiment, n is an integer from 1 to 3.
In one embodiment, n is 1 or 2.
In one embodiment, n is 5.
In one embodiment, n is 4.
In one embodiment, n is 3.
In one embodiment, n is 2.
In one embodiment, n is 1.
In one embodiment, n is 0.

If the phenyl group has less than the full complement of ring substituents, R$^A$, they may be arranged in any combination. For example, if n is 1, R$^A$ may be in the 2'-, 3'-, 4'-, 5'-, or 6'-position. Similarly, if n is 2, the two R$^A$ groups may be in, for example, the 2',3'-, 2',4'-, 2',5'-, 2',6'-, 3',4'-, or 3',5'-positions. If n is 3, the three R$^A$ groups may be in, for example, the 2',3',4'-, 2',3',5'-, 2',3',6'-, or 3',4',5'-positions.

In one embodiment, n is 0.
In one embodiment, n is 1, and the R$^A$ group is in the 4'-position.
In one embodiment, n is 2, and one R$^A$ group is in the 4'-position, and the other R$^A$ group is in the 2'-position.
In one embodiment, n is 2, and one R$^A$ group is in the 4'-position, and the other R$^A$ group is in the 3'-position.

The Cyclyl Group, Cy: Optionally Substituted Phenyl: Substituents

Examples of substituents on Cy (e.g., R$^A$), include, but are not limited to, those described under the heading "Substituents" below.

Further examples of substituents on Cy (e.g., $R^4$), include, but are not limited to, those described below.

In one embodiment, each of the substituents on Cy (e.g., each $R^4$), is independently selected from:
(1) ester;
(2) amido;
(3) acyl;
(4) halo;
(5) hydroxy;
(6) ether;
(7) $C_{1-7}$alkyl, including substituted $C_{1-7}$alkyl;
(8) $C_{5-20}$aryl, including substituted $C_{5-20}$aryl;
(9) sulfonyl;
(10) sulfonamido;
(11) amino;
(12) morpholino;
(13) nitro;
(14) cyano.

In one embodiment, each of the substituents on Cy (e.g., each $R^4$), is independently selected from:
(1) —C(=O)O$R^1$, wherein $R^1$ is independently $C_{1-7}$alkyl as defined in (7);
(2) —C(=O)N$R^2R^3$, wherein each of $R^2$ and $R^3$ is independently —H or $C_{1-7}$alkyl as defined in (7);
(3) —C(=O)$R^4$, wherein $R^4$ is independently $C_{1-7}$alkyl as defined in (7) or $C_{5-20}$aryl as defined in (8);
(4) —F, —Cl, —Br, —I;
(5) —OH;
(6) —O$R^5$, wherein $R^5$ is independently $C_{1-7}$alkyl as defined in (7) or $C_{5-20}$aryl as defined in (8);
(7) $C_{1-7}$alkyl, including substituted $C_{1-7}$alkyl, e.g.,
 halo-$C_{1-7}$alkyl;
 amino-$C_{1-7}$alkyl (e.g., —(CH$_2$)$_w$-amino);
 carboxy-$C_{1-7}$alkyl (e.g., —(CH$_2$)$_w$—COOH);
 hydroxy-$C_{1-7}$alkyl (e.g., —(CH$_2$)$_w$—OH);
 $C_{1-7}$alkoxy-$C_{1-7}$alkyl (e.g., —(CH$_2$)$_w$—O—$C_{1-7}$alkyl);
 $C_{5-20}$aryl-$C_{1-7}$alkyl;
 wherein w is 1, 2, 3, or 4;
(8) $C_{5-20}$aryl, including substituted $C_{5-20}$aryl;
(9) —SO$_2R^7$, wherein $R^7$ is independently $C_{1-7}$alkyl as defined in (7) or $C_{5-20}$aryl as defined in (8);
(10) —SO$_2$N$R^8R^9$, wherein each of $R^8$ and $R^9$ is independently —H or $C_{1-7}$alkyl as defined in (7);
(11) —N$R^{10}R^{11}$, wherein each of $R^{10}$ and $R^{11}$ is independently —H or $C_{1-7}$ alkyl as defined in (7);
(12) morpholino;
(13) nitro;
(14) cyano.

In one embodiment, each of the substituents on Cy (e.g., each $R^4$), is independently selected from:
(1) —C(=O)OMe, —C(=O)OEt, —C(=O)O(Pr), —C(=O)O(iPr), —C(=O)O(nBu), —C(=O)O(sBu), —C(=O)O(iBu), —C(=O)O(tBu), —C(=O)O(nPe); —C(=O)OCH$_2$CH$_2$OH, —C(=O)OCH$_2$CH$_2$OMe, —C(=O)OCH$_2$CH$_2$OEt;
(2) —(C=O)NH$_2$, —(C=O)NMe$_2$, —(C=O)NEt$_2$, —(C=O)N(iPr)$_2$, —(C=O)N(CH$_2$CH$_2$OH)$_2$;
(3) —(C=O)Me, —(C=O)Et, —(C=O)-cHex, —(C=O)Ph;
(4) —F, —Cl, —Br, —I;
(5) —OH;
(6) —OMe, —OEt, —O(iPr), —O(tBu), —OPh; —OCF$_3$, —OCH$_2$CF$_3$;
—OCH$_2$CH$_2$OH, —OCH$_2$CH$_2$OMe, —OCH$_2$CH$_2$OEt; —OCH$_2$CH$_2$NH$_2$, —OCH$_2$CH$_2$NMe$_2$, —OCH$_2$CH$_2$N(iPr)$_2$;
—OPh, —OPh-Me, —OPh-OH, —OPh-OMe, O-Ph-F, —OPh-Cl, —OPh-Br, —OPh-I;
(7) -Me, -Et, -nPr, -iPr, -nBu, -iBu, -sBu, -tBu, -nPe; —CF$_3$, —CH$_2$CF$_3$;
—CH$_2$CH$_2$OH, —CH$_2$CH$_2$OMe, —CH$_2$CH$_2$OEt;
—CH$_2$CH$_2$NH$_2$, —CH$_2$CH$_2$NMe$_2$, —CH$_2$CH$_2$N(iPr)$_2$;
—CH$_2$-Ph;
(8) -Ph, -Ph-Me, -Ph-OH, -Ph-OMe, -Ph-F, -Ph-Cl, -Ph-Br, -Ph-I;
(9) —SO$_2$Me, —SO$_2$Et, —SO$_2$Ph;
(10) —SO$_2$NH$_2$, —SO$_2$NMe$_2$, —SO$_2$NEt$_2$;
(11) —NMe$_2$, —NEt$_2$;
(12) morpholino;
(13) —NO$_2$;
(14) —CN.

In one embodiment, each of the substituents on Cy (e.g., each $R^4$), is independently selected from:
—C(=O)OMe, —C(=O)O(Pr), —C(=O)NHMe, —C(=O)Et, C(=O)Ph, —OCH$_2$CH$_2$OH, —OMe, —OPh, -nPr, iPr, —CF$_3$, —CH$_2$CH$_2$OH, —CH$_2$CH$_2$NMe$_2$, -Ph, -Ph-F, -Ph-Cl,
—SO$_2$Me, —SO$_2$Me$_2$, —NMe$_2$,
—F, —Cl, -Me, -Et, —OMe, —OEt, —CH$_2$-Ph, —O—CH$_2$-Ph.

In one embodiment, each of the substituents on Cy (e.g., each $R^4$), is independently selected from:
—F, —Cl, -Me, -Et, —OMe, —OEt, -Ph, —OPh, —CH$_2$-Ph, —O—CH$_2$-Ph.

Examples of some preferred substituents on Cy (e.g., $R^4$), include, but are not limited to, the following: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido (unsubstituted, i.e., —CONH$_2$), acetamido, acetyl, nitro, sulfonamido (unsubstituted, i.e., —SO$_2$NH$_2$), and phenyl.

The Cyclyl Leader Group, $Q^1$

In one embodiment, $Q^1$ is independently:
 a covalent bond; or
 a cyclyl leader group;
 and is optionally substituted.

In one embodiment, $Q^1$ is independently:
 a covalent bond.

In one embodiment, $Q^1$ is independently:
 a cyclyl leader group;
 and is optionally substituted.

In one embodiment, $Q^1$ is independently:
 a covalent bond;
 $C_{1-7}$alkylene; or
 $C_{1-7}$alkylene-X—$C_{1-7}$alkylene, —X—$C_{1-7}$alkylene, or $C_{1-7}$alkylene-X—;
 wherein X is —O— or —S—;
 and is optionally substituted.

In one embodiment, $Q^1$ is independently:
 a covalent bond; or
 a $C_{1-7}$alkylene group;
 and is optionally substituted.

In one embodiment, $Q^1$ is independently:
 a $C_{1-7}$alkylene group;
 and is optionally substituted.

In one embodiment, $Q^1$ is independently:
 $C_{1-7}$alkylene-X—$C_{1-7}$alkylene, —X—$C_{1-7}$alkylene, or $C_{1-7}$alkylene-X—;
 wherein X is —O— or —S—;
 and is optionally substituted.

In one embodiment, in the above alkylene groups, each alkylene group is independently:
(a) a saturated $C_{1-7}$alkylene group; or:
(b) a partially unsaturated $C_{2-7}$alkylene group; or:
(c) an aliphatic $C_{1-7}$alkylene group; or:
(d) a linear $C_{1-7}$alkylene group; or:
(e) a branched $C_{2-7}$alkylene group; or:
(f) a saturated aliphatic $C_{1-7}$alkylene group; or:
(g) a saturated linear $C_{1-7}$alkylene group; or
(h) a saturated branched $C_{2-7}$alkylene group; or
(i) a partially unsaturated aliphatic $C_{2-7}$alkylene group; or:
(j) a partially unsaturated linear $C_{2-7}$alkylene group; or:
(k) a partially unsaturated branched $C_{2-7}$alkylene group;
and is optionally substituted.

In one embodiment, the above alkylene groups have a maximum number of carbon atoms of 4, e.g., $C_{1-4}$alkylene, $C_{2-4}$alkylene.

In one embodiment, the above alkylene groups have a maximum number of carbon atoms of 3, e.g., $C_{1-3}$alkylene, $C_{2-3}$alkylene.

In one embodiment, $Q^1$ is selected so that the N-1 atom of the piperazin-1,4-diyl group is not connected to a carbon atom which is connected to another carbon atom via a non-aromatic carbon-carbon double bond (i.e., C=C). That is, the N-1 atom of the piperazin-1,4-diyl group is not adjacent to a non-aromatic carbon-carbon double bond (i.e., C=C). In this way, groups such as —CH=CH— and —CH$_2$—CH=CH— are excluded from $Q^1$, but groups such as —CH=CH—CH$_2$— are not. Additional embodiments include other embodiments described herein (e.g., those described above) further limited by this restriction upon $Q^1$.

The Cyclyl Leader Group, $Q^1$: Covalent Bond

In one embodiment:
$Q^1$ is independently a covalent bond;
$J^1$ is independently a covalent bond;
$J^2$ is independently —C(=O)—.

In one embodiment:
$Q^1$ is independently a covalent bond;
$J^1$ is independently —C(=O)—;
$J^2$ is independently —C(=O)—.

In one embodiment:
$Q^1$ is independently a covalent bond;
$J^1$ is independently a covalent bond;
$J^2$ is independently —S(=O)$_2$—.

In one embodiment:
$Q^1$ is independently a covalent bond;
$J^1$ is independently —C(=O)—;
$J^2$ is independently —S(=O)$_2$—.

The Cyclyl Leader Group, $Q^1$: Backbone Length

The group -$J^1$-$Q^1$- has a backbone length, as determined by the number of chain atoms in the shortest continuous chain of atoms linking the relevant Cy group and the N-1 atom of the piperazin-1,4-diyl group.

In one embodiment, the group -$J^1$-$Q^1$- has a backbone of:
from 1 to 7 atoms;
from 1 to 6 atoms;
from 1 to 5 atoms;
from 1 to 4 atoms; or,
from 1 to 3 atoms.

In one embodiment, the group -$J^1$-$Q^1$- has a backbone of at least 2 atoms. In this way, groups such as methylene (—CH$_2$—) and substituted methylene (—CR$_2$— and —CHR—) are excluded.

In one embodiment, the group -$J^1$-$Q^1$- has a backbone of at least 3 atoms.

In one embodiment, the group -$J^1$-$Q^1$- has a backbone of at least 4 atoms.

In one embodiment, the group -$J^1$-$Q^1$- has a backbone of at least 5 atoms.

In one embodiment, the group -$J^1$-$Q^1$- has a backbone of:
from 2 to 7 atoms;
from 2 to 6 atoms; or,
from 2 to 5 atoms.

In one embodiment, the group -$J^1$-$Q^1$- has a backbone of:
from 3 to 7 atoms;
from 3 to 6 atoms; or,
from 3 to 5 atoms.

In one embodiment, the group -$J^1$-$Q^1$- has a backbone of:
from 4 to 7 atoms;
from 4 to 6 atoms; or,
from 4 to 5 atoms.

In one embodiment, the group -$J^1$-$Q^1$- has a backbone of 1 atom.

In one embodiment, the group -$J^1$-$Q^1$- has a backbone of 2 atoms.

In one embodiment, the group -$J^1$-$Q^1$- has a backbone of 3 atoms.

In one embodiment, the group -$J^1$-$Q^1$- has a backbone of 4 atoms.

In one embodiment, the group -$J^1$-$Q^1$- has a backbone of 5 atoms.

In one embodiment, the backbone of "atoms" is a backbone of "carbon atoms."

Note that, for embodiments which are characterised by, or further characterised by, a backbone length limitation, corresponding changes in the description of that embodiment may be implicit. For example, for an embodiment wherein (a) $Q^1$ is a partially unsaturated $C_{2-7}$alkylene group and (b) $Q^1$ has a backbone of 4 carbon atoms, the term "$C_{2-7}$alkylene" group is necessarily, and implicitly, interpreted as "$C_{4-7}$alkylene."

The Cyclyl Leader Group, $Q^1$: Substituents

In one embodiment, $Q^1$, if other than a covalent bond, is unsubstituted.

In one embodiment, $Q^1$, if other than a covalent bond, is optionally substituted.

In one embodiment, $Q^1$, if other than a covalent bond, is substituted.

Examples of substituents on $Q^1$ include, but are not limited to, those described under the heading "Substituents" below.

In one embodiment, substituents on $Q^1$, if present, are as defined under the heading "The Cyclyl Group, Cy: Optionally Substituted Phenyl: Substituents."

In one embodiment, substituents on $Q^1$, if present, are independently: halo, hydroxy, ether (e.g., $C_{1-7}$alkoxy), $C_{5-20}$aryl, acyl, amino, amido, acylamido, or oxo.

In one embodiment, substituents on $Q^1$, if present, are independently: —F, —Cl, —Br, —I, —OH, —OMe, —OEt, —OPr, -Ph, —NH$_2$, —CONH$_2$, or =O.

In one embodiment, substituents on $Q^1$, if present, are independently —OH or -Ph.

In one embodiment, substituents on $Q^1$, if present, are independently -Ph.

For example, in one embodiment, $Q^1$ is unsubstituted methylene, and is —CH$_2$—; in one embodiment, $Q^1$ phenyl (-Ph) substituted methylene, and is —CH(Ph)-.

For example, in one embodiment, $Q^1$ is unsubstituted ethylene, and is —CH$_2$—CH$_2$—; in one embodiment, $Q^1$ is oxo (=O) substituted ethylene, and is —C(=O)—CH$_2$—; in one embodiment, $Q^1$ is hydroxy (—OH) substituted ethylene, and is —CH(OH)—CH$_2$—; in one embodiment, $Q^1$ is phenyl (-Ph) substituted ethylene, and is —CH$_2$CH(Ph)-.

Again, for the avoidance of doubt, it is intended that, if there is a —C(=O)— group immediately adjacent to the N-1 atom, of the piperazin-1-4-diyl group, then that —C(=O)— group must be assigned as $J^1$ (that is, $J^1$ is —C(=O)—) and not as part of $Q^1$ (e.g., as part of an oxo-substituted $Q^1$ group). For example, if the Cy-$Q^1$-$J^1$- group is Ph-CH$_2$—C(=O)—, then Cy is Ph-, $Q^1$ is —CH$_2$—, and $J^1$ is —C(=O)—.

The Cyclyl Leader Group, $Q^1$: Alkylene: Certain Embodiments

Note that, for embodiments excluding, e.g., a covalent bond, certain backbone lengths, absence of adjacent carbon-carbon double bonds, etc., it is to be understood that the corresponding species listed below are similarly excluded from the respective embodiments discussed below.

In one embodiment, $Q^1$ is independently selected from the following:
a covalent bond;
—CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—;
—CH(CH$_3$)—;
—CH(CH$_3$)CH$_2$—, —CH$_2$CH(CH$_3$)—;
—CH(CH$_3$)CH$_2$CH$_2$—, —CH$_2$CH(CH$_3$)CH$_2$—, —CH$_2$CH$_2$CH(CH$_3$)—;
—CH(CH$_3$)CH$_2$CH$_2$CH$_2$—, —CH$_2$CH(CH$_3$)CH$_2$CH$_2$—, —CH$_2$CH$_2$CH(CH$_3$)CH$_2$—, —CH$_2$CH$_2$CH$_2$CH(CH$_3$)—;
—CH(CH$_3$)CH$_2$CH$_2$CH$_2$CH$_2$—, —CH$_2$CH(CH$_3$)CH$_2$CH$_2$CH$_2$—, —CH$_2$CH$_2$CH(CH$_3$)CH$_2$CH$_2$—, —CH$_2$CH$_2$CH$_2$CH(CH$_3$)CH$_2$—, —CH$_2$CH$_2$CH$_2$CH$_2$CH(CH$_3$)—, —CH(CH$_3$)CH$_2$CH$_2$CH$_2$CH(CH$_3$);
—CH(CH$_2$CH$_3$)—;
—CH(CH$_2$CH$_3$)CH$_2$—, —CH$_2$CH(CH$_2$CH$_3$)—;
—CH(CH$_2$CH$_3$)CH$_2$CH$_2$—, —CH$_2$CH(CH$_2$CH$_3$)CH$_2$—, —CH$_2$CH$_2$CH(CH$_2$CH$_3$)—;
—CH(CH$_2$CH$_3$)CH$_2$CH$_2$CH$_2$—, —CH$_2$CH(CH$_2$CH$_3$)CH$_2$CH$_2$—, —CH$_2$CH$_2$CH(CH$_2$CH$_3$)CH$_2$—, —CH$_2$CH$_2$CH$_2$CH(CH$_2$CH$_3$)—;
—CH(CH$_2$CH$_3$)CH$_2$CH$_2$CH$_2$CH$_2$—, —CH$_2$CH(CH$_2$CH$_3$)CH$_2$CH$_2$CH$_2$—, —CH$_2$CH$_2$CH(CH$_2$CH$_3$)CH$_2$CH$_2$—, —CH$_2$CH$_2$CH$_2$CH(CH$_2$CH$_3$)CH$_2$—, —CH$_2$CH$_2$CH$_2$CH$_2$CH(CH$_2$CH$_3$)—;
—CH=CH—;
—CH=CHCH$_2$—, —CH$_2$CH=CH—;
—CH=CHCH$_2$CH$_2$—, —CH$_2$CH=CHCH$_2$—, —CH$_2$CH$_2$CH=CH—;
—CH=CHCH$_2$CH$_2$CH$_2$—, —CH$_2$CH=CHCH$_2$CH$_2$—, —CH$_2$CH$_2$CH=CHCH$_2$—, —CH$_2$CH$_2$CH$_2$CH=CH—;
—CH=CHCH$_2$CH$_2$CH$_2$CH$_2$—, —CH$_2$CH=CHCH$_2$CH$_2$CH$_2$—, —CH$_2$CH$_2$CH=CHCH$_2$CH$_2$—, —CH$_2$CH$_2$CH$_2$CH=CHCH$_2$—, —CH$_2$CH$_2$CH$_2$CH$_2$CH=CH—;
—C(CH$_3$)=CH—, —CH=C(CH$_3$)—;
—C(CH$_3$)=CHCH$_2$—, —CH=C(CH$_3$)CH$_2$—, —CH=CHCH(CH$_3$)—;
—CH(CH$_3$)CH=CH—, —CH$_2$C(CH$_3$)=CH—, —CH$_2$CH=C(CH$_3$)—;
—CH=CHCH=CH—;
—CH=CHCH=CHCH$_2$—, —CH$_2$CH=CHCH=CH—, —CH=CHCH$_2$CH=CH—;
—CH=CHCH=CHCH$_2$CH$_2$—, —CH=CHCH$_2$CH=CHCH$_2$—, —CH=CHCH$_2$CH$_2$CH=CH—, —CH$_2$CH=CHCH=CHCH$_2$—, —CH$_2$CH=CHCH$_2$CH=CH—, —CH$_2$CH$_2$CH=CHCH=CH—;
—C(CH$_3$)=CHCH=CH—, —CH=C(CH$_3$)CH=CH—, —CH=CHC(CH$_3$)=CH—, —CH=CHCH=C(CH$_3$)—;
—C≡C—;
—C≡CCH$_2$—, —CH$_2$C≡C—; —C≡CCH(CH$_3$)—, —CH(CH$_3$)C≡C—;
—C≡CCH$_2$CH$_2$—, —CH$_2$C≡CCH$_2$—, —CH$_2$CH$_2$C≡C—;
—C≡CCH(CH$_3$)CH$_2$—, —C≡CCH$_2$CH(CH$_3$)—; —CH(CH$_3$)C≡CCH$_2$—, —CH$_2$C≡CCH(CH$_3$)—; —CH(CH$_3$)CH$_2$C≡C—, —CH$_2$CH(CH$_3$)C≡C—;
—C≡CCH=CH—, —CH=CHC≡C—, —C≡CC≡C—;
—C≡CCH$_2$CH$_2$CH$_2$—, —CH$_2$CH$_2$CH$_2$C≡C—;
—C≡CCH$_2$CH$_2$CH$_2$CH$_2$—, —CH$_2$CH$_2$CH$_2$CH$_2$C≡C—;
—C≡CCH=CHCH=CH—, —CH=CHC≡C-CH=CH—, —CH=CHCH=CHC≡C—;
—C(CH$_3$)=CHC≡C—, —CH=C(CH$_3$)C≡C—, —C≡CC(CH$_3$)=CH—, —C≡CCH=C(CH$_3$)—.

In one embodiment, $Q^1$ is selected from:
a covalent bond;
—CH$_2$—, —(CH$_2$)$_2$—, —(CH$_2$)$_3$—, —(CH$_2$)$_4$—, —(CH$_2$)$_5$—, —(CH$_2$)$_6$—;
—CH(CH$_3$)CH$_2$CH$_2$CH$_2$—, —CH$_2$CH(CH$_3$)CH$_2$CH$_2$—, —CH$_2$CH$_2$CH(CH$_3$)CH$_2$—, —CH$_2$CH$_2$CH$_2$CH(CH$_3$)—;
—CH=CH—;
—CH=CHCH$_2$—, —CH=C(Me)CH$_2$—;
—CH=CH—CH=CH—;
—CH=CH—CH=CHCH$_2$—, —CH=CHCH$_2$CH$_2$CH$_2$—, —CH$_2$CH$_2$CH$_2$CH=CH—;
—CH=CHCH$_2$CH$_2$CH$_2$CH$_2$—, —CH$_2$CH$_2$CH$_2$CH$_2$CH=CH—;
—C(CH$_3$)=CHCH=CH—, —CH=C(CH$_3$)CH=CH—, —CH=CHC(CH$_3$)=CH—, —CH=CHCH=C(CH$_3$)—;

In one embodiment, $Q^1$ is selected from:
a covalent bond;
—CH$_2$—, —(CH$_2$)$_2$—, —(CH$_2$)$_3$—, —(CH$_2$)$_4$—, —(CH$_2$)$_5$—,
—CH=CH—;
—CH=CHCH$_2$—, —CH=C(Me)CH$_2$—;
—CH=CH—CH=CH—;
—C(CH$_3$)=CHCH=CH—, —CH=C(CH$_3$)CH=CH—, —CH=CHC(CH$_3$)=CH—, —CH=CHCH=C(CH$_3$)—;
—CH=CHCH$_2$CH$_2$—, —CH$_2$CH$_2$CH=CH—.

In one embodiment, $Q^1$ is independently selected from:
a covalent bond;
—CH$_2$—, —(CH$_2$)$_2$—, —(CH$_2$)$_3$—, —(CH$_2$)$_4$—, —(CH$_2$)$_6$;
—CH=CHCH$_2$—;
—CH=C(Me)CH$_2$—; and,
—CH=CH—CH=CHCH$_2$—.

In one embodiment, $Q^1$ is independently selected from:
a covalent bond;
—CH$_2$—;
—CH$_2$CH$_2$—;
—CH$_2$CH$_2$CH$_2$—;
—CH=CHCH$_2$—;
—CH=C(Me)CH$_2$—; and,
—CH=CH—CH=CHCH$_2$—.

In one embodiment, $Q^1$ is independently selected from:
a covalent bond;
—$CH_2$—;
—CH(*Ph)-;
—$CH_2CH_2$—;
—CH(*Ph)$CH_2$—;
—$CH_2$CH(*Ph)-;
—$CH_2CH_2CH_2$—;
—CH=CH$CH_2$—;
—CH=C(Me)$CH_2$—; and,
—CH=CH—CH=CH$CH_2$—;
wherein * indicates that the group (e.g., Ph) is optionally substituted with one or more substituents as defined above under the heading "The Cyclyl Group, Cy: Optionally Substituted Phenyl: Substituents."

The Cyclyl Leader Group, $Q^1$: Ethers and Thioethers: Certain Embodiments

Note that, for embodiments excluding, e.g., a covalent bond, certain backbone lengths, absence of adjacent carbon-carbon double bonds, etc., it is to be understood that the corresponding species listed below are similarly excluded from the respective embodiments discussed below.

In one embodiment, $Q^1$ is independently selected from the following:
—$(CH_2)_a$—X—$(CH_2)_b$—
wherein X is —O— or —S— and
a and b are each independently 1, 2, 3, 4, 5, 6, or 7;
and a+b is at least 1.

In one embodiment, $Q^1$ is independently selected from the following:
—O—$(CH_2)_a$—
—S—$(CH_2)_a$—
—$(CH_2)_a$—O—
—$(CH_2)_a$—S—
—$(CH_2)_a$—O—$(CH_2)_b$—
—$(CH_2)_a$—S—$(CH_2)_b$—
wherein a and b are each independently 1, 2, 3, 4, 5, 6, or 7.

In one embodiment, $Q^1$ is independently selected from the following:
—O—$CH_2$—; —O—$CH_2CH_2$—; —O—$CH_2CH_2CH_2$—;
—S—$CH_2$—; —S—$CH_2CH_2$—; —S—$CH_2CH_2CH_2$—;
—$CH_2$—O—; —$CH_2CH_2$—O—; —$CH_2CH_2CH_2$—O—;
—$CH_2$—S—; —$CH_2CH_2$—S—; —$CH_2CH_2CH_2$—S—;
—$CH_2$—O—$CH_2$—;       —$CH_2$—O—$CH_2CH_2$—;
—$CH_2CH_2$—O—$CH_2$—; and
—$CH_2CH_2$—O—$CH_2CH_2$—.

The Group -$Q^1$-$J^1$-: Certain Embodiments

In one embodiment, the group -$Q^1$-$J^1$- has a formula selected from:
—$CH_2$—;
—CH(*Ph)-;
—$CH_2CH_2$—;
—$CH_2$CH(*Ph)-;
—CH(*Ph)$CH_2$—;
—$CH_2CH_2CH_2$—;
—C(=O)—;
—$CH_2$—C(=O)—;
—CH(*Ph)C(=O)—;
—$CH_2CH_2$—C(=O)—;
—O—$CH_2$—;
—O—$CH_2CH_2$—;
—$CH_2$—O—;
—$CH_2CH_2$—O—; and,
—O—$CH_2$—C(=O)—.

wherein * indicates that the group (e.g., Ph) is optionally substituted with one or more substituents as defined above under the heading "The Cyclyl Group, Cy: Optionally Substituted Phenyl Substituents."

The Group Cy-$Q^1$-: Certain Embodiments

In one embodiment, the group Cy-$Q^1$- has a formula selected from:
*Ph-;
*Ph-$CH_2$—;
(*Ph)$_2$CH—;
*Ph-$CH_2CH_2$—;
(*Ph)$_2$-$CH_2CH_2$—;
*Ph-$CH_2$CH(*Ph)-;
*Ph-$CH_2CH_2CH_2$—;
*Ph-CH=CH$CH_2$—;
*Ph-CH=C(Me)$CH_2$;
*Ph-CH=CHCH=CH$CH_2$—;
(*pyrid-3-yl)-CH=CH$CH_2$—; and,
(*cyclohexyl)-$CH_2CH_2$—;
wherein * indicates that the group (e.g., Ph, pyrid-3-yl, cyclohexyl) is optionally substituted with one or more substituents as defined above under the heading "The Cyclyl Group, Cy: Optionally Substituted Phenyl: Substituents."

In one embodiment, * indicates that the group (e.g., Ph, pyrid-3-yl, cyclohexyl) is optionally substituted with one or more of: —F, —Cl, —Br, —I, —OH, —OMe, —OEt, —OPr, -Ph, —$NH_2$, and —$CONH_2$.

The Acid Leader Group, $Q^2$

The acid leader group, $Q^2$, is independently:
$C_{4-8}$alkylene;
and is optionally substituted;
and has a backbone length of at least 4 atoms;
or:
$C_{5-20}$arylene;
$C_{5-20}$arylene-$C_{1-7}$alkylene;
$C_{1-7}$alkylene-$C_{5-20}$arylene; or,
$C_{1-7}$alkylene-$C_{5-20}$arylene-$C_{1-7}$alkylene;
and is optionally substituted;
and has a backbone length of at least 4 atoms.

In one embodiment, the acid leader group, $Q^2$, is independently:
$C_{4-8}$alkylene;
and is optionally substituted;
and has a backbone length of at least 4 atoms.

In one embodiment, the acid leader group, $Q^2$, is independently:
$C_{5-20}$arylene;
$C_{5-20}$arylene-$C_{1-7}$alkylene;
$C_{1-7}$alkylene-$C_{5-20}$arylene;
$C_{1-7}$alkylene-$C_{5-20}$arylene-$C_{1-7}$alkylene; or,
and is optionally substituted;
and has a backbone length of at least 4 atoms.

The Acid Leader Group, $Q^2$: Backbone Length

The acid leader group, $Q^2$, has a backbone length, as determined by the number of chain atoms in the shortest continuous chain of atoms linking the N-4 atom of the piperazin-1,4-diyl group and the carbamic acid group, —C(=O)NHOH.

If $Q^2$ is alkylene, $Q^2$ necessarily has a backbone of at least 1 atom. Some examples are shown below.

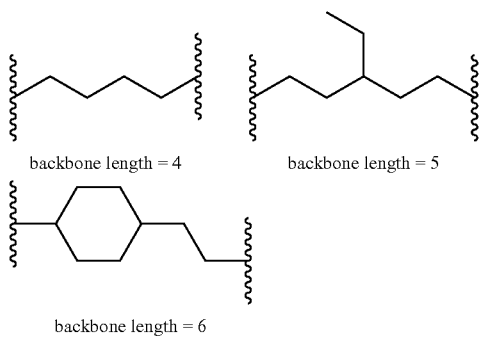

backbone length = 4    backbone length = 5 backbone length = 6

If $Q^2$ is arylene, arylene-alkylene, alkylene-arylene, alkylene-arylene-alkylene, $Q^2$ necessarily has a backbone of at least 2 atoms. Some examples are shown below.

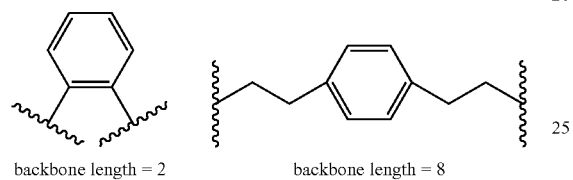

backbone length = 2    backbone length = 8

Without wishing to be bound to any particular theory, it is believed that $Q^2$ groups with shorter backbone lengths prevent or reduce the interaction of the carbamic acid group (—C(=O)NHOH) with HDAC (or its complexes), and thereby reduce the compound's activity as an HDAC inhibitor.

In one embodiment, $Q^2$ has a backbone of at least 4 atoms.
In one embodiment, $Q^2$ has a backbone of at least 5 atoms.
In one embodiment, $Q^2$ has a backbone of at least 6 atoms.
In one embodiment, $Q^2$ has a backbone of:
from 4 to 8 atoms;
from 4 to 7 atoms;
from 4 to 6 atoms; or,
from 4 to 5 atoms.
In one embodiment, $Q^2$ has a backbone of:
from 5 to 8 atoms; or
from 5 to 7 atoms; or
from 5 to 6 atoms.
In one embodiment, $Q^2$ has a backbone of from 5 to 6 atoms.
In one embodiment, $Q^2$ has a backbone of 4 atoms.
In one embodiment, $Q^2$ has a backbone of 5 atoms.
In one embodiment, $Q^2$ has a backbone of 6 atoms.
In one embodiment, $Q^2$ has a backbone of 7 atoms.
In one embodiment, $Q^2$ has a backbone of 8 atoms.
In one embodiment, the backbone of "atoms" is a backbone of "carbon atoms."

Note that, for embodiments which are characterised by, or further characterised by, a backbone length limitation, corresponding changes in the description of that embodiment may be implicit. For example, for an embodiment wherein (a) $Q^2$ is a partially unsaturated $C_{2-4}$alkylene group and (b) $Q^2$ has a backbone of 4 carbon atoms, the term "$C_{2-8}$alkylene" group is necessarily, and implicitly, interpreted as "$C_{4-8}$alkylene."

The Acid Leader Group, $Q^2$: Substitution
In one embodiment, $Q^2$ is unsubstituted.
In one embodiment, $Q^2$ is optionally substituted.
In one embodiment, $Q^2$ is substituted.

The backbone atoms of the acid leader group, $Q^2$, which link J and the carbamic acid group (—C(=O)NHOH), are denoted α, β, γ, δ, etc., starting with the backbone atom adjacent to the carbamic acid group. Some examples are illustrated below.

$Q^2$ is alkylene

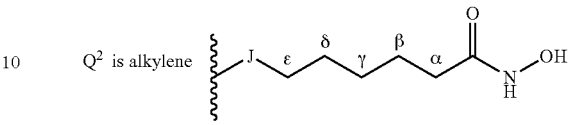

$Q^2$ is arylene

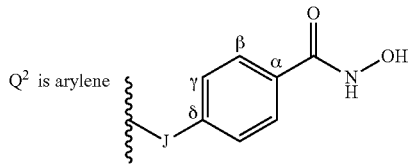

$Q^2$ is arylene-alkylene

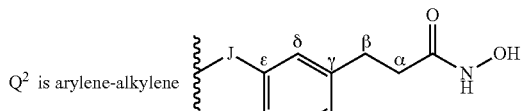

$Q^2$ is alkylene-arylene

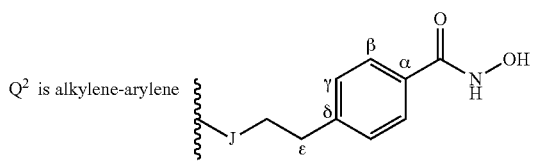

$Q^2$ is alkylene-arylene-alkylene

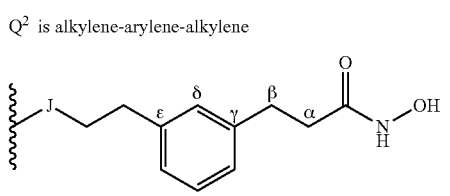

Without wishing to be bound to any particular theory, it is believed that groups (e.g., substituents), particularly bulky groups (e.g., substituents), at the α-position, or at either or both of the α- and β-positions, prevent or reduce the interaction of the carbamic acid group (—C(=O)NHOH) with HDAC (or its complexes), and thereby reduce the compound's activity as an HDAC inhibitor.

In one embodiment, $Q^2$ is, additionally, unsubstituted at the α-position.

In one embodiment, $Q^2$ is, additionally, unsubstituted at the α-position and unsubstituted at the β-position.

Note that, in some embodiments, $Q^2$ may have a non-linear alkylene group (for example, a branched alkylene) adjacent to the carbamic acid group. An example, wherein $Q^2$ is a branched saturated $C_6$-alkylene, having a methyl group at the α-position, is shown below. Although there is a group (i.e., a methyl group) at the α-position, such compounds are unsubstituted at the α-position, because the α-methyl group itself is considered to be part of the unsubstituted $Q^2$. Another example, wherein $Q^2$ is a branched saturated $C_6$-alkylene, having an amino group at the α-position and a methyl group at the β-position, is shown below; such compounds are α-substituted, β-unsubstituted.

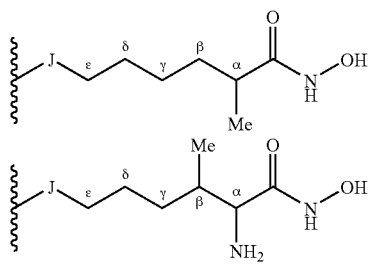

In one embodiment, in which $Q^2$ is a group as defined herein (e.g., $C_{4-8}$alkylene, $C_{5-20}$arylene-$C_{1-7}$alkylene, $C_{1-7}$alkylene-$C_{5-20}$arylene-$C_{1-7}$alkylene) having an alkylene group adjacent to the carbamic acid group, $Q^2$ is, additionally, unsubstituted at the α-position.

In one embodiment, in which $Q^2$ is a group as defined herein (e.g., $C_{4-8}$alkylene, $C_{5-20}$arylene-$C_{1-7}$alkylene, $C_{1-7}$alkylene-$C_{5-20}$arylene-$C_{1-7}$alkylene) having an alkylene group adjacent to the carbamic acid group, that adjacent alkylene group has a —CH$_2$— or =CH— group adjacent to the carbamic acid group (that is, at the α-position).

In one embodiment, in which $Q^2$ is a group as defined herein (e.g., $C_{4-8}$alkylene, $C_{5-20}$arylene-$C_{1-7}$alkylene, $C_{1-7}$alkylene-$C_{5-20}$arylene-$C_{1-7}$alkylene) having an alkylene group adjacent to the carbamic acid group, that adjacent alkylene group has a —CH$_2$— group adjacent to the carbamic acid group (that is, at the α-position).

In one embodiment, in which $Q^2$ is a group as defined herein (e.g., $C_{4-8}$alkylene, $C_{5-20}$arylene-$C_{1-7}$alkylene, $C_{1-7}$alkylene-$C_{5-20}$arylene-$C_{1-7}$alkylene) having an alkylene group adjacent to the carbamic acid group, that adjacent alkylene group has a =CH— group adjacent to the carbamic acid group (that is, at the α-position).

In one embodiment, in which $Q^2$ is a group as defined herein (e.g., $C_{4-8}$alkylene, $C_{5-20}$arylene-$C_{1-7}$alkylene, $C_{1-7}$alkylene-$C_{5-20}$arylene-$C_{1-7}$alkylene) having an alkylene group adjacent to the carbamic acid group, $Q^2$ is, additionally, unsubstituted at the α-position and unsubstituted at the β-position.

In one embodiment, in which $Q^2$ is a group as defined herein (e.g., $C_{4-8}$alkylene, $C_{5-20}$arylene-$C_{1-7}$alkylene, $C_{1-7}$alkylene-$C_{5-20}$arylene-$C_{1-7}$alkylene) having an alkylene group adjacent to the carbamic acid group, that adjacent alkylene group has a —CH$_2$CH$_2$—, —CH=CH—, or —C≡C— group adjacent to the carbamic acid group (that is, at the α,β-position).

In one embodiment, in which $Q^2$ is a group as defined herein (e.g., $C_{4-8}$alkylene, $C_{5-20}$arylene-$C_{1-7}$alkylene, $C_{1-7}$alkylene-$C_{5-20}$arylene-$C_{1-7}$alkylene) having an alkylene group adjacent to the carbamic acid group, that adjacent alkylene group has a —CH$_2$CH$_2$— or —CH=CH— group adjacent to the carbamic acid group (that is, at the α,β-position).

In one embodiment, in which $Q^2$ is a group as defined herein (e.g., $C_{4-8}$alkylene, $C_{5-20}$arylene-$C_{1-7}$alkylene, $C_{1-7}$alkylene-$C_{5-20}$arylene-$C_{1-7}$alkylene) having an alkylene group adjacent to the carbamic acid group, that adjacent alkylene group has a —CH$_2$CH$_2$— group adjacent to the carbamic acid group (that is, at the α,β-position).

In one embodiment, in which $Q^2$ is a group as defined herein (e.g., $C_{4-8}$alkylene, $C_{5-20}$arylene-$C_{1-7}$alkylene, $C_{1-7}$alkylene-$C_{5-20}$arylene-$C_{1-7}$alkylene) having an alkylene group adjacent to the carbamic acid group, that adjacent alkylene group has a —CH=CH— group adjacent to the carbamic acid group (that is, at the α,β-position).

Examples of substituents on $Q^2$ include, but are not limited to, those described under the heading "Substituents" below.

In one embodiment, the optional substituents on $Q^2$ are as defined under the heading "The Cyclyl Group, Cy: Optionally Substituted Phenyl: Substituents."

The Acid Leader Group, $Q^2$: Alkylene

In one embodiment, the acid leader group, $Q^2$, is $C_{4-8}$alkylene, and is optionally substituted, and has a backbone length of at least 4 atoms.

In one embodiment, $Q^2$ is independently a saturated $C_{4-8}$alkylene group.

In one embodiment, $Q^2$ is independently a partially unsaturated $C_{4-8}$alkylene group.

In one embodiment, $Q^2$ is independently an aliphatic $C_{4-8}$alkylene group

In one embodiment, $Q^2$ is independently a linear $C_{4-8}$alkylene group.

In one embodiment, $Q^2$ is independently a branched $C_{4-8}$alkylene group.

In one embodiment, $Q^2$ is independently an alicyclic $C_{4-8}$alkylene group.

In one embodiment, $Q^2$ is independently a saturated aliphatic $C_{4-8}$alkylene group.

In one embodiment, $Q^2$ is independently a saturated linear $C_{4-8}$alkylene group.

In one embodiment, $Q^2$ is independently a saturated branched $C_{4-8}$alkylene group.

In one embodiment, $Q^2$ is independently a saturated alicyclic $C_{4-8}$alkylene group.

In one embodiment, $Q^2$ is independently a partially unsaturated aliphatic $C_{4-8}$alkylene group.

In one embodiment, $Q^2$ is independently a partially unsaturated linear $C_{4-8}$alkylene group.

In one embodiment, $Q^2$ is independently a partially unsaturated branched $C_{4-8}$alkylene group.

In one embodiment, $Q^2$ is independently a partially unsaturated alicyclic $C_{4-8}$alkylene group.

Note that, for embodiments excluding, e.g., certain backbone lengths, absence of adjacent carbon-carbon double bonds, etc., it is to be understood that the corresponding species listed below are similarly excluded from the respective embodiments discussed below.

In one embodiment, $Q^2$ is independently selected from:
—(CH$_2$)$_4$—, —(CH$_2$)$_5$—, —(CH$_2$)$_6$—, —(CH$_2$)$_7$—, —(CH$_2$)$_8$—;
—CH(CH$_3$)CH$_2$CH$_2$CH$_2$—, —CH$_2$CH(CH$_3$)CH$_2$CH$_2$—, —CH$_2$CH$_2$CH(CH$_3$)CH$_2$—, —CH$_2$CH$_2$CH$_2$CH(CH$_3$)—;
—CH(CH$_3$)CH$_2$CH$_2$CH$_2$CH$_2$—, —CH$_2$CH(CH$_3$)CH$_2$CH$_2$CH$_2$—, —CH$_2$CH$_2$CH(CH$_3$)CH$_2$CH$_2$—, —CH$_2$CH$_2$CH$_2$CH(CH$_3$)CH$_2$—, —CH$_2$CH$_2$CH$_2$CH$_2$CH(CH$_3$)—, —CH(CH$_3$)CH$_2$CH$_2$CH$_2$CH(CH$_3$)—;
—CH(CH$_2$CH$_3$)CH$_2$CH$_2$CH$_2$—, —CH$_2$CH(CH$_2$CH$_3$)CH$_2$CH$_2$—, —CH$_2$CH$_2$CH(CH$_2$CH$_3$)CH$_2$—, —CH$_2$CH$_2$CH$_2$CH(CH$_2$CH$_3$)—;
—CH(CH$_2$CH$_3$)CH$_2$CH$_2$CH$_2$CH$_2$—, —CH$_2$CH(CH$_2$CH$_3$)CH$_2$CH$_2$CH$_2$—, —CH$_2$CH$_2$CH(CH$_2$CH$_3$)CH$_2$CH$_2$—, —CH$_2$CH$_2$CH$_2$CH(CH$_2$CH$_3$)CH$_2$—, —CH$_2$CH$_2$CH$_2$CH$_2$CH(CH$_2$CH$_3$)—;
—CH=CHCH$_2$CH$_2$—, —CH$_2$CH=CHCH$_2$—, —CH$_2$CH$_2$CH=CH—;
—CH=CHCH$_2$CH$_2$CH$_2$—, —CH$_2$CH=CHCH$_2$CH$_2$—, —CH$_2$CH$_2$CH=CHCH$_2$—, —CH$_2$CH$_2$CH$_2$CH=CH—;

—CH=CHCH$_2$CH$_2$CH$_2$CH$_2$—,
—CH$_2$CH=CHCH$_2$CH$_2$CH$_2$—,
—CH$_2$CH$_2$CH=CHCH$_2$CH$_2$—,
—CH$_2$CH$_2$CH$_2$CH=CHCH$_2$—,
—CH$_2$CH$_2$CH$_2$CH$_2$CH=CH—;
—CH=CHCH=CH—;
—CH=CHCH=CHCH$_2$—,
—CH$_2$CH=CHCH=CH—,
—CH=CHCH$_2$CH=CH—;
—CH=CHCH=CHCH$_2$CH$_2$—,
—CH=CHCH$_2$CH=CHCH$_2$—,
—CH=CHCH$_2$CH$_2$CH=CH—,
—CH$_2$CH=CHCH=CHCH$_2$—,
—CH$_2$CH=CHCH$_2$CH=CH—,
—CH$_2$CH$_2$CH=CHCH=CH—;
—C(CH$_3$)=CHCH=CH—, —CH=C(CH$_3$)CH=CH—, —CH=CHC(CH$_3$)=CH—, —CH=CHCH=C(CH$_3$);
—C≡CCH$_2$CH$_2$—, —CH$_2$C≡CCH$_2$—, —CH$_2$CH$_2$C≡C—;
—C≡CCH(CH$_3$)CH$_2$—, —C≡CCH$_2$CH(CH$_3$)—;
—CH(CH$_3$)C≡CCH$_2$—, —CH$_2$C≡CCH(CH$_3$)—;
—CH(CH$_3$)CH$_2$C≡C—, —CH$_2$CH(CH$_3$)C≡C—;
—C≡CCH=CH—, —CH=CHC≡C—, —C≡CC≡C—;
—C≡CCH$_2$CH$_2$CH$_2$—, —CH$_2$CH$_2$CH$_2$C≡C—;
—C≡CCH$_2$CH$_2$CH$_2$CH$_2$—, —CH$_2$CH$_2$CH$_2$CH$_2$C≡C—;
—C≡CCH=CHCH=CH—, —CH=CHC≡CCH=CH—, —CH=CHCH=CHC≡C—;
—C(CH$_3$)=CHC≡C—, —CH=C(CH$_3$)C≡C—, —C≡CC(CH$_3$)=CH—, —C≡CCH=C(CH$_3$)—;
cyclopentylene cyclopentenylene;
cyclohexylene, cyclohexenylene, cyclohexadienylene;

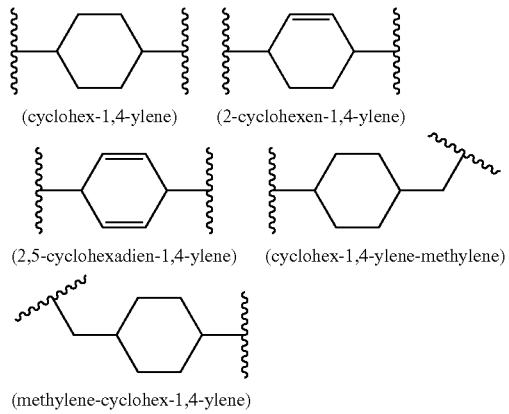

(cyclohex-1,4-ylene) (2-cyclohexen-1,4-ylene)
(2,5-cyclohexadien-1,4-ylene) (cyclohex-1,4-ylene-methylene)
(methylene-cyclohex-1,4-ylene)

In one preferred embodiment, Q$^2$ is independently selected from:
—(CH$_2$)$_5$—;
—(CH$_2$)$_6$—;
—(CH$_2$)$_7$—;
—(CH$_2$)$_8$—;
—CH(CH$_3$)CH$_2$CH$_2$CH$_2$CH$_2$—;
—CH$_2$CH$_2$CH$_2$CH$_2$CH(CH$_3$)—;
—CH$_2$CH$_2$CH(CH$_3$)CH$_2$CH$_2$—;
—CH(CH$_3$)CH$_2$CH$_2$CH$_2$CH(CH$_3$)—;
—CH$_2$CH$_2$CH$_2$CH=CH—;
—CH$_2$CH$_2$CH$_2$CH$_2$CH=CH—;

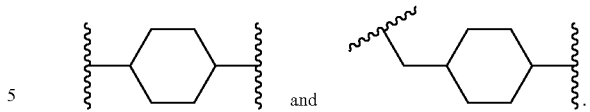

and

In one preferred embodiment, Q$^2$ is independently selected from:
—(CH$_2$)$_5$—;
—(CH$_2$)$_6$—;
—(CH$_2$)$_7$—;
—(CH$_2$)$_8$—;
—CH(CH$_3$)CH$_2$CH$_2$CH$_2$CH$_2$—;
—CH$_2$CH$_2$CH$_2$CH$_2$CH(CH$_3$)—;
—CH$_2$CH$_2$CH$_2$CH=CH—; and,
—CH$_2$CH$_2$CH$_2$CH$_2$CH=CH—.

In one preferred embodiment, Q$^2$ is independently selected from:
—(CH$_2$)$_5$—, —(CH$_2$)$_6$—, —(CH$_2$)$_7$—, and —(CH$_2$)$_8$—.

The Acid Leader Group, Q$^2$: Arylene

In one embodiment, the acid leader group, Q$^2$, is independently:
C$_{5-20}$arylene (denoted —Ar—),
and is optionally substituted,
and has a backbone length of at least 4 atoms.

In one embodiment, Q$^2$ is C$_{5-20}$arylene; and is optionally substituted.

In one embodiment, Q$^2$ is C$_{5-6}$arylene; and is optionally substituted.

In one embodiment, Q$^2$ is phenylene; and is optionally substituted.

In one embodiment, Q$^2$ additionally has a backbone length as described above under the heading "The Acid Leader Group, Q$^2$: Backbone Length."

The Acid Leader Group, Q$^2$:
Alkylene-Arylene, Arylene-Alkylene, and Alkylene-Arylene-Alkylene In one preferred embodiment, the acid leader group, Q$^2$, is independently:
C$_{5-20}$arylene-C$_{1-7}$alkylene;
C$_{1-7}$alkylene-C$_{5-20}$arylene; or,
C$_{1-7}$alkylene-C$_{5-20}$arylene-C$_{1-7}$alkylene;
and is optionally substituted;
and has a backbone length of at least 4 atoms.

In one preferred embodiment, the acid leader group, Q$^2$, is independently:
C$_{5-20}$arylene-C$_{1-7}$alkylene;
and is optionally substituted;
and has a backbone length of at least 4 atoms.

In one preferred embodiment, the acid leader group, Q$^2$, is independently:
C$_{1-7}$alkylene-C$_{5-20}$arylene; or,
and is optionally substituted;
and has a backbone length of at least 4 atoms.

In one preferred embodiment, the acid leader group, Q$^2$, is independently:
C$_{1-7}$alkylene-C$_{5-20}$arylene-C$_{1-7}$alkylene;
and is optionally substituted;
and has a backbone length of at least 4 atoms.

In one preferred embodiment, Q$^2$ is independently:
C$_{5-6}$arylene-C$_{1-7}$alkylene;
C$_{1-7}$alkylene-C$_{5-6}$arylene; or,
C$_{1-7}$alkylene-C$_{5-6}$arylene-C$_{1-7}$alkylene;
and is optionally substituted;
and has a backbone length of at least 4 atoms.

In one preferred embodiment, $Q^2$ is independently:
phenylene-$C_{1-7}$alkylene;
$C_{1-7}$alkylene-phenylene; or,
$C_{1-7}$alkylene-phenylene-$C_{1-7}$alkylene;
and is optionally substituted;
and has a backbone length of at least 4 atoms.

In one embodiment, $Q^2$ is $C_{1-7}$alkylene-$C_{5-20}$arylene; and is optionally substituted.

In one embodiment, $Q^2$ is $C_{1-7}$alkylene-$C_{5-6}$arylene; and is optionally substituted.

In one embodiment, $Q^2$ is independently $C_{1-7}$alkylene-phenylene; and is optionally substituted.

In one embodiment, $Q^2$ is $C_{5-20}$arylene-$C_{1-7}$alkylene; and is optionally substituted.

In one embodiment, $Q^2$ is $C_{5-6}$arylene-$C_{1-7}$alkylene; and is optionally substituted.

In one embodiment, $Q^2$ is independently phenylene-$C_{1-7}$alkylene; and is optionally substituted.

In one embodiment, $Q^2$ is $C_{1-7}$alkylene-$C_{5-20}$arylene-$C_{1-7}$alkylene; and is optionally substituted.

In one embodiment, $Q^2$ is $C_{1-7}$alkylene-$C_{5-20}$arylene-$C_{1-7}$alkylene; and is optionally substituted.

In one embodiment, $Q^2$ is independently $C_{1-7}$alkylene-phenylene-$C_{1-7}$alkylene; and is optionally substituted.

In the above arylene-alkylene (denoted —Ar—$R^{Q22}$—), alkylene-arylene (denoted —$R^{Q21}$—Ar—), and alkylene-arylene-alkylene (denoted —$R^{Q21}$—Ar—$R^{Q22}$—) groups, each of $R^{Q21}$ and $R^{Q22}$ is independently $C_{1-7}$alkylene.

In one embodiment, in the above arylene-alkylene, alkylene-arylene, and alkylene-arylene-alkylene groups, each alkylene group is independently:
(a) a saturated $C_{1-7}$alkylene group; or:
(b) a partially unsaturated $C_{2-7}$alkylene group; or:
(c) an aliphatic $C_{1-7}$alkylene group; or:
(d) a linear $C_{1-7}$alkylene group; or:
(e) a branched $C_{2-7}$alkylene group; or:
(f) a saturated aliphatic $C_{1-7}$alkylene group; or:
(g) a saturated linear $C_{1-7}$alkylene group; or
(h) a saturated branched $C_{2-7}$alkylene group; or
(i) a partially unsaturated aliphatic $C_{2-7}$alkylene group; or:
(j) a partially unsaturated linear $C_{2-7}$alkylene group; or:
(k) a partially unsaturated branched $C_{2-7}$alkylene group;
and is optionally substituted.

In one embodiment, $Q^2$ additionally has a backbone length as described above under the heading "The Acid Leader Group, $Q^2$: Backbone Length."

Alkylene Groups $R^{Q21}$ and $R^{Q22}$: Certain Embodiments

Note that, for embodiments excluding, e.g., certain backbone lengths, absence of adjacent carbon-carbon double bonds, etc., it is to be understood that the corresponding species listed below are similarly excluded from the respective embodiments discussed below.

In one embodiment, each of $R^{Q21}$ and $R^{Q22}$ is independently as defined for $Q^1$ under the heading "The Cyclyl Leader Group, $Q^1$: Alkylene: Certain Embodiments."

In one embodiment, $R^{Q21}$ is independently selected from:
—$CH_2$—, —$(CH_2)_2$—, —$(CH_2)_3$—, —$(CH_2)_4$—, —$(CH_2)_5$—, —$(CH_2)_6$—,
—$CH_2$—CH=CH—; and,
—$CH_2$—CH=CH—CH=CH—.

In one embodiment, $R^{Q21}$ is independently selected from:
—$CH_2$—, —$CH_2CH_2$—, and —$CH_2$—CH=CH—.

In one embodiment, $R^{Q21}$ is independently selected from:
—$CH_2$— and, —$CH_2CH_2$—.

In one embodiment, $R^{Q21}$ is independently —$CH_2$—.
In one embodiment, $R^{Q21}$ is independently —$CH_2CH_2$—.

In one embodiment, $R^{Q21}$ is independently —$CH_2$—CH=CH—.

In one embodiment, $R^{Q21}$ is independently cis —$CH_2$—CH=CH—.

In one embodiment, $R^{Q21}$ is independently trans —$CH_2$—CH=CH—.

In one embodiment, $R^{Q22}$ is independently selected from:
—$CH_2$—, —$(CH_2)_2$—, —$(CH_2)_3$—, —$(CH_2)_4$—, —$(CH_2)_5$—, —$(CH_2)_6$—;
—CH=CH—;
—$CH_2$—CH=CH—;
—CH=CH—CH=CH—; and,
—$CH_2$—CH=CH—CH=CH—.

In one embodiment, $R^{Q22}$ is independently selected from:
—$CH_2$—, —$CH_2CH_2$—, —CH=CH—, and —$CH_2$—CH=CH—.

In one embodiment, $R^{Q22}$ is independently selected from:
—$CH_2$—, —$CH_2CH_2$—, and —CH=CH—.

The Acid Leader Group, $Q^2$ Certain Phenylene-Containing Embodiments

In one embodiment, $Q^2$ is independently:
phenylene;
and is optionally substituted;
and has a backbone length of at least 4 atoms.

In one embodiment, $Q^2$ is independently:
methylene-phenylene;
ethylene-phenylene;
and is optionally substituted;
and has a backbone length of at least 4 atoms.

In one embodiment, $Q^2$ is independently:
phenylene-methylene;
phenylene-ethylene; or,
phenylene-ethenylene (also known as phenylene-vinylene);
and is optionally substituted;
and has a backbone length of at least 4 atoms.

In one embodiment, $Q^2$ is independently:
methylene-phenylene-methylene;
methylene-phenylene-ethylene;
methylene-phenylene-ethenylene;
ethylene-phenylene-methylene;
ethylene-phenylene-ethylene;
ethylene-phenylene-ethenylene;
and is optionally substituted;
and has a backbone length of at least 4 atoms.

In the above phenylene, phenylene-alkylene, alkylene-phenylene, and alkylene-phenylene-alkylene groups, the phenylene linkage may be ortho (i.e., 1,2-), meta (i.e., 1,3-), or para (i.e., 1,4-), and the phenylene group is optionally substituted with from 1 to 4 substituents, $R^B$:

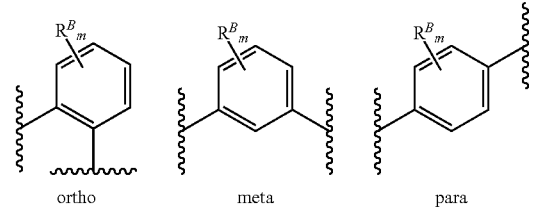

ortho      meta      para

In one embodiment, the phenylene linkage is meta or para.
In one embodiment, the phenylene linkage is meta.
In one embodiment, the phenylene linkage is para.
In one embodiment, m is an integer from 0 to 4.
In one embodiment, m is an integer from 0 to 3.

In one embodiment, m is an integer from 0 to 2.
In one embodiment, m is 0 or 1.
In one embodiment, m is an integer from 1 to 4.
In one embodiment, m is an integer from 1 to 3.
In one embodiment, m is 1 or 2.
In one embodiment, m is 4.
In one embodiment, m is 3.
In one embodiment, m is 2.
In one embodiment, m is 1.
In one embodiment, m is 0.
In one embodiment, the phenylene group is unsubstituted.
In one embodiment, the phenylene group is optionally substituted.
In one embodiment, the phenylene group is substituted.
Examples of substituents, $R^B$, include, but are not limited to, those described under the heading "Substituents" below.
In one embodiment, the substituents, $R^B$, are as defined under the heading "The Cyclyl Group, Cy: Optionally Substituted Phenyl: Substituents."
Examples of preferred substituents, $R^B$, include, but are not limited to, the following: fluoro, chloro, methyl, ethyl, isopropyl, t-butyl, trifluoromethyl, hydroxy, methoxy, ethoxy, isopropoxy, methylthio, amino, dimethylamino, diethylamino, morpholino, acetamido, nitro, and phenyl.

In one embodiment, the compounds have the following formula, in which $Q^2$ is para-arylene:

(9)

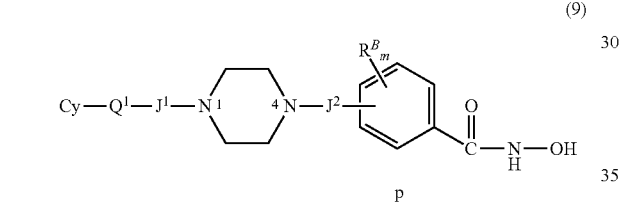

p

In one embodiment, the compounds have the following formula, in which $Q^2$ is alkylene-meta/para-arylene:

(10)

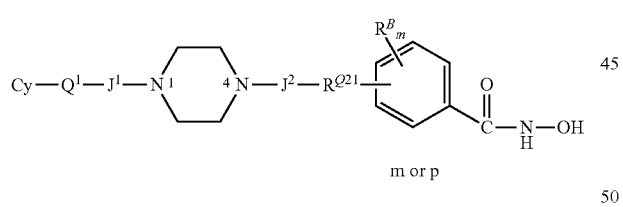

m or p

In one embodiment, the compounds have the following formula, in which $Q^2$ is arylene-meta/para-alkylene:

(11)

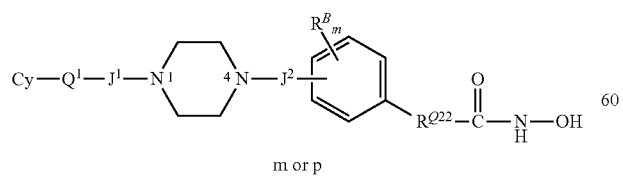

m or p

In one embodiment, the compounds have the following formula, in which $Q^2$ is alkylene-arylene-meta/para-alkylene:

(12)

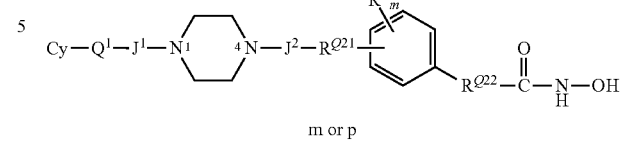

m or p

In one embodiment, $Q^2$ has the following formula (referred to herein as "para-phenylene"):

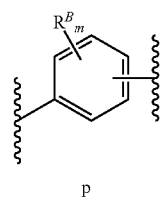

p

In one embodiment, $Q^2$ has the following formula (referred to herein as "methylene-meta/para-phenylene"):

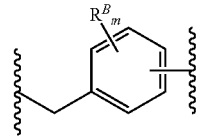

m or p

In one embodiment, $Q^2$ has the following formula (referred to herein as "methylene-meta-phenylene"):

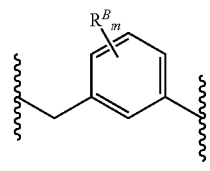

In one embodiment, $Q^2$ has the following formula (referred to herein as "unsubstituted methylene-meta-phenylene"):

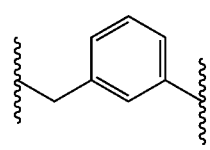

In one embodiment, $Q^2$ has the following formula (referred to herein as "ethylene-meta/para-phenylene"):

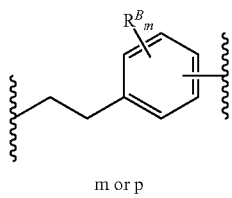

m or p

In one embodiment, $Q^2$ has the following formula (referred to herein as "ethylene-meta-phenylene"):

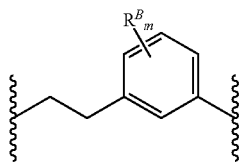

In one embodiment, $Q^2$ has the following formula (referred to herein as "unsubstituted ethylene-meta-phenylene"):

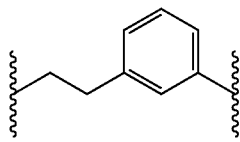

In one embodiment, $Q^2$ has the following formula (referred to herein as "phenylene-meta/para-methylene"):

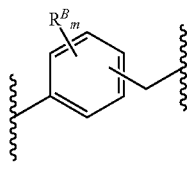

m or p

In one embodiment, $Q^2$ has the following formula (referred to herein as "phenylene-meta-methylene"):

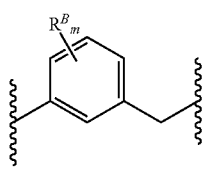

In one embodiment, $Q^2$ has the following formula (referred to herein as "unsubstituted phenylene-meta-methylene"):

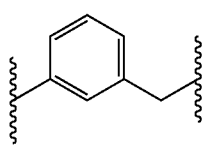

In one embodiment, $Q^2$ has the following formula (referred to herein as "methylene-phenylene-meta/para-methylene"):

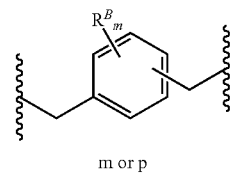

m or p

In one embodiment, $Q^2$ has the following formula (referred to herein as "methylene-phenylene-meta-methylene"):

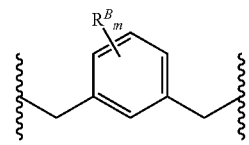

In one embodiment, $Q^2$ has the following formula (referred to herein as "unsubstituted methylene-phenylene-meta-methylene"):

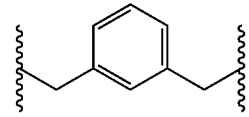

In one embodiment, $Q^2$ has the following formula (referred to herein as "ethylene-phenylene-meta/para-methylene"):

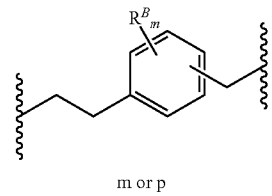

m or p

In one embodiment, $Q^2$ has the following formula (referred to herein as "ethylene-phenylene-meta-methylene"):

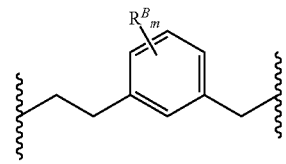

In one embodiment, $Q^2$ has the following formula (referred to herein as "unsubstituted ethylene-phenylene-meta-methylene"):

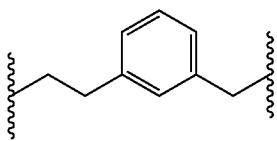

In one embodiment, $Q^2$ has the following formula (referred to herein as "phenylene-meta/para-trans-ethenylene"):

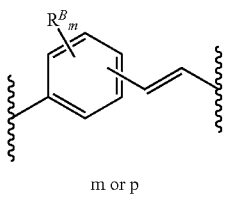

m or p

In one embodiment, $Q^2$ has the following formula (referred to herein as "unsubstituted phenylene-meta/para-trans-ethenylene"):

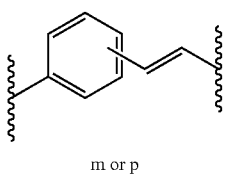

m or p

In one embodiment, $Q^2$ has the following formula (referred to herein as "phenylene-meta-trans-ethenylene"):

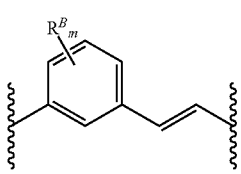

In one embodiment, $Q^2$ has the following formula (referred to herein as "unsubstituted phenylene-meta-trans-ethenylene"):

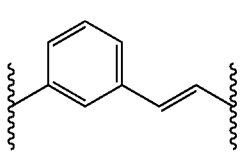

In one embodiment, $Q^2$ has the following formula (referred to herein as "phenylene-meta/para-ethylene"):

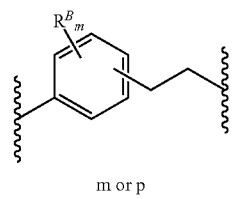

m or p

In one embodiment, $Q^2$ has the following formula (referred to herein as "phenylene-meta-ethylene"):

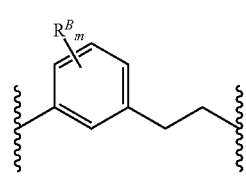

In one embodiment, $Q^2$ has the following formula (referred to herein as "unsubstituted phenylene-meta-ethylene"):

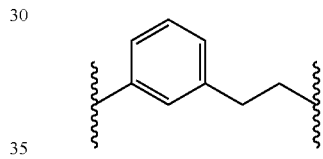

In one embodiment, $Q^2$ has the following formula (referred to herein as "methylene-phenylene-meta/para-trans-ethenylene"):

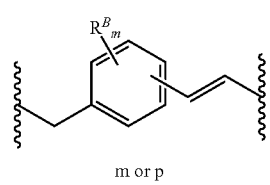

m or p

In one embodiment, $Q^2$ has the following formula (referred to herein as "unsubstituted methylene-phenylene-meta/para-trans-ethenylene"):

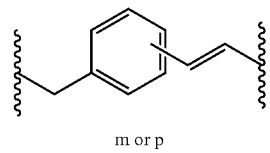

m or p

In one embodiment, $Q^2$ has the following formula (referred to herein as "methylene-phenylene-meta-trans-ethenylene"):

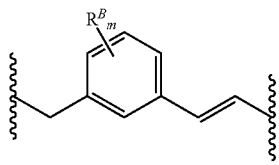

In one embodiment, $Q^2$ has the following formula (referred to herein as "unsubstituted methylene-phenylene-meta-trans-ethenylene"):

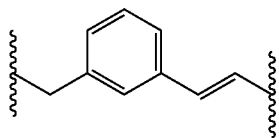

In one embodiment, $Q^2$ has the following formula (referred to herein as "methylene-phenylene-meta/para-ethylene"):

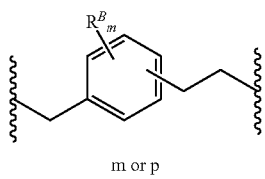

m or p

In one embodiment, $Q^2$ has the following formula (referred to herein as "methylene-phenylene-meta-ethylene"):

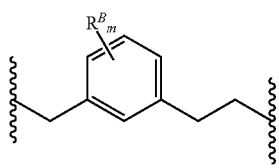

In one embodiment, $Q^2$ has the following formula (referred to herein as "unsubstituted methylene-phenylene-meta-ethylene"):

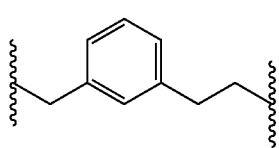

In one embodiment, $Q^2$ has the following formula (referred to herein as "ethylene-phenylene-meta/para-trans-ethenylene"):

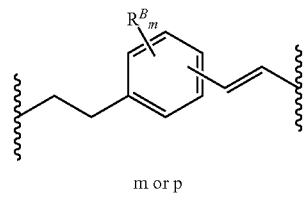

m or p

In one embodiment, $Q^2$ has the following formula (referred to herein as "ethylene-phenylene-meta-trans-ethenylene"):

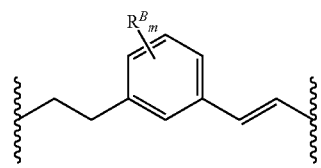

In one embodiment, $Q^2$ has the following formula (referred to herein as "unsubstituted ethylene-phenylene-meta-trans-ethenylene"):

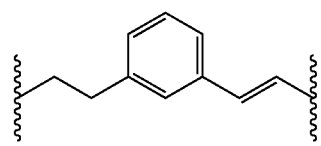

In one embodiment, $Q^2$ has the following formula (referred to herein as "ethylene-phenylene-meta/para-ethylene"):

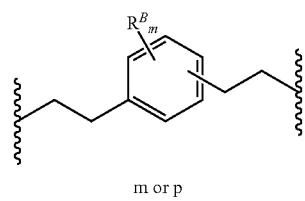

m or p

In one embodiment, $Q^2$ has the following formula (referred to herein as "ethylene-phenylene-meta-ethylene"):

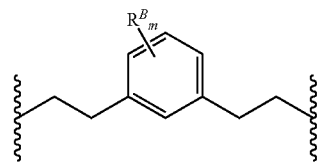

In one embodiment, Q² has the following formula (referred to herein as "unsubstituted ethylene-phenylene-meta-ethylene"):

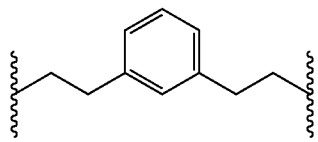

In one embodiment, Q² additionally has a backbone length as described above under the heading "The Acid Leader Group, Q²: Backbone Length."

Examples of Specific Embodiments

Some individual embodiments of the present invention include the following compounds.

1. 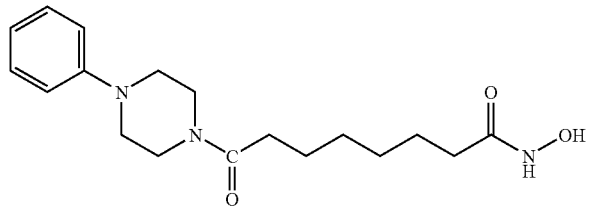 PX117402 (Ex 140)

2. 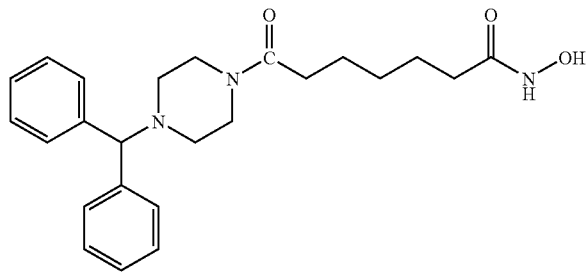 PX117403 (Ex 141)

3. 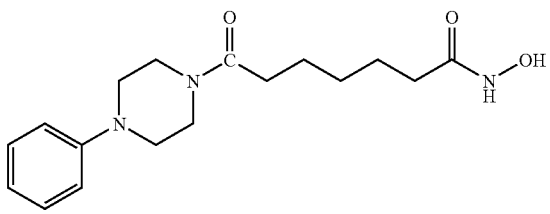 PX117404 (Ex 142)

4. 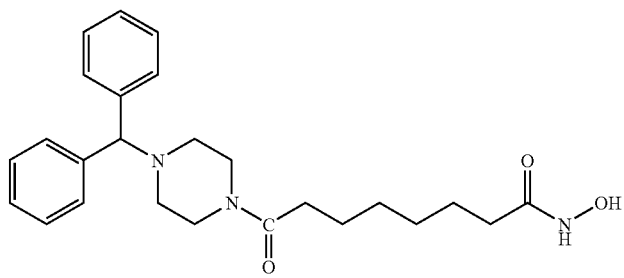 PX117764 (Ex 143)

5. 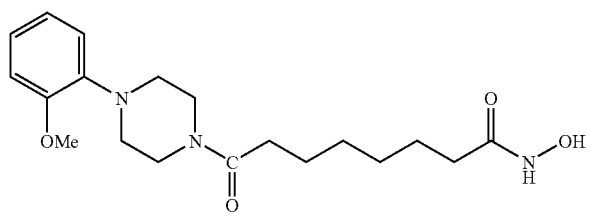 PX117768 (Ex 144)

-continued
| | | |
|---|---|---|
| 6. | 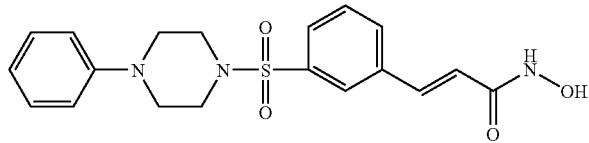 | PX118490 (Ex 40) |
| 7. | 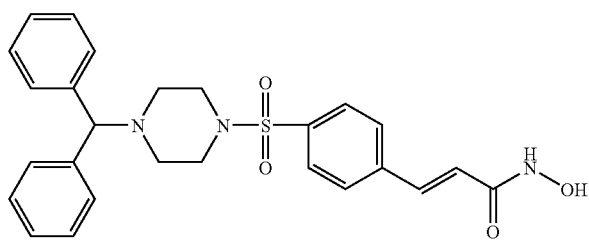 | PX118491 (Ex 41) |
| 8. | 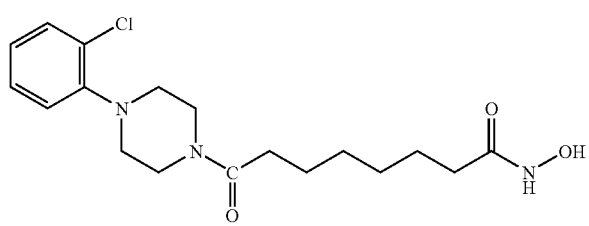 | PX118791 (Ex 145) |
| 9. | 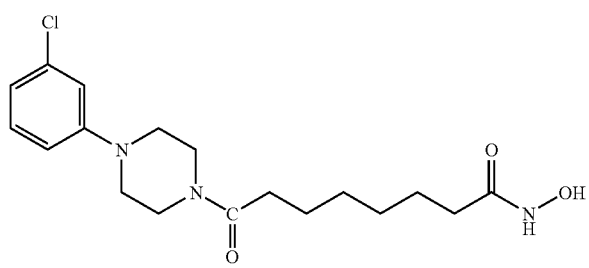 | PX118792 (Ex 146) |
| 10. | 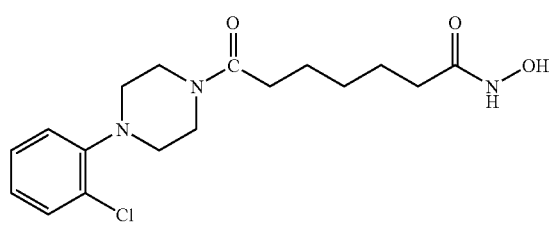 | PX118793 (Ex 147) |
| 11. | 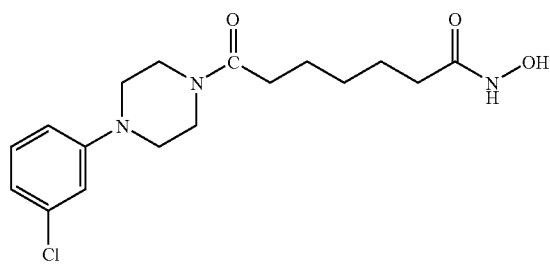 | PX118794 (Ex 148) |
| 12. | 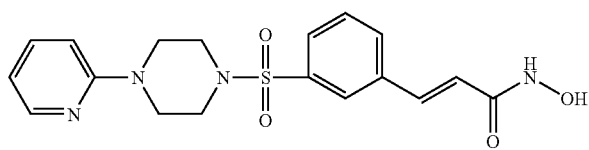 | PX118807 (Ex 45) |

-continued
| | | |
|---|---|---|
| 13. | 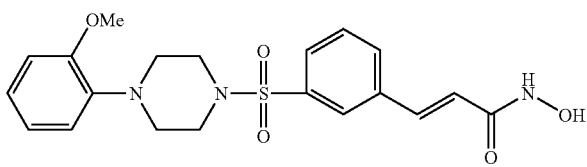 | PX118810 (Ex 42) |
| 14. | 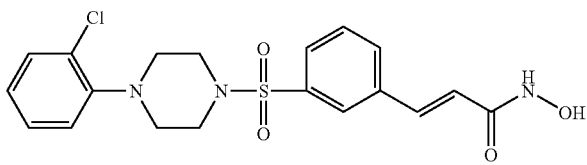 | PX118811 (Ex 43) |
| 15. | 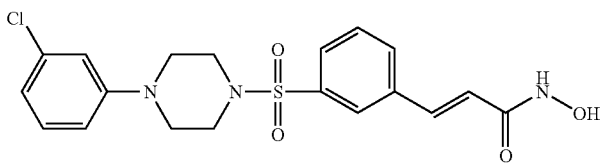 | PX118812 (Ex 44) |
| 16. | 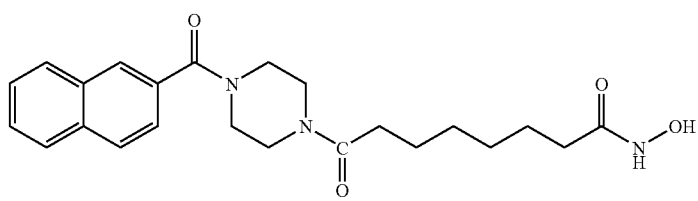 | PX118830 (Ex 149) |
| 17. | 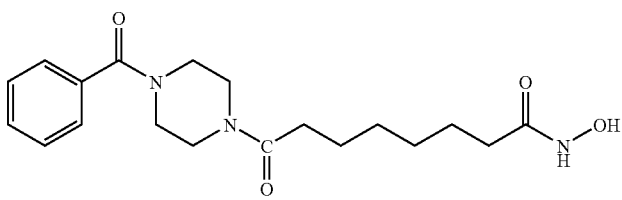 | PX118831 (Ex 150) |
| 18. | 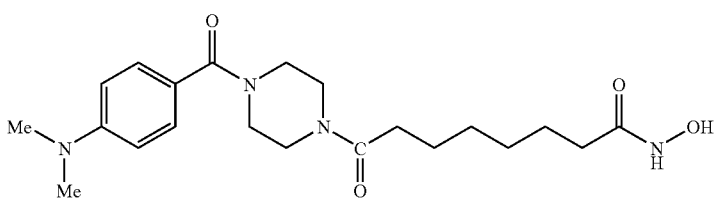 | PX118832 (Ex 151) |
| 19. | 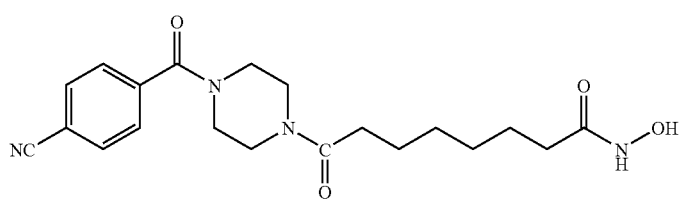 | PX118844 (Ex 163) |
| 20. | 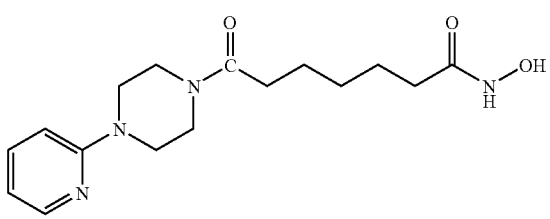 | PX118845 (Ex 164) |

| | | |
|---|---|---|
| 21. | 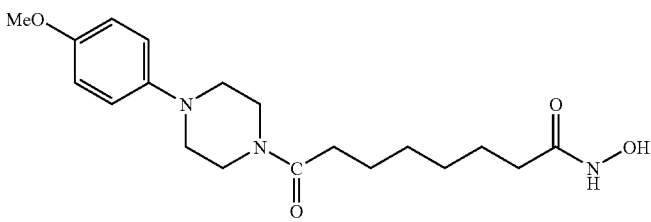 | PX118846 (Ex 152) |
| 22. | 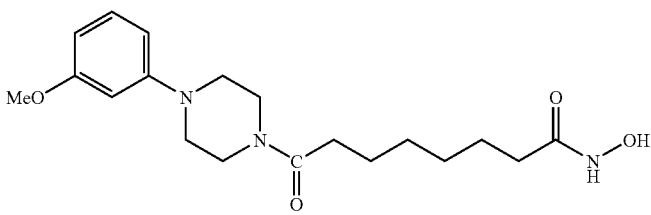 | PX118847 (Ex 153) |
| 23. | 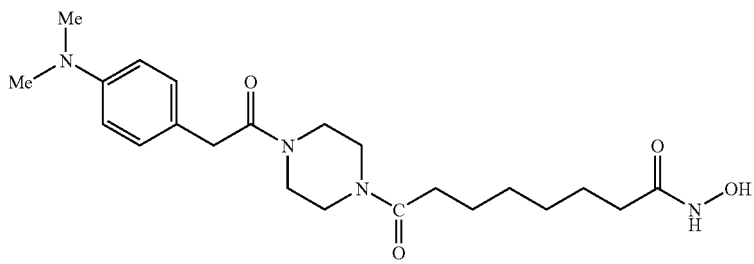 | PX118848 (Ex 165) |
| 24. | 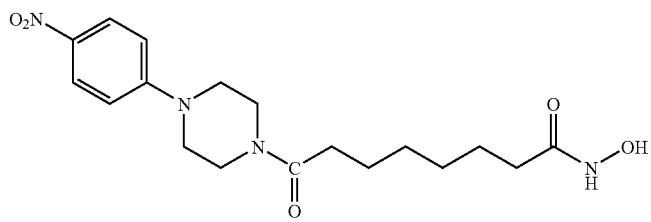 | PX118849 (Ex 154) |
| 25. | 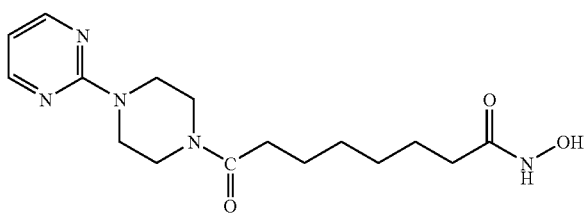 | PX118850 (Ex 166) |
| 26. | 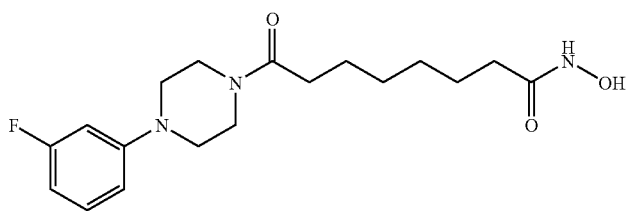 | PX118859 (Ex 174) |
| 27. | 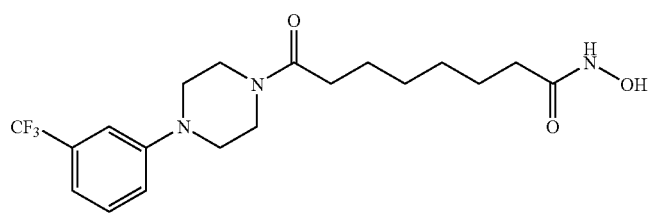 | PX118860 (Ex 175) |

| | | |
|---|---|---|
| 28. | [structure] | PX118870 (Ex 52) |
| 29. | [structure] | PX118871 (Ex 53) |
| 30. | [structure] | PX118872 (Ex 54) |
| 31. | [structure] | PX118873 (Ex 55) |
| 32. | [structure] | PX118874 (Ex 56) |
| 33. | [structure] | PX118875 (Ex 57) |
| 34. | [structure] | PX118876 (Ex 58) |
| 35. | [structure] | PX118877 (Ex 59) |
| 36. | [structure] | PX118878 (Ex 60) |

-continued
| | | |
|---|---|---|
| 37. | 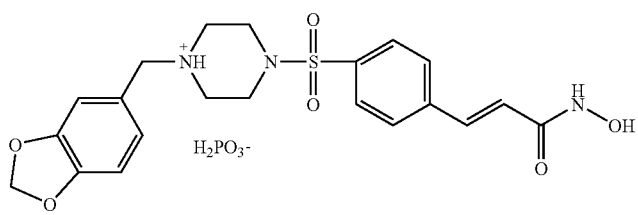 | PX118882 (Ex 72) |
| 38. | 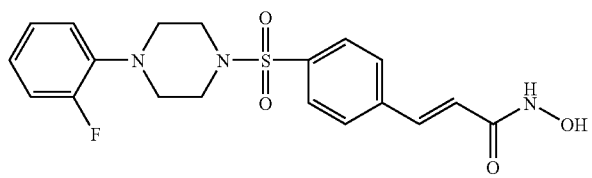 | PX118891 (Ex 74) |
| 39. | 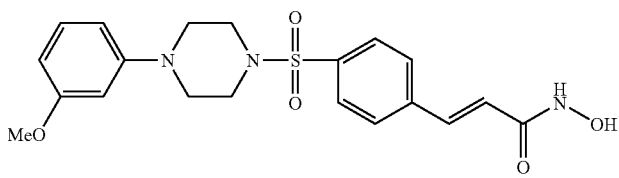 | PX118892 (Ex 75) |
| 40. | 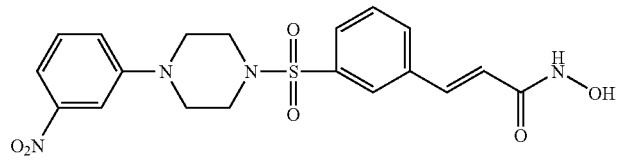 | PX118893 (Ex 61) |
| 41. | 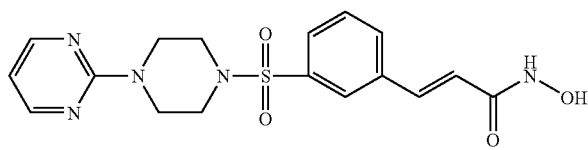 | PX118894 (Ex 62) |
| 42. | 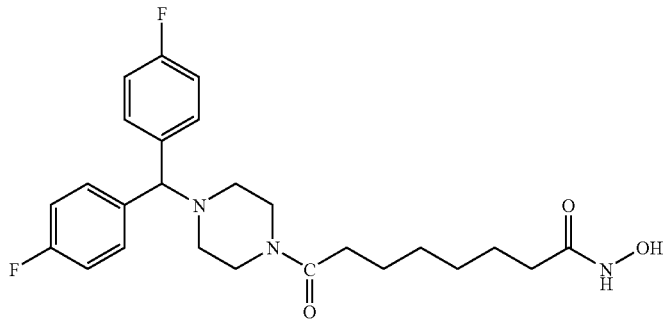 | PX118898 (Ex 176) |
| 43. | 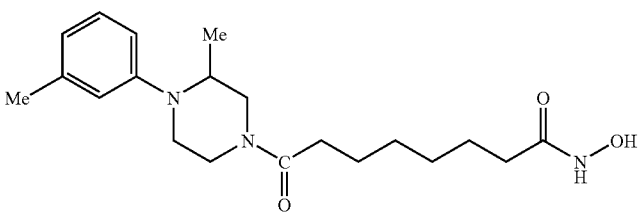 | PX118899 (Ex 177) |

-continued
| | | |
|---|---|---|
| 44. | 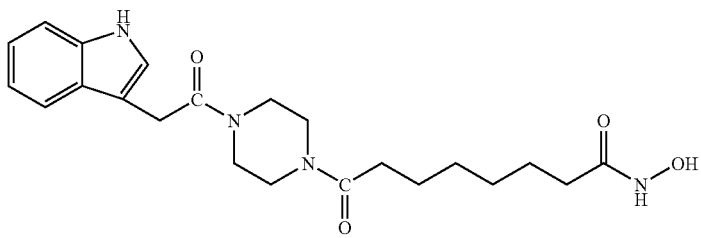 | PX118900 (Ex 178) |
| 45. | 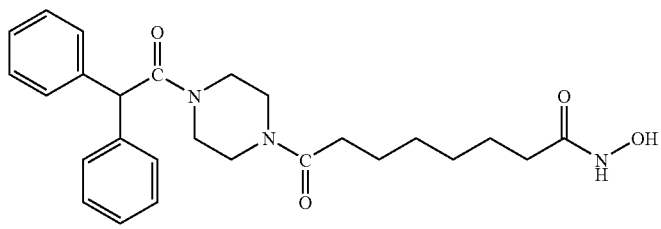 | PX118901 (Ex 179) |
| 46. | 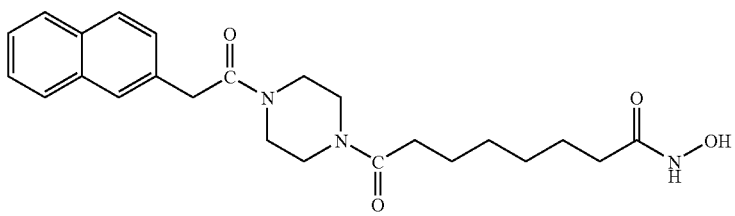 | PX118902 (Ex 180) |
| 47. | 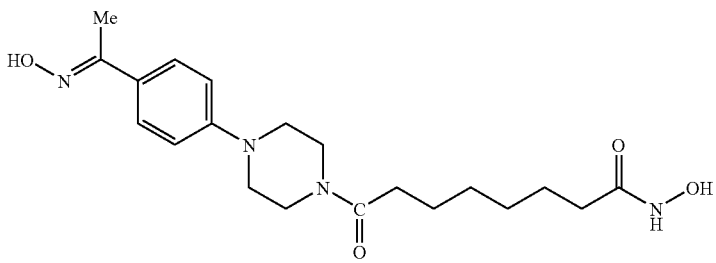 | PX118903 (Ex 181) |
| 48. | 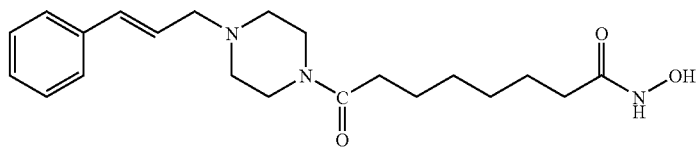 | PX118904 (Ex 182) |
| 49. | 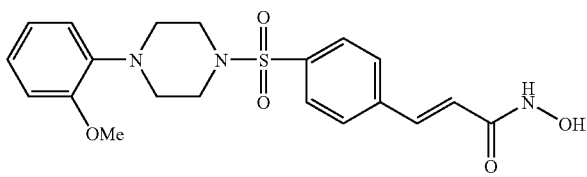 | PX118905 (Ex 76) |
| 50. | 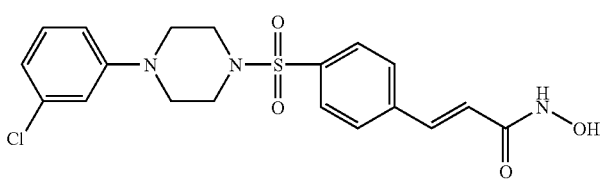 | PX118906 (Ex 77) |

-continued

| | | |
|---|---|---|
| 51. | [structure] | PX118907 (Ex 78) |
| 52. | [structure] | PX118908 (Ex 183) |
| 53. | [structure] | PX118909 (Ex 184) |
| 54. | [structure] | PX118910 (Ex 79) |
| 55. | [structure] | PX118911 (Ex 80) |
| 56. | [structure] | PX118913 (Ex 63) |
| 57. | [structure] | PX118914 (Ex 64) |

| | | |
|---|---|---|
| 58. | 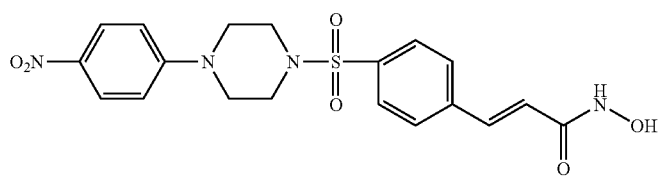 | PX118918 (Ex 73) |
| 59. | 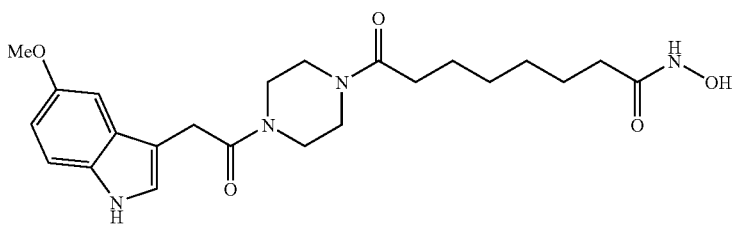 | PX118927 (Ex 155) |
| 60. | 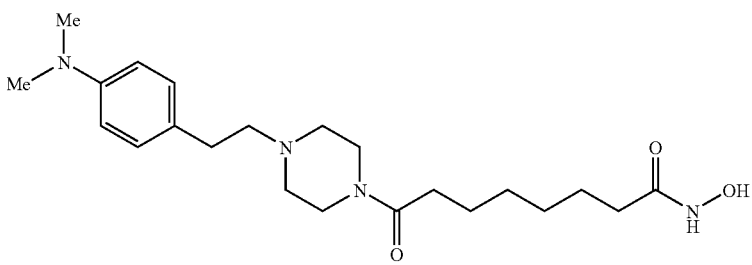 | PX118928 (Ex 167) |
| 61. | 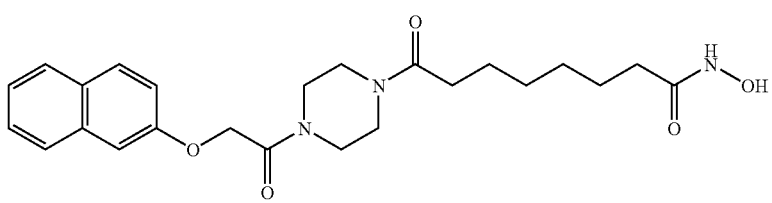 | PX118929 (Ex 168) |
| 62. | 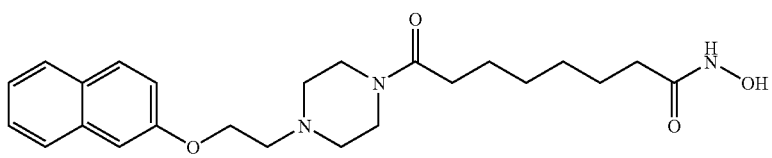 | PX118930 (Ex 156) |
| 63. | 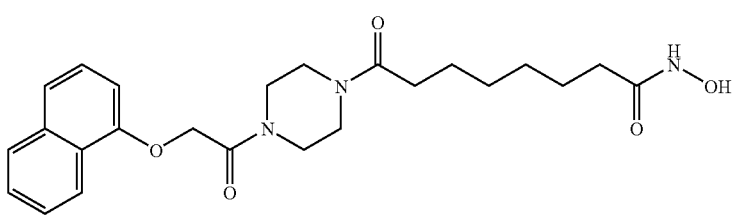 | PX118931 (Ex 157) |
| 64. | 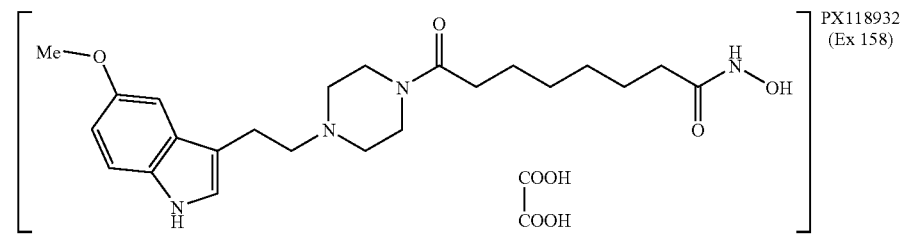 | PX118932 (Ex 158) |

-continued

| # | Structure | ID |
|---|---|---|
| 65. | (chemical structure) | PX118933 (Ex 46) |
| 66. | (chemical structure) | PX118934 (Ex 48) |
| 67. | (chemical structure) | PX118935 (Ex 49) |
| 68. | (chemical structure) | PX118937 (Ex 70) |
| 69. | (chemical structure) | PX118951 (Ex 47) |
| 70. | (chemical structure) | PX118965 (Ex 71) |
| 71. | (chemical structure) | PX118967 (Ex 159) |
| 72. | (chemical structure) | PX118968 (Ex 169) |

73. 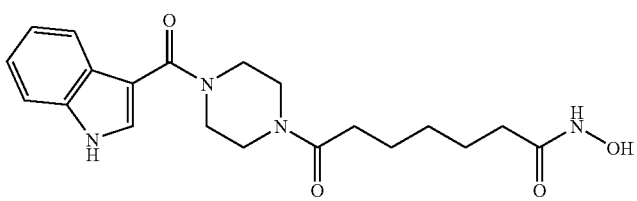 PX118969 (Ex 170)
74. 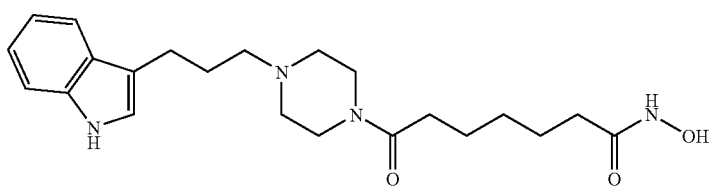 PX118970 (Ex 171)
75. 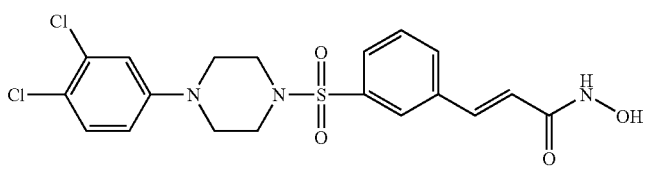 PX118971 (Ex 50)
76. 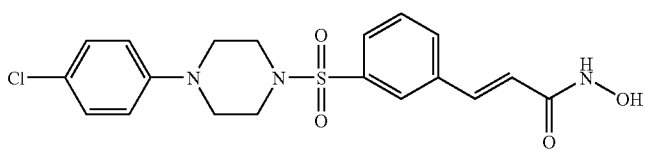 PX118972 (Ex 51)
77. 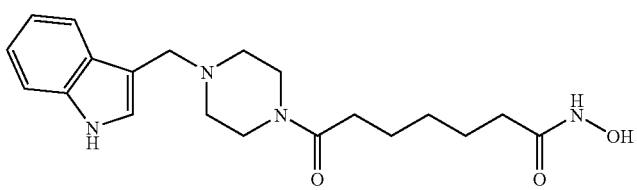 PX118978 (Ex 172)
78. 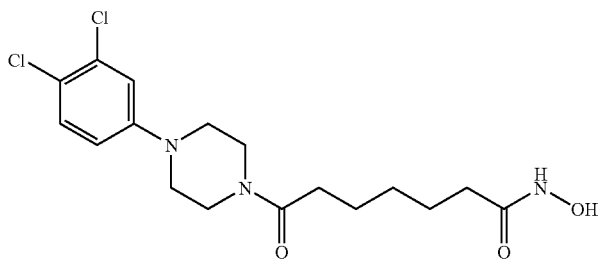 PX118989 (Ex 160)
79. 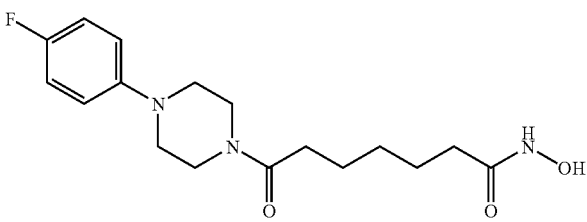 PX118990 (Ex 161)

-continued
| | | |
|---|---|---|
| 80. | 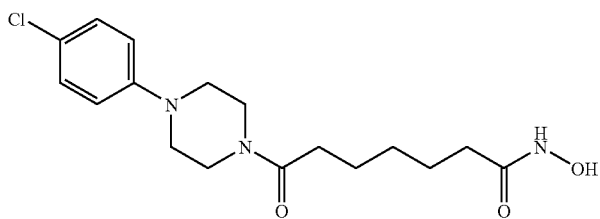 | PX118991 (Ex 162) |
| 81. | 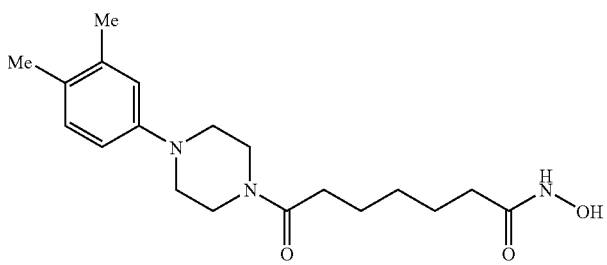 | PX118994 (Ex 173) |
| 82. | 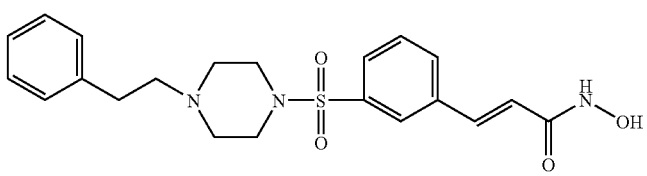 | |
| 83. | 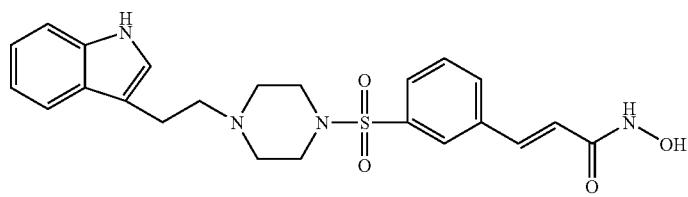 | |
| 84. | 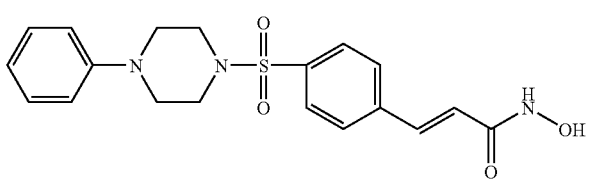 | |
| 85. | 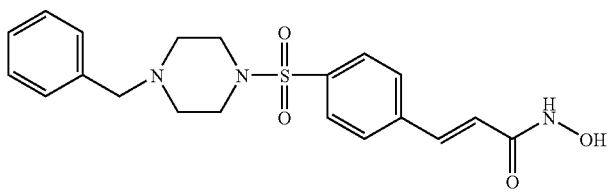 | |
| 86. | 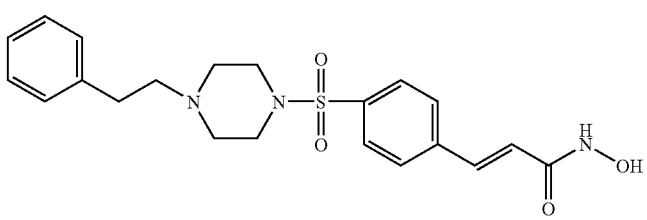 | |

87. 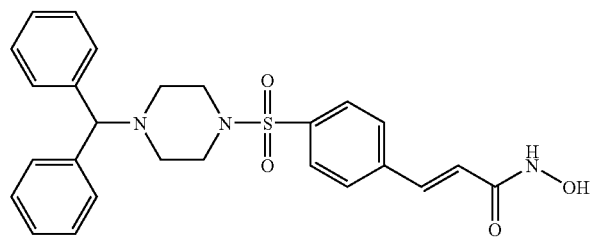
88. 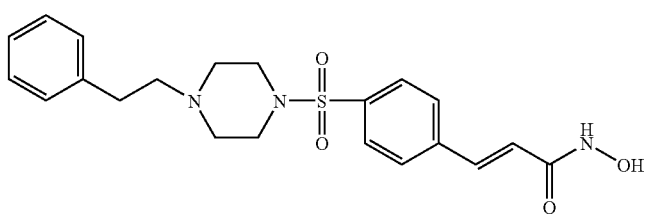
89. 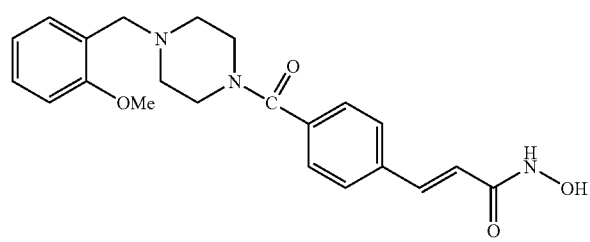
90. 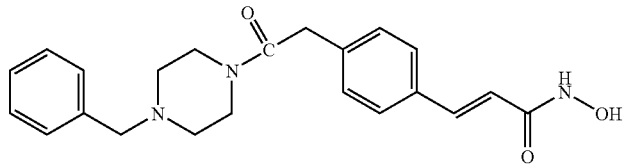
91. 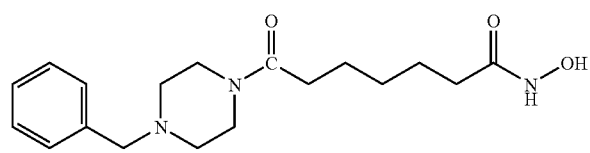
92. 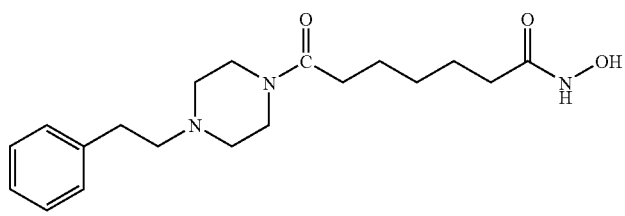
93. 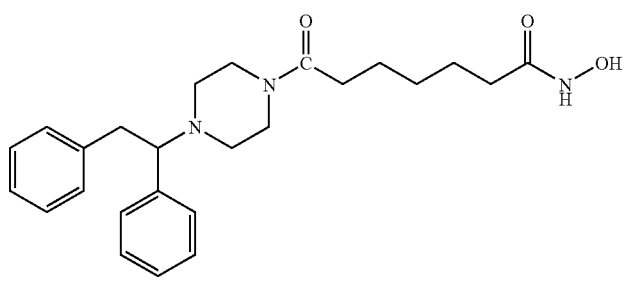

-continued
94. 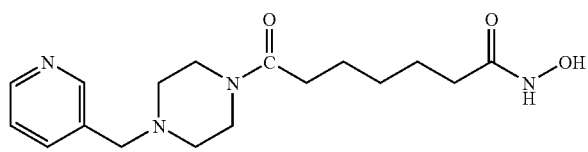
95. 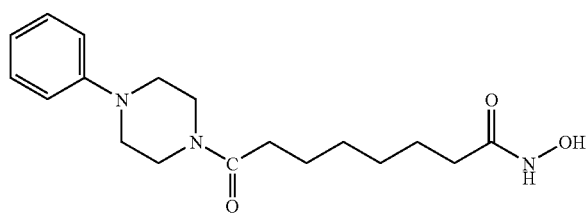
96. 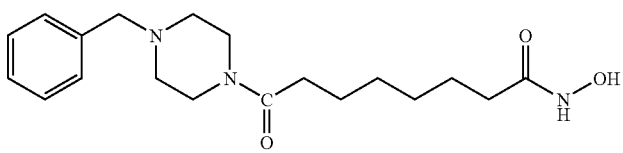
97. 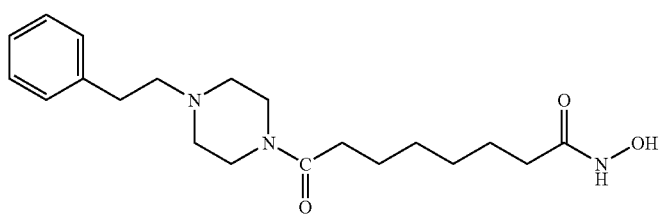
98. 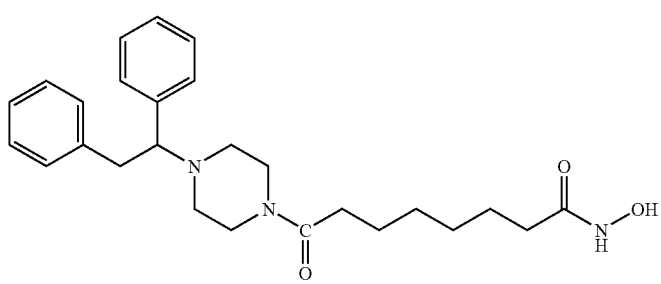
99. 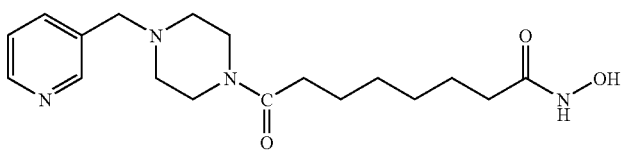
100. 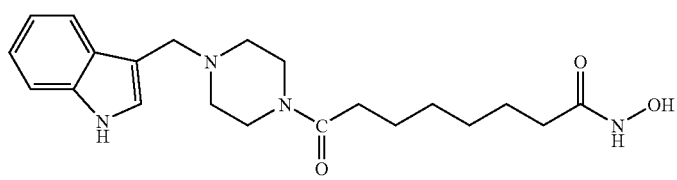

Note that, where the above examples are salts (e.g., PX118932, PX118882), other analogous salts may also be prepared.

Chemical Terms

The term "carbo," "carbyl," "hydrocarbon" and "hydrocarbyl," as used herein, pertain to compounds and/or groups which have only carbon and hydrogen atoms (but see "carbocyclic" below).

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "ring," as used herein, pertains to a closed ring of from 3 to 10 covalently linked atoms, more preferably 3 to 8 covalently linked atoms, yet more preferably 5 to 6 covalently linked atoms. A ring may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "carboaromatic ring," as used herein, pertains to an aromatic ring wherein all of the ring atoms are carbon atoms.

The term "heterocyclic ring," as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. Preferably, the heterocyclic ring has from 1 to 4 heteroatoms.

The term "cyclic compound," as used herein, pertains to a compound which has at least one ring. The term "cyclyl," as used herein, pertains to a monovalent moiety obtained by removing a hydrogen atom from a ring atom of a cyclic compound.

Where a cyclic compound has two or more rings, they may be fused (e.g., as in naphthalene), bridged (e.g., as in norbornane), spiro (e.g., as in spiro[3.3]heptane), or a combination thereof. Cyclic compounds with one ring may be referred to as "monocyclic" or "mononuclear," whereas cyclic compounds with two or more rings may be referred to as "polycyclic" or "polynuclear."

The term "carbocyclic compound," as used herein, pertains to a cyclic compound which has only carbocyclic ring(s).

The term "heterocyclic compound," as used herein, pertains to a cyclic compound which has at least one heterocyclic ring.

The term "aromatic compound," as used herein, pertains to a cyclic compound which has at least one aromatic ring.

The term "carboaromatic compound," as used herein, pertains to a cyclic compound which has only carboaromatic ring(s).

The term "heteroaromatic compound," as used herein, pertains to a cyclic compound which has at least one heteroaromatic ring.

The term "monodentate substituents," as used herein, pertains to substituents which have one point of covalent attachment.

The term "monovalent monodentate substituents," as used herein, pertains to substituents which have one point of covalent attachment, via a single bond. Examples of such substituents include halo, hydroxy, and alkyl.

The term "multivalent monodentate substituents," as used herein, pertains to substituents which have one point of covalent attachment, but through a double bond or triple bond. Examples of such substituents include oxo, imino, alkylidene, and alklidyne.

The term "bidentate substituents," as used herein, pertains to substituents which have two points of covalent attachment, and which act as a linking group between two other moieties. Examples of such substituents include alkylene and arylene.

Substituents

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

The substituents are described in more detail below.

Alkyl: The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated, partially unsaturated, or fully unsaturated. Thus, the term "alkyl" includes the subclasses alkenyl, alkynyl, cycloalkyl, etc., discussed below.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Cycloalkyl: The term "cycloalkyl," as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 20 ring atoms (unless otherwise specified). Preferably, each ring has from 3 to 7 ring atoms.

Examples of (unsubstituted) saturated cylcoalkyl groups include, but are not limited to, those derived from: cyclopropane ($C_3$), cyclobutane ($C_4$), cyclopentane ($C_5$), cyclohexane ($C_6$), cycloheptane ($C_7$), norbornane ($C_7$), norpinane ($C_7$), norcarane ($C_7$), adamantane ($C_{10}$), and decalin (decahydronaphthalene) ($C_{10}$).

Examples of (substituted) saturated cycloalkyl groups, which are also referred to herein as "alkyl-cycloalkyl" groups, include, but are not limited to, methylcyclopropyl, dimethylcyclopropyl, methylcyclobutyl, dimethylcyclobutyl, methylcyclopentyl, dimethylcyclopentyl, methylcyclohexyl, and dimethylcyclohexyl, menthane, thujane, carane, pinane, bornane, norcarane, and camphene.

Examples of (substituted) unsaturated cyclic alkenyl groups, which are also referred to herein as "alkyl-cycloalkenyl" groups, include, but are not limited to, methylcyclopropenyl, dimethylcyclopropenyl, methylcyclobutenyl, dimethylcyclobutenyl, methylcyclopentenyl, dimethylcyclopentenyl, methylcyclohexenyl, and dimethylcyclohexenyl.

Examples of (substituted) cycloalkyl groups, with one or more other rings fused to the parent cycloalkyl group, include, but are not limited to, those derived from: indene ($C_9$), indan (e.g., 2,3-dihydro-1H-indene) ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), aceanthrene ($C_{16}$). For example, 2H-inden-2-yl is a $C_5$cycloalkyl group with a substituent (phenyl) fused thereto.

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (—C(CH$_3$)=CH$_2$), butenyl ($C_4$), pentenyl ($C_5$), and hexenyl ($C_6$).

Examples of (unsubstituted) unsaturated cyclic alkenyl groups, which are also referred to herein as "cycloalkenyl" groups, include, but are not limited to, cyclopropenyl ($C_3$), cyclobutenyl ($C_4$), cyclopentenyl ($C_5$), and cyclohexenyl ($C_6$).

Alkynyl: The term "alkynyl," as used herein, pertains to an alkyl group having one or more carbon-carbon triple bonds. Examples of groups of alkynyl groups include $C_{2-4}$alkynyl, $C_{2-7}$alkynyl, $C_{2-20}$alkynyl.

Examples of (unsubstituted) unsaturated alkynyl groups include, but are not limited to, ethynyl (ethinyl, —C≡CH) and 2-propynyl (propargyl, —CH$_2$—C≡CH).

Alkylidene: The term "alkylidene," as used herein, pertains to a divalent monodentate moiety obtained by removing two hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidene groups include $C_{1-4}$alkylidene, $C_{1-7}$alkylidene, $C_{1-20}$alkylidene.

Examples of alkylidene groups include, but are not limited to, methylidene (=CH$_2$), ethylidene (=CH—CH$_3$), vinylidene (=C=CH$_2$), and isopropylidene (=C(CH$_3$)$_2$). An example of a substituted alkylidene is benzylidene (=CH-Ph).

Alkylidyne: The term "alkylidyne," as used herein, pertains to a trivalent monodentate moiety obtained by removing three hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidyne groups include $C_{1-4}$alkylidyne, $C_{1-7}$alkylidyne, $C_{1-20}$alkylidyne.

Examples of alkylidyne groups include, but are not limited to, methylidyne (≡CH) and ethylidyne (≡C—CH$_3$).

Carbocyclyl: The term "carbocyclyl," as used herein, pertains to a monovalent moiety obtained by removing a hydrogen atom from a ring atom of a carbocyclic compound, which moiety has from 3 to 20 ring atoms (unless otherwise specified). Preferably, each ring has from 3 to 7 ring atoms.

In this context, the prefixes (e.g., $C_{3-20}$, $C_{3-7}$, $C_{5-6}$, etc.) denote the number of ring atoms, or range of number of ring atoms. For example, the term "$C_{5-6}$carbocyclyl," as used herein, pertains to a carbocyclyl group having 5 or 6 ring atoms. Examples of groups of carbocyclyl groups include $C_{3-20}$carbocyclyl, $C_{3-10}$carbocyclyl, $C_{5-10}$carbocyclyl, $C_{3-7}$carbocyclyl, and $C_{5-7}$carbocyclyl.

Examples of carbocyclic groups include, but are not limited to, those described above as cycloalkyl groups; and those described below as carboaryl groups.

Heterocyclyl: The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{3-7}$heterocyclyl, $C_{5-7}$heterocyclyl, and $C_{5-6}$heterocyclyl.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include saccharides, in cyclic form, for example, furanoses ($C_5$), such as arabinofuranose, lyxofuranose, ribofuranose, and xylofuranose, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{3-20}$ $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{3-12}$aryl, $C_{5-12}$aryl, $C_{5-7}$aryl, and $C_{5-6}$aryl.

The ring atoms may be all carbon atoms, as in "carboaryl groups" (e.g., $C_{5-20}$carboaryl).

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indene ($C_9$), isoindene ($C_9$), and fluorene ($C_{13}$).

Alternatively, the ring atoms may include one or more heteroatoms, as in "heteroaryl groups" (e.g., $C_{5-20}$heteroaryl).

Examples of monocyclic heteroaryl groups include, but are not limited to, those derived from:
$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heterocyclic groups (some of which are also heteroaryl groups) which comprise fused rings, include, but are not limited to:
$C_9$heterocyclic groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);
$C_{10}$heterocyclic groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);
$C_{13}$heterocyclic groups (with 3 fused rings) derived from carbazole ($N_1$), dibenzofuran ($O_1$), dibenzothiophene ($S_1$), carboline ($N_2$), perimidine ($N_2$), pyridoindole ($N_2$); and,
$C_{14}$heterocyclic groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substituents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N= group may be substituted in the form of an N-oxide, that is, as —N(→O)= (also denoted —N⁺(→O⁻)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms.

Monocyclic examples of such groups include, but are not limited to, those derived from:
$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidinone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:
$C_9$: indenedione;
$C_{10}$: tetralone, decalone;
$C_{14}$: anthrone, phenanthrone;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$);
$N_4$: purinone ($C_9$) (e.g., guanine).

Still more examples of cyclic groups which bear one or more oxo (=O) groups on ring carbon atoms include, but are not limited to, those derived from:
cyclic anhydrides (—C(=O)—O—C(=O)— in a ring), including but not limited to maleic anhydride ($C_5$), succinic anhydride ($C_5$), and glutaric anhydride ($C_6$);
cyclic carbonates (—O—C(=O)—O— in a ring), such as ethylene carbonate ($C_5$) and 1,2-propylene carbonate ($C_5$);
imides (—C(=O)—NR—C(=O)— in a ring), including but not limited to, succinimide ($C_5$), maleimide ($C_5$), phthalimide, and glutarimide ($C_6$);
lactones (cyclic esters, —O—C(=O)— in a ring), including, but not limited to, β-propiolactone, γ-butyrolactone, δ-valerolactone (2-piperidone), and ε-caprolactone;
lactams (cyclic amides, —NR—C(=O)— in a ring), including, but not limited to, β-propiolactam ($C_4$), γ-butyrolactam (2-pyrrolidone) ($C_5$), δ-valerolactam ($C_6$), and ε-caprolactam ($C_7$);
cyclic carbamates (—O—C(=O)—NR— in a ring), such as 2-oxazolidone ($C_5$);
cyclic ureas (—NR—C(=O)—NR— in a ring), such as 2-imidazolidone ($C_5$) and pyrimidine-2,4-dione (e.g., thymine, uracil) ($C_6$).

The above alkyl, alkylidene, alkylidyne, heterocyclyl, and aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$alkyl group, a $C_{3-20}$heterocyclyl group, or a $C_{5-20}$aryl group, preferably a $C_{1-7}$alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$alkyl group, a $C_{3-20}$heterocyclyl group, or a $C_{5-20}$aryl group, preferably a $C_{1-7}$alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Acylhalide (haloformyl, halocarbonyl): —C(=O)X, wherein X is —F, —Cl, —Br, or —I, preferably —Cl, —Br, or —I.

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$alkyl group, a $C_{3-20}$heterocyclyl group, or a $C_{5-20}$aryl group, preferably hydrogen or a $C_{1-7}$alkyl group, and R$^2$ is an acyl substituent, for example, a $C_{1-7}$alkyl group, a $C_{3-20}$heterocyclyl group, or a $C_{5-20}$aryl group, preferably hydrogen or a $C_{1-7}$alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

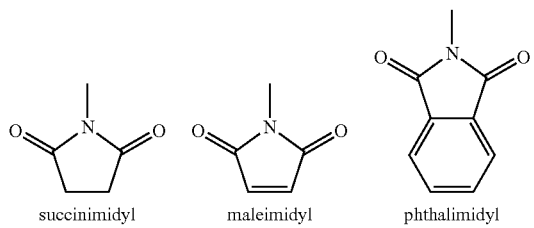

succinimidyl    maleimidyl    phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$,"—C(=S)N(CH$_3$)$_2$, and —C(=S)NHCH$_2$CH$_3$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a C$_{1-7}$alkyl group, a C$_{3-20}$heterocyclyl group, or a C$_{5-20}$aryl group, preferably hydrogen or a C$_{1-7}$alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$,

Tetrazolyl: a five membered aromatic ring having four nitrogen atoms and one carbon atom,

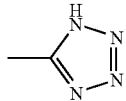

Amino: —NR$^1$R$^2$, wherein R$^1$ and R$^2$ are independently amino substituents, for example, hydrogen, a C$_{1-7}$alkyl group (also referred to as C$_{1-7}$alkylamino or di-C$_{1-7}$alkylamino), a C$_{3-20}$heterocyclyl group, or a C$_{5-20}$aryl group, preferably H or a C$_{1-7}$alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, for example, hydrogen, a C$_{1-7}$alkyl group, a C$_{3-20}$heterocyclyl group, or a C$_{5-20}$aryl group, preferably H or a C$_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a C$_{1-7}$alkyl group, a C$_{3-20}$heterocyclyl group, or a C$_{5-20}$aryl group, preferably H or a C$_{1-7}$alkyl group. Examples of amidine groups include, but are not limited to, —C(=NH)NH$_2$, —C(=NH)NMe$_2$, and —C(=NMe)NMe$_2$.

Nitro: —NO$_2$.

Cyano(nitrile, carbonitrile): —CN.

Isocyano: —NC.

Cyanato: —OCN.

Isocyanato: —NCO.

Isothiocyano(isothiocyanato): —NCS.

Sulfhydryl (thiol, mercapto): —SH.

Thioether (sulfide): —SR, wherein R is a thioether substituent, for example, a C$_{1-7}$alkyl group (also referred to as a C$_{1-7}$alkylthio group), a C$_{3-20}$heterocyclyl group, or a C$_{5-20}$aryl group, preferably a C$_{1-7}$alkyl group. Examples of C$_{1-7}$alkylthio groups include, but are not limited to, —SCH$_3$ and —SCH$_2$CH$_3$.

Disulfide: —SS—R, wherein R is a disulfide substituent, for example, a C$_{1-7}$alkyl group, a C$_{3-20}$heterocyclyl group, or a C$_{5-20}$aryl group, preferably a C$_{1-7}$alkyl group (also referred to herein as C$_{1-7}$alkyl disulfide). Examples of C$_{1-7}$alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a C$_{1-7}$alkyl group, a C$_{3-20}$heterocyclyl group, or a C$_{5-20}$aryl group, preferably a C$_{1-7}$alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a C$_{1-7}$alkyl group, a C$_{5-20}$heterocyclyl group, or a C$_{5-20}$aryl group, preferably a C$_{1-7}$alkyl group, including, for example, a fluorinated or perfluorinated C$_{1-7}$alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$ C$_4$F$_9$ (nonaflyl), —S(=O)$_2$CH$_2$CF$_3$ (tresyl), —S(=O)$_2$ CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a C$_{1-7}$alkyl group, a C$_{3-20}$heterocyclyl group, or a C$_{5-20}$aryl group, preferably a C$_{1-7}$alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a C$_{1-7}$alkyl group, a C$_{3-20}$heterocyclyl group, or a C$_{5-20}$aryl group, preferably a C$_{1-7}$alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a C$_{1-7}$alkyl group, a C$_{3-20}$heterocyclyl group, or a C$_{5-20}$aryl group, preferably a C$_{1-7}$alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a C$_{1-7}$alkyl group, a C$_{3-20}$heterocyclyl group, or a C$_{5-20}$aryl group, preferably a C$_{1-7}$alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a C$_{1-7}$alkyl group, a C$_{3-20}$heterocyclyl group, or a C$_{5-20}$aryl group, preferably a C$_{1-7}$alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$alkyl group, a C$_{3-20}$heterocyclyl group, or a C$_{5-20}$aryl group, preferably a C$_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$alkyl group, a C$_{3-20}$heterocyclyl group, or a C$_{5-20}$aryl group, preferably a C$_{1-7}$alkyl group. Examples of sulfinamino groups include, but are not limited to, —NHS(=O)CH$_3$ and —N(CH$_3$)S(=O)C$_6$H$_5$.

In many cases, substituents may themselves be substituted. For example, a C$_{1-7}$alkyl group may be substituted with, for example, hydroxy (also referred to as a C$_{1-7}$hydroxyalkyl group), C$_{1-7}$alkoxy (also referred to as a C$_{1-7}$alkoxyalkyl group), amino (also referred to as a C$_{1-7}$aminoalkyl group), halo (also referred to as a C$_{1-7}$haloalkyl group), carboxy (also referred to as a C$_{1-7}$carboxyalkyl group), and C$_{5-20}$aryl (also referred to as a C$_{5-20}$aryl-C$_{1-7}$alkyl group).

Similarly, a C$_{5-20}$aryl group may be substituted with, for example, hydroxy (also referred to as a C$_{5-20}$hydroxyaryl group), halo (also referred to as a C$_{5-20}$haloaryl group), amino (also referred to as a C$_{5-20}$aminoaryl group, e.g., as in aniline), C$_{1-7}$alkyl (also referred to as a C$_{1-7}$alkyl-C$_{5-20}$aryl group, e.g., as in toluene), and C$_{1-7}$alkoxy (also referred to as a C$_{1-7}$alkoxy-C$_{5-20}$aryl group, e.g., as in anisole).

These and other specific examples of such substituted-substituents are described below.

C$_{1-7}$haloalkyl group: The term "C$_{1-7}$haloalkyl group," as used herein, pertains to a C$_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a C$_{1-7}$ perhaloalkyl group." Examples of C$_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

C$_{1-7}$haloalkoxy: —OR, wherein R is a C$_{1-7}$haloalkyl group. Examples of C$_{1-7}$haloalkoxy groups include, but are not limited to, —OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$.

C$_{1-7}$hydroxyalkyl: The term "C$_{1-7}$hydroxyalkyl group," as used herein, pertains to a C$_{1-7}$alkyl group in which at least one hydrogen atom has been replaced with a hydroxy group. Examples of C$_{1-7}$hydroxyalkyl groups include, but are not limited to, —CH$_2$OH, —CH$_2$CH$_2$OH, and —CH(OH)CH$_2$OH.

C$_{1-7}$carboxyalkyl: The term "C$_{1-7}$carboxyalkyl group," as used herein, pertains to a C$_{1-7}$alkyl group in which at least one hydrogen atom has been replaced with a carboxy group. Examples of C$_{1-7}$carboxyalkyl groups include, but are not limited to, —CH$_2$COOH and —CH$_2$CH$_2$COOH.

C$_{1-7}$aminoalkyl: The term "C$_{1-7}$aminoalkyl group," as used herein, pertains to a C$_{1-7}$alkyl group in which at least one hydrogen atom has been replaced with an amino group. Examples of C$_{1-7}$aminoalkyl groups include, but are not limited to, —CH$_2$NH$_2$, —CH$_2$CH$_2$NH$_2$, and —CH$_2$CH$_2$N(CH$_3$)$_2$.

C$_{1-7}$aminoalkylamino: The term "C$_{1-7}$aminoalkylamino," as used herein, pertains to an amino group, —NR$^1$R$^2$, in which one of the substituents, R$^1$ or R$^2$, is itself a C$_{1-7}$aminoalkyl group (—C$_{1-7}$alkyl-NR$^1$R$^2$). The C$_{1-7}$aminoalkylamino may be represented, for example, by the formula —NR$^1$—C$_{1-7}$alkyl-NR$^1$R$^2$. Examples of amino-C$_{1-7}$alkylamino groups include, but are not limited to, groups of the formula —NR$^1$(CH$_2$)$_n$NR$^1$R$^2$, where n is 1 to 6, for example, —NHCH$_2$NH$_2$, —NH(CH$_2$)$_2$NH$_2$, —NH(CH$_2$)$_3$NH$_2$, —NH(CH$_2$)$_4$NH$_2$, —NH(CH$_2$)$_5$NH$_2$, —NH(CH$_2$)$_6$NH$_2$, —NHCH$_2$NH(Me), —NH(CH$_2$)$_2$NH(Me), —NH(CH$_2$)$_3$NH(Me), —NH(CH$_2$)$_4$NH(Me), —NH(CH$_2$)$_5$NH(Me), —NH(CH$_2$)$_6$NH(Me), —NHCH$_2$NH(Et), —NH(CH$_2$)$_2$NH(Et), —NH(CH$_2$)$_3$NH(Et), —NH(CH$_2$)$_4$NH(Et), —NH(CH$_2$)$_5$NH(Et), and —NH(CH$_2$)$_6$NH(Et).

C$_{1-7}$alkyl-C$_{5-20}$aryl: The term "C$_{1-7}$alkyl-C$_{5-20}$aryl," as used herein, describes certain C$_{5-20}$aryl groups which have been substituted with a C$_{1-7}$alkyl group. Examples of such groups include, but are not limited to, tolyl (from toluene), xylyl (from xylene), mesityl (from mesitylene), and cumenyl (or cumyl, from cumene), and duryl (from durene).

C$_{1-7}$alkyl-C$_{5-20}$aryloxy: The term "C$_{1-7}$alkyl-C$_{5-20}$aryloxy," as used herein, describes certain C$_{5-20}$aryloxy groups which have been substituted with a C$_{1-7}$alkyl group. Examples of such groups include, but are not limited to, tolyloxy, xylyloxy, mesityloxy, cumenyloxy, and duryloxy.

C$_{5-20}$aryl-C$_{1-7}$alkyl: The term "C$_{5-20}$aryl-C$_{1-7}$alkyl," as used herein, describers certain C$_{1-7}$alkyl groups which have been substituted with a C$_{5-20}$aryl group. Examples of such groups include, but are not limited to, benzyl (phenylmethyl, PhCH$_2$—), benzhydryl (Ph$_2$CH—), trityl (triphenylmethyl, Ph$_3$C—), phenethyl (phenylethyl, Ph-CH$_2$CH$_2$—), styryl (Ph-CH=CH—), cinnamyl (Ph-CH=CH—CH$_2$—).

C$_{5-20}$aryl-C$_{1-7}$alkoxy: The term "C$_{5-20}$aryl-C$_{1-7}$alkoxy," as used herein, describes certain C$_{1-7}$alkoxy groups which have been substituted with a C$_{5-20}$aryl group. Examples of such groups include, but are not limited to, benzyloxy, benzhydryloxy, trityloxy, phenethoxy, styryloxy, and cimmamyloxy.

C$_{5-20}$haloaryl: The term "C$_{5-20}$haloaryl," as used herein, describes certain C$_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Bidentate Substituents

The term "bidentate substituents," as used herein, pertains to substituents which have two points of covalent attachment, and which act as a linking group between two other moieties.

In some cases (A), a bidentate substituent is covalently bound to a single atom. In some cases (B), a bidentate substituent is covalently bound to two different atoms, and so serves as a linking group therebetween.

Within (B), in some cases (C), a bidentate substituent is covalently bound to two different atoms, which themselves are not otherwise covalently linked (directly, or via intermediate groups). In some cases (D), a bidentate substituent is covalently bound to two different atoms, which themselves are already covalently linked (directly, or via intermediate groups); in such cases, a cyclic structure results. In some cases, the bidentate group is covalently bound to vicinal atoms, that is, adjacent atoms, in the parent group.

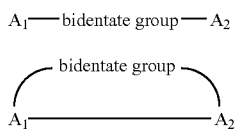

In some cases (A and D), the bidentage group, together with the atom(s) to which it is attached (and any intervening atoms, if present) form an additional cyclic structure. In this way, the bidentate substituent may give rise to a cyclic or polycyclic (e.g., fused, bridged, spiro) structure, which may be aromatic.

Examples of bidentate groups include, but are not limited to, $C_{1-7}$alkylene groups, $C_{3-20}$heterocyclylene groups, and $C_{5-20}$arylene groups, and substituted forms thereof.

Alkylene

Alkylene: The term "alkylene," as used herein, pertains to a bidentate moiety obtained by removing two hydrogen atoms, either both from the same carbon atom, or one from each of two different carbon atoms, of a hydrocarbon compound having from 1 to 20 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkylene," as used herein, pertains to an alkylene group having from 1 to 4 carbon atoms. Examples of groups of alkylene groups include $C_{1-4}$alkylene ("lower alkylene"), $C_{1-7}$alkylene, and $C_{1-20}$alkylene.

Examples of linear saturated $C_{1-7}$alkylene groups include, but are not limited to, —$(CH_2)_n$— where n is an integer from 1 to 7, for example, —$CH_2$— (methylene), —$CH_2CH_2$— (ethylene), —$CH_2CH_2CH_2$— (propylene), and —$CH_2CH_2CH_2CH_2$— (butylene).

Examples of branched saturated $C_{1-7}$alkylene groups include, but are not limited to, —CH($CH_3$>, —CH($CH_3$)$CH_2$—, —CH($CH_3$)$CH_2CH_2$—, —CH($CH_3$)$CH_2CH_2CH_2$—, —$CH_2$CH($CH_3$)$CH_2$—, —$CH_2$CH($CH_3$)$CH_2CH_2$—, —CH($CH_2CH_3$)—, —CH($CH_2CH_3$)$CH_2$—, and —$CH_2$CH($CH_2CH_3$)$CH_2$—.

Examples of linear partially unsaturated $C_{1-7}$alkylene groups include, but is not limited to, —CH=CH— (vinylene), —CH=CH—$CH_2$—, —CH=CH—$CH_2$—$CH_2$—, —CH=CH—$CH_2$—$CH_2$—$CH_2$—, —CH=CH—CH=CH—, —CH=CH—CH=CH—$CH_2$—, —CH=CH—CH=CH—$CH_2$—$CH_2$—, —CH=CH—$CH_2$—CH=CH—, and —CH=CH—$CH_2$—$CH_2$—CH=CH—.

Examples of branched partially unsaturated $C_{1-7}$alkylene groups include, but is not limited to, —C($CH_3$)=CH—, —C($CH_3$)=CH—$CH_2$—, and —CH=CH—CH($CH_3$)—.

Examples of alicyclic saturated $C_{1-7}$alkylene groups include, but are not limited to, cyclopentylene (e.g., cyclopent-1,3-ylene), and cyclohexylene (e.g., cyclohex-1,4-ylene).

Examples of alicyclic partially unsaturated $C_{1-7}$alkylene groups include, but are not limited to, cyclopentenylene (e.g., 4-cyclopenten-1,3-ylene), cyclohexenylene (e.g., 2-cyclohexen-1,4-ylene; 3-cyclohexen-1,2-ylene; 2,5-cyclohexadien-1,4-ylene).

Arylene

Arylene: The term "arylene," as used herein, pertains to a bidentate moiety obtained by removing two hydrogen atoms, one from each of two different aromatic ring atoms of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$arylene," as used herein, pertains to an arylene group having 5 or 6 ring atoms. Examples of groups of arylene groups include $C_{3-20}$arylene, $C_{3-12}$arylene, $C_{5-12}$arylene, $C_{5-7}$arylene, and $C_{5-6}$arylene.

The ring atoms may be all-carbon atoms, as in "carboarylene groups" (e.g., $C_{5-20}$carboarylene).

Alternatively, the ring atoms may include one or more heteroatoms, as in "heteroarylene groups" (e.g., $C_{5-20}$heteroarylene).

Examples of $C_{5-20}$arylene groups which do not have ring heteroatoms (i.e., $C_{5-20}$carboarylene groups) include, but are not limited to, those derived from the compounds discussed above in regard to carboaryl groups.

Examples of $C_{5-20}$heteroarylene groups include, but are not limited to, those derived from the compounds discussed above in regard to heteroaryl groups.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—$N^+HR^1R^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Isomers, Salts, Solvates, Protected Forms, and Prodrugs

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

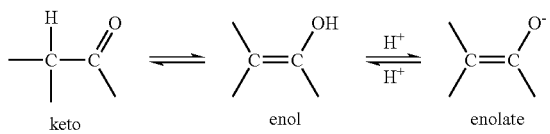

keto          enol          enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether, a benzyl, benzhydryl (diphenylmethyl), or trityl (triphenylmethyl)ether; a trimethylsilyl or t-butyldimethylsilyl ether; or an acetyl ester (—OC(=O)$CH_3$, —OAc).

For example, an aldehyde or ketone group may be protected as an acetal (R—CH(OR)$_2$) or ketal ($R_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—$CH_3$); a benzyloxy amide (—NHCO—$OCH_2C_6H_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2C_6H_4C_6H_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O.).

For example, a carboxylic acid group may be protected as an ester for example, as: an $C_{1-7}$alkyl ester (e.g., a methyl ester; a t-butyl ester); a $C_{1-7}$haloalkyl ester (e.g., a $C_{1-7}$trihaloalkyl ester); a $triC_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$alkyl (e.g., -Me, -Et, -nPr, -iPr, -nBu, -sBu, -iBu, -tBu);
$C_{1-7}$aminoalkyl (e.g., aminoethyl; 2-(N,N-diethylamino)ethyl; 2-(4-morpholino)ethyl); and
acyloxy-$C_{1-7}$alkyl
(e.g., acyloxymethyl;
acyloxyethyl;
pivaloyloxymethyl;
acetoxymethyl;
1-acetoxyethyl;
1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy)carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

Synthesis

Methods for the chemical synthesis of compounds of the present invention are described herein. These methods may be modified and/or adapted in known ways in order to facilitate the synthesis of additional compounds within the scope of the present invention.

The compounds of the present invention may be prepared, for example, by the methods described herein, or by adapting these or other well known methods in well known ways.

In one method, a suitable chloro sulfonate (also having a protected carboxylic acid group, e.g., ester) is prepared, for example, from an aldehyde, by reaction with, e.g., H$_2$SO$_4$ and SO$_3$, followed by reaction with, e.g., a suitable phosphate, e.g., (MeO)$_2$P(O)R, followed by reaction with, e.g., SO$_2$Cl$_2$. An example of such a method is illustrated in the following scheme.

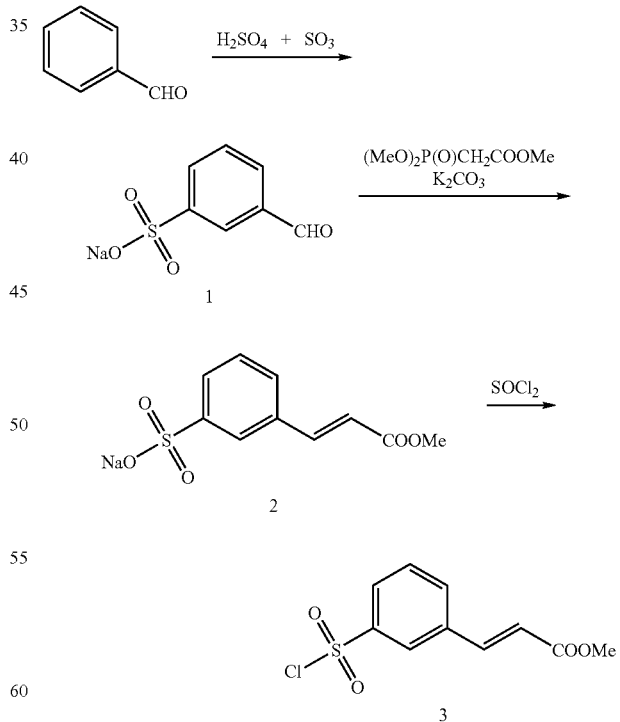

The chloro sulfonate is then reacted with a suitable piperazine, to give the corresponding piperazino sulfonamide. An example of such a method is illustrated in the following scheme (see also Method A below).

Scheme 2

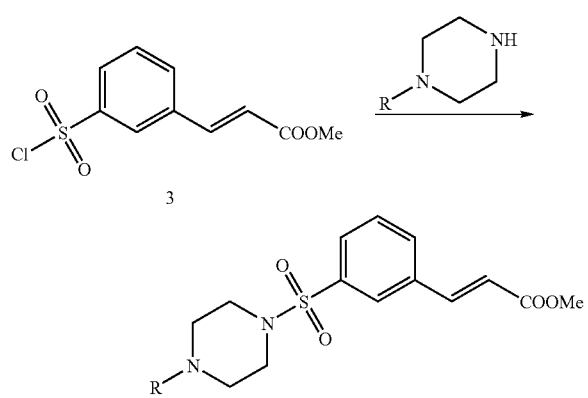

The protected carboxylic acid group (e.g., ester) is then converted to a hydroxamic acid, for example, by deprotection with NaOH, followed by reaction with $(COCl)_2$, followed by reaction with $NH_2OH$. An example of such a method is illustrated in the following scheme (see also Methods B, C, and D below).

Scheme 3

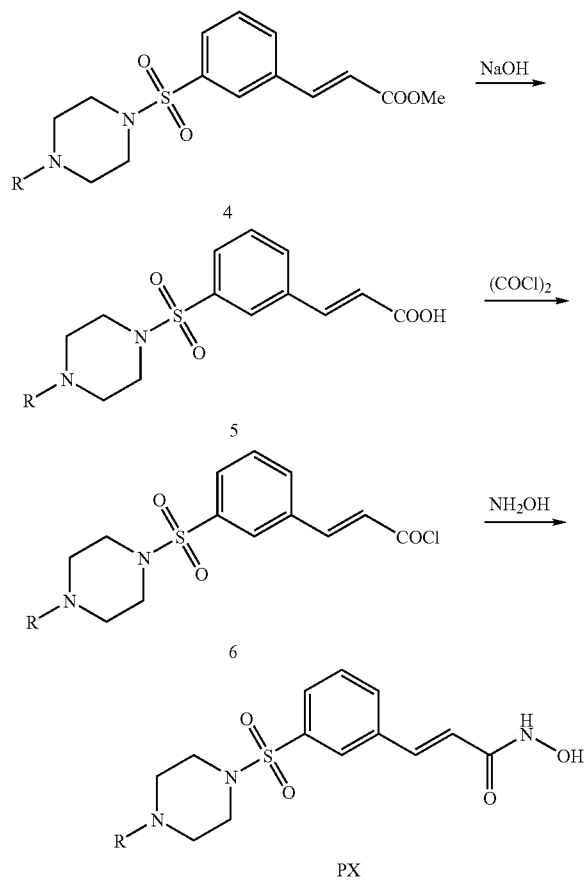

In another method, a suitable phenylacrylic acid is reacted with, e.g., chlorosulfonic acid ($HSO_3Cl$) to form the corresponding para-chlorosulfonylphenyl acrylic acid, which is then reacted with piperazine to form the corresponding piperazino sulfonamide. An example of such a method is illustrated in the following scheme.

Scheme 4

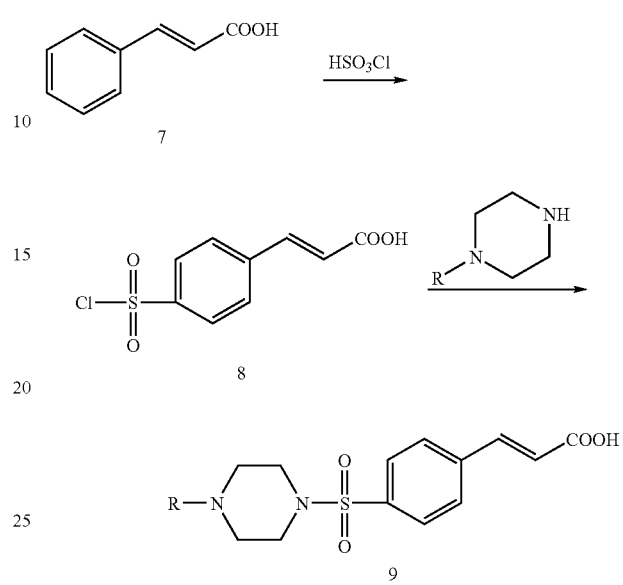

The carboxylic acid group (e.g., ester) is then converted to a chloroacyl group, for example, by reaction with $(COCl)_2$, and is then converted to a hydroxamic acid by reaction with, for example, $NH_2OH$. An example of such a method is illustrated in the following scheme.

Scheme 5

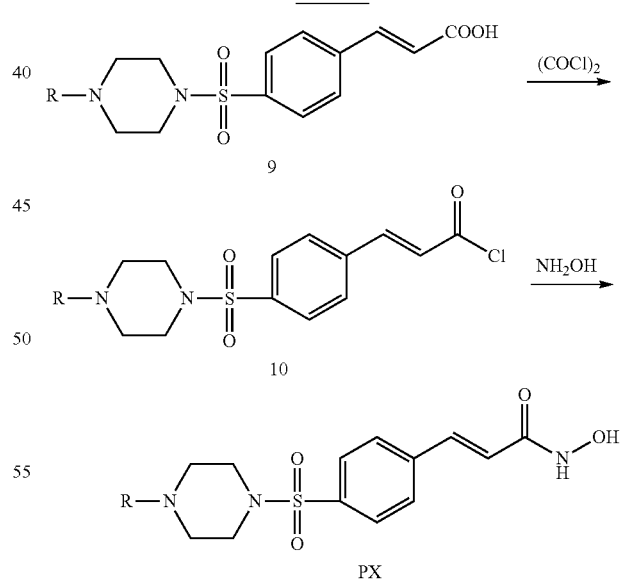

In another method, suitable piperazine compounds are prepared by reaction of piperazine with a suitable carboxylic acid (R—COOH), for example, in the presence of hydroxybenzotriazole, to give the corresponding amide. An example of such a method is illustrated in the following scheme (see also Method E below).

Scheme 6

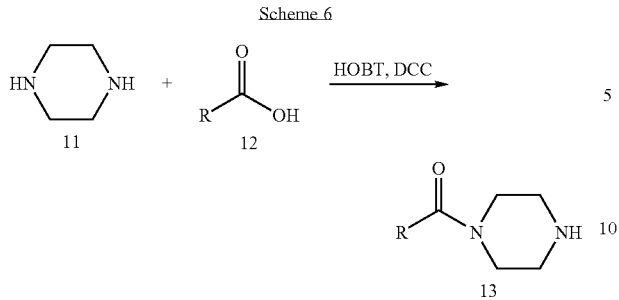

In another method, a suitably protected (e.g., t-butoxycarbonyl protected) piperazine is reacted with, for example, a haloacyl compound (e.g., chloroacylbenzene, PhCOCl) or a suitable carboxylic acid (R—COOH), to give the corresponding amide, followed by deprotection (e.g., with HCl/MeOH and NaOH). An example of such a method is illustrated in the following scheme (see also Methods F and G, below).

Scheme 7

[structure of Boc-piperazine 14 + acyl chloride/acid 12 → CDI/DMFA → intermediate 15 → 1) HCl/MeOH 2) NaOH → 13]

In another method, the piperazine amide is hydrogenated, for example, by reaction with LiAlH₄/THF, to give the corresponding N-substituted piperazine. An example of such a method is illustrated in the following scheme (see also Method H below).

Scheme 8

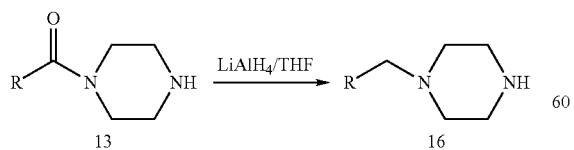

A number of N-substituted piperazine compounds are commercially available, and/or can be readily prepared using well known methods. Examples of such compounds include the following:

N-phenylpiperazine (17a);
1-(diphenylmethyl)piperazine (17b);
1-(2-methoxyphenyl)piperazine hydrochloride (17c);
1-(2-chlorophenyl)piperazine (17d);
1-(3-chlorophenyl)piperazine (17e);
1-(4-methoxyphenyl)piperazine (17f);
1-(3-methoxyphenyl)piperazine (17g);
1-(4-nitrophenyl)piperazine (17h);
1-(3,4-dichlorophenyl)piperazine (17i);
1-(4-fluorophenyl)piperazine (17j);
1-(4-chlorophenyl)piperazine (17k);
1-(2-pyridinyl)piperazine (17l);
2-(1-piperazinyl)pyrimidine (17m); and
1-(3,4-dimethylphenyl)piperazine (17n).

In another method, a suitable carboxylic acid (also having a protected carboxylic acid group) is reacted with a suitable piperazine, for example, in the presence of carbonyldiimidazole (CDI). An example of such a method is illustrated in the following scheme (see also Methods J, K, and L, below).

Scheme 9

The protected carboxylic acid group (e.g., ester) is then converted to a hydroxamic acid, for example, by reaction with NH₂OH and NaOMe in methanol. An example of such a method is illustrated in the following scheme (see also Methods Q and R, below).

Scheme 10

[structure 19] →(NaOMe/MeOH, NH₂OH)→ [structure PX]

In another method, a suitable carboxylic acid (also having a protected carboxylic acid group) is reacted with (COCl)₂ and H₂NOBn, to give the corresponding benzyloxyamide. The protected carboxylic acid group is then deprotected, for example, by reaction with NaOH, and then reacted with a suitable piperazine to give the corresponding piperazine amide. The benzyloxyamide is then converted to a carbamic acid, for example, by reaction with $H_2$ over Pd(C). An example of such a method is illustrated in the following scheme (see also Methods M, N, P, and S, below).

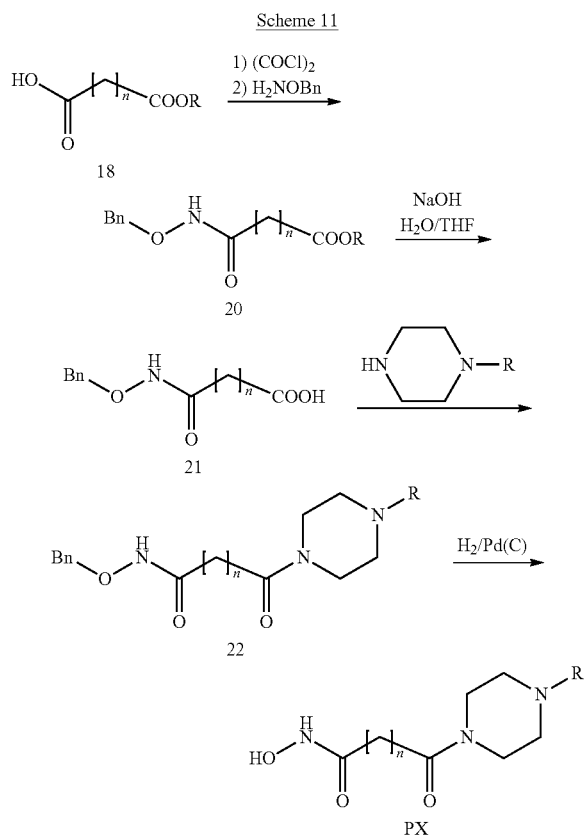

Use

The present invention provides active compounds, specifically, active carbamic acids, as described herein.

The term "active," as used herein, specifically includes both compounds with intrinsic activity (drugs) as well as prodrugs of such compounds, which prodrugs may themselves exhibit little or no intrinsic activity.

The present invention also provides active compounds which inhibit HDAC activity.

The present invention also provides methods of inhibiting HDAC in a cell, comprising contacting said cell with an effective amount of an active compound. Such a method may be practised in vitro or in vivo. In one embodiment, the method is performed in vitro. In one embodiment, the method is performed in vivo. Preferably, the active compound is provided in the form of a pharmaceutically acceptable composition.

The term "inhibiting HDAC," as used herein, includes: inhibiting HDAC activity; inhibiting the formation of HDAC complexes; and inhibiting the activity of HDAC complexes.

One of ordinary skill in the art is readily able to determine whether or not a candidate compound inhibits HDAC activity. For example, one assay which may conveniently be used in order to assess the HDAC inhibition offered by a particular compound is described in the examples below.

The present invention also provides active compounds which (a) regulate (e.g., inhibit) cell proliferation; (b) inhibit cell cycle progression; (c) promote apoptosis; or (d) a combination of one or more of these.

Thus, the present invention also provides methods of (a) regulating (e.g., inhibiting) cell proliferation; (b) inhibiting cell cycle progression; (c) promoting apoptosis; or (d) a combination of one or more of these, in vitro or in vivo, comprising contacting a cell with an effective amount of an active compound, as described herein.

One of ordinary skill in the art is readily able to determine whether or not a candidate compound regulate (e.g., inhibit) cell proliferation, etc. For example, assays which may conveniently be used to assess the activity offered by a particular compound are described in the examples below.

For example, a sample of cells (e.g., from a tumour) may be grown in vitro and an active compound brought into contact with said cells, and the effect of the compound on those cells observed. As an example of "effect," the morphological status of the cells (e.g., alive or dead, etc.) may be determined. Where the active compound is found to exert an influence on the cells, this may be used as a prognostic or diagnostic marker of the efficacy of the compound in methods of treating a patient carrying cells of the same cellular type.

Methods of Treatment, Etc.

The invention further provides methods of treatment, comprising administering to a subject in need of treatment a therapeutically-effective amount of an active compound, preferably in the form of a pharmaceutical composition.

The invention further provides active compounds for use in a method of treatment of the human or animal body by therapy, for example, in the treatment of a condition mediated by HDAC, a condition known to be treated by HDAC inhibitors (such as, e.g., trichostatin A), cancer, a proliferative condition, or other condition as described herein.

The invention further provides the use of an active compound for the manufacture of a medicament, for example, for the treatment of a condition mediated by HDAC, a condition known to be treated by HDAC inhibitors (such as, e.g., trichostatin A), cancer, a proliferative condition, or other condition as described herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount," as used herein, pertains to that amount of an active compound, or a material, composition or dosage form comprising an active compound, which is effective for producing some desired therapeutic effect, commensurate with a reasonable benefit/risk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Active compounds may also be used, as described above, in combination therapies, that is, in conjunction with other agents, for example, cytotoxic agents.

Anti-HDAC Applications

The present invention also provides active compounds which are anti-HDAC agents, and which treat a condition mediated by HDAC.

The term "a condition mediated by HDAC," as used herein pertains to a condition in which HDAC and/or the action of HDAC is important or necessary, e.g., for the onset, progress, expression, etc. of that condition, or a condition which is known to be treated by HDAC inhibitors (such as, e.g., trichostatin A).

Examples of such conditions include, but are not limited to, the following:

Cancer (see, e.g., Vigushin et al., 2001).
Psoriasis (see, e.g., Iavarone et al., 1999).
Fibroproliferative disorders (e.g., liver fibrosis) (see, e.g., Niki et al., 1999; Corneil et al., 1998).
Smooth muscle proliferative disorder (e.g., atherosclerosis, restenosis) (see, e.g., Kimura et al., 1994).
Neurodegenerative diseases (e.g., Alzheimer's, Parkinson's, Huntington's chorea, amyotropic lateral sclerosis, spinocerebellar degeneration) (see, e.g., Kuusisto et al., 2001).
Inflammatory disease (e.g., osteoarthritis, rheumatoid arthritis) (see, e.g., Dangond et al., 1998; Takahashi et al., 1996).
Diseases involving angiogenesis (e.g., cancer, rheumatoid arthritis, psoriasis, diabetic retinopathy) (see, e.g., Kim et al., 2001).
Haematopoietic disorders (e.g., anaemia, sickle cell anaemia, thalassaeimia) (see, e.g., McCaffrey et al., 1997).
Fungal infection (see, e.g., Bernstein et al., 2000; Tsuji et al., 1976).
Parasitic infection (e.g., malaria, trypanosomiasis, helminthiasis, protozoal infections (see, e.g., Andrews et al., 2000).
Bacterial infection (see, e.g., Onishi et al., 1996).
Viral infection (see, e.g., Chang et al., 2000).
Conditions treatable by immune modulation (e.g., multiple sclerosis, autoimmune diabetes, lupus, atopic dermatitis, allergies, asthma, allergic rhinitis, inflammatory bowel disease; and for improving grafting of transplants) (see, e.g., Dangond et al., 1998; Takahashi et al., 1996).

One of ordinary skill in the art is readily able to determine whether or not a candidate compound treats a condition mediated by HDAC for any particular cell type. For example, assays which may conveniently be used to assess the activity offered by a particular compound are described in the examples below.

Anticancer Applications

The present invention also provides active compounds which are anticancer agents, and treat cancer.

Thus, the present invention also provides methods of treating cancer, comprising administering to a subject in need of treatment a therapeutically-effective amount of an active compound, as described herein, preferably in the form of a pharmaceutical composition.

One of ordinary skill in the art is readily able to determine whether or not a candidate compound treats a cancerous condition for any particular cell type. For example, assays which may conveniently be used to assess the activity offered by a particular compound are described in the examples below.

The term "anticancer agent" as used herein, pertains to a compound which treats a cancer (i.e., a compound which is useful in the treatment of a cancer). The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). Examples of cancers are discussed below.

Antiproliferative Applications

The present invention also provides active compounds which are antiproliferative agents. The term "antiproliferative agent" as used herein, pertain to a compound which treats a proliferative condition (i.e., a compound which is useful in the treatment of a proliferative condition).

Thus, the present invention also provides methods of treating a proliferative condition, comprising administering to a subject in need of treatment a therapeutically-effective amount of an active compound, as described herein, preferably in the form of a pharmaceutical composition.

One of ordinary skill in the art is readily able to determine whether or not a candidate compound treats a proliferative condition for any particular cell type. For example, assays which may conveniently be used to assess the activity offered by a particular compound are described in the examples below.

The terms "cell proliferation," "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g., lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g., of connective tissues), and atherosclerosis.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

Additional Uses

Active compounds may also be used as cell culture additives to inhibit HDAC, for example, in order to regulate (e.g., inhibit) cell proliferation in vitro.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other HDAC inhibitors, other anticancer agents, other antiproliferative agents, etc.

The compounds of the present invention may also be used in methods of improving protein production by cultured cells (see, e.g., Furukawa et al., 1998).

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject

The subject may be a prokaryote (e.g., bacteria) or a eukaryote (e.g., protoctista, fungi, plants, animals).

The subject may be a protoctista, an alga, or a protozoan.

The subject may be a plant, an angiosperm, a dicotyledon, a monocotyledon, a gymnosperm, a conifer, a ginkgo, a cycad, a fern, a horsetail, a clubmoss, a liverwort, or a moss.

The subject may be an animal.

The subject may be a chordate, an invertebrate, an echinoderm (e.g., starfish, sea urchins, brittlestars), an arthropod, an annelid (segmented worms) (e.g., earthworms, lugworms, leeches), a mollusk (cephalopods (e.g., squids, octopi), pelecypods (e.g., oysters, mussels, clams), gastropods (e.g., snails, slugs)), a nematode (round worms), a platyhelminthes (flatworms) (e.g., planarians, flukes, tapeworms), a cnidaria (e.g., jelly fish, sea anemones, corals), or a porifera (e.g., sponges).

The subject may be an arthropod, an insect (e.g., beetles, butterflies, moths), a chilopoda (centipedes), a diplopoda (millipedes), a crustacean (e.g., shrimps, crabs, lobsters), or an arachnid (e.g., spiders, scorpions, mites).

The subject may be a chordate, a vertebrate, a mammal, a bird, a reptile (e.g., snakes, lizards, crocodiles), an amphibian (e.g., frogs, toads), a bony fish (e.g., salmon, plaice, eel, lungfish), a cartilaginous fish (e.g., sharks, rays), or a jawless fish (e.g., lampreys, hagfish).

The subject may be a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig) ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject may be any of its forms of development, for example, a spore, a seed, an egg, a larva, a pupa, or a foetus.

Formulations

While it is possible for the active compound to be used (e.g., administered) alone, it is often preferable to present it as a formulation.

Thus, one aspect of the present invention pertains to a composition comprising a compound, as described herein, and a carrier.

In one embodiment, the composition is a pharmaceutical composition (e.g., formulation, preparation, medicament) comprising a compound, as described herein, and a pharmaceutically acceptable carrier.

In one embodiment, the composition is a pharmaceutical composition comprising at least one compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, N.Y., USA), *Remington's Pharmaceutical Sciences*, 18th edition, Mack Publishing Company, Easton, Pa., 1990; and *Handbook of Pharmaceutical Excipients*, 2nd edition, 1994.

Another aspect of the present invention pertains to methods of making a pharmaceutical composition comprising admixing at least one active compound, as defined above, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in a the form of a depot or reservoir.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, lozenges, pastilles, as well as patches, adhesive plasters, depots, and reservoirs. Lozenges typically comprise the active compound in a flavored basis, usually sucrose and acacia or tragacanth. Pastilles typically comprise the active compound in an inert matrix, such as gelatin and glycerin, or sucrose and acacia. Mouthwashes typically comprise the active compound in a suitable liquid carrier.

Formulations suitable for sublingual administration include tablets, lozenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, lozenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the active compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the active compound is dissolved or suspended in a suitable carrier, especially an aqueous solvent for the active compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the active compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the active compounds, and compositions comprising the active compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 0.1 to about 250 mg per kilogram body weight of the subject per day. Where the active compound is a salt, an ester, an amide, a prodrug, or the like, the amount administered is calculated on the basis of the parent compound and so the actual weight to be used is increased proportionately.

Kits

One aspect of the invention pertains to a kit comprising (a) the active ingredient, preferably provided in a suitable container and/or with suitable packaging; and (b) instructions for use, for example, written instructions on how to administer the active compound, etc.

The written instructions may also include a list of indications for which the active ingredient is a suitable treatment.

EXAMPLES

The following are examples are provided solely to illustrate the present invention and are not intended to limit the scope of the invention, as described herein.

General $^1$H NMR spectra were recorded at ambient temperature with WH-90/DS or Mercury 200 (Varian) spectrometers. The HPLC measurements were performed on a Gilson Model 302 system equipped with a spectrophotometer. Elemental analyses were obtained with a Carlo Erba EA 1108 instrument. Melting points were measured on a "Boëtius" micro melting point apparatus and are uncorrected. Silicagel, 0.035-0.070 mm, (Acros) was employed for column chromatography. All the solvents were purified before use by routine techniques. To isolate reaction products the solvents were removed by evaporation using a vacuum rotary evaporator, the water bath temperature not exceeding 40° C.

Various reagents were purchased from Sigma-Aldrich (The Old Brickyard, New Road, Gillingham, Dorset, UK), Acros Organics (Janssens Pharmaceuticalaan 3A, 2440 Geel, Belgium), Lancaster Synthesis Ltd. (Eastgate, White Lund, Morecambe, Lancashire, LA3 3DY, UK), and Bapeks Ltd. (Riga, Latvia).

Example 1

3-Formylbenzenesulfonic acid, Sodium Salt (1)

Oleum (5 mL) was placed in a reaction vessel and benzaldehyde (2.00 g, 18.84 mmol) was slowly added not exceeding the temperature of the reaction mixture more than 30° C. The obtained solution was stirred at 40° C. for 10 hours and at ambient temperature overnight. The reaction mixture was poured into ice and extracted with ethyl acetate. The aqueous phase was treated with $CaCO_3$ until the evolution of $CO_2$ ceased (pH~6-7), then the precipitated $CaSO_4$ was filtered off and washed with water. The filtrate was treated with $Na_2CO_3$ until the pH of the reaction medium increased to pH 8, obtained $CaCO_3$ was filtered off and water solution was evaporated in vacuum. The residue was washed with methanol, the washings were evaporated and the residue was dried in desiccator over $P_2O_5$ affording the title compound (2.00 g, 51%). $^1$H NMR ($D_2O$), δ: 7.56-8.40 (4H, m); 10.04 (1H, s).

Example 2

3-(3-Sulfophenyl)acrylic acid methyl ester, Sodium Salt (2)

Sodium salt of 3-formylbenzenesulfonic acid (1) (1.00 g, 4.80 mmol), potassium carbonate (1.32 g, 9.56 mmol), trimethyl phosphonoacetate (1.05 g, 5.77 mmol) and water (2 mL) were stirred at ambient temperature for 30 min, and the precipitated solid was filtered and washed with methanol. The filtrate was evaporated and to give the title compound as a white solid (0.70 g, 55%). $^1$H NMR (DMSO-$d_6$, HMDSO), δ: 3.68 (3H, s); 6.51 (1H, d, J=16.0 Hz); 7.30-7.88 (5H, m).

Example 3

3-(3-Chlorosulfonylphenyl)acrylic acid methyl ester (3)

To the sodium salt of 3-(3-sulfophenyl)acrylic acid methyl ester (2) (0.670 g, 2.53 mmol) benzene (2 mL), thionyl chloride (1.508 g, 0.9 mL, 12.67 mmol) and 3 drops of dimethylformamide were added and the resultant suspension was stirred at reflux for one hour. The reaction mixture was evaporated, the residue was dissolved in benzene (3 mL), filtered and the filtrate was evaporated to give the title compound (0.640 g, 97%).

Method A—General Synthesis of methyl (E)-3-(3-{[4-substituted 1-piperazinyl]sulfonyl}phenyl)-2-propenoates (4a-l)

A solution of 3-(3-chlorosulfonylphenyl)acrylic acid methyl ester (3) (0.40 g, 1.53 mmol) in dioxane (5.0 mL) was added to a mixture of appropriate piperazine (1.53 mmol) in dioxane (2.0 mL) and NaHCO$_3$ (0.26 g, 3.06 mmol) in water (3.0 mL) (in the case of piperazine hydrochlorides the amount of NaHCO$_3$ was increased by 1 eq), and the resultant solution was stirred at room temperature until initial compounds disappeared (1-2 hours). Water was added to the reaction mixture. In the case of a precipitate formation, it was filtered, washed with water, ether, and dried to give the corresponding methyl (E)-3-(3-{[4-substituted 1-piperazinyl]sulfonyl}phenyl)-2-propenoate (4). Otherwise, the reaction mixture was extracted with ethyl acetate, washed successively with water, brine, dried (Na$_2$SO$_4$), and solvent removed to give the corresponding methyl (E)-3-(3-{[4-substituted 1-piperazinyl]sulfonyl}phenyl)-2-propenoate (4).

Example 4

Methyl (E)-3-(3-{[4-phenyl-1-piperazinyl]sulfonyl}phenyl)-2-propenoate (4a)

The title compound was obtained from 3-(3-chlorosulfonylphenyl)acrylic acid methyl ester (3) and 1-phenylpiperazine, using Method A, yield 84%. $^1$H NMR (DMSO-d$_6$, HMDSO), δ: 2.94-3.39 (8H, m); 3.74 (3H, s); 6.65-7.03 (4H, m); 7.05-7.32 (2H, m); 7.60-7.92 (3H, m); 7.94-8.20 (2H, m).

Example 5

Methyl (E)-3-(3-{[4-benzhydryl-1-piperazinyl]sulfonyl}phenyl)-2-propenoate (4b)

The title compound was obtained from 3-(3-chlorosulfonylphenyl)acrylic acid methyl ester (3) and 1-benzhydrylpiperazine, using Method A, yield 96%. $^1$H NMR (DMSO-d$_6$, HMDSO), δ: 2.16-2.60 (4H, m); 2.78-3.07 (4H, m); 3.78 (3H, s); 4.32 (1H, s); 6.73 (1H, d, J=16.0 Hz); 7.12-8.27 ppm (15H, m).

Example 6

Methyl (E)-3-(3-{[4-(2-methoxyphenyl)-1-piperazinyl]sulfonyl}phenyl)-2-propenoate (4c)

The title compound was obtained from 3-(3-chlorosulfonylphenyl)acrylic acid methyl ester (3) and 1-(2-methoxyphenyl)-piperazine hydrochloride, using Method A, yield 87%. $^1$H NMR (CDCl$_3$, HMDSO), δ: 3.03-3.29 (8H, m); 3.78 (3H, s); 3.83 (3H, s); 6.48 (1H, d, J=16.0 Hz); 6.76-7.07 (4H, m); 7.42-7.94 (4H, m); 7.72 ppm (1H, d, J=16.0 Hz).

Example 7

Methyl (E)-3-(3-{[4-(2-chlorophenyl)-1-piperazinyl]sulfonyl}phenyl)-2-propenoate (4d)

The title compound was obtained from 3-(3-chlorosulfonylphenyl)acrylic acid methyl ester (3) and 1-(2-chlorophenyl)-piperazine hydrochloride, using Method A, yield 81%. $^1$H NMR (CDCl$_3$, HMDSO), δ: 2.94-3.38 (8H, m); 3.85 (3H, s); 6.54 (1H, d, J=16.0 Hz); 6.87-7.43 (3H, m); 7.12 (1H, d, J=16.0 Hz); 7.42-7.94 ppm (5H, m).

Example 8

Methyl (E)-3-(3-{[4-(3-chlorophenyl)-1-piperazinyl]sulfonyl}phenyl)-2-propenoate (4e)

The title compound was obtained from 3-(3-chlorosulfonylphenyl)acrylic acid methyl ester (3) and 1-(3-chlorophenyl)-piperazine hydrochloride, using Method A, yield 71%. $^1$H NMR (CDCl$_3$, HMDSO), δ: 2.94-3.45 (8H, m); 3.83 (3H, s); 6.56 (1H, d, J=116.0 Hz); 6.60-6.98 (3H, m); 7.16 (1H, d, J=16.0 Hz); 7.45-8.05 ppm (5H, m).

Example 9

Methyl (E)-3-(3-{[4-(2-pyridinyl)-1-piperazinyl]sulfonyl}phenyl)-2-propenoate (4f)

The title compound was obtained from 3-(3-chlorosulfonylphenyl)acrylic acid methyl ester (3) and 1-(2-pyridyl)piperazine, using Method A, yield 82%. $^1$H NMR (CDCl$_3$, HMDSO), δ: 2.94-3.25 (4H, m); 3.43-3.72 (4H, m); 3.78 (3H, s); 6.49 (1H, d, J=16.0 Hz); 6.47-6.72 (2H, m); 7.27-7.94 (6H, m); 8.00-8.20 ppm (1H, m).

Example 10

Methyl (E)-3-(3-{[4-(4-acetylphenyl)-1-piperazinyl]sulfonyl}phenyl)-2-propenoate (4g)

The title compound was obtained from 3-(3-chlorosulfonylphenyl)acrylic acid methyl ester (3) and 4'-piperazinoacetophenone, using Method A, yield 90%. $^1$H NMR (DMSO-d$_6$ HMDSO), δ: 2.45 (3H, s); 2.94-3.25 (4H, m); 3.32-3.65 (4H, m, overlapped with a signal of water); 3.78 (3H, s); 6.85 (1H, d, J=16.0 Hz); 6.86-7.16 (2H, m); 7.65-7.96 (5H, m); 8.05-8.27 ppm (2H, m).

Example 11

Methyl (E)-3-[3-({4-[4-(dimethylamino)phenethyl]-1-piperazinyl}sulfonyl)phenyl]-2-propenoate (4h)

The title compound was obtained from 3-(3-chlorosulfonylphenyl)acrylic acid methyl ester (3) and 1-(4-dimethylaminophenetyl)piperazine, using Method A, yield 91%. $^1$H NMR (DMSO-d$_6$, HMDSO), δ: 2.14-2.63 (8H, m, overlapped with a signal of DMSO); 2.80 (6H, s); 2.81-3.05 (4H, m); 3.78 (3H, s); 6.63 (2H, d, J=9.4 Hz); 6.84 (1H, d, J=16.0 Hz); 7.00 (2H, d, J=9.4 Hz); 7.61-7.88 (2H, m); 7.83 (1H, d, J=16.0 Hz); 7.99-8.28 ppm (2H, m).

Example 12

Methyl (E)-3-[3-({4-[2-(1-naphthyloxy)ethyl]-1-piperazinyl}sulfonyl)phenyl]-2-propenoate (4i)

The title compound was obtained from 3-(3-chlorosulfonylphenyl)acrylic acid methyl ester (3) and 1-[2-(1-naphthyloxy)ethyl]piperazine, using Method A, yield 78%. $^1$H NMR (DMSO-d$_6$. HMDSO), δ: 2.36-2.77 (8H, m, overlapped with a signal of DMSO); 2.78-3.09 (4H, m); 3.72 (3H, s); 6.76 (1H, d, J=15.7 Hz); 7.20-7.53 (3H, m); 7.54-7.94 (7H, m); 7.96-8.20 ppm (2H, m).

Example 13

Methyl (E)-3-[3-({4-[2-(2-naphthyloxy)ethyl]-1-piperazinyl}sulfonyl)phenyl]-2-propenoate (4j)

The title compound was obtained from 3-(3-chlorosulfonylphenyl)acrylic acid methyl ester (3) and 1-[2-(2-naphthyloxy)ethyl]piperazine, using Method A, yield 94%. $^1$H NMR (DMSO-$d_6$, HMDSO), δ: 2.38-2.65 (6H, m, overlapped with a signal of DMSO); 2.76 (2H, t, J=5.0 Hz); 2.83-3.05 (2H, m); 3.71 (3H, s); 4.11 (2H, t, J=5.3 Hz); 6.76 (1H, d, J=16.0 Hz); 6.98-7.56 (4H, m); 7.60-7.92 (6H, m); 7.93-8.18 ppm (2H, m).

Example 14

Methyl (E)-3-(3-{[4-(3,4-dichlorophenyl)-1-piperazinyl]sulfonyl}phenyl)-2-propenoate (4k)

The title compound was obtained from 3-(3-chlorosulfonylphenyl)acrylic acid methyl ester (3) and 1-(3,4-dichlorophenyl)-piperazine, using Method A, yield 85%. $^1$H NMR (DMSO-$d_6$, HMDSO), δ: 2.76-3.12 (4H, m); 3.13-3.38 (4H, m, overlapped with a signal of water); 3.66 (3H, s); 6.76 (1H, d, J=15.9 Hz); 6.87 (1H, dd, J=2.8 and 8.4 Hz); 7.10 (1H, d, J=2.8 Hz); 7.38 (1H, d, J=8.4 Hz); 7.78 (1H, d, J=15.9 Hz); 7.60-7.93 (2H, m); 7.95-8.27 ppm (2H, m).

Example 15

Methyl (E)-3-(3-{[4-(4-chlorophenyl)-1-piperazinyl]sulfonyl}phenyl)-2-propenoate (4l)

The title compound was obtained from 3-(3-chlorosulfonylphenyl)acrylic acid methyl ester (3) and 1-(4-chlorophenyl)-piperazine, using Method A, yield 84%. $^1$H NMR (DMSO-$d_6$, HMDSO), δ: 2.76-3.34 (8H, m); 3.72 (3H, s); 6.80 (1H, d, J=15.9 Hz); 6.92 (2H, d, J=8.9 Hz); 7.23 (2H, d, J=8.9 Hz); 7.80 (1H, d, J=15.9 Hz); 7.56-7.96 (2H, m); 7.98-8.25 ppm (2H, m).

Method B—General Synthesis of (E)-3-(3-{[4-substituted 1-piperazinyl]sulfonyl}phenyl-2-propenoic acids (5a-l)

To a suspension or solution of appropriate methyl (E)-3-(3-{[4-substituted 1-piperazinyl]sulfonyl}phenyl)-2-propenoate (4a-l) (1.29 mmol) in methanol-tetrahydrofuran (2:3) mixture (5.0 mL), 1N NaOH solution (3.87 mL, 3.87 mmol) was added and the resultant mixture was stirred at ambient temperature overnight. The reaction mixture was partitioned between ethyl acetate and water. The aqueous layer was acidified with 1 N $KH_2PO_4$ solution. In the case of a precipitate formation, it was filtered, washed with water, ether (or other suitable solvent), and dried to give the corresponding (E)-3-(3-{[4-substituted 1-piperazinyl]sulfonyl}phenyl)-2-propenoic acid (5). Otherwise, the reaction mixture was extracted with ethyl acetate, washed successively with water, brine, dried ($Na_2SO_4$), and solvent removed to give the corresponding (E)-3-(3-{[4-substituted 1-piperazinyl]sulfonyl}phenyl)-2-propenoic acid (5).

Example 16

(E)-3-(3-{[4-Phenyl-1-piperazinyl]sulfonyl}phenyl)-2-propenoic acid (5a)

The title compound was obtained from methyl (E)-3-(3-{[4-phenyl-1-piperazinyl]sulfonyl}phenyl)-2-propenoate (4a) as a white solid, using Method B, yield 61%. $^1$H NMR (DMSO-$d_6$, HMDSO), δ: 2.87-3.65 (8H, m); 6.54-6.98 (4H, m); 7.00-7.36 (2H, m); 7.58-7.92 (3H, m); 7.94-8.23 (2H, m).

Example 17

(E)-3-(3-[{4-Benzhydryl-1 piperazinyl]sulfonyl}phenyl)-2-propenoic acid (5b)

The title compound was obtained from methyl (E)-3-(3-{[4-benzhydryl-1-piperazinyl]sulfonyl}phenyl)-2-propenoate (4b) as a white solid, using Method B, yield 70%. $^1$H NMR (DMSO-$d_6$ HMDSO), δ: 2.20-2.56 (4H, m); 2.80-3.07 (4H, m); 4.27 (1H, s); 6.67 (1H, d, J=16.0 Hz); 7.05-8.16 ppm (15H, m).

Example 18

(E)-3-(3-{[4-(2-Methoxyphenyl)-1-piperazinyl]sulfonyl}phenyl)-2-propenoic acid (5c)

The title compound was obtained from methyl (E)-3-(3-{[4-(2-methoxyphenyl)-1-piperazinyl]sulfonyl}phenyl)-2-propenoate (4c) as a white solid, using Method B, yield 84%. $^1$H NMR (DMSO-$d_6$, HMDSO), δ: 2.76-3.25 (8H, m); 3.72 (3H, s); 6.74 (1H, d, J=16.0 Hz); 6.76-7.14 (4H, m); 7.60-7.94 (2H, m); 7.76 (1H, d, J=16.0 Hz); 7.94-8.27 ppm (2H, m).

Example 19

(E)-3-(3-{[4-(2-Chlorophenyl)-1-piperazinyl]sulfonyl}phenyl)-2-propenoic acid (5d)

The title compound was obtained from methyl (E)-3-(3-{[4-(2-chlorophenyl)-1-piperazinyl]sulfonyl}phenyl)-2-propenoate (d), using Method B, yield 83%. $^1$H NMR (DMSO-$d_6$, HMDSO), δ: 2.72-3.27 (8H, m); 6.72 (1H, d, J=16.0 Hz); 6.89-7.52 (4H, m); 7.60-7.92 (2H, m); 7.74 (1H, d, J=16.0 Hz); 7.96-8.25 ppm (2H, m).

Example 20

(E)-3-(3-{[443-Chlorophenyl)-1-piperazinyl]sulfonyl}phenyl)-2-propenoic acid (5e)

The title compound was obtained from methyl (E)-3-(3-{[4-(3-chlorophenyl)-1-piperazinyl]sulfonyl}phenyl)-2-propenoate (4e), using Method B, yield 89%. $^1$H NMR (DMSO-$d_6$, HMDSO), δ: 2.87-3.16 (6H, m); 3.17-3.67 (2H, m, overlapped with a signal DMSO); 6.67 (1H, d, J=16.0 Hz); 6.68-7.00 (3H, m); 7.02-7.34 (1H, m); 7.56-7.87 (2H, m); 7.72 (1H, d, J=16.0 Hz); 7.94-8.23 ppm (2H, m).

Example 21

(E)-3-(3-{[4-(2-Pyridinyl)-1-piperazinyl]sulfonyl}phenyl)-2-propenoic acid (5f)

The title compound was obtained from methyl (E)-3-(3-{[4-(2-pyridinyl)-1-piperazinyl]sulfonyl}phenyl)-2-propenoate (4f) using Method B, yield 91%. $^1$H NMR (DMSO-$d_6$, HMDSO), δ: 2.83-3.14 (4H, m); 3.43-3.69 (4H, m); 6.52-6.89 (2H, m); 6.67 (1H, d, J=16.0 Hz); 7.36-7.83 (3H, m); 7.69 (1H, d, J=16.0 Hz); 7.94-8.18 ppm (3H, m).

Example 22

(E)-3-(3-{[4-(4-Acetylphenyl)-1-piperazinyl]sulfonyl}phenyl)-2-propenoic acid (5g)

The title compound was obtained from methyl (E)-3-(3-{[4-(4-acetylphenyl)-1-piperazinyl]sulfonyl}phenyl)-2-propenoate (4g), using Method B, yield 85%. $^1$H NMR (DMSO-d$_6$, HMDSO), δ: 2.38 (3H, s); 2.89-3.20 (4H, m); 3.21-3.67 (4H, m, overlapped with a signal of water); 6.69 (1H, d, J=16.0 Hz); 6.70-7.11 (2H, m); 7.53-7.94 (5H, m); 7.96-8.20 ppm (2H, m).

Example 23

(E)-3-[3-({4-[4-(Dimethylamino)phenethyl]-1-piperazinyl}sulfonyl)phenyl]-2-propenoic acid (5h)

The title compound was obtained from methyl (E)-3-[3-({4-[4-(dimethylamino)phenethyl]-1-piperazinyl}sulfonyl)phenyl]-2-propenoate (4h), using Method B, yield 80%. $^1$H NMR (DMSO-d$_6$ HMDSO), δ: 2.23-2.67 (8H, m, overlapped with a signal of DMSO); 2.80 (6H, s); 2.72-3.09 (4H, m); 6.63 (2H, d, J=8.0 Hz); 6.74 (1H, d, J=16.0 Hz); 6.99 (2H, d, J=8.0 Hz); 7.51-7.89 (3H, m); 7.90-8.32 ppm (2H, m).

Example 24

(E)-3-[3-({4-[2-(1-Naphthyloxy)ethyl]-1-piperazinyl}sulfonyl)phenyl]-2-propenoic acid (5i)

The title compound was obtained from methyl (E)-3-[3-({4-[2-(1-naphthyloxy)ethyl]-1-piperazinyl}sulfonyl)phenyl]-2-propenoate (4i), using Method B, yield 90%. $^1$H NMR (DMSO-d$_6$, HMDSO), δ: 2.36-2.76 (6H, m, overlapped with a signal of DMSO); 2.78-3.07 (6H, m); 6.69 (1H, d, J=15.7 Hz); 7.22-7.56 (3H, m); 7.58-7.92 (7H, m); 7.93-8.16 ppm (2H, m).

Example 25

(E)-3-[3-({4-[2-(2-Naphthyloxy)ethyl]-1-piperazinyl}sulfonyl)phenyl]-2-propenoic acid (5j)

The title compound was obtained from methyl (E)-3-[3-({4-[2-(2-naphthyloxy)ethyl]-1-piperazinyl}sulfonyl)phenyl]-2-propenoate (4j), using Method B, yield 84%. $^1$H NMR (DMSO-d$_6$, HMDSO), δ: 2.36-2.58 (6H, m, overlapped with a signal of DMSO); 2.76 (2H, t, J=5.0 Hz); 2.82-3.05 (2H, m); 4.11 (2H, t, J=5.3 Hz); 6.67 (1H, d, J=16.0 Hz); 6.98-7.52 (4H, m); 7.53-7.87 (6H, m); 7.88-8.16 ppm (2H, m).

Example 26

(E)-3-(3-{[4-(3,4-Dichlorophenyl)-1-piperazinyl]sulfonyl}phenyl)-2-propenoic acid (5k)

The title compound was obtained from methyl (E)-3-(3-{[4-(3,4-dichlorophenyl)-1-piperazinyl]sulfonyl}phenyl)-2-propenoate (4k), using Method B, yield 87%. $^1$H NMR (DMSO-d$_6$, HMDSO), δ: 2.69-3.1.6 (4H, m); 3.17-3.47 (4H, m); 6.69 (1H, d, J=116.0 Hz); 6.92 (1H, dd, J=2.8 and 8.4 Hz); 7.13 (1H, d, J=2.8 Hz); 7.38 (1H, d, J=8.4 Hz); 7.54 (1H, d, J=16.0 Hz); 7.58-7.92 (2H, m); 7.93-8.18 ppm (2H, m).

Example 27

(E)-3-(3-{[4-(4-Chlorophenyl)-1-piperazinyl]sulfonyl}phenyl)-2-propenoic acid (5l)

The title compound was obtained from methyl (E)-3-(3-{[4-(4-chlorophenyl)-1-piperazinyl]sulfonyl}phenyl)-2-propenoate (4l), using Method B, yield 75%. $^1$H NMR (DMSO-d$_6$, HMDSO), δ: 2.83-3.49 (8H, m, overlapped with a signal of water); 6.67 (1H, d, J=15.9 Hz); 6.89 (1H, d, J=8.9 Hz); 7.18 (2H, d, J=8.9 Hz); 7.49-7.87 (2H, m); 7.69 (1H, d, J=15.9 Hz); 7.88-8.20 ppm (2H, m).

Method C—General Synthesis of (E)-3-(3-{[substituted 1-piperazinyl]sulfonyl}phenyl)-2-propenoyl chlorides (6a-l)

To a suspension of appropriate (E)-3-(3-{[4-substituted 1-piperazinyl]sulfonyl}phenyl)-2-propenoic acid (5a-l) (0.78 mmol) in dichloromethane (4.0 mL) oxalyl chloride (0.21 mL, 2.37 mmol) and one drop of dimethylformamide were added. The reaction mixture was stirred at 40° C. for one hour and concentrated under reduced pressure to give crude (E)-3-(3-{[4-substituted 1-piperazinyl]sulfonyl}phenyl)-2-propenoyl chloride (6).

Example 28

(E)-3-(3-{[4-Phenyl-1-piperazinyl]sulfonyl}phenyl)-2-propenoyl chloride (6a)

The title compound was obtained from (E)-3-(3-{[4-phenyl-1-piperazinyl]sulfonyl}phenyl)-2-propenoic acid (5a), using Method C, in a form of a crude product.

Example 29

(E)-3-(3-{[4-Benzhydryl-1-piperazinyl]sulfonyl}phenyl)-2-propenoyl chloride (6b)

The title compound was obtained from (E)-3-(3-{[4-benzhydryl-1-piperazinyl]sulfonyl}phenyl)-2-propenoic acid (5b), using Method C, in a form of a crude product.

Example 30

(E)-3-(3-{[4-(2-Methoxyphenyl)-1-piperazinyl]sulfonyl}phenyl)-2-propenoyl chloride (6c)

The title compound was obtained from (E)-3-(3-{[4-(2-methoxyphenyl)-1-piperazinyl]sulfonyl}phenyl)-2-propenoic acid (i), using Method C, in a form of a crude product.

Example 31

(E)-3-(3-{[4-(2-Chlorophenyl)-1-piperazinyl]sulfonyl}phenyl)-2-propenoyl chloride (6d)

The title compound was obtained from (E)-3-(3-{[4-(2-chlorophenyl)-1-piperazinyl]sulfonyl}phenyl)-2-propenoic acid (5d), using Method C, in a form of a crude product.

Example 32

(E)-3-(3-{[4-(3-Chlorophenyl)-1-piperazinyl]sulfonyl}phenyl)-2-propenoyl chloride (6e)

The title compound was obtained from (E)-3-(3-{[4-(3-chlorophenyl)-1-piperazinyl]sulfonyl}phenyl)-2-propenoic acid (5e), using Method C, in a form of a crude product.

Example 33

(E)-3-(3-{[4-(2-Pyridinyl)-1-piperazinyl]sulfonyl}phenyl)-2-propenoyl chloride (6f)

The title compound was obtained from (E)-3-(3-{[4-(2-pyridinyl)-1-piperazinyl]sulfonyl}phenyl)-2-propenoic acid (5f), using Method C, in a form of a crude product.

Example 34

(E)-3-[3-({4-[4-(1-Chlorovinyl)phenyl]-1-piperazinyl}sulfonyl)phenyl]-2-propenoyl chloride (6g)

The title compound was obtained from (E)-3-(3-{[4-(4-acetylphenyl)-1-piperazinyl]sulfonyl}phenyl)-2-propenoic acid (5g), using Method C, in a form of a crude product.

Example 35

(E)-3-[3-({4-[4-(Dimethylamino)phenethyl]-1-piperazinyl}sulfonyl)phenyl]-2-propenoyl chloride (6h)

The title compound was obtained from (E)-3-[3-({4-[4-(dimethylamino)phenethyl]-1-piperazinyl}sulfonyl)phenyl]-2-propenoic acid (5h), using Method C, in a form of a crude product.

Example 36

(E)-3-[3-({4-[2-(1-Naphthyloxy)ethyl]-1-piperazinyl}sulfonyl)phenyl]-2-propenoyl chloride (6i)

The title compound was obtained from (E)-3-[3-({4-[2-(1-naphthyloxy)ethyl]-1-piperazinyl}sulfonyl)phenyl]-2-propenoic acid (5i), using Method C, in a form of a crude product.

Example 37

(E)-3-[3-({4-[2-(2-Naphthyloxy)ethyl]-1-piperazinyl}sulfonyl)phenyl]-2-propenoyl chloride (6j)

The title compound was obtained from (E)-3-[3-({4-[2-(2-naphthyloxy)ethyl]-1-piperazinyl}sulfonyl)phenyl]-2-propenoic acid (5j), using Method C, in a form of a crude product.

Example 38

(E)-3-(3-{[4-(3,4-Dichlorophenyl)-1-piperazinyl]sulfonyl}phenyl)-2-propenoyl chloride (6k)

The title compound was obtained from (E)-3-(3-{[4-(3,4-dichlorophenyl)-1-piperazinyl]sulfonyl}phenyl)-2-propenoic acid (5k), using Method C, in a form of a crude product.

Example 39

(E)-3-(3-{[4-(4-Chlorophenyl)-1-piperazinyl]sulfonyl}phenyl)-2-propenoyl chloride (6l)

The title compound was obtained from (E)-3-(3-{[4-(4-chlorophenyl)-1-piperazinyl]sulfonyl}phenyl)-2-propenoic acid (5l), using Method C, in a form of a crude product.

Method D—General Synthesis of (E)-N-hydroxy-3-(3-{[4-substituted 1-piperazinyl]sulfonyl}phenyl)-2-propenamides To a suspension of hydroxylamine hydrochloride (0.27 g, 3.90 mmol) in tetrahydrofuran (6.0 mL) a saturated NaHCO$_3$ solution (6.9 mL) was added and the resultant mixture was stirred at ambient temperature for 10 minutes. To the reaction mixture an appropriate (E)-3-(3-{[4-substituted 1-piperazinyl]sulfonyl}phenyl)-2-propenoyl chloride (6a-l) (ca. 0.78 mmol) solution in tetrahydrofuran (4.0 mL) was added and the obtained mixture was stirred at ambient temperature for ca. one hour. The organic layer was separated, the water layer was supplemented with water (ca. 5 mL) and extracted with ethyl acetate. The organic extracts were combined, washed successively with water, brine, and dried (Na$_2$SO$_4$). The solvent was removed and the crude product was washed with an appropriate solvent (ether, methanol, ethyl acetate, acetonitrile etc.) or crystallized from ether, methanol, ethyl acetate or acetonitrile, or their mixtures to give the corresponding target (E)-N-hydroxy-3-(3-{[4-substituted 1-piperazinyl]sulfonyl}phenyl)-2-propenamide. Otherwise, the crude reaction product was chromatographed on silica gel with chloroform-methanol as eluents to give the corresponding (E)-N-hydroxy-3-(3-{[4-substituted 1-piperazinyl]sulfonyl}phenyl)-2-propenamide.

Example 40

(E)-N-Hydroxy-3-{3-[(4-phenyl-1-piperazinyl)sulfonyl]phenyl}-2-propenamide (PX118490)

The title compound was obtained from (E)-3-(3-{[4-phenyl-1-piperazinyl]sulfonyl}phenyl)-2-propenoyl chloride (6a) as white crystals, using Method D, yield 73% (on 5a). M.p. 201° C. $^1$H NMR (DMSO-d$_6$, HMDSO), δ: 2.91-3.39 (8H, m, overlapped with a signal of water); 6.62 (1H, d, J=16.0 Hz); 6.74-6.99 (3H, m); 7.06-7.34 (2H, m); 7.57 (1H, d, J=16.0 Hz); 7.56-8.12 (4H, m); 9.11 (1H, brs); 10.79 (1H, s). HPLC analysis on Zorbax SB-C$_{18}$ column: impurities 1.3% (column size 4.6×150 mm; mobile phase acetonitrile-0.1% H$_3$PO$_4$, gradient from 50:50 to 100:0; sample concentration 0.5 mg/ml; flow rate 1.5 mL/min.; detector: UV 254 nm). Anal. Calcd for C$_{19}$H$_{21}$N$_3$O$_4$S, %: C, 58.90; H, 5.46; N, 10.84. Found, %: C, 58.73; H, 5.34; N, 10.69.

Example 41

(E)-N-Hydroxy-3-{3-[(4-benzhydryl-1-piperazinyl)sulfonyl]phenyl}-2-propenamide (PX118491)

The Title Compound was obtained from (E)-3-(3-{[4-Benzhydryl-1-piperazinyl]sulfonyl}phenyl)-2-propenoyl chloride (6b) as white crystals, using Method D, yield 57% (on 5b). M.p. 156° C. $^1$H NMR (DMSO-d$_6$, HMDSO), δ: 2.18-2.54 (4H, m, overlapped with a signal of DMSO); 2.75-3.11 (4H, m); 4.31 (1H, s); 6.64 (1H, d, J=116.0 Hz); 7.01-8.11 (15H, m); 9.15 (1H, brs); 10.83 (1H, s). HPLC analysis on Symmetry C$_{18}$ column: impurities 7% (column size 3.9×150 mm; mobile phase acetonitrile-0.1M phosphate buffer (pH 2.5), 50:50; sample concentration 1 mg/ml; flow rate 0.75 mL/min.; detector UV 220 nm). Anal. Calcd for C$_{26}$H$_{27}$N$_3$O$_4$S*0.7H$_2$O, %: C, 63.71; H, 5.84; N, 8.57. Found, %: C, 63.81; H, 5.77; N, 8.34.

Example 42

(E)-N-Hydroxy-3-{3-[(4-(2-methoxyphenyl)-1-piperazinyl)sulfonyl]phenyl}-2-propenamide (PX118810)

The title compound was obtained from (E)-3-(3-{[4-(2-methoxyphenyl)-1-piperazinyl]sulfonyl}phenyl)-2-propenoyl chloride (6c) as white crystals, using Method D, yield 59% (on 5c). M.p. 190° C. $^1$H NMR (DMSO-d$_8$, HMDSO), δ: 2.72-3.25 (8H, m); 3.67 (3H, s); 6.65 (1H, d, J=16.0 Hz); 6.76-7.12 (4H, m); 7.61 (1H, d, J=16.0 Hz); 7.60-8.07 (4H, m); 9.09 (1H, br s); 10.78 (1H, s). HPLC analysis on Zorbax SB C$_{18}$ column: impurities 2% (column size 4.6×150 mm; mobile phase acetonitrile-0.1% H$_3$PO$_4$, 50:50 10 min, 100:0 5 min; sample concentration 1 mg/ml; flow rate 1.5 mL/min.; detector UV 254 nm). Anal. Calcd for C$_{20}$H$_{23}$N$_3$O$_5$S, %: C, 57.54; H, 5.55; N, 10.06. Found, %: C, 57.26; H, 5.46; N, 9.99.

Example 43

(E)-N-Hydroxy-3-{3-[(4-(2-chlorophenyl)-1-piperazinyl)sulfonyl]phenyl}-2-propenamide (PX118811)

The title compound was obtained from (E)-3-(3-{[4-(2-chlorophenyl)-1-piperazinyl]sulfonyl}phenyl)-2-propenoyl chloride (d), using Method D, yield 84% (on 5d). M.p. 183° C. $^1$H NMR (DMSO-d$_6$, HMDSO), δ: 2.76-3.32 (8H, m); 6.63 (1H, d, J=16.0 Hz); 6.92-7.48 (4H, m); 7.59 (1H, d, J=16.0 Hz); 7.58-8.12 (4H, m); 9.12 (1H, br s); 10.80 (1H, s). HPLC analysis on Zorbax SB C$_{18}$ column: impurities 2% (column size 4.6×150 mm; mobile phase acetonitrile-0.1% H$_3$PO$_4$, 50:50 10 min, 100:0 5 min; sample concentration 0.5 mg/ml; flow rate 1.5 mL/min; detector: UV 254 nm). Anal. Calcd for C$_{19}$H$_{20}$ClN$_3$O$_4$S, %: C, 54.09; H, 4.78; N, 9.96. Found, %: C, 53.99; H, 4.73; N, 9.80.

Example 44

(E)-N-Hydroxy-3-{3-[(4-(3-chlorophenyl)-1-piperazinyl)sulfonyl]phenyl}-2-propenamide (PX118812)

The title compound was obtained from (E)-3-(3-{[4-(3-chlorophenyl)-1-piperazinyl]sulfonyl}phenyl)-2-propenoyl chloride (6e), using Method D, yield 75% (on 5e). M.p. 201° C. $^1$H NMR (DMSO-d$_6$, HMDSO), δ: 2.83-3.45 (8H, m); 6.63 (1H, d, J=16.0 Hz); 6.68-7.02 (3H, m); 7.16 (1H, t, J=7.8 Hz); 7.58 (1H, d, J=16.0 Hz); 7.60-8.07 (4H, m); 9.16 (1H, br s); 10.72 (1H, s). HPLC analysis on Symmetry C$_8$ column: impurities 3.3% (column size 3.9×150 mm; mobile phase acetonitrile-0.1M phosphate buffer (pH 2.5), 45:55; sample concentration 0.5 mg/ml; flow rate 1.4 mL/min; detector UV 254 nm). Anal. Calcd for C$_{19}$H$_{20}$ClN$_3$O$_4$S, containing 4% of inorganic impurities, %: C, 51.93; H, 4.59; N, 9.56. Found, %: C, 52.00; H, 4.59; N, 9.39.

Example 45

(E)-N-Hydroxy-3-{3-[(4-(2-pyridinyl)-1-piperazinyl)sulfonyl]phenyl}-2-propenamide (PX118807)

The title compound was obtained from (E)-3-(3-{[4-(2-pyridinyl)-1-piperazinyl]sulfonyl}phenyl)-2-propenoyl chloride (6f), using Method D, yield 63% (on 5f). M.p. 112° C. $^1$H NMR (DMSO-d$_6$, HMDSO), δ: 2.78-3.18 (4H, m); 3.41-3.76 (4H, m); 6.45-6.91 (3H, m); 7.38-8.19 (7H, m); 9.13 (1H, br s); 10.78 (1H, br s). HPLC analysis on Symmetry C$_8$ column: impurities 4% (column size 3.9×150 mm; mobile phase acetonitrile-0.1M phosphate buffer (pH 2.5), 35:65; sample concentration 0.5 mg/ml; flow rate 1.3 mL/min; detector UV 254 nm). Anal. Calcd for C$_{18}$H$_{20}$N$_4$O$_4$S*H$_2$O, containing 1.5% of inorganic impurities, %: C, 52.39; H, 5.37; N, 13.58. Found, %: C, 52.45; H, 5.23; N, 13.39.

Example 46

(E)-3-[3-({4-[4-(1-Chlorovinyl)phenyl]-1-piperazinyl}sulfonyl)phenyl]-N-hydroxy-2-propenamide (PX118933)

The title compound was obtained from (E)-3-[3-({4-[4-(1-chlorovinyl)phenyl]-1-piperazinyl}sulfonyl)phenyl]-2-propenoyl chloride (6g), using Method D, yield 24% (on 5g). M.p. 203° C. (dec.). TLC: single spot at R$_f$ 0.3 (ethyl acetate-methanol, 4:1; detection—UV-254 nm). $^1$H NMR (DMSO-d$_6$, HMDSO), δ: 2.94-3.20 (4H, m); 3.21-3.63 (4H, m, overlapped with a signal of water); 5.38 (1H, d, J=4.0 Hz); 5.83 (1H, d, J=4.0 Hz); 6.63 (1H, d, J=16.0 Hz); 6.93 (2H, d, J=9.0 Hz); 7.54 (2H, d, J=9.0 Hz); 7.60 (1H, d, J=16.0 Hz); 7.43-8.05 (4H, m); 9.16 (1H, br s); 10.85 ppm (1H, br s). Anal. Calcd for C$_{21}$H$_{22}$ClN$_3$O$_4$S, containing 1.9% of inorganic material, %: C, 55.24; H, 4.86; N, 9.20. Found, %: C, 55.22; H, 4.78; N, 9.45.

Example 47

(E)-3-[3-({4-[4-(Dimethylamino)phenethyl]-1-piperazinyl}sulfonyl)phenyl]-N-hydroxy-2-propenamide (PX118951)

The title compound was obtained from (E)-3-[3-({4-[4-(dimethylamino)phenethyl]-1-piperazinyl}sulfonyl)phenyl]-2-propenoyl chloride (6h), using Method D, yield 17% (on 5h). M.p. 189° C. $^1$H NMR (DMSO-d$_6$, HMDSO), δ: 2.36-2.57 (8H, m, overlapped with a signal of DMSO); 2.80 (6H, s); 2.83-2.94 (4H, m); 6.60 (2H, d, J=8.0 Hz); 6.61 (1H, d, J=15.7 Hz); 6.96 (2H, d, J=8.0 Hz); 7.57 (1H, d, J=15.7 Hz); 7.66-7.75 (2H, m); 7.83-7.97 (2H, m); 9.17 (1H, br s); 10.83 (1H, br s). HPLC analysis on Alltima C$_{18}$ column: impurities 3% (column size 4.6×150 mm; mobile phase acetonitrile-0.1 M phosphate buffer (pH 2.5), 15:85; sample concentration 1.0 mg/ml; flow rate 1.0 mL/min; detector UV 220 nm). Anal. Calcd for C$_{23}$H$_{30}$N$_4$O$_4$S, %: C, 60.24; H, 6.59; N, 12.22. Found, %: C, 60.05; H, 6.52; N, 12.16.

Example 48

(E)-N-Hydroxy-3-[3-({4-[2-(1-naphthyloxy)ethyl]-1-piperazinyl}-sulfonyl)phenyl]-2-propenamide (PX118934)

The title compound was obtained from (E)-3-[3-({4-[2-(1-naphthyloxy)ethyl]-1-piperazinyl}sulfonyl)phenyl]-2-propenoyl chloride (61), using Method D, yield 68% (on 5l). M.p. 178° C. $^1$H NMR (DMSO-d$_6$, HMDSO), δ: 2.41-2.68 (6H, m, overlapped with a signal of DMSO); 2.75-3.00 (6H, m); 6.61 (1H, d, J=16.0 Hz); 7.34 (1H, d, J=8.4 Hz); 7.39-7.52 (2H, m); 7.57 (1H, d, J=16.0 Hz); 7.63-7.97 (8H, m); 9.17 (1H, br s); 10.84 ppm (1H, br s). HPLC analysis on Omnispher C$_{18}$ column: impurities 2.2% (column size 4.6×150 mm; mobile phase acetonitrile-0.2 M acetate buffer (pH 5.0), 40:60; sample concentration 0.5 mg/ml; flow rate 1.5 mL/min; detector UV 230 nm). Anal. Calcd for C$_{25}$H$_{27}$N$_3$O$_5$S, %: C, 62.35; H, 5.65; N, 8.73. Found, %: C, 62.42; H, 5.56; N, 8.69.

Example 49

(E)-N-Hydroxy-3-[3-({4-[2-(2-naphthyloxy)ethyl]-1-piperazinyl}-sulfonyl)phenyl]-2-propenamide (PX118935)

The title compound was obtained from (E)-3-[3-({4-[2-(2-naphthyloxy)ethyl]-1-piperazinyl}sulfonyl)phenyl]-2-propenoyl chloride (6j), using Method D, yield 57% (on 5j). M.p. 130° C. $^1$H NMR (DMSO-d$_6$, HMDSO), δ: 2.54-2.68 (4H, m, overlapped with a signal of DMSO); 2.76 (2H, t, J=5.0 Hz); 2.82-3.03 (4H, m); 4.12 (2H, t, J=5.3 Hz); 6.60 (1H, d, J=16.0 Hz); 7.10 (1H, dd, J=8.9 and 2.0 Hz); 7.28 (1H, d, J=2.0 Hz);

7.31 (1H, t, J=7.9 Hz); 7.43 (1H, t, J=7.6 Hz); 7.55 (1H, d, J=16.0 Hz); 7.62-7.95 (7H, m); 9.19 (1H, br s); 10.82 ppm (1H, br s). HPLC analysis on Omnispher $C_{18}$ column: impurities 3.3% (column size 4.6×150 mm; mobile phase acetonitrile-0.2 M acetate buffer (pH 5.0), 40:60; sample concentration 0.25 mg/ml; flow rate 1.5 mL/min; detector UV 230 nm). Anal. Calcd for $C_{25}H_{27}N_3O_5S$, containing 6% of inorganic impurities, %: C, 58.61; H, 5.31; N, 8.20. Found, %: C, 58.63; H, 5.33; N, 8.01.

Example 50

(E)-3-(3-{[4-(3,4-Dichlorophenyl)-1-piperazinyl]sulfonyl}phenyl)-N-hydroxy-2-propenamide (PX118971)

The title compound was obtained from (E)-3-(3-{[4-(3,4-dichlorophenyl)-1-piperazinyl]sulfonyl}phenyl)-2-propenoyl chloride (6k), using Method D, yield 71% (on 5k). M.p. 193° C. $^1$H NMR (DMSO-$d_6$, HMDSO), δ: 2.89-3.09 (4H, m); 3.18-3.33 (4H, m, overlapped with a signal of water); 6.61 (1H, d, J=15.9 Hz); 6.89 (1H, dd, J=2.8 and 8.4 Hz); 7.11 (1H, d, J=2.8 Hz); 7.38 (1H, d, J=8.4 Hz); 7.57 (1H, d, J=15.9 Hz); 7.66-7.82 (2H, m); 7.87-8.00 (2H, m); 9.16 (1H, s); 10.82 (1H, s). HPLC analysis on Omnispher $C_{18}$ column: impurities 3.3% (column size 4.6×150 mm; mobile phase acetonitrile-0.2 M acetate buffer (pH 5.0), 50:50; sample concentration 0.5 mg/ml; flow rate 1.3 mL/min; detector UV 254 nm). Anal. Calcd for $C_{19}H_{19}Cl_2N_3O_4S$, %: C, 50.01; H, 4.20; N, 9.21. Found, %: C, 49.94; H, 4.06; N, 9.10.

Example 51

(E)-3-(3-{[4-(4-Chlorophenyl)-1-piperazinyl]sulfonyl}phenyl)-N-hydroxy-2-propenamide (PX118972)

The title compound was obtained from (E)-3-(3-{[4-(4-chlorophenyl)-1-piperazinyl]sulfonyl}phenyl)-2-propenoyl chloride (6l), using Method D, yield 79% (on 5l). M.p. 215° C. $^1$H NMR (DMSO-$d_6$, HMDSO), δ: 2.89-3.12 (4H, m); 3.12-3.27 (4H, m); 6.61 (1H, d, J=15.9 Hz); 6.91 (2H, d, J=8.9 Hz); 7.21 (2H, d, J=8.9 Hz); 7.57 (1H, d, J=15.9 Hz); 7.67-7.85 (2H, m); 7.86-8.05 (2H, m); 9.26 (1H, br s); 10.65 (1H, br s). HPLC analysis on Alltima $C_{18}$ column: impurities <1% (column size 4.6×150 mm; mobile phase acetonitrile-0.1 M phosphate buffer (pH 2.5), 50:50; sample concentration 0.5 mg/ml; flow rate 1.5 mL/min; detector UV 254 nm). Anal. Calcd for $C_{19}H_{20}ClN_3O_4S$, %: C, 54.09; H, 4.78; N, 9.96. Found, %: C, 54.08; H, 4.62; N, 9.90.

Example 52

(E)-N-Hydroxy-3-[3-({4-[(E)-3-phenyl-2-propenyl]-1-piperazinyl}sulfonyl)phenyl]-2-propenamide (PX118870)

The title compound was obtained using methods analogous to those described above. M.p. 178° C. $^1$H NMR (DMSO-$d_6$, TMS) δ: 2.60-3.49 (8H, m, partly overlapped with a signal of water), 3.09 (2H, d, J=6.0 Hz); 6.13 (1H, dt, J=16.0 and 6.0 Hz), 6.49 (1H, d, J=16.0 Hz); 6.60 (1H, d, J=16.0 Hz); 7.16-7.56 (5H, m); 7.57-8.00 (5H, m); 9.20 (1H, br s); 10.78 ppm (1H, br s). HPLC analysis on an Omnispher 5 $C_{18}$ column: impurities 1.0% (column size: 4.6×150 mm—mobile phase: acetonitrile-0.1 M phosphate buffer (pH 2.5), 25:75; sample concentration 0.16 mg/ml; flow rate: 1.3 mL/min; detector UV 254 nm). Anal. Calcd. for $C_{22}H_{23}N_3O_4S$, %: C, 61.81; H, 5.89; N, 9.83. Found, % C, 61.43; H, 5.84; N, 9.65.

Example 53

(E)-N-Hydroxy-3-(3-{[4-(4-methoxyphenyl)-1-piperazinyl]-sulfonyl}phenyl)-2-propenamide (PX118871)

The title compound was obtained using methods analogous to those described above. M.p. 203° C. $^1$H NMR (DMSO-$d_6$, HMDSO) δ: 2.96-3.12 (8H, m); 3.66 (3H, s); 6.62 (1H, d, J=15.7 Hz); 6.79 (2H, d, J=9.4 Hz); 6.85 (2H, d, J=9.4 Hz); 7.59 (1H, d, J=15.7 Hz); 7.62-7.70 (2H, m); 7.92-8.05 (2H, m); 9.15 (1H, br s); 10.82 ppm (1H, br s). HPLC analysis on an Omnispher 5 $C_{18}$ column: impurities 1.3%. (column size 4.6×150 mm; mobile phase acetonitrile-0.1 M phosphate buffer (pH 2.5), 40:60; sample concentration 0.5 mg/ml; flow rate 1.5 mL/min; detector UV 220 nm). Anal. Calcd. for $C_{20}H_{23}N_3O_5S$, %: C, 57.54; H, 5.55; N, 10.06. Found, %: C, 57.55; H, 5.41; N, 9.98.

Example 54

(E)-N-hydroxy-3-(3-{[4(3-methoxyphenyl)piperazinyl]sulfonyl}phenyl)-2-propenamide (PX118872)

The title compound was obtained using methods analogous to those described above. M.p. 196° C. $^1$H NMR (DMSO-$d_6$, HMDSO) δ: 2.96-3.10 (4H, m), 3.13-3.26 (4H, m); 3.68 (3H, s); 6.34-6.52 (3H, m); 6.61 (1H, d, J=15.7 Hz); 7.08 (1H, t, J=7.9 Hz); 7.57 (1H, d, J=15.7 Hz); 7.64-7.80 (2H, m); 7.89-7.98 (2H, m); 9.15 (1H, br s); 10.81 ppm (1H, br s). HPLC analysis on an Alltima $C_{18}$ column: impurities 3.5% (column size 4.6×150 mm; mobile phase acetonitrile-0.1 M phosphate buffer (pH 2.5), 50:50; sample concentration 0.5 mg/ml; flow rate 1.4 mL/min; detector UV 220 nm). Anal. Calcd for $C_{20}H_{23}N_3O_5S$, containing 1.5% of inorganic impurities, %: C, 56.68; H, 5.47; N, 9.91. Found, %: C, 56.79; H, 5.31; N, 9.81.

Example 55

(E)-3-(3-{[4-(1,3-Benzodioxol-5-ylmethyl)-1-piperazinyl]sulfonyl}-phenyl)-N-hydroxy-2-propenamide (PX118873)

The title compound was obtained using methods analogous to those described above. M.p. 172° C. $^1$H NMR (DMSO-d 6, HMDSO) δ: 2.32-2.45 (4H, m), 2.82-2.97 (4H, m); 3.34 (2H, s, overlapped with a signal of water); 5.94 (2H, s); 6.60 (1H, d, J=15.7 Hz); 6.67 (1H, d, J=7.9 Hz); 6.76 (1H, s); 6.78 (1H, d, J=8.3 Hz); 7.56 (1H, d, J=15.7 Hz); 7.66-7.74 (2H, m); 7.83-7.96 (2H, m); 9.14 (1H, br s); 10.80 ppm (1H, br s). HPLC analysis on an Omnispher 5 $C_{18}$ column: impurities 1.3% (column size 4.6×150 mm; mobile phase acetonitrile-0.1 M phosphate buffer (pH 2.5), 35:65; sample concentration 1.0 mg/ml; flow rate: 1.3 mL/min; detector UV 254 nm). Anal. Calcd. for $C_{21}H_{23}N_3O_6S$, %: C, 56.62; H, 5.20; N, 9.43. Found, %: C, 56.35; H, 5.02; N, 9.24.

Example 56

(E)-3-{3-[(4-Benzyl-1-piperazinyl)sulfonyl]phenyl}-N-hydroxy-2-propenamide (PX118874)

The title compound was obtained using methods analogous to those described above. M.p. 185° C. $^1$H NMR (DMSO-$d_6$, HMDSO) δ: 2.42 (4H, m), 2.91 (4H, m); 3.45 (2H, s); 6.59 (1H, d, J=15.7 Hz); 7.15-7.31 (5H, m); 7.56 (1H, d, J=15.7 Hz); 7.62-7.76 (2H, m); 7.81-7.98 (2H, m); 9.14 (1H, br s); 10.80 ppm (1H, br s). HPLC analysis on an Omnispher 5 $C_{18}$ column: impurities 2.3% (column size 4.6×150 mm; mobile phase acetonitrile-0.1 M phosphate buffer (pH 2.5), 40:60; sample concentration 0.33 mg/ml; flow rate 1.3 mL/min; detector UV 220 nm). Anal Calcd. for $C_{20}H_{23}N_3O_4S$, %: C, 59.83; H, 5.77; N, 10.47. Found, %: C, 59.67; H, 5.62; N, 10.34.

Example 57

(E)-3-[3-({4-[Bis(4-fluorophenyl)methyl]-1-piperazinyl}sulfonyl)phenyl]-N-hydroxy-2-propenamide (PX118875)

The title compound was obtained using methods analogous to those described above. M.p. foam. $^1$H NMR (DMSO-$d_6$, HMDSO) δ: 2.18-2.45 (4H, m), 2.78-3.09 (4H, m); 4.36 (1H, s); 6.58 (1H, d, J=16.0 Hz); 6.89-7.20 (4H, m); 7.22-7.58 (5H, m); 7.60-8.05 (4H, m); 9.98 ppm (2H, br s). HPLC analysis on an Alltima $C_{18}$ column: impurities 6.5% (column size 4.6× 150 mm; mobile phase acetonitrile-0.1 M phosphate buffer (pH 2.5), 60:40; sample concentration 0.5 mg/ml; flow rate 1.5 mL/min; detector: UV 220 nm). Anal Calcd. for $C_{26}H_{25}F_2N_3O_4S$, %: C, 60.31; H, 5.24; N, 7.54. Found, %: C, 60.13; H, 5.17; N, 7.51.

Example 58

(E)-N-Hydroxy-3-(3-{[3-methyl-4-(4-methylphenyl)-1-piperazinyl]sulfonyl}phenyl)-2-propenamide (PX118876)

The title compound was obtained using methods analogous to those described above. M.p. 186° C. $^1$H NMR (DMSO-$d_6$, HMDSO) δ: 0.94 (3H, d, J=6.4 Hz); 2.20 (3H, s); 2.56-2.83 (1H, m, partly overlapped with a signal of water); 2.84-3.67 (5H, m); 3.80-4.16 (1H, m); 6.45-6.78 (4H, m); 6.94-7.20 (1H, m); 7.60 (1H, d, J=16.0 Hz); 7.69-8.14 (4H, m); 9.98 (2H, br s). HPLC analysis on an Alltima $C_{18}$ column: impurities 3.0% (column size 4.6×150 mm; mobile phase acetonitrile-0.1 M phosphate buffer (pH 2.5), 50:50; sample concentration 1.0 mg/ml; flow rate 1.0 ml/min; detector UV 220 nm). Anal. Calcd. for $C_{21}H_{25}N_3O_4S$*0.1EtOH, %: C, 60.58; H, 6.13; N, 9.90. Found, %: C, 60.46; H, 6.05; N, 9.84.

Example 59

(E)-3-(3-{[4-(2-Fluorophenyl)-1-piperazinyl]sulfonyl}phenyl)-N-hydroxy-2-propenamide (PX118877)

The title compound was obtained using methods analogous to those described above. M.p. 176° C. $^1$H NMR (DMSO-$d_6$, HMDSO) δ: 2.83-3.15 (8H, m); 6.63 (1H, d, J=16.0 Hz); 6.83-7.27 (4H, m); 7.60 (1H, d, J=16.0 Hz); 7.65-8.05 (4H, m); 9.12 (1H, br s); 10.83 ppm (1H, br s). HPLC analysis on Ultra JBD: impurities 1.0% (column size 4.6×150 mm; mobile phase acetonitrile-0.1 M phosphate buffer (pH 2.5), 60:40; sample concentration 1.0 mg/ml; flow rate 1.0 mL/min; detector UV 230 nm). Anal Calcd. for $C_{19}H_{20}FN_3O_4S$, %: C, 56.29; H, 4.97; N, 10.36. Found, %: C, 56.25; H, 4.89; N, 10.16.

Example 60

(E)-N-Hydroxy-3-[3-({4-[3-(trifluoromethyl)phenyl]-1-piperazinyl}sulfonyl)phenyl]-2-propenamide (PX118878)

The title compound was obtained using methods analogous to those described above. M.p. 173° C. $^1$H NMR (DMSO-$d_6$, HMDSO) δ: 2.94-3.25 (8H, m); 6.63 (1H, d, J=16.0 Hz); 6.98-7.29 (3H, m); 7.39 (1H, d, J=7.6 Hz); 7.69 (1H, d, J=16.0 Hz); 7.60-8.09 (4H, m); 10.05 ppm (2H, br s). HPLC analysis on Alltima $C_1$: impurities 5.5% (column size 4.6×150 mm; mobile phase acetonitrile-0.1 M phosphate buffer (pH 2.5), 50:50; sample concentration 1.0 mg/ml; flow rate 1.5 mL/min; detector UV 220 nm.) Anal. Calcd. for $C_{20}H_{20}F_3N_3O_4S$*0.1EtOAc, %: C, 52.78; H, 4.52; N, 9.05. Found, %: C, 52.74; H, 4.36; N, 8.88.

Example 61

(E)-N-Hydroxy-3-(3-{[4-(3-nitrophenyl)-1-piperazinyl]sulfonyl}phenyl)-2-propenamide (PX118893)

The Title Compound was Obtained Using Methods Analogous to Those Described Above. M.p. 162° C. $^1$H NMR (DMSO-$d_6$, HMDSO) δ: 2.94-3.20 (4H, m); 3.45-3.69 (4H, m); 6.65 (1H, d, J=16.0 Hz); 7.02 (2H, d, J=9.0 Hz); 7.58 (1H, d, J=16.0 Hz); 7.62-7.83 (2H, m); 7.84-8.20 (4H, m); 10.20 (2H, br s). HPLC analysis on Omnisphere 5 $C_{18}$: impurities 2.0% (column size 4.6×150 mm; mobile phase acetonitrile-0.1 M phosphate buffer (pH 2.5), 40:60; sample concentration 0.3 mg/ml; flow rate 1.5 mL/min; detector UV 220 nm). Anal. Calcd. for $C_{19}H_{20}N_4O_6S$ containing 2.3% inorganic material, %: C, 51.56; H, 4.55; N, 12.66. Found, %: C, 51.54; H, 4.50; N, 12.57.

Example 62

(E)-N-Hydroxy-3-(3{-[4-(2-pyrimidinyl)-1-piperazinyl]sulfonyl}-phenyl)-2-propenamide (PX118894)

The title compound was obtained using methods analogous to those described above. M.p. 200° C. $^1$H NMR (DMSO-$d_6$, HMDSO), δ: 2.78-3.15 (4H, m); 3.63-3.94 (4H, m); 6.58 (1H, d, J=16.0 Hz); 6.63 (1H, t, J=6.4 Hz); 7.56 (1H, d, J=16.0 Hz); 7.57-8.12 (4H, m); 8.34 (2H, d, J=6.4 Hz); 9.16 (1H, br s); 10.80 ppm (1H, br s). HPLC analysis on Alltima $C_{18}$: impurities 4.8% (column size: 4.6×150 mm; mobile phase acetonitrile-0.1 M phosphate buffer (pH 2.5), 30:70; sample concentration 1.0 mg/ml; flow rate 1.15 mL/min; detector UV 254 nm.) Anal. Calcd for $C_{17}H_{19}N_5O_4S$, %: C, 52.43; H, 4.92; N, 17.98. Found, %: C, 52.37; H, 4.89; N, 17.69.

Example 63

(E)-3-(3-{[4-(2,2-Diphenylethyl)-1-piperazinyl]sulfonyl}phenyl)-N-hydroxy-2-propenamide (PX118913)

The title compound was obtained using methods analogous to those described above.
M.p. 117° C. (decomposes). $^1$H NMR (DMSO-$d_6$, HMDSO), δ: 2.42-2.62 (4H, m, overlapped with a signal of DMSO); 2.70-2.87 (4H, m); 2.92 (2H, d, J=7.3 Hz); 4.18 (1H t, J=7.3 Hz); 6.58 (1H, d, J=15.8 Hz); 7.02-7.35 (10H, m); 7.53 (1H, d, J=15.8 Hz); 7.61-7.70 (2H, m); 7.80-7.92 (2H, m); 9.14 (1H, br s); 10.80 ppm (1H, br s). HPLC analysis on Omnisphere $C_{18}$: impurities 4.5% (column size 4.6×150 mm; mobile phase acetonitrile-0.1 M phosphate buffer (pH 2.5); 40:60; sample concentration 0.5 mg/ml; flow rate: 1.2 mL/min; detector UV 220 nm.) Anal. Calcd. for $C_{27}H_{29}N_3O_4S$*0.2 M $Et_2O$ containing 1.8% of inorganic impurities, %: C, 64.75; H, 6.06; N, 8.15. Found, %: C, 64.76; H, 6.07; N, 8.19.

Example 64

(E)-N-Hydroxy-3-[3-({4-[2-(2naphthyl)ethyl]-1-piperazinyl}sulfonyl)phenyl]-2-propenamide (PX118914)

The title compound was obtained using methods analogous to those described above. M.p. 184° C. $^1$H NMR (DMSO-$d_6$, HMDSO), δ: 2.38-3.07 (12H, m, partly overlapped with a signal of DMSO); 6.63 (1H, d, J=16.0 Hz); 7.20-7.54 (4H, m); 7.57-7.98 (8H, m); 9.16 (1H, br s); 10.78 ppm (1H, br s). HPLC analysis on Alltima $C_{18}$: impurities 1.0% (column size 4.6×150 mm; mobile phase acetonitrile-0.1 M phosphate buffer (pH 2.5), 35:65; sample concentration 1.0 mg/ml; flow rate 1.2 mL/min; detector UV 220 nm). Anal. Calcd. for $C_{25}H_{27}N_3O_4S$, %: C, 64.50; H, 5.85; N, 9.03. Found, %: C, 64.34; H, 5.74; N, 9.02.

Example 65

3-(4-Chlorosulfonylphenyl)acrylic acid (8)

To neat chlorosulfonic acid (26.5 mL, 0.4 mol) at 18° C. temperature slowly cinnamic acid (7) (7.35 g, 0.05 mol) was added. As the reaction proceeded, hydrogen chloride gas evolved. The reaction mixture was stirred successively at 20° C. for 3 hours and at 42° C. for 3 hours. The dark, viscous syrup was poured into ice water, and the precipitated solid was filtered and washed with water. The title compound was obtained (6.8 g, 55%) as a white solid. $^1$H NMR (DMSO-$d_6$, HMDSO), δ: 6.55 (1H, d, J=16.0 Hz); 7.58 (1H, d, J=16.0 Hz); 7.65 (4H, s); 8.15 (1H, br s).

Example 66

(E)-3-[4-({4-[3-(Trifluoromethyl)phenyl]-1-piperazinyl}sulfonyl)phenyl]-2-propenoic acid (9a)

To a suspension of 1-(α,α,α-trifluoro-m-tolyl)piperazine hydrochloride (0.43 g, 1.62 mmol) in dioxane (5 mL) a solution of $NaHCO_3$ (0.27 g, 3.24 mmol) in water (4 mL) and a solution of 3-(4-chlorosulfonyl-phenyl)-acrylic acid (8) (0.40 g, 1.62 mmol) were added and the resultant mixture was stirred at ambient temperature for 20 hours. The reaction mixture was poured into water (50 mL) and the pH of the medium was brought to ~4 with 2 N HCl. The precipitated solid was filtered, washed with water, and dried in vacuum to give the title compound (0.59 g, 82%). $^1$H NMR (DMSO-$d_6$, HMDSO), δ: 2.96-3.67 (8H, m, overlapped with a signal of water); 6.74 (1H, d, J=16.3 Hz); 7.01-7.57 (4H, m); 7.67 (1H, d, J=16.3 Hz); 7.82 (2H, d, J=8.4 Hz); 8.00 (2H, d, J=8.4 Hz); 12.71 (1H, br s).

Example 67

(E)-3-[(4-({4-[Bis(4-fluorophenyl)methyl]-1-piperazinyl}sulfonyl)phenyl]-2-propenoic acid (9b)

To a suspension of 1-bis(4-fluorophenyl)methyl piperazine (0.47 g, 1.62 mmol) in dioxane (5 mL) a solution of $NaHCO_3$ (0.27 g, 3.24 mmol) in water (4 mL) and a solution of 3-(4-chlorosulfonyl-phenyl)-acrylic acid (8) (0.40 g, 1.62 mmol) were added and the resultant mixture was stirred at ambient temperature for 20 hours. The reaction mixture was poured into water (50 mL), the pH of the medium was brought to ~4 with 2 N HCl, and extracted with ethyl acetate. The extract was washed successively with water, brine, and dried ($Na_2SO_4$). The solvent was removed and the crude product was crystallized from dioxane to give the title compound (0.58 g, 63%) as a white solid. $^1$H NMR (DMSO-$d_6$, HMDSO), δ: 2.19-2.50 (4H, m, overlapped with a signal of DMSO); 2.80-3.12 (4H, m); 4.42 (1H, s); 6.78 (1H, d, J=16.0 Hz); 7.11 (4H, t, J=9.0 Hz); 7.41 (4H, dd, J=8.6 and 5.6 Hz); 7.72 (1H, d, J=116.0 Hz); 7.78 (2H, d, J=8.2 Hz); 8.00 (2H, d, J=8.2 Hz); 12.68 (1H, br s).

Example 68

(E)-3-[4-({4-[3-(Trifluoromethyl)phenyl]-1-piperazinyl}sulfonyl)phenyl]-2-propenoyl chloride (10a)

To a suspension of (E)-3-[4-({4-[3-(trifluoromethyl)phenyl]-1-piperazinyl}sulfonyl)phenyl]-2-propenoic acid (9a) (0.30 g, 0.69 mmol) in dichloromethane (7 mL) oxalyl chloride (0.2 mL, 2.4 mmol) and a drop of dimethylformamide were added. The reaction mixture was stirred at ambient temperature for 0.5 hours and at 42° C. for 1 hour. The reaction mixture was evaporated and the residue was dried in vacuum to give (E)-3-[4-({4-[3-(trifluoromethyl)phenyl]-1-piperazinyl}sulfonyl)phenyl]-2-propenoyl chloride (10a) (0.31 g) in a form of a crude product.

Example 69

(E)-3-[4-({4-[Bis(4-fluorophenyl)methyl]-1-piperazinyl}sulfonyl)phenyl]-2-propenoyl chloride (10b)

To a solution of (E)-3-[4-({4-[bis(4-fluorophenyl)methyl]-1-piperazinyl}sulfonyl)phenyl]-2-propenoic acid (b) (0.25 g, 0.5 mmol) in dichloromethane (7 mL) oxalyl chloride (0.15 mL, 1.75 mmol) and a drop of dimethylformamide were added. The reaction mixture was stirred at ambient temperature for 1 hour, then the mixture was evaporated and the residue was dried in vacuum to give (E)-3-[4-({4-[bis(4-fluorophenyl)methyl]-1-piperazinyl}sulfonyl)phenyl]-2-propenoyl chloride (10b) (0.26 g) in a form of a crude product.

Example 70

(E)-N-Hydroxy-3-[4-({4-[3-(trifluoromethyl)phenyl]-1-piperazinyl}-sulfonyl)phenyl]-2-propenamide (PX118937)

To a suspension of hydroxylamine hydrochloride (0.24 g, 3.4 mmol) in tetrahydrofuran (5.0 mL) a solution of $NaHCO_3$ (0.40 g, 4.8 mmol) in water (6 mL) was added and the resultant mixture was stirred at ambient temperature for 5 minutes. The reaction mixture was added to a suspension of (E)-3-[4-({4-[3-(trifluoromethyl)phenyl]-1-piperazinyl}sulfonyl)phenyl]-2-propenoyl chloride (10a) (0.31 g) in tetrahydrofuran (5 mL) and the mixture was stirred at ambient temperature for 0.5 hours. The mixture was poured into water (25 mL), the precipitate was filtered, washed with water, ether, and dried to give the title compound (0.23 g, 73%). M.p. 178-179° C. $^1$H NMR (DMSO-$d_6$, HMDSO), δ: 2.95-3.10 (4H, m); 3.23-3.40

(4H, m, overlapped with a signal of water); 6.62 (1H, d, J=15.9 Hz); 7.09 (1H, d, J=7.7 Hz); 7.16 (1H, s); 7.19 (1H, d, J=8.0 Hz); 7.40 (1H, t, J=7.7 Hz); 7.54 (1H, d, J=15.9 Hz); 7.80 (2H, d, J=8.4 Hz); 7.83 (2H, d, J=8.4 Hz); 9.35 (1H, br s); 10.72 (1H, br s). HPLC analysis on Omnispher 5 $C_{18}$ column: impurities 3.5% (column size 4.6×150 mm; mobile phase acetonitrile-0.1M acetate buffer (pH 5.0), 50:50; sample concentration 1 mg/ml; flow rate 1.3 mL/min; detector UV 254 nm). Anal. Calcd for $C_{20}H_{20}F_3N_3O_4S$, %: C, 52.74; H, 4.43; N, 9.23; S, 7.04. Found, %: C, 52.04; H, 4.29; N, 8.86; S, 7.20.

Example 71

(E)-3-[4-({4-[Bis(4-fluorophenyl)methyl]-1-piperazinyl}sulfonyl)phenyl]-N-hydroxy-2-propenamide (PX118965)

To a suspension of hydroxylamine hydrochloride (0.18 g, 2.5 mmol) in tetrahydrofuran (5.0 mL) a solution of NaHCO₃ (0.30 g, 3.5 mmol) in water (5 mL) was added and the resultant mixture was stirred at ambient temperature for 5 minutes. The reaction mixture was added to a solution of (E)-3-[4-({4-[bis(4-fluorophenyl)methyl]-1-piperazinyl}sulfonyl)phenyl]-2-propenoyl chloride (10b) (0.26 g) in tetrahydrofuran (5 mL) and the obtained mixture was stirred at ambient temperature for 0.5 hours. The mixture was poured into water (25 mL), extracted with ethyl acetate, the extract was washed with water, brine, and dried (Na₂SO₄). The solvent was removed and the residue was chromatographed on silica gel with chloroform-isopropanol (9:1) as eluent to give the title compound (0.087 g, 34%). M.p. 125-126° C. ¹H NMR (DMSO-d₆, HMDSO), δ: 2.26-2.42 (4H, m); 2.81-3.00 (4H, m); 4.39 (1H, s); 6.64 (1H, d, J=15.8 Hz); 7.07 (4H, t, J=8.6 Hz); 7.37 (4H, dd, J=8.4 and 5.6 Hz); 7.57 (1H, d, J=15.8 Hz); 7.74 (2H, d, J=8.0 Hz); 7.83 (2H, d, J=8.0 Hz); 9.19 (1H, s); 10.93 (1H, s). HPLC analysis on Alltima $C_{18}$ column: impurities 2% (column size 4.6×150 mm; mobile phase acetonitrile-0.1M phosphate buffer (pH 2.5), 70:30; sample concentration 1.0 mg/ml; flow rate 1.0 mL/min; detector: UV 215 nm). Anal. Calcd for $C_{26}H_{25}F_2N_3O_4S$*0.3 Et₂O*0.2 iso-PrOH*0.1CHCl₃ (an exhaustively dried material contains all the indicated traces of solvents (PMR)), %: C, 59.87; H, 5.35; N, 7.51; S, 5.73. Found, %: C, 59.85; H, 5.36; N, 7.29; S, 5.60.

Example 72

1-(1,3-Benzodioxol-5-ylmethyl)-4-({-[(E)-3-(hydroxyamino)-3-oxo-1-propenyl]phenyl}sulfonyl) piperazin-1-ium dihydrogen phosphate (PX118882)

The title compound was obtained using methods analogous to those described above. M.p. 210-211° C. ¹H NMR (DMSO-d₆, HMDSO) δ: 2.30-2.45 (4H, m, overlapped with a signal of DMSO); 2.82-2.96 (4H, m); 3.36 (2H, s); 3.89-4.67 (br s, interchangeable protons); 5.95 (2H, s); 6.62 (1H, d, J=15.8 Hz); 6.68 (1H, d, J=7.8 Hz); 6.77 (1H, s); 6.79 (1H, d, J=7.8 Hz); 7.53 (2H, d, J=15.8 Hz); 7.73 (2H, d, J=8.0 Hz); 7.81 (2H, d, J=8.0 Hz). HPLC analysis on Omnispher 5 $C_{18}$: impurities 2.5% (column size 4.6×150 mm; mobile phase acetonitrile-0.1M phosphate buffer (pH 2.5), 20:80; sample concentration 0.5 mg/ml; flow rate 1.5 ml/min; detector UV 220 nm). Anal. Calcd. for $C_{21}H_{23}N_3O_6S$*$H_3PO_4$*0.25 NaH₂PO₄, %: C, 43.98; H, 4.66; N, 7.33; S, 5.59. Found, %: C, 43.59; H, 4.75; N, 7.50; S, 5.70.

Example 73

(E)-N-Hydroxy-3-(4-{[4-(4-nitrophenyl)-1-piperazinyl]sulfonyl}phenyl)-2-propenamide (PX118918)

The title compound was obtained using methods analogous to those described above. M.p. 199-200° C. ¹H NMR (DMSO-d₆, HMDSO) δ: 2.97-3.09 (4H, m); 3.49-3.62 (4H, m); 6.61 (1H, d, J=15.7 Hz); 6.99 (2H, d, J=9.2 Hz); 7.52 (1H, d, J=15.7 Hz); 7.78 (2H, d, J=9.0 Hz); 7.81 (2H, d, J=9.0 Hz); 8.02 (2H, d, J=9.2 Hz); 9.17 (1H, s); 10.91 (1H, s). HPLC analysis on Omnispher 5 $C_{18}$: impurities 3.0% (column size 4.6×150 mm; mobile phase acetonitrile-0.1M phosphate buffer (pH 2.5), 40:60; sample concentration 0.25 mg/ml; flow rate 1.5 mL/min; detector UV 270 nm). Anal. Calcd. for $C_{19}H_{20}N_4O_6S$, %: C, 52.77; H, 4.66; N, 12.96; S, 7.41. Found, %: C, 52.56; H, 4.74; N, 12.41; S, 7.28.

Example 74

(E)-3-(4-{[4-(2-Fluorophenyl)-1-piperazinyl] sulfonyl}phenyl)-N-hydroxy-2-propenamide (PX118891)

The title compound was obtained using methods analogous to those described above. M.p. 196-197° C. ¹H NMR (DMSO-d₆, HMDSO) δ: 3.00-3.14 (8H, m); 6.63 (1H, d, J=15.8 Hz); 6.92-7.18 (4H, m); 7.55 (1H, d, J=15.8 Hz); 7.80 (2H, d, J=8.6 Hz); 7.84 (2H, d, J=8.6 Hz); 9.16 (1H, s); 10.92 (1H, s). HPLC analysis on Alltima $C_{18}$: impurities 3.5% (column size 4.6×150 mm; mobile phase acetonitrile-0.1M phosphate buffer (pH 2.5), 50:50; sample concentration 1.0 mg/ml; flow rate 1.0 mL/min; detector UV 254 nm.) Anal. Calcd. for $C_{19}H_{20}FN_3O_4S$*0.2 EtOAc, %: C, 56.21; H, 5.15; N, 9.93; S, 7.58. Found, %: C, 56.07; H, 5.10; N, 9.97; S, 7.60.

Example 75

(E)-N-Hydroxy-3-(4-{[4-(3-methoxyphenyl)-1-piperazinyl]sulfonyl}phenyl)-2-propenamide (PX118892)

The title compound was obtained using methods analogous to those described above. M.p. 199-200° C. ¹H NMR (DMSO-d₆, HMDSO) δ: 2.95-3.06 (4H, m); 3.13-3.25 (4H, m); 3.68 (3H, s); 6.38 (1H, d, J=8.0 Hz); 6.42 (1H, s); 6.47 (1H, d, J=8.2 Hz); 6.61 (1H, d, J=16.0 Hz); 7.09 (1H, t, J=8.0 Hz); 7.54 (1H, d, J=16.0 Hz); 7.78 (2H, d, J=8.4 Hz); 7.83 (2H, d, J=8.4 Hz); 9.17 (1H, s); 10.91 (1H, br s). HPLC analysis on Omnispher 5 $C_{18}$: impurities 4.5% (column size 4.6×150 mm; mobile phase acetonitrile-0.1M phosphate buffer (pH 2.5), 45:55; sample concentration 0.15 mg/ml; flow rate 1.2 mL/min; detector UV 254 nm). Anal. Calcd. for $C_{20}H_{23}N_3O_5S$*0.1 EtOAc*0.2H₂O, %: C, 57.00; H, 5.67; N, 9.77; S, 7.46. Found, %: C, 57.04; H, 5.52; N, 9.64; S, 7.38.

Example 76

(E)-N-Hydroxy-3-(4-{[4-(2-methoxyphenyl)-1-piperazinyl]sulfonyl}phenyl)-2-propenamide (PX118905)

The title compound was obtained using methods analogous to those described above. M.p. 225-226° C. ₁H NMR (DMSO-d$_6$, HMDSO) δ: 2.89-3.13 (8H, m); 3.70 (3H, s); 6.63 (1H, d, J=15.8 Hz); 6.83-7.00 (4H, m); 7.56 (1H, d, J=15.8 Hz); 7.80 (2H, d, J=8.2 Hz); 7.85 (2H, d, J=8.2 Hz); 9.18 (1H, br s); 10.93 (1H, br s). HPLC analysis on Omnispher 5 C$_{18}$: impurities 4.5%. (column size 4.6×150 mm; mobile phase acetonitrile-0.1M phosphate buffer (pH 2.5), 40:60; sample concentration 0.2 mg/ml; flow rate 1.2 mL/min; detector UV 254 nm). Anal. Calcd. for C$_{20}$H$_{23}$N$_3$O$_5$S*0.2 EtOAc*0.2H$_2$O, %: C, 56.95; H, 5.74; N, 9.58; S, 7.31. Found, %: C, 56.95; H, 5.66; N, 9.40; S, 7.54.

Example 77

3-(4-[4-(3-Chloro-phenyl)-piperazine-1-sulfonyl]-phenyl)-N-hydroxy-acrylamide (PX118906)

The Title Compound was Obtained Using Methods Analogous to Those Described Above.

Example 78

N-Hydroxy-3-[4-(4-pyrimidin-2-yl-piperazine-1-sulfonyl)-phenyl]-acrylamide (PX118907)

The title compound was obtained using methods analogous to those described above.

Example 79

3-[4-(4-Benzhydryl-piperazine-1-sulfonyl)-phenyl-N-hydroxy-acrylamide (PX118910)

The title compound was obtained using methods analogous to those described above.

Example 80

N-Hydroxy-3-[4-(3-methyl-4-m-tolyl-piperazine-1-sulfonyl)-phenyl]-acrylamide (PX118911)

The title compound was obtained using methods analogous to those described above.

Method E—General Synthesis of 1-Acylpiperazines

Appropriate carboxylic acid (1-2 mmol) and hydroxybenztriazole (1 eq) were suspended in chloroform (2 ml/1 mmol) and a solution of 1,3-dicylcohexylcarbodiimide (DCC) (1 eq) in a minimal amount of dimethylformamide was added. The mixture was stirred for 30 minutes at room temperature to give white suspension. The mixture was transferred slowly to a pre-cooled solution of anhydrous piperazine (5 eq) in chloroform (1 mL/1 mmol). The reaction was stirred for 4 hours at room temperature, the white suspension (DCU) was filtered, and the filtrate was extracted with 2 M HCl. The HCl extracts were basified with 2 M NaOH to pH 9, extracted with ethyl acetate, and the organic extract was washed with brine, dried (Na$_2$SO$_4$), and evaporated under reduced pressure. The crude product was used without further purification, or was purified on silica gel (20 g) with methanol-NH$_4$OH (ca. 95:5 to 90:10) as eluent.

Example 81

2-Naphthyl(1-piperazinyl)methanone (13a)

The title compound was prepared from naphthalene 2-carboxylic acid (2a), using Method E, yield 94%. $^1$H NMR (CDCl$_3$, HMDS), δ: 1.92 (s, 1H); 2.87 (t, J=5.0 Hz, 4H); 3.63 (t, J=5.0 Hz, 4H); 7.43-7.74 (m, 3H); 7.89-8.12 (m, 4H).

Example 82

2-(5-Methoxy-1H-indol-3-yl)-1-(1-piperazinyl)-1-ethanone (13b)

The title compound was prepared from 2-(5-methoxy-1H-indol-3-yl)acetic acid (12b), using Method E, yield 75%. $^1$H NMR (CDCl$_3$, HMDS), δ: 1.61 (s, 1H); 2.63 (t, J=5.0 Hz, 2H); 2.78 (t, J=5.0 Hz, 2H); 3.45 (t, J=5.0 Hz, 2H); 3.65 (t, J=5.0 Hz, 2H); 3.78 (s, 2H); 3.83 (s, 3H); 6.78 (dd, J=8.8 and 3.0 Hz, 1H); 7.06 (t, J=3.0 Hz, 2H); 7.22 (d, J=8.8 Hz, 1H); 8.27 (s, 1H).

Example 83

2-(2-Naphthyloxy)-1-(1-piperazinyl)-1-ethanone (13c)

The title compound was prepared from 2-(2-naphthyloxy) acetic acid (2c), using Method E, yield 97%. $^1$H NMR (CDCl$_3$, HMDS), δ: 1.69 (s, 1H); 2.83 (t, J=5.0 Hz, 4H); 3.61 (t, J=5.0 Hz, 4H); 4.81 (s, 2H); 7.12-7.58 (m, 4H); 7.69-7.92 (m, 3H).

Example 84

2-(1-Naphthyloxy)-1-(1-piperazinyl)-1-ethanone (13d)

The title compound was prepared from 2-(1-naphthyloxy) acetic acid (d), using Method E, yield 82%. $^1$H NMR (CDCl$_3$, HMDS), δ: 1.87 (s, 1H); 2.63 (t, J=5.0 Hz, 2H); 2.83 (t, J=5.0 Hz, 2H); 3.45 (t, J=5.0 Hz, 2H); 3.65 (t, J=5.0 Hz, 2H); 3.89 (s, 2H); 7.29-7.61 (m, 3H); 7.65-7.96 (m, 4H).

Example 85

2-(1-Benzothiophen-3-yl)-1-(1-piperazinyl)-1-ethanone (13e)

The title compound was prepared from 2-(1-benzothiophen-3-yl)acetic acid (2e), using Method E, yield 92%. $^1$H NMR (CDCl$_3$, HMDS), δ: 1.61 (s, 1H); 2.67 (t, J=5.0 Hz, 2H); 2.83 (t, J=5.0 Hz, 2H); 3.43 (t, J=5.0 Hz, 2H); 3.67 (t, J=5.0 Hz, 2H); 3.81 (s, 2H); 7.21-7.54 (m, 3H); 7.69-7.98 (m, 2H).

Example 86

3-(1H-Indol-3-yl)-1-(1-piperazinyl)-1-propanone (13f)

The title compound was prepared from 3-(1H-indol-3-yl) propanoic acid (12f), using Method E, yield 79%. $^1$H NMR (CDCl$_3$, HMDS), δ: 2.03 (s, 1H); 2.54-2.89 (m, 6H); 3.03-3.21 (m, 2H); 3.34 (t, J=5.0 Hz, 2H); 3.58 (t, J=5.0 Hz, 2H); 7.00-7.45 (m, 4H); 7.52-7.74 (m, 1H); 8.13 (bs, 1H).

Example 87

1H-Indol-3-yl(1-piperazinyl)methanone (13g)

The title compound was prepared from 1H-indole-3-carboxylic acid (12g), using Method E, yield 39%. $^1$H NMR (CDCl₃, HMDS), δ: 1.67 (s, 1H); 2.89 (t, J=5.0 Hz, 4H); 3.69 (t, J=5.0 Hz, 4H); 7.09-7.43 (m, 4H); 7.63-7.87 (m, 1H); 9.27 (bs, 1H).

Example 88

Tert-butyl 4-benzoyl-1-piperazinecarboxylate (15h)

To a solution of N-Boc-piperazine (14) (1.00 g, 5.37 mmol) in dioxane (5 mL), a solution of NaOH (0.50 g, 12.9 mmol) in water (5 mL) followed by a solution of benzoyl chloride (0.75 mL, 6.44 mmol) in dioxane (2 mL) under vigorous stirring were added. The reaction mixture was stirred at ambient temperature for 4 hours, diluted with brine (20 mL), and extracted with ethyl acetate (2×25 mL). The organic extract was washed successively with brine (20 mL), saturated NaHCO₃ (20 mL), saturated KH₂PO₄ (20 mL), and dried (Na₂SO₄). The solvents were evaporated to give the title compound (1.400 g, 90%) which was used in the next step of the synthesis without further purification. ¹H NMR (CDCl₃, HMDS), δ: 1.41 (s, 9H); 2.86 (t, J=5.0 Hz, 4H); 3.62 (t, J=5.0 Hz, 4H); 7.34 (s, 5H).

Method F—General Synthesis of Tert-Butyl 1-Piperazinecarboxylates

A solution of appropriate acid 12i-k (2.75 mmol) in anhydrous dimethylformamide (4.5 mL) was cooled in ice bath under argon and carbonyldiimidazole (0.490 g, 3.01 mmol) was added. The mixture was stirred for 30 minutes, then a solution of N-Boc-piperazine 14 (2.75 mmol) in dimethylformamide (3 mL) was added. The mixture was stirred at ice bath temperature for 1 hour, followed by 20 hours at room temperature, diluted with brine (20 mL), and extracted with ethyl acetate (3×25 mL). The organic phase was washed successively with brine (20 mL), saturated KH₂PO₄ (20 mL), brine (20 mL), and dried (Na₂SO₄). The solvent was evaporated and the crude product was used in a further step of the synthesis without additional purification, or was purified on silica gel (20 g) with ethyl acetate as eluent.

Example 89 tert-Butyl 4-[4-(dimethylamino)benzoyl]-1-piperazinecarboxylate (15i)

The title compound was prepared from 4-(dimethylamino)benzoic acid (12i), using Method F, yield 61%. ¹H NMR (CDCl₃, HMDS), δ: 1.45 (s, 9H); 2.98 (s, 6H); 3.29-3.74 (m, 8H); 6.69 (d, J=8.8 Hz, 2H); 7.36 (d, J=8.8 Hz, 2H).

Example 90 tert-Butyl 4-(4-cyanobenzoyl)-1-piperazinecarboxylate (15j)

The title compound was prepared from 4-cyanobenzoic acid (12j), using Method F, yield 96%. ¹H NMR (CDCl₃, HMDS), δ: 1.40 (s, 9H); 2.87 (t, J=5.0 Hz, 4H); 3.63 (t, J=5.0 Hz, 4H); 6.70 (d, J=8.8 Hz, 2H); 7.12 (d, J=8.8 Hz, 2H).

Example 91 tert-Butyl 4-{2-[4-(dimethylamino)phenyl]acetyl}-1-piperazinecarboxylate (15k)

The title compound was prepared from 2-[4-(dimethylamino)phenyl]acetic acid (12k), using Method F, yield 60%. ¹H NMR (CDCl₃, HMDS), δ: 1.43 (s, 9H); 2.92 (s, 6H); 3.07-3.78 (m, 8H); 3.65 (s, 2H); 6.72 (d, J=8.8 Hz, 2H); 7.14 (d, J=8.8 Hz, 2H).

Method G—General Synthesis of 1-Acylpiperazines

A solution of an appropriate N-Boc-piperazine derivative 15h-k (2.5 mmol) in 1 N HCl methanol (12.5 mL) (made in situ from AcCl and MeOH) was stirred for 2 hours at ambient temperature, and then the mixture was evaporated. To the residue, water (30 mL) was added, the mixture was washed with diethyl ether, and the pH of the aqueous phase was brought to 9 with 2 M NaOH. The reaction product was extracted with chloroform (3×25 mL), the organic extract was washed with brine (25 mL), and dried (Na₂SO₄). The solvent was evaporated and the crude product was used in a further step of the synthesis without additional purification, or was purified on silica gel (20 g) with methanol-NH₄OH (9:1) as eluent.

Example 92

Phenyl(1-piperazinyl)methanone (13h)

The title compound was prepared from tert-butyl 4-benzoyl-1-piperazinecarboxylate (15h), using Method G, yield 87%. ¹H NMR (CDCl₃, HMDS), δ: 1.81 (s, 1H); 2.76 (t, J=5.0 Hz, 4H); 3.56 (bs, 4H); 7.41 (s, 5H).

Example 93

[4-(Dimethylamino)phenyl](1-piperazinyl)methanone (13i)

The title compound was prepared from tert-butyl 4-[4-(dimethylamino)benzoyl]-1-piperazinecarboxylate (15i), using Method G, yield 82%. ¹H NMR (CDCl₃, HMDS), δ: 1.91 (s, 1H); 2.87 (t, J=5.0 Hz, 4H); 2.98 (s, 6H); 3.63 (t, J=5.0 Hz, 4H); 6.67 (d, J=8.8 Hz, 2H); 7.34 (d, J=8.8 Hz, 2H).

Example 94

4-(1-piperazinylcarbonyl)benzonitrile (13j)

The title compound was prepared from tert-butyl 4-(4-cyanobenzoyl)-1-piperazinecarboxylate (15j), using Method G, yield 62%. ¹H NMR (CDCl₃ HMDS), δ: 1.92 (s, 1H); 2.69-3.02 (m, 4H); 3.14-3.92 (m, 4H); 7.49 (d, J=8.8 Hz, 2H); 7.72 (d, J=8.8 Hz, 2H).

Example 95

8-(4-{2-[4-(Dimethylamino)phenyl]acetyl}-1-piperazinyl)-N-hydroxy-8-oxooctanamide (13k)

The title compound was prepared from tert-butyl 4-{2-[4-(dimethylamino)phenyl]acetyl}-1-piperazinecarboxylate (15k) using Method G, yield 80%. ¹H NMR (CDCl₃, HMDS), δ: 1.63 (s, 1H); 2.63 (t, J=5.0 Hz, 2H); 2.78 (t, J=5.0 Hz, 2H); 2.92 (s, 6H); 3.41 (t, J=5.0 Hz, 2H); 3.58 (t, J=5.0 Hz, 2H); 3.65 (s, 2H); 6.99 (d, J=8.8 Hz, 2H); 7.11 (d, J=8.8 Hz, 2H).

Method H—General Synthesis of N-Monosubstituted Piperazines

To a suspension of LiAlH₄ (2.5 eq) in anhydrous tetrahydrofuran (2-3 mL/mmol) under argon atmosphere, a solution of appropriate N-acylpiperazine 13b,c,f,g,k (1 eq) in tetrahydrofuran (1.5 mL/1 mmol) was added, and the mixture was stirred at reflux temperature until the initial compound disappeared (3-7 hours on average). The reaction mixture was allowed to cool to room temperature and methanol, water, and 1N NaOH were carefully added. The reaction mixture was stirred for 2 hours at room temperature and the mixture passed through a celite pad. The filtrate was evaporated and the residue was purified on silica gel (20 g) with methanol-NH$_4$OH (9:1) as eluent to give the expected piperazine product.

Example 96

5-Methoxy-3-[2-(1-piperazinyl)ethyl]-1H-indole (16b)

The title compound was prepared from 2-(5-methoxy-1H-indol-3-yl)-1-(1-piperazinyl)-1-ethanone (13b), using Method H, yield 38%. $^1$H NMR (CDCl$_3$, HMDS), δ: 1.61 (s, 1H); 2.47-2.81 (m, 6H); 2.87-3.09 (m, 6H); 3.85 (s, 3H); 6.85 (dd, J=8.8 and 3.0 Hz, 1H); 7.05 (t, J=3.0 Hz, 2H); 7.25 (d, J=8.8 Hz, 1H); 7.83 (s, 1H).

Example 97

1-[2-(2-Naphthyloxy)ethyl]piperazine (16c)

The title compound was prepared from 2-(2-naphthyloxy)-1-(1-piperazinyl)-1-ethanone (13c), using Method H, yield 43%. $^1$H NMR (CDCl$_3$, HMDS), δ: 1.48 (s, 1H); 2.56 (t, J=5.0 Hz, 4H); 2.85 (t, J=6.0 Hz, 2H); 2.92 (t, J=5.0 Hz, 4H); 4.25 (t, J=6.0 Hz, 2H); 7.05-7.58 (m, 4H); 7.65-7.89 (m, 3H).

Example 98

3-[3-(1-piperazinyl)propyl]-1H-indole (16f)

The title compound was prepared from 3-(1H-indol-3-yl)-1-(1-piperazinyl)-1-propanone (13f), using Method H, yield 74%. $^1$H NMR (DMSO, HMDS), δ: 1.69 (t, J=7.0 Hz, 1H); 1.78 (t, J=7.0 Hz, 1H); 2.12-2.34 (m, 6H); 2.36-2.47 (1H, overlapped with DMSO signal); 2.49-2.76 (m, 6H); 6.67-7.00 (m, 3H); 7.05-7.45 (m, 2H); 10.49 (s, 1H).

Example 99

3-(1-piperazinylmethyl)-1H-indole (16g)

The title compound was prepared from 1H-indol-3-yl(1-piperazinyl)methanone (13g) using Method H, yield 63%. $^1$H NMR (CDCl$_3$, HMDS), δ: 1.81 (s, 1H); 2.49 (t, J=5.0 Hz, 4H); 2.89 (t, J=5.0 Hz, 4H); 3.72 (s, 2H); 7.05-7.52 (m, 4H); 7.65-7.83 (m, 1H); 8.14 (bs, 1H).

Example 100

N,N-Dimethyl-4-[2-(1-piperazinyl)ethyl]aniline (16k)

The title compound was prepared from 8-(4-{2-[4-(dimethylamino)phenyl]acetyl}-1-piperazinyl)-N-hydroxy-8-oxooctanamide (13k), using Method H, yield 82%. $^1$H NMR (CDCl$_3$, HMDS), δ: 1.74 (s, 1H); 2.34-2.72 (m, 8H); 2.89 (s, 6H); 2.81-3.03 (m, 4H); 6.72 (d, J=8.8 Hz, 2H); 7.09 (d, J=8.8 Hz, 2H).

Method J—General Synthesis of Amidoesters

A solution of dicarbonic acid monoethyl (or monomethyl) ester 18a or 18b (2.73 mmol) in anhydrous tetrahydrofuran (5 mL) under argon atmosphere was cooled in an ice bath and to the solution carbonyldiimidazole (0.500 g, 3.08 mmol) was added. The mixture was stirred for 1 hour at ice bath temperature, then appropriate piperazine (2.73 mmol) was added. The reaction mixture was stirred at room temperature for 20 hours, concentrated under vacuum, and partitioned between brine (30 mL) and ethyl acetate (40 mL). The organic layer was washed successively with water (25 mL), 5% citric acid (25 mL), brine (25 mL), and dried (MgSO$_4$). The solvent was evaporated and the residue was chromatographed on silica gel (20 g) with petroleum ether-ethyl acetate as eluent affording the corresponding reaction product.

Example 101

8-Oxo-8-(4-phenyl-piperazin-1-yl)-octanoic acid methyl ester (19a)

The title compound was obtained from suberic acid monomethyl ester (18b) and N-phenylpiperazine (17a) (commercially available) using Method J, yield 88%. $^1$H NMR (DMSO-d$_6$, HMDSO), δ: 1.05-1.72 (m, 8H); 2.02-2.30 (m, 8H); 3.30-3.60 (m, 4H); 3.51 (s, 3H); 7.21-7.51 (m, 5H).

Example 102

Ethyl 7-(4-benzhydryl-1-piperazinyl)-7-oxoheptanoate (19b)

The title compound was obtained from pimelic acid monoethyl ester (18a) and 1-(diphenylmethyl)piperazine (17b) (commercially available) using Method J, yield 80%. $^1$H NMR (DMSO-d$_6$, HMDSO), δ: 1.04-1.62 (m, 9H); 2.12-2.36 (m, 8H); 3.35-3.50 (m, 4H); 4.17 (q, 2H, J=7.3 Hz); 4.31 (s, 1H); 7.02-7.59 (m, 10H).

Example 103

Ethyl 7-oxo-7-(4-phenyl-1-piperazinyl)heptanoate (19c)

The title compound was obtained from pimelic acid monoethyl ester (18a) and N-phenylpiperazine (17a) (commercially available) using Method J, yield 88%. $^1$H NMR (DMSO-d$_6$, HMDSO), δ: 1.12-1.62 (m, 9H); 1.97-2.35 (m, 8H); 3.27-3.59 (m, 4H); 4.17 (q, 2H, J=7.2 Hz); 7.03-7.51 (m, 5H).

Example 104

Methyl 8-(4-benzhydryl-1-piperazinyl)-8-oxooctanoate (19d)

The title compound was obtained from suberic acid monomethyl ester (b) and 1-(diphenylmethyl)piperazine (17b) (commercially available) using Method J, yield 91%. $^1$H NMR (DMSO-d$_6$, HMDSO), δ: 1.02-1.67 (m, 8H); 2.09-2.38 (m, 8H); 3.33-3.51 (m, 4H); 3.56 (s, 3H); 4.29 (s, 1H); 7.09-7.56 (m, 10H).

Example 105

Methyl 8-[4-(2-methoxyphenyl)-1-piperazinyl]-8-oxooctanoate (19e)

The title compound was obtained from suberic acid monomethyl ester (18b) and 1-(2-methoxyphenyl)piperazine hydrochloride (17c) (commercially available) (before the addition of hydrochloride (17c), triethylamine (3.0 mmol) was added to the reaction mixture), using Method J, yield 87%. $^1$H NMR (DMSO-d$_6$, HMDSO), δ: 1.12-1.60 (m, 8H); 1.97-2.82 (m, 8H, overlapped with a signal of DMSO); 3.40-3.62 (m, 7H); 3.75 (s, 3H); 6.92-7.15 (m, 4H).

Method K—General Synthesis of Amidoesters

To a solution of dicarbonic acid monoethyl (or monomethyl) ester 18a or 18b (2.75 mmol) in anhydrous dichloromethane (10 mL) oxalyl chloride (0.84 mL, 9.63 mmol) and a drop of dimethylformamide were added, and the resulting mixture was stirred for 30 minutes at room temperature followed by 1 hour at 40° C. The solution was carefully evaporated under reduced pressure and the residue was dried in vacuum at 40° C. The resulting chloride was dissolved in anhydrous tetrahydrofuran (3 mL) and the obtained solution to a cold suspension (ice bath) of piperazine (2.75 mmol), tetrahydrofuran (10 mL), and saturated NaHCO$_3$ (10 mL) under vigorous stirring was added. The stirring was continued for 1 hour at ice bath temperature and 20 hours at room temperature. The mixture was diluted with brine (30 mL) and extracted with ethyl acetate (3×25 mL). The organic phase was washed with brine and dried (Na$_2$SO$_4$). The solvent was evaporated and the residue was chromatographed on silica gel (20 g) with benzene-ethyl acetate as eluent to give the corresponding reaction product.

Example 106

Ethyl 8-[4-(2-chlorophenyl)-1-piperazinyl]-8-oxooctanoate (19f)

The title compound was obtained from suberic acid monoethyl ester (18c) and 1-(2-chlorophenyl)piperazine (17d) (commercially available) using Method K, yield 80%. $^1$H NMR (CDCl$_3$, HMDSO), δ: 1.13 (t, J=7.0 Hz, 3H); 1.18-1.91 (m, 8H); 2.29 (t, J=6.0 Hz, 2H); 2.38 (t, J=6.0 Hz, 2H); 3.02 (t, J=5.0 Hz, 4H); 3.50-3.90 (m, 4H); 4.11 (q, J=7.0 Hz, 2H); 6.85-7.09 (m, 2H); 7.14-7.48 (m, 2H).

Example 107

Ethyl 8-[4-(3-chlorophenyl)-1-piperazinyl]-8-oxooctanoate (19g)

The title compound was obtained from suberic acid monoethyl ester (8c) and 1-(3-chlorophenyl)piperazine (17e) (commercially available) using Method K, yield 88%. $^1$H NMR (CDCl$_3$, HMDSO), δ: 1.23 (t, J=7.0 Hz, 3H); 1.18-1.79 (m, 8H); 2.29 (t, J=6.0 Hz, 2H); 2.36 (t, J=6.0 Hz, 2H); 3.14 (t, J=5.0 Hz, 4H); 3.44-3.87 (m, 4H); 4.11 (q, J=7.0 Hz, 2H); 6.66-6.92 (m, 2H); 7.05-7.37 (m, 2H).

Example 108

Ethyl 7-[4-(2-chlorophenyl)-1-piperazinyl]-7-oxoheptanoate (19h)

The title compound was obtained from pimelic acid monoethyl ester (18a) and 1-(2-chlorophenyl)piperazine (17d) (commercially available) using Method K, yield 79%. $^1$H NMR (CDCl$_3$, HMDSO), δ: 1.23 (t, J=7.0 Hz, 3H); 1.18-1.89 (m, 6H); 2.29 (t, J=6.0 Hz, 2H); 2.38 (t, J=6.0 Hz, 2H); 3.00 (t, J=5.0 Hz, 4H); 3.49-3.89 (m, 4H); 4.12 (q, J=7.0 Hz, 2H); 6.85-7.09 (m, 2H); 7.14-7.48 (m, 2H).

Example 109

Ethyl 7-[4-(3-chlorophenyl)-1-piperazinyl]-7-oxoheptanoate (19i)

The title compound was obtained from pimelic acid monoethyl ester (18a) and 1-(3-chlorophenyl)piperazine (17e) (commercially available) using Method K, yield 78%. $^1$H NMR (CDCl$_3$, HMDSO), δ: 1.23 (t, J=7.0 Hz, 3H); 1.18-1.89 (m, 6H); 2.29 (t, J=6.0 Hz, 2H); 2.36 (t, J=6.0 Hz, 2H); 3.14 (t, J=5.0 Hz, 4H); 3.45-3.89 (m, 4H); 4.12 (q, J=7.0 Hz, 2H); 6.67-6.94 (m, 2H); 7.05-7.38 (m, 2H).

Method L—General Synthesis of Amidoesters

A solution of dicarbonic acid monomethyl (or monoethyl) ester 18a-c (2.75 mmol) in anhydrous dimethylformamide (3 mL) was cooled in ice bath under argon atmosphere and carbonyldiimidazole (490 mg, 3.01 mmol) was added. The mixture was stirred at ice bath temperature for 30 minutes and a solution of appropriate piperazine (2.75 mmol) in dimethylformamide (3 mL) was added (if the piperazine was used in a hydrochloride form triethylamine (1.0 mL) before the piperazine hydrochloride to the reaction mixture was added). The mixture was stirred at ice bath temperature for 1 hour followed by 20 hours at room temperature. Then the reaction mixture was diluted with brine (50 mL) and extracted with ethyl acetate (3×25 mL). The organic phase was washed with brine, dried (Na$_2$SO$_4$), and the solvent was evaporated. The residue was chromatographed on silica gel with appropriate eluent to give the corresponding reaction product.

Example 110

Ethyl 8-[4-(2-naphthoyl)-1-piperazinyl]-8-oxooctanoate (19j)

The title compound was obtained from suberic acid monoethyl ester (18c) and 2-naphthyl(1-piperazinyl)methanone (3a) using Method L, yield 79%. $^1$H NMR (CDCl$_3$, HMDSO), δ: 1.16 (t, J=7.0 Hz, 3H); 1.18-1.65 (m, 8H); 2.25 (t, J=6.0 Hz, 2H); 2.38 (t, J=6.0 Hz, 2H); 3.36-3.65 (m, 8H); 4.02 (q, J=7.0 Hz, 2H); 7.43-7.74 (m, 3H); 7.89-8.12 (m, 4H).

Example 111

Ethyl 8-(4-benzoyl-1-piperazinyl)-8-oxooctanoate (19k)

The title compound was obtained from suberic acid monoethyl ester (18c) and phenyl(1-piperazinyl)methanone (13h) using Method L, yield 89%. $^1$H NMR (CDCl$_3$, HMDSO), δ: 1.28 (t, J=7.0 Hz, 3H); 1.14-1.83 (m, 8H); 2.16 (t, J=7.0 Hz, 2H); 2.23 (t, J=7.0 Hz, 2H); 3.00-3.25 (m, 4H); 3.49-3.83 (m, 4H); 3.98 (q, J=7.0 Hz, 2H); 7.39 (s, 5H).

Example 112

Ethyl 8-{4-[4-(dimethylamino)benzoyl]-1-piperazinyl}-8-oxooctanoate (19l)

The title compound was obtained from suberic acid monoethyl ester (1c) and [4-(dimethylamino)phenyl](1-piperazinyl)methanone (31) using Method L, yield 81%. $^1$H NMR (CDCl$_3$, HMDSO), δ: 1.27 (t, J=7.0 Hz, 3H); 1.15-1.88 (m, 8H); 2.34 (t, J=7.0 Hz, 2H); 2.52 (t, J=6.0 Hz, 2H); 2.88 (s, 6H); 3.00-3.21 (m, 4H); 3.49-3.87 (m, 4H); 4.11 (q, J=7.0 Hz, 2H); 7.08 (d, J=8.8 Hz, 2H); 7.35 (s, 5H).

Example 113

Ethyl 8-[4-(4-methoxyphenyl)-1-piperazinyl]-8-oxooctanoate (19m)

The title compound was obtained from suberic acid monoethyl ester (18c) and 1-(4-methoxyphenyl)piperazine (17f) (commercially available) using Method L, yield 76%. $^1$H NMR (CDCl$_3$, HMDSO), δ: 1.16 (t, J=7.0 Hz, 3H); 1.05-1.76 (m, 8H); 2.22 (t, J=7.0 Hz, 2H); 2.29 (t, J=7.0 Hz, 2H); 2.85-3.07 (m, 4H); 3.43-3.78 (m, 4H); 3.72 (s, 3H); 4.05 (q, J=7.0 Hz, 2H); 6.83 (s, 4H).

Example 114

Ethyl 8-[4-(3-methoxyphenyl)-1-piperazinyl]-8-oxooctanoate (19n)

The title compound was obtained from suberic acid monoethyl ester (18c) and 1-(3-methoxyphenyl)piperazine (17g) (commercially available) using Method L, yield 62%. $^1$H NMR (CDCl$_3$, HMDSO), δ: 1.29 (t, J=7.0 Hz, 3H); 1.16-1.85 (m, 8H); 2.16 (t, J=7.0 Hz, 2H); 2.22 (t, J=7.0 Hz, 2H); 3.00-3.25 (m, 4H); 3.49-3.83 (m, 4H); 3.65 (s, 3H); 3.98 (q, J=7.0 Hz, 2H); 6.36-6.67 (m, 3H); 7.05-7.23 (m, 1H).

Example 115

Ethyl 8-[4-(4-nitrophenyl)-1-piperazinyl]-8-oxooctanoate (19o)

The title compound was obtained from suberic acid monoethyl ester (18c) and 1-(4-nitrophenyl)piperazine (17h) (commercially available) using Method L, yield 67%. $^1$H NMR (CDCl$_3$, HMDSO), δ: 1.23 (t, J=7.0 Hz, 3H); 1.07-1.89 (m, 8H); 2.29 (t, J=7.0 Hz, 2H); 2.36 (t, J=7.0 Hz, 2H); 3.25-3.92 (m, 8H); 4.12 (q, J=7.0 Hz, 2H); 6.83 (d, J=8.8 Hz, 2H); 8.14 (d, J=8.8 Hz, 2H).

Example 116

Methyl 8-{4-[2-(5-methoxy-1H-indol-3-yl)acetyl]-1-piperazinyl}-8-oxooctanoate (19p)

The title compound was obtained from suberic acid monomethyl ester (18b) and 2-(5-methoxy-1H-indol-3-yl)-1-(1-piperazinyl)-1-ethanone (13b) using Method L, yield 76%. $^1$H NMR (CDCl$_3$, HMDSO), δ: 1.12-1.89 (m, 8H); 2.29 (t, J=7.0 Hz, 4H); 3.09-3.74 (m, 8H); 3.65 (s, 3H); 3.83 (s, 2H); 3.85 (s, 3H); 6.89 (dd, J=8.8 and 3.0 Hz, 1H); 7.07 (t, J=3.0 Hz, 2H); 7.16-7.35 (m, 1H); 8.31 (bs, 1H).

Example 117

Methyl 8-{4-[2-(2-naphthyloxy)ethyl]-1-piperazinyl}-8-oxooctanoate (19r)

The title compound was obtained from suberic acid monomethyl ester (18b) and 1-[2-(2-naphthyloxy)ethyl]piperazine (16c) using Method L, yield 56%. $^1$H NMR (CDCl$_3$, HMDSO), δ: 1.14-1.81 (m, 8H); 2.29 (t, J=7.0 Hz, 4H); 2.43-2.69 (m, 4H); 2.87 (t, J=5.0 Hz, 2H); 3.32-3.74 (m, 4H); 3.63 (s, 3H); 4.23 (t, J=5.0 Hz, 2H); 7.03-7.23 (m, 2H); 7.29-7.52 (m, 2H); 7.61-7.83 (m, 2H).

Example 118

Ethyl 8-{4-[2-(1-naphthyloxy)acetyl]-1-piperazinyl}-8-oxooctanoate (19s)

The title compound was obtained from suberic acid monoethyl ester (18c) and 2-(1-naphthyloxy)-1-(1-piperazinyl)-1-ethanone (13d) using Method L, yield 65%. $^1$H NMR (CDCl$_3$, HMDSO), δ: 1.23 (t, J=7.0 Hz, 3H); 1.18-1.85 (m, 8H); 2.27 (t, J=7.0 Hz, 4H); 3.10-3.81 (m, 8H); 3.92 (s, 2H); 4.12 (q, J=7.0 Hz, 2H); 7.32-7.59 (m, 3H); 7.65-7.94 (m, 4H).

Example 119

Methyl 8-{4-[2-(5-methoxy-1H-indol-3-yl)ethyl]-1-piperazinyl}-8-oxooctanoate (19t)

The title compound was obtained from suberic acid monomethyl ester (18b) and 5-methoxy-3-[2-(1-piperazinyl)ethyl]-1H-indole (16b) using Method L, yield 89%. $^1$H NMR (CDCl$_3$, HMDSO), δ: 1.18-1.78 (m, 8H); 2.34 (t, J=7.0 Hz, 4H); 2.52 (t, J=6.0 Hz, 4H); 2.65-2.89 (m, 4H); 3.38-3.74 (m, 4H); 3.67 (s, 3H); 3.85 (s, 3H); 6.87 (dd, J=8.8 and 3.0 Hz, 1H); 7.03 (t, J=3.0 Hz, 2H); 7.25 (d, J=8.8 Hz, 1H); 8.01 (s, 1H).

Example 120

Ethyl 8-{4-[2-(1-benzothiophen-3-yl)acetyl]-1-piperazinyl}-8-oxooctanoate (19u)

The title compound was obtained from suberic acid monoethyl ester (18c) and 2-(1-benzothiophen-3-yl)-1-(1-piperazinyl)-1-ethanone (13e) using Method L, yield 83%. $^1$H NMR (CDCl$_3$, HMDSO), δ: 1.23 (t, J=7.0 Hz, 3H); 1.16-1.87 (m, 8H); 2.29 (t, J=7.0 Hz, 4H); 3.27-3.83 (m, 8H); 3.94 (s, 2H); 4.12 (q, J=7.0 Hz, 2H); 7.18-7.52 (m, 2H); 7.72-7.96 (m, 2H).

Example 121

Ethyl 7-[4-(3,4-dichlorophenyl)-1-piperazinyl]-7-oxoheptanoate (19y)

The title compound was obtained from pimelic acid monoethyl ester (8a) and 1-(3,4-dichlorophenyl)piperazine (17) (commercially available) using Method L, yield 73%. $^1$H NMR (CDCl$_3$, HMDSO), δ: 1.23 (t, J=7.0 Hz, 3H); 1.14-1.87 (m, 6H); 2.16-2.49 (m, 4H); 2.98-3.23 (m, 4H); 3.47-3.83 (m, 4H); 4.09 (q, J=7.0 Hz, 2H); 6.74 (dd, J=8.8 and 3.0 Hz, 1H); 6.96 (d, J=3.0 Hz, 1H); 7.32 (d, J=8.8 Hz, 1H).

Example 122

Ethyl 7-[4-(4-fluorophenyl)-1-piperazinyl]-7-oxoheptanoate (19v)

The title compound was obtained from pimelic acid monoethyl ester (18a) and 1-(4-fluorophenyl)piperazine (17j) (commercially available) using Method L, yield 74%. $^1$H NMR (CDCl$_3$, HMDSO), δ: 1.22 (t, J=7.0 Hz, 3H); 1.16-1.89 (m, 6H); 2.16-2.49 (m, 4H); 2.93-3.18 (m, 4H); 3.49-3.87 (m, 4H); 4.09 (q, J=7.0 Hz, 2H); 6.77-7.14 (m, 4H).

Example 123

Ethyl 7-[4-(4-chlorophenyl)-1-piperazinyl]-7-oxoheptanoate (19w)

The title compound was obtained from pimelic acid monoethyl ester (18a) and 1-(4-chlorophenyl)piperazine (17k) (commercially available) using Method L, yield 75%. $^1$H NMR (CDCl$_3$, HMDSO), δ: 1.23 (t, J=7.0 Hz, 3H); 1.16-1.87 (m, 6H); 2.16-2.49 (m, 4H); 3.00-3.21 (m, 4H); 3.49-3.87 (m, 4H); 4.11 (q, J=7.0 Hz, 2H); 6.85 (d, J=8.8 Hz, 2H); 7.23 (d, J=8.8 Hz, 2H).

Method M—Synthesis of O-Benzylhydroxamate Esters

To a solution of dicarbonic acid monoethyl (or monomethyl) ester 18a-c (2.75 mmol) in anhydrous dichloromethane (10 mL) oxalyl chloride (0.84 mL, 9.63 mmol) and a drop of dimethylformamide were added, and the resulting mixture was stirred for 30 minutes at room temperature followed by 1 hour at 40° C. The solution was carefully evaporated under reduced pressure and the residue was dried in vacuum at 40° C. The resulting chloride was dissolved in anhydrous tetrahydrofuran (3 mL) and the obtained solution to a cold suspension (ice bath) of benzylhydroxylamine hydrochloride (2.75 mmol), tetrahydrofuran (10 mL), and saturated NaHCO$_3$ (10 mL) was added under vigorous stirring. The stirring was continued for 1 hour at ice bath temperature and 20 hours at room temperature. The mixture was diluted with brine (30 mL) and extracted with ethyl acetate (3×25 mL). The organic phase was washed with brine and dried (Na$_2$SO$_4$). The solvent was evaporated and the residue was chromatographed on silica gel (20 g) with chloroform-ethyl acetate (gradient from 100:0 to 50:50) as eluent to give the corresponding reaction product (20a-c) in 80-90% yield.

Example 124

Ethyl 7-[(benzyloxy)amino]-7-oxoheptanoate (20a)

The title product was obtained from heptanedioic acid monoethyl ester, using Method M. $^1$H NMR (CDCl$_3$, HMDSO), δ: 1.22 (t, J=7.0 Hz, 3H); 1.07-1.88 (m, 6H); 1.89-2.26 (m, 2H); 2.29 (t, J=7.0 Hz, 2H); 4.11 (q, J=7.0 Hz, 2H); 4.88 (s, 2H); 7.31 (s, 5H).

Example 125

Methyl 8-[(benzyloxy)amino]-8-oxooctanoate (20b)

The title product was obtained from octanedioic acid monomethyl ester, using Method M. $^1$H NMR (CDCl$_3$, HMDSO), δ: 1.09-1.83 (m, 8H); 1.87-2.27 (m, 2H); 2.27 (t, J=7.0 Hz, 2H); 3.63 (s, 3H); 4.87 (s, 2H); 7.29 (s, 5H).

Example 126

Ethyl 8-[(benzyloxy)amino]-8-oxooctanoate (20c)

The title product was obtained from octanedioic acid monoethyl ester, using Method M. $^1$H NMR (CDCl$_3$, HMDSO), δ: 1.23 (t, J=7.0 Hz, 3H); 1.09-1.83 (m, 8H); 1.87-2.27 (m, 2H); 2.27 (t, J=7.0 Hz, 2H); 4.12 (q, J=7.0 Hz, 2H); 4.87 (s, 2H); 7.29 (s, 5H).

Method N—Synthesis of O-Benzylhydroxamate Carboxylic Acids

To a solution of appropriate ester 20a-c (1, 5-2 mmol) in tetrahydrofuran (5 mL), a saturated aqueous solution of LiOH (5 mL) was added. The mixture was stirred for 5 hours at room temperature. The organic volatiles were evaporated under reduced pressure and the mixture was supplemented with water (20 mL). The mixture was washed with diethyl ether and aqueous phase was acidified with 2 M HCl to pH 3. The crude product was extracted with ethyl acetate (3×20 mL). The organic layer was washed with brine (3×10 mL) and dried (Na$_2$SO$_4$). The solvent was evaporated and the residue was dried in vacuum to give expected product 21a or 21b in 60-70% yield.

Example 127

7-[(Benzyloxy)amino]-7-oxoheptanoic acid (21a)

The title product was obtained from ethyl 7-[(benzyloxy)amino]-7-oxoheptanoate (20a), using Method N. $^1$H NMR (CDCl$_3$, HMDSO), δ: 1.07-1.88 (m, 6H); 1.89-2.26 (m, 2H); 2.29 (t, J=7.0 Hz, 2H); 4.88 (s, 2H); 7.32 (s, 5H).

Example 128

8-[(Benzyloxy)amino]-8-oxooctanoic acid (21b)

The title product was obtained from methyl 8-[(benzyloxy)amino]-8-oxooctanoate (20b) or ethyl 8-[(benzyloxy)amino]-8-oxooctanoate (20c), using Method N. $^1$H NMR (CDCl$_3$, HMDSO), δ: 1.09-1.81 (m, 8H); 1.88-2.29 (m, 2H); 2.27 (t, J=7.0 Hz, 2H); 4.86 (s, 2H); 7.30 (s, 5H).

Method P—General Synthesis of O-Benzyl Hydroxamates

A solution of dicarbonic acid N-benzyloxy monoamide 21a or 21b (1 eq) in anhydrous dimethylformamide (2 mL/mmol) was cooled in ice bath under argon atmosphere, and carbonyldiimidazole (1.1 eq.) was added. The mixture was stirred at ice bath temperature for 30 minutes and a solution of appropriate piperazine (1 eq) in dimethylformamide (2 mL/mmol) was added (if the piperazine was used in a hydrochloride form, triethylamine (3 eq) was added to the reaction mixture prior to the piperazine hydrochloride). The mixture was stirred at ice bath temperature for 1 hour followed by 20 hours at room temperature. Then the reaction mixture was diluted with brine and extracted with ethyl acetate. The organic phase was washed with brine, dried (Na$_2$SO$_4$), and the solvent was evaporated. The residue was chromatographed on silica gel with appropriate eluent (chloroform-ethyl acetate for less polar and ethyl acetate-methanol for more polar compounds) to give the corresponding reaction product 22a-k.

Example 129

N-(Benzyloxy)-8-[4-(4-cyanobenzoyl)-1-piperazinyl]-8-oxooctanamide (22a)

The title compound was obtained from 8-[(benzyloxy)amino]-8-oxooctanoic acid (21b) and 4-(1-piperazinylcarbonyl)benzonitrile (13j), using Method P, yield 79%. $^1$H NMR (CDCl$_3$, HMDSO), δ: 1.09-1.81 (m, 8H); 1.87-2.17 (m, 2H); 2.18-2.42 (m, 2H); 3.32-3.69 (m, 8H); 4.89 (s, 2H); 7.38 (s, 5H); 7.52 (d, J=8.8 Hz, 2H); 7.76 (d, J=8.8 Hz, 2H); 8.03 (s, 1H).

Example 130

N-(Benzyloxy)-7-oxo-7-[4-(2-pyridinyl)-1-piperazinyl]heptanamide (22b)

The title compound was obtained from 7-[(benzyloxy)amino]-7-oxoheptanoic acid (21a) and 1-(2-pyridinyl)piperazine (17l) (commercially available), using Method P, yield 50%. ¹H NMR (CDCl₃, HMDSO), δ: 1.16-1.81 (m, 6H); 2.36 (t, J=7.0 Hz, 2H); 3.21 (q, J=6.0 Hz, 2H); 3.36-3.85 (m, 8H); 4.76 (bs, 1H); 5.09 (s, 2H); 6.58-6.74 (m, 2H); 7.34 (s, 5H); 7.41-7.63 (m, 1H); 8.12-8.29 (m, 1H).

Example 131

N-(Benzyloxy)-8-(4-{2-[4-(dimethylamino)phenyl] acetyl}-1-piperazinyl)-8-oxooctanamide (22c)

The title compound was obtained from 8-[(benzyloxy) amino]-8-oxooctanoic acid (21b) and 2-[4-(dimethylamino) phenyl]-1-(1-piperazinyl)-1-ethanone (13k), using Method P, yield 68%. ¹H NMR (CDCl₃, HMDSO), δ: 1.05-1.81 (m, 8H); 1.85-2.32 (m, 4H); 2.89 (s, 6H); 3.07-3.69 (m, 8H); 3.65 (s, 2H); 4.87 (s, 2H); 6.67 (d, J=8.8 Hz, 2H); 7.07 (d, J=8.8 Hz, 2H); 7.36 (s, 5H); 8.00 (s, 1H).

Example 132

N-(Benzyloxy)-8-oxo-8-[4-(2-pyrimidinyl)-1-piperazinyl]octanamide (22d)

The title compound was obtained from 8-[(benzyloxy) amino]-8-oxooctanoic acid (2b) and 2-(1-piperazinyl)pyrimidine (17m) (commercially available), using Method P, yield 64%. ¹H NMR (CDCl₃, HMDSO), δ: 1.14-1.81 (m, 8H); 1.96-2.25 (m, 2H); 2.36 (t, J=7.0 Hz, 2H); 3.43-3.94 (m, 8H); 4.89 (s, 2H); 6.54 (t, J=5.0 Hz, 1H); 7.38 (s, 5H); 7.92-8.03 (m, 1H); 8.32 (d, J=5.0 Hz, 2H).

Example 133

N-(Benzyloxy)-8-(4-{3-[3-(dimethylamino)phenyl] propyl}-1-piperazinyl)-8-oxooctanamide (22e)

The title compound was obtained from 8-[(benzyloxy) amino]-8-oxooctanoic acid (21b) and N,N-dimethyl-3-[3-(1-piperazinyl)propyl]aniline (16k), using Method P, yield 63%. ¹H NMR (CDCl₃, HMDSO), δ: 1.18-1.83 (m, 8H); 2.07-2.38 (m, 4H); 2.43-2.76 (m, 8H); 2.92 (s, 6H); 3.38-3.80 (m, 4H); 4.92 (s, 2H); 6.71 (d, J=8.8 Hz, 2H); 7.12 (d, J=8.8 Hz, 2H); 7.41 (s, 5H); 8.07-8.36 (m, 1H).

Example 134

N-(Benzyloxy)-8-{4-[2-(2-naphthyloxy)acetyl]-1-piperazinyl}-8-oxooctanamide (22f)

The title compound was obtained from 8-[(benzyloxy) amino]-8-oxooctanoic acid (21b) and 2-(2-naphthyloxy)-1-(1-piperazinyl)-1-ethanone (13c), using Method P, yield 66%. ¹H NMR (CDCl₃, HMDSO), δ: 1.14-1.76 (m, 8H); 1.94-2.40 (m, 4H); 3.29-3.74 (m, 8H); 4.83 (s, 2H); 4.88 (s, 2H); 7.07-7.30 (m, 3H); 7.36 (s, 5H); 7.31-7.58 (m, 1H); 7.65-7.92 (m, 3H); 8.25 (bs, 1H).

Example 135

N-(Benzyloxy)-7-{4-[3-(1H-indol-3-yl)propanoyl]-1-piperazinyl}-7-oxoheptanamide (22g)

The title compound was obtained from 7-[(benzyloxy) amino]-7-oxoheptanoic acid (21a) and 3-(1H-indol-3-yl)-1-(1-piperazinyl)-1-propanone (13f), using Method P, yield 63%. ¹H NMR (CDCl₃, HMDSO), δ: 1.09-1.85 (m, 6H); 1.92-2.41 (m, 4H); 2.58-3.00 (m, 4H); 3.05-3.72 (m, 8H); 4.89 (s, 2H); 6.91-7.39 (m, 5H); 7.38 (s, 5H); 7.52-7.74 (m, 1H); 8.25-8.76 (m, 1H).

Example 136

N-(Benzyloxy)-7-[4-(1H-indol-3-ylcarbonyl)-1-piperazinyl]-7-oxoheptanamide (22h)

The title compound was obtained from 7-[(benzyloxy) amino]-7-oxoheptanoic acid (21a) and 1H-indol-3-yl(1-piperazinyl)methanone (13g), using Method P, yield 69%. ¹H NMR (CDCl₃, HMDSO), δ: 1.14-1.78 (m, 6H); 1.87-2.45 (m, 4H); 3.34-3.78 (m, 8H); 4.87 (s, 2H); 7.14-7.54 (m, 5H); 7.41 (s, 5H); 7.58-7.83 (m, 1H); 9.14-9.38 (m, 1H).

Example 137

N-(Benzyloxy)-7-{4-[3-(1H-indol-3-yl)propyl]-1-piperazinyl}-7-oxoheptanamide (22i)

The title compound was obtained from 7-[(benzyloxy) amino]-7-oxoheptanoic acid (21a) and 3-[3-(1-piperazinyl) propyl]-1H-indole (16f), using Method P, yield 87%. ¹H NMR (CDCl₃, HMDSO), δ: 1.14-2.00 (m, 8H); 2.12-2.56 (m, 8H); 2.67-2.96 (m, 4H); 3.32-3.71 (m, 4H); 4.89 (s, 2H); 6.92-7.36 (m, 5H); 7.38 (s, 5H); 7.49-7.69 (m, 1H); 7.85-8.00 (m, 1H).

Example 138

N-(Benzyloxy)-7-[4-(H-indol-3-ylmethyl)-1-piperazinyl]-7-oxoheptanamide (22j)

The title compound was obtained from 7-[(benzyloxy) amino]-7-oxoheptanoic acid (21a) and 3-(1-piperazinylmethyl)-1H-indole (16g), using Method P, yield 59%. ¹H NMR (CDCl₃, HMDSO), δ: 1.16-1.87 (m, 6H); 2.03-2.60 (m, 8H); 3.32-3.69 (m, 4H); 3.72 (s, 2H); 4.89 (s, 2H); 7.05-7.34 (m, 5H); 7.38 (s, 5H); 7.60-7.85 (m, 1H); 8.03-8.41 (m, 1H).

Example 139

N-(Benzyloxy)-7-[4-(3,4-dimethylphenyl)-1-piperazinyl]-7-oxoheptanamide (22k)

The title compound was obtained from 7-[(benzyloxy) amino]-7-oxoheptanoic acid (21a) and 1-(3,4-dimethylphenyl)piperazine (17n) (commercially available), using Method P, yield 71%. ¹H NMR (CDCl₃, HMDSO), δ: 1.14-1.80 (m, 6H); 2.11 (s, 3H) 2.16 (s, 3H); 2.36-2.49 (m, 4H); 3.36-3.85 (m, 8H); 4.89 (s, 2H); 6.70 (dd, J=8.8 and 3.0 Hz, 1H); 6.86 (d, J=3.0 Hz, 1H); 7.02 (d, J=8.8 Hz, 1H), 7.34 (s, 5H).

Method Q—General Synthesis of Hydroxamic Acids from Amidoesters

To a 1 M solution of hydroxylamine hydrochloride in methanol (5 mL, 5 mmol) a 5 M solution of sodium methylate (1 mL, 5 mmol) was added, and the precipitate was filtered off. To the filtrate, a solution of appropriate amidoester (19a-e) (2.47 mmol) in methanol (3 mL) was added and the resultant mixture was stirred at room temperature for 24 hours. The mixture was acidified with acetic acid to pH 5 and the solvent was evaporated. The residue was extracted with ethyl acetate (50 mL), the extract was washed with water, brine, and dried (MgSO₄). The extract was filtrated, concentrated to ca. 5-10 mL, and allowed to crystallize. The precipitate was filtered, washed with ethyl acetate, and dried in vacuum to give the corresponding hydroxamic acid.

Example 140

8-Oxo-8-(4-phenyl-piperazin-1-yl)-octanoic acid hydroxyamide (PX117402)

The title compound was obtained from 8-oxo-8-(4-phenyl-piperazin-1-yl)-octanoic acid methyl ester (19a) by Method Q, yield 42%. M.p. 134-136° C. $^1$H NMR (DMSO-d$_6$, HMDSO), δ: 1.16-1.38 (m, 4H); 1.38-1.60 (m, 4H); 1.93 (t, 2H, J=7.4 Hz); 2.33 (t, 2H, J=7.2 Hz); 3.09 (m, 4H); 3.57 (m, 4H); 6.80 (t, 1H, J=7.1 Hz); 6.94 (d, 2H, J=8.0 Hz); 7.22 (t, 2H, J=7.7 Hz); 8.66 (s, 1H); 10.33 (s, 1H). HPLC analysis on Symmetry C$_8$ column: impurities 1.3% (column size 3.9×150 mm; mobile phase acetonitrile-0.1% H$_3$PO$_4$, 30:70; detector UV 220 nm; sample concentration 0.5 mg/ml; flow rate 1.1 mL/min). Anal. Calcd for C$_{18}$H$_{27}$N$_3$O$_3$, %: C, 64.84; H, 8.16; N, 12.60. Found, %: C, 64.71; H, 8.20; N, 12.52.

Example 141

7-(4-Benzhydryl-piperazin-1-yl)-7-oxo-heptanoic acid hydroxyamide (PX117403)

The title compound was obtained from ethyl 7-(4-benzhydryl-1-piperazinyl)-7-oxoheptanoate (19b) by Method Q, yield 29%. M.p. 157-159° C. $^1$H NMR (DMSO-d$_6$, HMDSO) δ: 1.08-1.32 (m, 2H); 1.35-1.60 (m, 4H); 1.82-2.02 (m, 2H); 2.03-2.40 (m, 6H); 3.23-3.60 (m, 4H overlapped with a water signal of DMSO); 4.30 (s, 1H); 7.09-7.52 (m, 10H); 8.68 (s, 1H); 10.34 (s, 1H). HPLC analysis on Zorbax Rx-C$_{18}$ column: impurities 1.5% (column size 4.6×150 mm; mobile phase acetonitrile-water, 80:20; detector UV 220 nm; sample concentration 1.0 mg/ml; flow rate 1.0 mL/min). Anal. Calcd for C$_{24}$H$_{31}$N$_3$O$_3$, %: C, 70.39; H, 7.63; N, 10.26. Found, %: C, 70.09; H, 7.67; N, 10.11.

Example 142

7-Oxo-7-(4-phenyl-piperazin-1-yl)-heptanoic acid hydroxyamide (PX117404)

The title compound was obtained from ethyl 7-oxo-7-(4-phenyl-1-piperazinyl)heptanoate (19c) by Method Q, yield 27%. M.p. 107-109° C. $^1$H NMR (DMSO-d$_6$, HMDSO) δ: 1.15-1.36 (m, 2H); 1.38-1.60 (m, 4H); 1.93 (t, 2H, J=7.1 Hz); 2.33 (t, 2H, J=7.3 Hz); 3.09 (m, 4H); 3.58 (m, 4H); 6.80 (t, 1H, J=7.3 Hz); 6.95 (d, 2H, J=8.2 Hz); 7.22 (t, 2H, J=7.9 Hz); 8.69 (s, 1H); 10.35 (s, 1H). HPLC analysis on Zorbax SB-C$_{18}$ column: impurities 3% (column size 4.6×150 mm; mobile phase methanol-0.1% H$_3$PO$_4$, gradient from 50:50 to 90:10; detector UV 220 nm; sample concentration 0.55 mg/ml; flow rate 1.5 mL/min). Anal. Calcd for C$_{17}$H$_{25}$N$_3$O$_3$, %: C, 63.93; H, 7.89; N, 13.16. Found, %: C, 63.80; H, 7.89; N, 13.06.

Example 143

8-(4-Benzhydryl-piperazin-1-yl)-8-oxo-heptanoic acid hydroxyamide (PX117764)

The title compound was obtained from methyl 8-(4-benzhydryl-1-piperazinyl)-4-oxooctanoate (19d) by Method Q, yield 32%. M.p. 126-129° C. $^1$H NMR (DMSO-d$_6$, HMDSO), δ: 1.14-1.30 (m, 4H); 1.34-1.54 (m, 4H); 1.91 (t, 2H, J=7.3 Hz); 2.15-2.32 (m, 6H); 3.38-3.50 (m, 4H); 4.30 (s, 1H); 7.17-7.50 (m, 10H); 8.66 (s, 1H); 10.32 (s, 1H). HPLC analysis on Symmetry C$_8$ column: impurities 3.3% (column size 3.9×150 mm; mobile phase acetonitrile-0.1M phosphate buffer (pH 2.5), 50:50; detector UV 220 nm; sample concentration 0.5 mg/ml; flow rate 1.3 mL/min). Anal. Calcd for C$_{25}$H$_{33}$N$_3$O$_3$, %: C, 70.89; H, 7.85; N, 9.92. Found, %: C, 70.81; H, 7.63; N, 10.11.

Example 144

8-[4-(2-Methoxy-phenyl)-piperazin-1-yl]-8-oxo-octanoic acid hydroxyamide (PX117768)

The title compound was obtained from methyl 8-[4-(2-methoxyphenyl)-1-piperazinyl]-8-oxooctanoate (19e) by Method Q, yield 34%. M.p. 135-137° C. $^1$H NMR (DMSO-d$_6$, HMDSO), δ: 1.18-1.38 (m, 4H); 1.38-1.60 (m, 4H); 1.93 (t, 2H, J=7.3 Hz); 2.31 (t, 2H, J=7.2 Hz); 2.82-2.98 (m, 4H); 3.50-3.62 (m, 4H); 3.78 (s, 3H); 6.84-7.02 (m, 4H); 8.66 (s, 1H); 10.33 (s, 1H). HPLC analysis on Symmetry C$_8$ column: impurities <1.0% (column size 3.9×150 mm; mobile phase acetonitrile-0.1M phosphate buffer (pH 2.5), 30:70; detector UV 220 nm; sample concentration 0.5 mg/ml; flow rate 1.1 mL/min). Anal. Calcd for C$_{19}$H$_{29}$N$_3$O$_4$, %: C, 62.79; H, 8.04; N, 11.56. Found, %: C, 62.71; H, 8.07; N, 11.64.

Method R—General Synthesis of Hydroxamic Acids from Amidoesters

To a solution of amidoester 19f-w (1 mmol) in methanol (3-5 mL), a solution of hydroxylamine hydrochloride (0.278 g, 4 mmol) in methanol (3 mL) followed by a solution of NaOH (0.320 g, 8 mmol) in water (1 mL) were added. After stirring for 15-45 minutes at ambient temperature, the reaction mixture was diluted with brine and extracted with ethyl acetate (3×30 mL). The organic phase was washed with brine, evaporated under reduced pressure by adding benzene to remove traces of water several times, and dried in vacuum. The crude product was crystallized or chromatographed on silica gel to give the corresponding hydroxamic acid.

Example 145

8-[4-(2-Chloro-phenyl)-piperazin-1-yl]-8-oxo octanoic acid hydroxyamide (PX118791)

The title compound was obtained from methyl ethyl 8-[4-(2-chlorophenyl)-1-piperazinyl]-8-oxooctanoate (19f) using Method R. The crude product was crystallized from acetonitrile, yield 65%. M.p. 131-132° C. $^1$H NMR (DMSO-d$_6$, HMDSO), δ: 1.18-1.37 (m, 4H); 1.40-1.60 (m, 4H); 1.93 (t, J=7.0 Hz, 2H); 2.33 (t, J=7.3 Hz, 2H); 2.83-3.20 (m, 4H); 3.53-3.66 (m, 4H); 7.06 (dt, J=1.6 and 7.8 Hz, 1H); 7.15 (dd, J=1.4 and 8.2 Hz, 1H); 7.30 (dt, J=1.4 and 8.2 Hz, 1H); 7.43 (dd, J=1.6 and 7.8 Hz, 1H); 8.66 (s, 1H); 10.33 (s, 1H). HPLC analysis on Omnispher 5 C$_{18}$ column: impurities <1% (column size 4.6×150 mm; mobile phase 45% acetonitrile+55% 0.1M phosphate buffer (pH 2.5); detector UV 254 nm; sample concentration 1.0 mg/ml; flow rate 1.0 mL/min). Anal. Calcd for C$_{18}$H$_{28}$ClN$_3$O$_3$*0.4H$_2$O, %: C, 57.64; H, 7.20; N, 11.20. Found, %: C, 57.72; H, 7.03; N, 11.24.

Example 146

8-[4-(3-Chloro-phenyl)-piperazin-1-yl]-8-oxo octanoic acid hydroxyamide (PX118792)

The title compound was obtained from ethyl 8-[4-(3-chlorophenyl)-1-piperazinyl]-8-oxooctanoate (19g) using Method R. The crude product was crystallized from acetonitrile, yield 56%. M.p. 122-124° C. $^1$H NMR (DMSO-d$_6$, HMDSO), δ: 1.19-1.38 (m, 4H); 1.40-1.61 (m, 4H); 1.93 (t, J=7.2 Hz, 2H); 2.29 (t, J=7.4 Hz, 2H); 2.80-3.20 (m, 4H); 3.55-3.66 (m, 4H); 6.81 (d, J=7.8 Hz, 1H); 6.87-6.99 (m, 2H); 7.22 (t, J=7.8 Hz, 1H); 8.65 (d, J=1.4 Hz, 1H); 10.33 (s, 1H). HPLC analysis on Zorbax SB C$_{18}$ column: impurities ~2.5% (column size 4.6×150 mm; mobile phase acetonitrile-0.1M phosphate buffer (pH 2.5), gradient from 30:70 to 100:0; detector UV 254 nm; sample concentration 1.0 mg/ml; flow rate 1.5 mL/min). Anal. Calcd for C$_{18}$H$_{26}$ClN$_3$O$_3$, %: C, 58.77; H, 7.12; N, 11.42. Found, %: C, 58.41; H, 7.07; N, 11.44.

Example 147

7-[4-(2-Chloro-phenyl)-piperazin-1-yl]-7-oxo heptanoic acid hydroxyamide (PX118793)

The title compound was obtained from ethyl 7-[4-(2-chlorophenyl)-1-piperazinyl]-7-oxoheptanoate (19h) using Method R. The crude product was crystallized from acetonitrile, yield 62%. M.p. 128-130° C. $^1$H NMR (DMSO-d$_6$, HMDSO), δ: 1.17-1.36 (m, 2H); 1.41-1.62 (m, 4H); 1.94 (t, J=7.0 Hz, 2H); 2.33 (t, J=7.3 Hz, 2H); 2.80-3.20 (m, 4H); 3.54-3.67 (m, 4H); 7.06 (dt, J=1.6 and 7.8 Hz, 1H); 7.15 (dd, J=1.8 and 8.0 Hz, 1H); 7.30 (dt, J=1.8 and 8.0 Hz, 1H); 7.43 (dd, J=1.6 and 7.8 Hz, 1H); 8.67 (d, J=1.8 Hz, 1H); 10.33 (s, 1H). HPLC analysis on Omnispher 5 C$_{18}$ column: impurities ~1.8% (column size 4.6×150 mm; mobile phase 40% acetonitrile+60% 0.1M phosphate buffer (pH 2.5); detector UV 220 nm; sample concentration 1.0 mg/ml; flow rate 1.5 mL/min). Anal. Calcd for C$_{17}$H$_{24}$ClN$_3$O$_3$, %: C, 57.70; H, 6.84; N, 11.88. Found, %: C, 57.76; H, 6.87; N, 11.79.

Example 148

7-[4-(3-Chloro-phenyl)-piperazin-1-yl]-7-oxo heptanoic acid hydroxyamide (PX118794)

The title compound was obtained from ethyl 7-[4-(3-chlorophenyl)-1-piperazinyl]-7-oxoheptanoate (19i) using Method R. The crude product was crystallized from acetonitrile, yield 48%. M.p. 120-122° C. $^1$H NMR (DMSO-d$_6$, HMDSO), δ: 1.17-1.34 (m, 2H); 1.40-1.59 (m, 4H); 1.93 (t, J=7.3 Hz, 2H); 2.32 (t, J=7.3 Hz, 2H); 3.07-3.24 (m, 4H); 3.47-3.67 (m, 4H); 6.80 (dd, J=1.5 and 8.0 Hz, 1H); 6.86-6.98 (m, 2H); 7.22 (t, J=7.8 Hz, 1H); 8.65 (d, J=1.8 Hz, 1H); 10.33 (s, 1H). HPLC analysis on Zorbax SB C$_{18}$ column: impurities ~3% (column size 4.6×150 mm; mobile phase acetonitrile-0.1M phosphate buffer (pH 2.5), gradient from 30:70 to 100:0; detector UV 254 nm; sample concentration 0.5 mg/ml; flow rate 1.5 mL/min). Anal. Calcd for C$_{17}$H$_{24}$ClN$_3$O$_3$, %: C, 57.70; H, 6.84; N, 11.88. Found, %: C, 57.74; H, 6.86; N, 11.79.

Example 149

8-[4-(Naphthalene-2-carbonyl)-piperazin-1-yl]-8-oxo octanoic acid hydroxyamide (PX118830)

The title compound was obtained from ethyl 8-[4-(2-naphthoyl)-1-piperazinyl]-8-oxooctanoate (19j) using Method R. The crude product was crystallized from acetonitrile, yield 54%. M.p. 133.5-134.5° C. $^1$H NMR (DMSO-d$_6$, HMDSO), δ: 1.20-1.60 (m, 8H); 1.92 (t, J=7.2 Hz, 2H); 2.20-2.40 (m, 2H); 3.28-3.76 (m, 8H); 7.50-7.66 (m, 3H); 7.94-8.10 (m, 4H); 8.66 (d, J=1.6 Hz, 1H); 10.32 (s, 1H). HPLC analysis on Alltima C$_{18}$ column: impurities 3% (column size 4.6×150 mm; mobile phase 40% acetonitrile+60% 0.1M phosphate buffer (pH 2.5); detector UV 220 nm; sample concentration 0.5 mg/ml; flow rate 1.3 mL/min). Anal. Calcd for C$_{23}$H$_{29}$N$_3$O$_4$, %: C, 67.13; H, 7.10; N, 10.21. Found, %: C, 66.90; H, 7.09; N, 10.23.

Example 150

8-(4-Benzoyl-piperazin-1-yl)-8-oxo octanoic acid hydroxyamide (PX118831)

The title compound was obtained from ethyl 8-(4-benzoyl-1-piperazinyl)-8-oxooctanoate (19k) using Method R. The crude product was crystallized from acetonitrile, yield 29%. M.p. 100-101° C. $^1$H NMR (DMSO-d$_6$, HMDSO), δ: 1.18-1.36 (m, 4H); 1.38-1.58 (m, 4H); 1.92 (t, J=7.4 Hz, 2H); 2.30 (t, J=6.6 Hz, 2H); 3.49 (m, 8H); 7.38-7.50 (m, 5H); 8.66 (s, 1H); 10.32 (s, 1H). HPLC analysis on Alltima C$_{18}$ column: impurities 2.5% (column size 4.6×150 mm; mobile phase 20% acetonitrile+80% 0.1M phosphate buffer (pH 2.5); detector UV 254 nm; sample concentration 1.0 mg/ml; flow rate 1.7 mL/min). Anal. Calcd for C$_{19}$H$_{27}$N$_3$O$_4$*0.35H$_2$O, %: C, 62.06; H, 7.59; N, 11.43. Found, %: C, 62.03; H, 7.50; N, 11.33.

Example 151

8-[4-(4-Dimethylamino-benzoyl-piperazin-1-yl]-8-oxo octanoic acid hydroxyamide (PX118832)

The Title Compound was Obtained from Ethyl 8-{4-[4-(Dimethylamino)Benzoyl]-1-piperazinyl}-8-oxooctanoate (19l) using Method R. The crude product was crystallized from acetonitrile, yield 74%. M.p. 90-92° C. $^1$H NMR (DMSO-d$_6$, HMDSO), δ: 1.18-1.30 (m, 4H); 1.40-1.60 (m, 4H); 1.93 (t, J=7.2 Hz, 2H); 2.30 (t, J=7.0 Hz, 2H); 2.95 (s, 6H); 3.44-3.52 (m, 8H); 6.70 (d, J=8.6 Hz, 2H); 7.29 (d, J=8.6 Hz, 2H); 8.64 (s, 1H); 10.32 (s, 1H). HPLC analysis on Zorbax SB C$_{18}$ column: impurities ~10% (column size 4.6×150 mm; mobile phase gradient 15 min 10% acetonitrile/90% 0.1M phosphate buffer (pH 2.5)-100% 0.1M phosphate buffer; detector UV 254 nm; sample concentration 0.5 mg/ml; flow rate 1.0 mL/min). Anal. Calcd for C$_{21}$H$_{32}$N$_4$O$_4$*0.5H$_2$O, %: C, 61.00; H, 8.04; N, 13.55. Found, %: C, 60.98; H, 7.85; N, 13.37.

Example 152

8-[4-(4-Methoxyphenyl)-piperazin-1-yl]-8-oxo octanoic acid hydroxyamide (PX118846)

The title compound was obtained from ethyl 8-[4-(4-methoxyphenyl)-1-piperazinyl]-8-oxooctanoate (19m) using Method R. The crude product was crystallized from acetonitrile, yield 48%. M.p. 149-150° C. $^1$H NMR (DMSO-d$_6$, HMDSO), δ: 1.18-1.33 (m, 4H); 1.39-1.58 (m, 4H); 1.93 (t, J=7.2 Hz, 2H); 2.32 (t, J=7.4 Hz, 2H); 2.88-3.03 (m, 4H); 3.52-3.61 (m, 4H); 3.68 (s, 3H); 6.83 (dt, J=9.6 and 2.8 Hz, 2H); 6.90 (dt, J=9.6 and 2.8 Hz, 2H); 8.64 (s, 1H); 10.32 (s, 1H). HPLC analysis on Alltima C$_{18}$ column: impurities 1.5% (column size 4.6×150 mm; mobile phase 25% acetonitrile+75% 0.1M phosphate buffer (pH 2.5); detector UV 220 nm; sample concentration 0.5 mg/ml; flow rate 1.5 mL/min).

Anal. Calcd for $C_{19}H_{29}N_3O_4$, %: C, 62.79; H, 8.04; N, 11.56. Found, %: C, 62.65; H, 8.09; N, 11.53.

Example 153

8-[4-(3-Methoxyphenyl)-piperazin-1-yl]-8-oxo octanoic acid hydroxyamide (PX118847)

The title compound was obtained from ethyl 8-[4-(3-methoxyphenyl)-1-piperazinyl]-8-oxooctanoate (19n) using Method R. The crude product was crystallized from acetonitrile, yield 69%. M.p. 122-122.5° C. $^1$H NMR (DMSO-d$_5$, HMDSO), δ: 1.18-1.36 (m, 4H); 1.39-1.58 (m, 4H); 1.93 (t, J=7.0 Hz, 2H); 2.32 (t, J=7.6 Hz, 2H); 3.03-3.17 (m, 4H); 3.50-3.63 (m, 4H); 3.71 (s, 3H); 6.39 (dd, J=8.0 and 2.0 Hz, 1H); 6.46 (t, J=2.0 Hz, 1H); 6.52 (dd, J=8.0 and 2.0 Hz, 1H); 7.12 (t, J=8.0 Hz, 1H); 8.63 (d, J=1.6 Hz, 1H); 10.31 (s, 1H). HPLC analysis on Alltima $C_{18}$ column: impurities 1% (column size 4.6×150 mm; mobile phase 25% acetonitrile+75% 0.1M phosphate buffer (pH 2.5); detector UV 220 nm; sample concentration 0.5 mg/ml; flow rate 1.5 mL/min). Anal. Calcd for $C_{19}H_{29}N_3O_4$, %: C, 62.79; H, 8.04; N, 11.56. Found, %: C, 62.65; H, 8.06; N, 11.43.

Example 154

N-Hydroxy-8-[4-(4-nitrophenyl)-1-piperazinyl]-8-oxooctanamide (PX118849)

The title compound was obtained from ethyl 8-[4-(4-nitrophenyl)-1-piperazinyl]-8-oxooctanoate (19o) using Method R. The crude product was crystallized from acetonitrile, yield 31%. M.p. 125-127° C. $^1$H NMR (DMSO-d$_6$, HMDSO), δ: 1.20-1.28 (m, 4H); 1.33-1.50 (m, 4H); 1.93 (t, J=7.6 Hz, 2H); 2.33 (t, J=7.2 Hz, 2H); 3.40-3.70 (m, 8H); 7.00 (d, J=9.0 Hz, 2H); 8.07 (d, J=9.0 Hz, 2H); 8.67 (s, 1H); 10.33 (s, 1H). HPLC analysis on Alltima $C_{18}$ column: impurities 2.5% (column size 4.6×150 mm; mobile phase 40% acetonitrile+60% 0.1M phosphate buffer (pH 2.5); detector UV 215 nm; sample concentration 0.5 mg/ml; flow rate 1.5 mL/min). Anal. Calcd for $C_{18}H_{26}N_4O_5$, %: C, 57.13; H, 6.93; N, 14.80. Found, %: C, 57.06; H, 6.94; N, 14.72.

Example 155

N-Hydroxy-8-{4-[2-(5-methoxy-1H-indol-3-yl)acetyl]-1-piperazinyl}-8-oxooctanamide (PX118927)

The title compound was obtained from methyl 8-{4-[2-(5-methoxy-1H-indol-3-yl)acetyl]-1-piperazinyl}-8-oxooctanoate (19p) using Method R. The crude product was chromatographed on reverse phase Silasorb CL18 with methanol-0.1% $H_3PO_4$ as eluent. The eluate was evaporated, the residue was dissolved in ethyl acetate, the extract was washed with water, evaporated, and dried. Yield 35%. Foam. $^1$H NMR (DMSO-d$_6$, HMDSO), δ: 1.13-1.32 (m, 4H); 1.34-1.55 (m, 4H); 1.91 (t, J=7.3 Hz, 2H); 2.17-2.31 (m, 2H); 3.24-3.57 (m, 8H, overlapped with a signal of water); 3.73 (s, 3H); 3.75 (s, 2H); 6.71 (dd, J=8.8 and 2.4 Hz, 1H); 7.05 (d, J=2.4 Hz, 1H); 7.16 (br s, 1H); 7.22 (d, J=8.8 Hz, 1H); 8.67 (s, 1H); 10.33 (s, 1H); 10.75 (s, 1H). HPLC analysis on Kromasil $C_{18}$ column: impurities 5% (column size 4.6×150 mm; mobile phase 20% acetonitrile+80% 0.2M acetate buffer (pH 5.0); detector UV 230 nm; sample concentration 1.0 mg/ml; flow rate 1.5 mL/min). Anal. Calcd for $C_{23}H_{32}N_4O_5$*0.25$H_2O$, containing 4% of inorganic impurities, %: C, 59.06; H, 7.00; N, 11.98. Found, %: C, 59.01; H, 7.02; N, 11.97.

Example 156

N-Hydroxy-8-{4-[2-(2-naphthyloxy)ethyl]-1-piperazinyl}-8-oxooctanamide (PX118930)

The title compound was obtained from methyl 8-{4-[2-(2-naphthyloxy)ethyl]-1-piperazinyl}-8-oxooctanoate (19r) using Method R. The crude product was precipitated from diethyl ether, yield 35%. Foam. $^1$H NMR (DMSO-d$_6$, HMDSO), δ: 1.16-1.31 (m, 4H); 1.37-1.54 (m, 4H); 1.93 (t, J=7.2 Hz, 2H); 2.27 (t, J=7.4 Hz, 2H); 2.41-2.55 (m, 4H, overlapped with a signal of DMSO); 2.79 (t, J=5.9 Hz, 2H); 3.39-3.49 (m, 4H); 4.21 (t, J=5.9 Hz, 2H); 7.16 (dd, J=8.8 and 2.4 Hz, 1H); 7.29-7.50 (m, 3H); 7.76-7.86 (m, 3H); 8.67 (s, 1H); 10.33 (s, 1H). HPLC analysis on Alltima $C_{18}$ column: impurities 1% (column size 4.6×150 mm; mobile phase 25% acetonitrile+75% 0.1M phosphate buffer (pH 2.5); detector UV 220 nm; sample concentration 1.0 mg/ml; flow rate 1.3 mL/min). Anal. Calcd for $C_{24}H_{33}N_3O_4$*1.25$H_2O$, %: C, 64.05; H, 7.95; N, 9.34. Found, %: C, 64.17; H, 7.91; N, 9.28.

Example 157

N-Hydroxy-8-{4-[2-(1-naphthyloxy)acetyl]-1-piperazinyl}-8-oxooctanamide (PX118931)

The title compound was obtained from ethyl 8-{4-[2-(1-naphthyloxy)acetyl]-1-piperazinyl}-8-oxooctanoate (19s) using Method R. The crude product was precipitated from diethyl ether, yield 34%. Foam. $^1$H NMR (DMSO-d$_6$, HMDSO), δ: 1.14-1.33 (m, 4H); 1.37-1.56 (m, 4H); 1.92 (t, J=7.0 Hz, 2H); 2.21-2.36 (m, 2H); 3.22-3.61 (m, 8H, overlapped with a signal of $H_2O$); 3.92 (s, 2H); 7.34-7.57 (m, 3H); 7.80-7.95 (m, 4H); 8.66 (s, 1H); 10.32 (s, 1H). HPLC analysis on Alltima $C_{18}$ column: impurities 1% (column size 4.6×150 mm; mobile phase 50% acetonitrile+50% 0.1M phosphate buffer (pH 2.5); detector UV 220 nm; sample concentration 1.0 mg/ml; flow rate 1.0 mL/min). Anal. Calcd for $C_{24}H_{31}N_3O_5$, %: C, 65.29; H, 7.08; N, 9.52. Found, %: C, 65.15; H, 7.45; N, 9.40.

Example 158

N-Hydroxy-8-{4-[2-(5-methoxy-1H-indol-3-yl)ethyl]-1-piperazinyl}-8-oxooctanamide oxalate (PX118932)

The title compound was obtained from methyl 8-{4-[2-(5-methoxy-1H-indol-3-yl)ethyl]-1-piperazinyl}-8-oxooctanoate (19t) using Method R. The crude product (ca. 0.33 mmol) was dissolved in abs. ethanol (1.5 mL) and a solution of oxalic acid dihydrate (0.1 g, 0.79 mmol) in abs. ethanol (1 mL) was added. The reaction mixture was stirred for 2 hours at ambient temperature, the precipitate was filtered and washed with diethyl ether. The product was crystallized from ethanol and dried, yield 70%. M.p. 122-125° C. $^1$H NMR (DMSO-d$_6$, HMDSO), δ: 1.17-1.35 (m, 4H); 1.39-1.57 (m, 4H); 1.93 (t, J=7.6 Hz, 2H); 2.32 (t, J=7.4 Hz, 2H); 2.93-3.17 (m, 8H); 3.56-3.72 (m, 4H); 3.77 (s, 3H); 6.73 (dd, J=8.8 and 2.2 Hz, 1H); 7.03 (d, J=2.2 Hz, 1H); 7.16 (d, J=2.2 Hz, 1H); 7.23 (d, J=8.8 Hz, 2H); 10.35 (s, 1H); 10.75 (s, 1H). HPLC analysis on Zorbax SB $C_{18}$ column: impurities ~7% (column size 4.6×150 mm; mobile phase 15 min gradient: acetonitrile-0.1M phosphate buffer (pH 2.5); 30/70-100/0; detector UV

Example 159

8-{4-[2-(1-Benzothiophen-3-yl)acetyl]-1-piperazinyl}-N-hydroxy-8-oxooctanamide (PX118967)

The title compound was obtained from ethyl 8-{4-[2-(1-benzothiophen-3-yl)acetyl]-1-piperazinyl}-8-oxooctanoate (19u) using Method R. The crude product was crystallized from acetonitrile, yield 35%. M.p. 140-141° C. $^1$H NMR (DMSO-$d_6$, HMDSO), δ: 1.15-1.34 (m, 4H); 1.37-1.56 (m, 4H); 1.92 (t, J=7.3 Hz, 2H); 2.29 (t, J=7.3 Hz, 2H); 3.36-3.60 (m, 8H); 3.98 (s, 2H); 7.34-7.44 (m, 2H); 7.51 (s, 1H); 7.78-7.85 (m, 1H); 7.93-8.05 (m, 1H); 8.65 (s, 1H); 10.32 (s, 1H). HPLC analysis on Omnispher 5 $C_{18}$ column: impurities 1% (column size 4.6×150 mm; mobile phase 50% acetonitrile+50% 0.1M phosphate buffer (pH 2.5); detector UV 215 nm; sample concentration 0.5 mg/ml; flow rate 1.3 mL/min). Anal. Calcd for $C_{22}H_{29}N_3O_4S$, %: C, 61.23; H, 6.77; N, 9.74. Found, %: C, 60.76; H, 6.71; N, 9.82.

Example 160

7-[4-(3,4-Dichlorophenyl)-1-piperazinyl]-N-hydroxy-7-oxoheptanamide (PX118989)

The title compound was obtained from ethyl 7-[4-(4-dichlorophenyl)-1-piperazinyl]-7-oxoheptanoate (19v) using Method R. The crude product was crystallized from ethyl acetate-methanol (9:1), yield 43%. M.p. 125-126° C. $^1$H NMR (DMSO-$d_6$, HMDSO), δ: 1.14-1.34 (m, 2H); 1.38-1.59 (m, 4H); 1.93 (t, J=7.3 Hz, 2H); 2.32 (t, J=7.0 Hz, 2H); 3.07-3.26 (m, 4H); 3.48-3.63 (m, 4H); 6.94 (dd, J=8.8 and 2.9 Hz, 1H); 7.14 (d, J=2.9 Hz, 1H); 7.40 (d, J=8.8 Hz, 1H); 8.67 (d, J=1.5 Hz, 1H); 10.33 (s, 1H). HPLC analysis on Omnispher 5 $C_{18}$ column: impurities 1% (column size 4.6×150 mm; mobile phase 40% acetonitrile+60% 0.1M phosphate buffer (pH 2.5); detector UV 215 nm; sample concentration 1.0 mg/ml; flow rate 1.3 mL/min). Anal. Calcd for $C_{17}H_{23}Cl_2N_3O_3$, %: C, 52.59; H, 5.97; N, 10.82. Found, %: C, 52.50; H, 5.90; N, 10.75.

Example 161

7-[4-(4-Fluorophenyl)-1-piperazinyl]-N-hydroxy-7-oxoheptanamide (PX118990)

The title compound was obtained from ethyl 7-[4-(4-fluorophenyl)-1-piperazinyl]-7-oxoheptanoate (19v) using Method R. The crude product was crystallized from ethyl acetate-methanol (9:1), yield 29%. M.p. 119-120° C. $^1$H NMR (DMSO-$d_6$, HMDSO), δ: 1.18-1.34 (m, 2H); 1.39-1.59 (m, 4H); 1.93 (t, J=7.3 Hz, 2H); 2.32 (t, J=7.3 Hz, 2H); 2.94-3.11 (m, 4H); 3.51-3.62 (m, 4H); 6.92-7.13 (m, 4H); 8.67 (s, 1H); 10.33 (s, 1H). HPLC analysis on Alltima $C_{18}$ column: impurities 2% (column size 4.6×150 mm; mobile phase 35% acetonitrile+65% 0.1M phosphate buffer (pH 2.5); detector UV 254 nm; sample concentration 1.0 mg/ml; flow rate 1.0 mL/min). Anal. Calcd for $C_{17}H_{24}FN_3O_3$, %: C, 60.52; H, 7.17; N, 12.45. Found, %: C, 60.42; H, 7.22; N, 12.32.

Example 162

7-[4-(4-Chlorophenyl)-1-piperazinyl]-N-hydroxy-7-oxoheptanamide (PX118991)

The title compound was obtained from ethyl 7-[4-(4-chlorophenyl)-1-piperazinyl]-7-oxoheptanoate (19w) using Method R. The crude product was crystallized from ethyl acetate-methanol (9:1), yield 21%. M.p. 119-121° C. $^1$H NMR (DMSO-$d_6$, HMDSO), δ: 1.19-1.34 (m, 2H); 1.39-1.59 (m, 4H); 1.93 (t, J=7.3 Hz, 2H); 2.33 (t, J=7.3 Hz, 2H); 3.01-3.18 (m, 4H); 3.50-3.64 (m, 4H); 6.95 (d, J=8.8 Hz, 2H); 7.24 (d, J=8.8 Hz, 2H); 8.67 (s, 1H); 10.33 (s, 1H). HPLC analysis on Omnispher 5 $C_{18}$ column: impurities 2.2% (column size 4.6×150 mm; mobile phase 35% acetonitrile+65% 0.1M phosphate buffer (pH 2.5); detector UV 215 nm; sample concentration 1.0 mg/ml; flow rate 1.3 mL/min). Anal. Calcd for $C_{17}H_{24}ClN_3O_3$, %: C, 57.70; H, 6.84; N, 11.88. Found, %: C, 57.75; H, 6.84; N, 11.80.

Method S—General Synthesis of Hydroxamic Acids from O-benzyl Hydroxamates

To a solution of O-benzylhydroxamate 22a-k (1 mmol) in methanol (5-10 mL), 5% palladium on activated carbon catalyst (0.050 g) was added and the black suspension was vigorously stirred under hydrogen atmosphere until initial compound disappeared. The reaction mixture was filtered through a small amount of silica gel (ca. 1-2 cm thin layer), the sorbent was washed with methanol, and the filtrate was evaporated in vacuum. The crude product was crystallized or chromatographed on silica gel to give the corresponding hydroxamic acid.

Example 163

8-[4-(4-Cyanobenzoyl)-piperazin-1-yl]-8-oxo octanoic acid hydroxyamide (PX118844)

The title compound was obtained from N-(benzyloxy)-8-[4-(4-cyanobenzoyl)-1-piperazinyl]-8-oxooctanamide (22a, using Method S, yield 74%. M.p. 150-150.5° C. $^1$H NMR (DMSO-$d_6$, HMDSO), δ: 1.18-1.38 (m, 4H); 1.40-1.60 (m, 4H); 1.92 (t, J=7.0 Hz, 2H); 2.22-2.40 (m, 2H); 3.20-3.70 (m, overlapped with a signal of $H_2O$); 7.61 (d, J=8.0 Hz, 2H); 7.94 (d, J=8.0 Hz, 2H); 8.64 (s, 1H); 10.32 (s, 1H). HPLC analysis on Omnispher 5 $C_{18}$ column: impurities 2% (column size 4.6×150 mm; mobile phase 20% acetonitrile+80% 0.1M phosphate buffer (pH 2.5); detector UV 254 nm; sample concentration 0.5 mg/ml; flow rate 1.0 mL/min). Anal. Calcd for $C_{20}H_{26}N_4O_4$*0.5$H_2O$, %: C, 60.74; H, 6.88; N, 14.17. Found, %: C, 60.83; H, 6.82; N, 13.88.

Example 164

7-Oxo-7-(4-pyridin-2-yl-piperazin-1-yl]-heptanoic acid hydroxyamide oxalate (PX118845)

The title compound was obtained from N-(benzyloxy)-7-oxo-7-[4-(2-pyridinyl)-1-piperazinyl]heptanamide (22b), using Method S. The crude product (ca. 0.33 mmol) was dissolved in abs. ethanol (1.5 mL) and a solution of oxalic acid dihydrate (0.1 g, 0.79 mmol) in abs. ethanol (1 mL) was added. The reaction mixture was stirred for 2 hours at ambient temperature, the precipitate was filtered and washed with diethyl ether. The product was crystallized from ethanol and dried, yield 65%. M.p. 118-122° C. $^1$H NMR (DMSO-$d_6$, HMDSO), δ: 1.20-1.40 (m, 2H); 1.42-1.65 (m, 4H); 2.35 (t, J=7.2 Hz, 2H); 2.77 (t, J=7.2 Hz, 2H); 3.37-3.63 (m, 8H); 6.65

(dd, J=7.2 and 5.0 Hz, 1H); 6.83 (d, J=8.2 Hz, 1H); 7.55 (ddd, J=8.2, 7.2 and 1.8 Hz, 1H); 8.11 (dd, J=5.0 and 1.8 Hz, 1H). HPLC analysis on Ultra Aqueous $C_{18}$ column: impurities 2.3% (column size 4.6×150 mm; mobile phase 5% acetonitrile+95% 0.1M phosphate buffer (pH 2.5); detector UV 215 nm; sample concentration 0.5 mg/mL; flow rate 1.5 mL/min). Anal. Calcd for $C_{16}H_{24}N_4O_3*0.5C_2H_2O_4*0.5H_2O$, %: C, 54.53; H, 7.00; N, 14.96. Found, %: C, 54.43; H, 7.20; N, 14.84.

Example 165

8-(4-{2-[4-(Dimethylamino)phenyl]acetyl}-1-piperazinyl)-N-hydroxy-8-oxooctanamide (PX118848)

The Title Compound was Obtained from N-(Benzyloxy)-8-(4-{2-[4-(dimethylamino)phenyl]acetyl}-1-piperazinyl)-8-oxooctanamide (22c), using Method S. The crude product was precipitated from diethyl ether, yield 63%. M.p. 77-79° C. $^1H$ NMR (DMSO-$d_6$, HMDSO), δ: 1.18-1.34 (m, 4H); 1.36-1.56 (m, 4H); 1.92 (t, J=7.2 Hz, 2H); 2.27 (t, J=7.2 Hz, 2H); 2.85 (s 6H); 3.25-3.50 (m, 8H, overlapped with a signal of $H_2O$); 3.58 (s, 2H); 6.66 (d, J=8.2, 2H); 7.03 (d, J=8.2 Hz, 2H); 8.65 (s, 1H); 10.32 (s, 1H). HPLC analysis on Alltima $C_{18}$ column: impurities 4% (column size 4.6×150 mm; mobile phase 15% acetonitrile+85% 0.1M phosphate buffer (pH 2.5); detector UV 215 nm; sample concentration 0.5 mg/ml; flow rate 1.5 mL/min). Anal. Calcd for $C_{22}H_{34}N_4O_4*0.5H_2O$, %: C, 61.80; H, 8.25; N, 13.10. Found, %: C, 61.90; H, 8.18; N, 13.11.

Example 166

N-Hydroxy-8-oxo-8-[4-(2-pyrimidinyl)-1-piperazinyl]octanamide (PX118850)

The title compound was obtained from N-(benzyloxy)-8-oxo-8-[4-(2-pyrimidinyl)-1-piperazinyl]octanamide (22d), using Method S. The crude product was crystallized from methanol, yield 37%. M.p. 132-133.5° C. $^1H$ NMR (DMSO-$d_6$, HMDSO), δ: 1.18-1.36 (m, 4H); 1.38-1.59 (m, 4H); 1.93 (t, J=7.3 Hz, 2H); 2.33 (t, J=7.3 Hz, 2H); 3.46-3.58 (m, 4H); 3.62-3.80 (m, 4H); 6.65 (t, J=4.8 Hz, 1H); 8.37 (d, J=4.8 Hz, 2H); 8.65 (br s, 1H); 10.29 (br s, 1H). HPLC analysis on Alltima $C_{18}$ column: impurities 1% (column size 4.6×150 mm; mobile phase 20% acetonitrile+80% 0.1M phosphate buffer (pH 2.5); detector UV 230 nm; sample concentration 0.5 mg/ml; flow rate 1.5 mL/min). Anal. Calcd for $C_{16}H_{25}N_5O_3$, %: C, 57.30; H, 7.51; N, 20.88. Found, %: C, 57.23; H, 7.58; N, 20.80.

Example 167

8-{4-[4-(Dimethylamino)phenethyl]-1-piperazinyl}-N-hydroxy-8-oxooctanamide (PX118928)

The title compound was obtained from N-(benzyloxy)-8-(4-{3-[3-(dimethylamino)phenyl]propyl}-1-piperazinyl)-8-oxooctanamide (22e), using Method S. The crude product was crystallized from acetonitrile, yield 45%. M.p. 103-105° C. $^1H$ NMR (DMSO-$d_6$, HMDSO), δ: 1.11-1.33 (m, 4H); 1.35-1.54 (m, 4H); 1.92 (t, J=7.2 Hz, 2H); 2.26 (t, J=7.4 Hz, 2H); 2.24-2.66 (m, 8H, partially overlapped with a signal of DMSO); 2.83 (s, 6H); 3.25-3.50 (m, 4H, partially overlapped with a signal of water); 6.64 (d, J=8.6 Hz, 2H); 7.00 (d, J=8.6 Hz, 2H); 8.67 (s, 1H); 10.33 (s, 1H). HPLC analysis on Alltima $C_{18}$ column: impurities 1% (column size 4.6×150 mm; mobile phase 8% acetonitrile+92% 0.1M phosphate buffer (pH 2.5); detector UV 215 nm; sample concentration 1.0 mg/ml; flow rate 1.3 mL/min). Anal. Calcd for $C_{22}H_{35}N_4O_3$, containing 1% of inorganic impurities, %: C, 64.66; H, 8.88; N, 13.71. Found, %: C, 64.64; H, 8.94; N, 13.70.

Example 168

N-Hydroxy-8-{4-[2-(2-naphthyloxy)acetyl]-1-piperazinyl}-8-oxooctanamide (PX118929)

The title compound was obtained from N-(benzyloxy)-8-{4-[2-(2-naphthyloxy)acetyl]-1-piperazinyl}-8-oxooctanamide (22f), using Method S. The crude product was crystallized from acetonitrile, yield 45%. M.p. 139-140.5° C. $^1H$ NMR (DMSO-$d_6$, HMDSO), δ: 1.17-1.35 (m, 4H); 1.37-1.56 (m, 4H); 1.93 (t, J=7.2 Hz, 2H); 2.32 (t, J=7.0 Hz, 2H); 3.39-3.60 (m, 8H, overlapped with a signal of $H_2O$); 4.97 (s, 2H); 7.17-7.51 (m, 4H); 7.37-7.89 (m, 3H); 8.67 (s, 1H); 10.34 (s, 1H). TLC: single spot at $R_f$ 0.3 (ethyl acetate-methanol, 4:1; detection—UV-254 nm). Anal. Calcd for $C_{24}H_{31}N_3O_5$, containing 1% of inorganic impurities, %: C, 64.64; H, 7.01; N, 9.42. Found, %: C, 64.64; H, 6.96; N, 9.45.

Example 169

N-Hydroxy-7-{4-[3-(1H-indol-3-yl)propanoyl]-1-piperazinyl}-7-oxoheptanamide (PX118968)

The title compound was obtained from N-(benzyloxy)-7-{4-[3-(1H-indol-3-yl)propanoyl]-1-piperazinyl}-7-oxoheptanamide (22g), using Method S. The crude product was crystallized from methanol-ethyl acetate (1:2), yield 40%. M.p. 152.5-153.5° C. $^1H$ NMR (DMSO-$d_6$, HMDSO), δ: 1.13-1.33 (m, 2H); 1.36-1.57 (m, 4H); 1.92 (t, J=7.0 Hz, 2H); 2.27 (t, J=7.0 Hz, 2H); 2.67 (t, J=7.3 Hz, 2H); 2.93 (t, J=7.3 Hz, 2H); 3.25-3.52 (m, 8H, overlapped with a signal of $H_2O$); 6.96 (t, J=7.3 Hz, 1H); 7.05 (t, J=7.3 Hz, 1H); 7.14 (d, J=2.0 Hz, 1H); 7.33 (d, J=7.3 Hz, 1H); 7.51 (d, J=7.3 Hz, 1H); 8.67 (s, 1H); 10.34 (s, 1H); 10.78 (s, 1H). HPLC analysis on Alltima $C_{18}$ column: impurities 1% (column size 4.6×150 mm; mobile phase 20% acetonitrile+80% 0.1M phosphate buffer (pH 2.5); detector UV 215 nm; sample concentration 0.25 mg/ml; flow rate 1.5 mL/min). Anal. Calcd for $C_{22}H_{30}N_4O_4*0.5H_2O*0.1EtOAc$, %: C, 62.59; H, 7.42; N, 12.81. Found, %: C, 62.61; H, 7.35; N, 12.92.

Example 170

N-Hydroxy-7-[4-(1H-indol-3-ylcarbonyl)-1-piperazinyl]-7-oxoheptanamide (PX118969)

The title compound was obtained from N-(benzyloxy)-7-[4-(1H-indol-3-ylcarbonyl)-1-piperazinyl]-7-oxoheptanamide (22h), using Method S. The crude product was crystallized from methanol-ethyl acetate (2:3), yield 52%. M.p. 86-88° C. $^1H$ NMR (DMSO-$d_6$, HMDSO), δ: 1.16-1.35 (m, 2H); 1.39-1.59 (m, 4H); 1.93 (t, J=7.3 Hz, 2H); 2.32 (t, J=7.3 Hz, 2H); 3.43-3.70 (m, 8H); 7.04-7.21 (m, 2H); 7.44 (dd, J=7.3 and 1.5 Hz, 1H); 7.66-7.75 (m, 2H); 8.67 (s, 1H); 10.34 (s, 1H); 11.62 (s, 1H). HPLC analysis on Omnisphere 5 $C_{18}$ column: impurities 2% (column size 4.6×150 mm; mobile phase 20% acetonitrile+80% 0.1M phosphate buffer (pH 2.5); detector UV 215 nm; sample concentration 0.5 mg/ml; flow rate 1.3 mL/min). Anal. Calcd for $C_{20}H_{26}N_4O_4$*0.5$H_2O$*0.2 $CH_2Cl_2$, containing 2% of inorganic impurities, %: C, 58.18; H, 6.56; N, 13.30. Found, %: C, 58.12; H, 6.54; N, 13.33.

Example 171

N-Hydroxy-7-{4-[3-(1H-indol-3-yl)propyl]-1-piperazinyl}-7-oxoheptanamide (PX118970)

The title compound was obtained from N-(benzyloxy)-7-{4-[3-(1H-indol-3-yl)propyl]-1-piperazinyl}-7-oxoheptanamide (22i), using Method S. The crude product was crystallized from methanol-ethyl acetate (2:3), yield 23%. M.p. 165-166° C. $^1$H NMR (DMSO-$d_6$, HMDSO), δ: 1.11-1.32 (m, 2H); 1.35-1.57 (m, 4H); 1.79 (t, J=7.3 Hz, 2H); 1.92 (t, J=7.0 Hz, 2H); 2.18-2.41 (m, 10H); 2.68 (t, J=7.3 Hz, 2H); 3.42 (br s, 4H); 6.90-7.06 (m, 2H); 7.10 (s, 1H); 7.31 (d, J=7.3 Hz, 1H); 7.49 (d, J=7.3 Hz, 1H); 8.66 (s, 1H); 10.32 (s, 1H); 10.74 (s, 1H). HPLC analysis on μ Bondasphere Phenyl column: impurities 2.5% (column size 4.6×150 mm; mobile phase 20% acetonitrile+80% 0.1M phosphate buffer (pH 2.5); detector UV 210 nm; sample concentration 0.5 mg/ml; flow rate 1.5 mL/min). Anal. Calcd for $C_{22}H_{32}N_4O_3$, %: C, 65.97; H, 8.05; N, 13.99. Found, %: C, 65.85; H, 8.10; N, 13.97.

Example 172

N-Hydroxy-7-[4-(1H-indol-3-ylmethyl)-1-piperazinyl]-7-oxoheptanamide (PX118978)

The title compound was obtained from N-(benzyloxy)-7-[4-(1H-indol-3-ylmethyl)-1-piperazinyl]-7-oxoheptanamide (22j), using Method S. The crude product was crystallized from methanol-ethyl acetate (2:3), yield 52%. M.p. 65-67° C. $^1$H NMR (DMSO-$d_6$, HMDSO), δ: 1.10-1.30 (m, 2H); 1.34-1.56 (m, 4H); 1.91 (t, J=7.3 Hz, 2H); 2.24 (t, J=7.0 Hz, 2H); 2.23-2.50 (m, 4H, overlapped with a signal of DMSO); 3.25-3.48 (m, 4H, overlapped with a signal of water); 3.65 (s, 2H); 6.97 (t, J=7.3 Hz, 1H); 7.07 (t, J=7.3 Hz, 1H); 7.23 (s, 1H); 7.34 (d, J=7.3 Hz, 1H); 7.63 (d, J=7.3 Hz, 1H); 8.66 (s, 1H); 10.32 (s, 1H); 10.96 (s, 1H). HPLC analysis on Omnispher $C_{18}$ column: impurities 2% (column size 4.6×150 mm; mobile phase 15% acetonitrile+85% 0.1M phosphate buffer (pH 2.5); detector UV 210 nm; sample concentration 0.5 mg/ml; flow rate 1.0 mL/min). Anal. Calcd for $C_{20}H_{28}N_4O_3$*0.4$H_2O$*0.25 EtOAc, containing 4% of inorganic material, %: C, 60.49; H, 7.86; N, 13.44. Found, %: C, 60.65; H, 7.43; N, 13.39.

Example 173

7-[4-(3,4-Dimethylphenyl)-1-piperazinyl]-N-hydroxy-7-oxoheptanamide (PX118994)

The title compound was obtained from N-(benzyloxy)-7-[4-(3,4-dimethylphenyl)-1-piperazinyl]-7-oxoheptanamide (22k), using Method S. The crude product was crystallized from acetonitrile, yield 73%. M.p. 119.5-120.5° C. $^1$H NMR (DMSO-$d_8$, HMDSO), δ: 1.18-1.34 (m, 2H); 1.39-1.59 (m, 4H); 1.93 (t, J=7.3 Hz, 2H); 2.11 (s, 3H); 2.16 (s, 3H); 2.32 (t, J=7.3 Hz, 2H); 2.93-3.09 (m, 4H); 3.49-3.61 (m, 4H); 6.66 (dd, J=8.8 and 2.2 Hz, 1H); 6.76 (d, J=2.2 Hz, 1H); 6.97 (d, J=8.8 Hz, 1H); 8.67 (d, J=1.5 Hz, 1H); 10.34 (s, 1H). HPLC analysis on Alltima $C_{18}$ column: impurities <2% (column size 4.6×150 mm; mobile phase 25% acetonitrile+75% 0.1M phosphate buffer (pH 2.5); detector UV 210 nm; sample concentration 1.0 mg/ml; flow rate 1.5 mL/min). Anal. Calcd for $C_{19}H_{29}N_3O_3$, %: C, 65.68; H, 8.41; N, 12.09. Found, %: C, 65.65; H, 8.54; N, 12.09.

Example 174

8-[4-(3-Fluorophenyl)-piperazin-1-yl]-8-oxooctanoic acid hydroxyamide (PX118859)

The title compound was obtained using methods analogous to those described above. M.p. 149-150.5° C. $^1$H NMR (DMSO-$d_6$, HMDSO) δ: 1.19-1.37 (m, 4H); 1.39-1.58 (m, 4H); 1.93 (t, J=7.5 Hz, 2H); 2.32 (t, J=7.4 Hz, 2H); 2.88-3.04 (m, 4H); 3.54-3.65 (m, 4H); 6.93-7.22 (m, 4H); 8.65 (br s, 1H); 10.32 (s, 1H). HPLC analysis on Alltima $C_{18}$: ~1% impurities (column size 4.6×150 mm; mobile phase 35% acetonitrile+65% 0.1M phosphate buffer (pH 2.5); detector UV 220 nm; sample concentration 0.5 mg/ml; flow rate 1.5 mL/min). Anal. Calcd. for $C_{18}H_{26}FN_3O_3$, %: C, 61.52; H, 7.46; N, 11.96. Found, %: C, 61.45; H, 7.48; N, 11.88.

Example 175

8-Oxo-8-[4-(3-trifluoromethylphenyl)-piperazin-1-yl]-octanoic acid hydroxyamide (PX118860)

The title compound was obtained using methods analogous to those described above. M.p. 126-128° C. $^1$H NMR (DMSO-$d_6$, HMDSO) δ: 1.16-1.37 (m, 4H); 1.38-1.59 (m, 4H); 1.93 (t, J=7.4 Hz, 2H); 2.33 (t, J=7.0 Hz, 2H); 3.14-3.39 (m, 4H, overlapped with a signal of water); 3.52-3.65 (m, 4H); 7.09 (d, J=7.6 Hz, 1H); 7.18 (s, 1H); 7.22 (d, J=8.4 Hz, 1H); 7.43 (t, J=8.0 Hz, 1H); 8.64 (s, 1H); 10.32 (s, 1H). HPLC analysis on Omnispher 5 $C_{18}$: <1% impurities (column size 4.6×150 mm; mobile phase 40% acetonitrile+60% 0.1M phosphate buffer (pH 2.5); detector UV 254 nm; sample concentration 0.5 mg/ml; flow rate 1.5 mL/min). Anal. Calcd for $C_{19}H_{26}F_3N_3O_3$, %: C, 56.85; H, 6.53; N, 10.47. Found, %: C, 56.62; H, 6.48; N, 10.40.

Example 176

8-{4-[Bis-(4-fluorophenyl)-methyl]-piperazin-1-yl}-8-oxo octanoic acid hydroxyamide (PX118898)

The title compound was obtained using methods analogous to those described above. M.p. foam. $^1$H NMR (DMSO-$d_6$, HMDSO) δ: 1.16-1.35 (m, 4H); 1.38-1.58 (m, 4H); 1.91 (t, J=7.4 Hz, 2H); 2.15-2.30 (m, 6H); 3.52-3.65 (m, 4H, overlapped with a signal of water); 4.39 (s, 1H); 7.13 (t, J=8.6 Hz, 4H); 7.44 (dd, J=8.6 and 5.6 Hz, 4H); 8.65 (br s, 1H); 10.31 (br s, 1H). HPLC analysis on Alltima $C_{18}$: ~3.5% impurities. (column size 4.6×150 mm; mobile phase 70% acetonitrile+30% 0.1M phosphate buffer (pH 2.5); detector UV 220 nm; sample concentration 1.0 mg/ml; flow rate 1.3 mL/min). Anal. Calcd for $C_{25}H_{31}F_2N_3O_3$*0.25$H_2O$, %: C, 64.71; H, 6.84; N, 9.06. Found, %: C, 64.50; H, 6.81; N, 8.90.

Example 177

8-(3-Methyl-4-m-tolyl-piperazin-1-yl)-8-oxo octanoic acid hydroxyamide (PX118899)

The title compound was obtained using methods analogous to those described above. M.p. 75-76° C. $^1$H NMR (DMSO-$d_6$, HMDSO) δ: 0.82 and 0.90 (d and d, J=6.6 Hz, 3H); 1.14-1.35 (m, 4H); 1.39-1.59 (m, 4H); 1.93 (t, J=7.2 Hz, 2H);

2.24 (s, 3H); 2.13-2.42 (m, 2H); 2.80-3.53 (m, 5H, partly overlapped with a signal of H$_2$O); 3.62-4.31 (m, 2H); 6.59 (d, J=7.8 Hz, 1H); 6.69 (d, J=7.8 Hz, 1H); 6.72 (s, 1H); 7.09 (t, J=7.8 Hz, 1H); 8.65 (s, 1H); 10.32 (s, 1H). HPLC analysis on Omnispher 5 C$_{18}$: ~1.8% impurities (column size 4.6×150 mm; mobile phase 30% acetonitrile+70% 0.1M phosphate buffer (pH 2.5); detector UV 220 nm; sample concentration 1.0 mg/ml; flow rate 1.2 mL/min). Anal. Calcd. for C$_{20}$H$_{31}$N$_3$O$_3$, %: C, 66.45; H, 8.64; N, 11.62. Found, %: C, 66.43; H, 8.67; N, 11.52.

Example 178

8-[4-(2-1H-Indol-3-yl-acetyl)-piperazin-1-yl]-8-oxo octanoic acid hydroxyamide (PX118900)

The title compound was obtained using methods analogous to those described above. M.p. foam. $^1$H NMR (DMSO-d$_6$, HMDSO) δ: 1.10-1.31 (m, 4H); 1.34-1.56 (m, 4H); 1.93 (t, J=7.2 Hz, 2H); 2.18-2.35 (m, 2H); 3.20-3.58 (m, 8H, overlapped with a signal of H$_2$O); 3.79 (s, 2H); 6.96 (t, J=7.0 Hz, 1H); 7.07 (t, J=7.0 Hz, 1H); 7.21 (s, 1H); 7.34 (d, J=7.8 Hz, 1H); 7.55 (d, J=7.8 Hz, 1H); 8.65 (s, 1H); 10.32 (s, 1H); 10.93 (s, 1H). HPLC analysis on Alltima C$_{18}$: ~7.5% impurities (column size 4.6×150 mm; mobile phase 30% acetonitrile+70% 0.1M phosphate buffer (pH 2.5); detector UV 220 nm; sample concentration 1.0 mg/ml; flow rate 1.0 mL/min). Anal. Calcd. for C$_{22}$H$_{30}$N$_4$O$_4$*0.1H$_2$O*0.1EtOAc., containing 3% of inorganic impurities, %: C, 61.39; H, 7.13; N, 12.78. Found, %: C, 61.45; H, 7.08; N, 12.81.

Example 179

8-(4-Diphenylacetyl-piperazin-1-yl)-8-oxo octanoic acid hydroxyamide (PX118901)

The title compound was obtained using methods analogous to those described above. M.p. foam. $^1$H NMR (DMSO-d$_6$, HMDSO) δ: 1.14-1.30 (m, 4H); 1.34-1.54 (m, 4H); 1.93 (t, J=7.2 Hz, 2H); 2.17-2.32 (m, 2H); 3.09-3.21 (m, 2H); 3.30-3.58 (m, 6H, overlapped with a signal of H$_2$O); 5.55 (s, 1H); 7.15-7.37 (m, 10H); 8.66 (s, 1H); 0.33 (s, 1H). HPLC analysis on Omnispher 5 C$_{18}$: ~2.2% impurities. (column size 4.6×150 mm; mobile phase 60% acetonitrile+40% 0.1M phosphate buffer (pH 2.5); detector UV 220 nm; sample concentration 0.5 mg/ml; flow rate 1.2 mL/min.) Anal Calcd for C$_{26}$H$_{33}$N$_3$O$_4$*0.5 MeOH, %: C, 68.07; H, 7.54; N, 8.99. Found, %: C, 68.04; H, 7.23; N, 8.99.

Example 180

8-[4-(2-Naphthalen-2-yl-acetyl)-piperazin-1-yl]-8-oxo octanoic acid hydroxyamide (PX118902)

The title compound was obtained using methods analogous to those described above. M.p. foam. $^1$H NMR (DMSO-d$_6$, HMDSO) δ: 1.12-1.32 (m, 4H); 1.35-1.56 (m, 4H); 1.92 (t, J=7.4 Hz, 2H); 2.28 (t, J=6.8 Hz, 2H); 3.26-3.58 (m, 8H, overlapped with a signal of H$_2$O); 3.91 (s, 2H); 7.39 (dd, J=8.4 and 1.8 Hz, 1H); 7.45-7.54 (m, 2H); 7.73 (s, 1H); 7.79-7.92 (m, 3H); 8.67 (s, 1H); 10.33 (s, 1H). HPLC analysis on Alltima C$_{18}$: ~5% impurities (column size 4.6×150 mm; mobile phase 40% acetonitrile+60% 0.1M phosphate buffer (pH 2.5); detector UV 220 nm; sample concentration 0.5 mg/ml; flow rate 1.3 mL/min.) Anal. Calcd. for C$_{24}$H$_{31}$N$_3$O$_4$*0.75H$_2$O, %: C, 65.66; H, 7.46; N, 9.57. Found, %: C, 65.52; H, 7.40; N, 9.43.

Example 181

8-{4-[4-(1-Hydroxyimino-ethyl)-phenyl]-piperazin-1-yl}-8-oxo octanoic acid hydroxyamide (PX118903)

The title compound was obtained using methods analogous to those described above. M.p. 147-147.5° C. $^1$H NMR (DMSO-d$_6$, HMDSO) δ: 1.18-1.35 (m, 4H); 1.37-1.57 (m, 4H); 1.93 (t, J=7.4 Hz, 2H); 2.09 (s, 3H); 2.33 (t, J=7.2 Hz, 2H); 3.06-3.25 (m, 4H); 3.51-3.65 (m, 4H); 6.94 (d, J=8.8 Hz, 2H); 7.51 (d, J=8.8 Hz, 2H); 8.65 (s, 1H); 10.32 (s, 1H); 10.86 (s, 1H). HPLC analysis on Zorbax SB 5 C$_{18}$: ~5% of acetophenone derivative (sample contains ca. 5% of the corresponding methylketone 8-[4-(4-acetylphenyl)-1-piperazinyl]-N-hydroxy-8-oxooctanamide). (column size 4.6×150 mm; mobile phase acetonitrile-0.1M phosphate buffer (pH 2.5), gradient 15 min from 20:80 to 100:0; detector UV 254 nm; sample concentration 0.5 mg/ml; flow rate 1.0 mL/min.) Anal. Calcd. for C$_{20}$H$_{30}$N$_4$O$_4$ containing 5% of the acetophenone C$_{20}$H$_{29}$N$_3$O$_4$, %: C, 61.63; H, 7.75; N, 14.20. Found, %: C, 61.67; H, 7.76; N, 13.76.

Example 182

8-Oxo-8[4-(3-phenylallyl)-piperazin-1-yl]-octanoic acid hydroxyamide (PX118904)

The title compound was obtained using methods analogous to those described above. M.p. foam. $^1$H NMR (DMSO-d$_6$, HMDSO) δ: 1.14-1.32 (m, 4H); 1.36-1.55 (m, 4H); 1.93 (t, J=7.3 Hz, 2H); 2.19-2.45 (m, 6H); 3.10 (d, J=6.6 Hz, 2H); 3.27-3.51 (m, 4H, overlapped with a signal of H$_2$O); 6.29 (dt, J=6.60 and 16.2 Hz, 1H); 6.54 (d, J=16.2 Hz, 1H); 7.15-7.48 (m, 3H); 7.44 (d, J=6.6 Hz, 2H); 8.67 (br s, H); 10.33 (s, 1H). HPLC analysis on Alltima C$_{18}$: ~5% impurities (column size 4.6×150 mm; mobile phase 20% acetonitrile+80% 0.1M phosphate buffer (pH 2.5); detector UV 220 nm; sample concentration 1.0 mg/ml; flow rate 1.5 mL/min.) Anal. Calcd. for C$_{21}$H$_{31}$N$_3$O$_3$*0.5H$_2$O, %: C, 65.94; H, 8.43; N, 10.99. Found, %: C, 66.05; H, 8.28; N, 10.94.

Example 183

8-[4-(2-Naphthalen-2-yl-ethyl)-piperazin-1-yl]-8-oxo octanoic acid hydroxyamide (PX118908)

The title compound was obtained using methods analogous to those described above. M.p. 118-120° C. $^1$H NMR (DMSO-d$_6$, HMDSO) δ: 1.16-1.34 (m, 4H); 1.36-1.56 (m, 4H); 1.92 (t, J=7.3 Hz, 2H); 2.27 (t, J=7.6 Hz, 2H); 2.34-2.55 (m, 4H, overlapped with a signal of DMSO); 2.63 (t, J=8.4 Hz, 2H); 2.92 (t, J=8.4 Hz, 2H); 3.28-3.52 (m, 4H, overlapped with a signal of H$_2$O); 7.37-7.53 (m, 3H); 7.73 (s, 1H); 7.77-7.91 (m, 3H); 8.67 (s, 1H); 10.33 (s, 1H). HPLC analysis on Omnispher 5 C$_{18}$: ~1.5% impurities (column size 4.6×150 mm; mobile phase 25% acetonitrile+75% 0.1M phosphate buffer (pH 2.5); detector UV 220 nm; sample concentration 0.5 mg/ml; flow rate 1.2 mL/min.) Anal. Calcd. for C$_{24}$H$_{33}$N$_3$O$_3$, %: C, 70.04; H, 8.08; N, 10.21. Found, %: C, 69.31; H, 8.11; N, 10.20.

Example 184

8-[4-(2,2-Diphenyl-ethyl)-piperazin-1-yl]-8-oxo octanoic acid hydroxyamide (PX118909)

The title compound was obtained using methods analogous to those described above. M.p. 117-118° C. $^1$H NMR (DMSO-d$_6$, HMDSO) δ: 1.12-1.31 (m, 4H); 1.34-1.54 (m, 4H); 1.91 (t, J=7.4 Hz, 2H); 2.23 (t, J=7.4 Hz, 2H); 2.31-2.48 (m, 4H, overlapped with a signal of DMSO); 2.94 (d, J=7.6 Hz, 2H); 3.26-3.48 (m, 4H, overlapped with a signal of H$_2$O); 4.26 (t, J=7.6 Hz, 1H); 7.09-7.40 (m, 10H); 8.65 (s, 1H); 10.31 (s, 1H). HPLC analysis on Alltima C$_{18}$: <1% impurities. (column size: 4.6×150 mm; mobile phase 25% acetonitrile+75% 0.1M phosphate buffer (pH 2.5); detector UV 215 nm; sample concentration 1.0 mg/ml; flow rate 1.15 mL/min.) Anal. Calcd. for C$_{26}$H$_{35}$N$_3$O$_3$, %: C, 71.37; H, 8.06; N, 9.60. Found, %: C, 71.01; H, 8.11; N, 9.59.

Biological Activity

Candidate compounds were assessed for their ability to inhibit deacetylase activity (biochemical assays) and to inhibit cell proliferation (cell-based antiproliferation assays), as described below.

Primary Assay (1): Deacetylase Activity

Briefly, this assay relies on the release of radioactive acetate from a radioactively labelled histone fragment by the action of HDAC enzyme. Test compounds, which inhibit HDAC, reduce the yield of radioactive acetate. Signal (e.g., scintillation counts) measured in the presence and absence of a test compound provide an indication of that compound's ability to inhibit HDAC activity. Decreased activity indicates increased inhibition by the test compound.

The histone fragment was an N-terminal sequence from histone H4, and it was labelled with radioactively labelled acetyl groups using tritiated acetylcoenzyme A (coA) in conjunction with an enzyme which is the histone acetyltransferase domain of the transcriptional coactivator p300. 0.33 mg of peptide H4 (the N-terminal 20 amino acids of histone H4, synthesized using conventional methods) were incubated with His6-tagged p300 histone acetyltransferase domain (amino acids 1195-1673, expressed in *E. coli* strain BLR (DE3)pLysS (Novagen, Cat. No. 69451-3) and 3H-acetyl coA (10 µL of 3.95 Ci/mmol; from Amersham) in a total volume of 300 µL of HAT buffer (50 mM TrisCl pH 8, 5% glycerol, 50 mM KCl, 0.1 mM ethylenediaminetetraacetic acid (EDTA), 1 mM dithiothreitol (DTT) and 1 mM 4-(2-aminoethyl)-benzenesulfonylfluoride (AEBSF)). The mixture was incubated at 30° C. for 45 min after which the His-p300 was removed using nickel-trinitriloacetic acid agarose (Qiagen, Cat No. 30210). The acetylated peptide was then separated from free acetyl coA by size exclusion chromatography on Sephadex G-15 (Sigma G-15-120), using distilled H$_2$O as the mobile phase.

After purification of the radiolabelled histone fragment, it was incubated with a source of HDAC (e.g., an extract of HeLa cells (a rich source of HDAC), recombinantly produced HDAC1 or HDAC2) and any released acetate was extracted into an organic phase and quantitatively determined using scintillation counting. By including a test compound with the source of HDAC, that compound's ability to inhibit the HDAC was determined.

Primary Assay (2): Deacetylase Activity: Fluorescent Assay

Alternatively, the activity of the compounds as HDAC inhibitors was determined using a commercially available fluorescent assay kit: (Fluor de Lys™, BioMol Research Labs, Inc., Plymouth Meeting, USA). HeLa extract was incubated for 1 hour at 37° C. in assay buffer (25 mM HEPES, 137 mM NaCl, 2.7 mM KCl, 1 mM MgCl$_2$, pH 8.0) with 15 µM acetylated substrate in the presence of test compound (HDAC inhibitor). The extent of deacetylation was determined by the addition of 50 µL of a 1-in-500 dilution of Developer, and measurement of the fluorescence (excitation 355 nm, emission 460 nm), according to the instructions provided with the kit.

Extensive comparative studies have shown that Primary Assay (1) and Primary Assay (2), discussed above, yield equivalent results. Primary Assay results reported herein are (a) exclusively from (1); (b) exclusively from (2); or (c) from both (1) and (2).

HeLa Cell Extract

The HeLa cell extract was made from HeLa cells (ATCC Ref. No. CCL-2) by freeze-thawing three times in 60 mM TrisCl pH 8.0, 450 mM NaCl, 30% glycerol. Two cell volumes of extraction buffer were used, and particulate material was centrifuged out (20800 g, 4° C., 10 min). The supernatant extract having deacetylase activity was aliquoted and frozen for storage.

Recombinantly Produced HDAC1 and HDAC2

Recombinant plasmids were prepared as follows.

Full length human HDAC1 was cloned by PCR using a λgt11 Jurkat cDNA library (Clontech-HL5012b). The amplified fragment was inserted into the EcoRI-SalI sites of pFlag-CTC vector (Sigma-E5394), in frame with the Flag tag. A second PCR was carried out in order to amplify a fragment containing the HDAC1 sequence fused to the Flag tag. The resulting fragment was subcloned into the EcoRI-Sac1 sites of the baculovirus transfer vector pAcHTL-C (Pharmingen-21466P).

Full length mouse HDAC2 was subcloned into pAcHLT-A baculovirus transfer vector (Pharmingen-21464P) by PCR amplification of the EcoRI-Sac1 fragment from a HDAC2-pFlag-CTC construct.

Recombinant protein expression and purification was performed as follows.

HDAC1 and HDAC2 recombinant baculoviruses were constructed using BaculoGold Transfection Kit (Pharmingen-554740). Transfer vectors were co-transfected into SF9 insect cells (Pharmingen-21300C). Amplification of recombinant viruses was performed according to the Pharmingen Instruction Manual. SF9 cells were maintained in serum-free SF900 medium (Gibco 10902-096).

For protein production, 2×10$^7$ cells were infected with the appropriate recombinant virus for 3 days. Cells were then harvested and spun at 3,000 rpm for 5 minutes. They were then washed twice in PBS and resuspended in 2 pellet volumes of lysis buffer (25 mM HEPES pH 7.9, 0.1 mM EDTA, 400 mM KCl, 10% glycerol, 0.1% NP-40, 1 mM AEBSF). Resuspended cells were frozen on dry ice and thawed at 37° C. 3 times and centrifuged for 10 minutes at 14,000 rpm. The supernatant was collected and incubated with 300 µl of 50% Ni-NTA agarose bead slurry (Qiagen-30210). Incubation was carried out at 4° C. for 1 hour on a rotating wheel. The slurry was then centrifuged at 500 g for 5 minutes. Beads were washed twice in 1 ml of wash buffer (25 mM HEPES pH7.9, 0.1 mM EDTA, 150 mM KCl, 10% glycerol, 0.1% NP-40, 1 mM AEBSF). Protein was eluted 3 times in 300 µl elution buffer (25 mM HEPES pH 7.9, 0.1 mM EDTA, 250 mM KCl, 10% glycerol, 0.1% NP-40, 1 mM AEBSF) containing increasing concentrations of imidazole: 0.2 M, 0.5 M and 1 M. Each elution was performed for 5 minutes at room temperature. Eluted protein was kept in 50% glycerol at −70° C.

Assay Method

A source of HDAC (e.g., 2 µL of crude HeLa extract, 5 µL of HDAC1 or HDAC2; in elution buffer, as above) was incubated with 3 µL of radioactively labelled peptide along with appropriate dilutions of candidate compounds (1.5 µL) in a total volume of 150 µL of buffer (20 mM Tris pH 7.4, 10% glycerol). The reaction was carried out at 37° C. for one hour, after which the reaction was stopped by adding 20 µL of 1 M HCl/0.4 M sodium acetate. Then, 750 µL of ethyl acetate was added, the samples vortexed and, after centrifugation (14000 rpm, 5 min), 600 µL from the upper phase were transferred to a vial containing 3 mL of scintillation liquid (UltimaGold, Packard, Cat. No. 6013329). Radioactivity was measured using a Tri-Carb 2100TR Liquid Scintillation Analyzer (Packard).

Percent activity (% activity) for each test compound was calculated as:

% activity={$(S^C-B)/(S^o-B)$}×100 wherein $S^C$ denotes signal measured in the presence of enzyme and the compound being tested, $S^o$ denotes signal measured in the presence of enzyme but in the absence of the compound being tested, and B denotes the background signal measured in the absence of both enzyme and compound being tested. The IC50 corresponds to the concentration which achieves 50% activity.

IC50 data for several compounds of the present invention, as determined using this assay, are also shown in Table 1, below.

Measurement of cell viability in the presence of increasing concentration of test compound at different time points is used to assess both cytotoxicity and the effect of the compound on cell proliferation.

Secondary Assay: Cell Proliferation

Compounds with HDAC inhibition activity, as determined using the primary assay, were subsequently evaluated using secondary cell-based assays. The following cell lines were used:

HeLa—Human cervical adenocarcinoma cell line (ATCC ref. No. CCL-2).

K11—HPV E7 transformed human keratinocyte line provided by Pidder Jansen-Duerr, Institut für Biomedizinische Altemsforschung, Innsbruck, Austria.

NHEK-Ad—Primary human adult keratinocyte line (Cambrex Corp., East Rutherford, N.J., USA).

JURKAT—Human T-cell line (ATCC no. TIB-152).

Assay Method

Cells were cultured, exposed to candidate compounds, and incubated for a time, and the number of viable cells was then assessed using the Cell Proliferation Reagent WST-1 from Boehringer Mannheim (Cat. No. 1 644 807), described below.

Cells were plated in 96-well plates at 3-10×$10^3$ cells/well in 100 µL of culture medium. The following day, different concentrations of candidate compounds were added and the cells incubated at 37° C. for 48 h. Subsequently, 10 µL/well of WST-1 reagent was added and the cells reincubated for 1 hour. After the incubation time, absorbance was measured.

WST-1 is a tetrazolium salt which is cleaved to formazan dye by cellular enzymes. An expansion in the number of viable cells results in an increase in the overall activity of mitochondrial dehydrogenases in the sample. This augmentation in the enzyme activity leads to an increase in the amount of formazan dye formed, which directly correlates to the number of metabolically active cells in the culture. The formazan dye produced is quantified by a scanning multiwell spectrophotometer by measuring the absorbance of the dye solution at 450 nm wavelength (reference wavelength 690 nm).

Percent activity (% activity) in reducing the number of viable cells was calculated for each test compound as:

% activity={$(S^C-B)/(S^o-B)$}×100 wherein $S^C$ denotes signal measured in the presence of the compound being tested, $S^o$ denotes signal measured in the absence of the compound being tested, and B denotes the background signal measured in blank wells containing medium only. The IC50 corresponds to the concentration which achieves 50% activity. IC50 values were calculated using the software package Prism 3.0 (GraphPad Software Inc., San Diego, Calif.), setting top value at 100 and bottom value at 0.

IC50 data for several compounds of the present invention, as determined using this assay, are also shown in Table 2, below.

Measurement of cell viability in the presence of increasing concentration of test compound at different time points is used to assess both cytotoxicity and the effect of the compound on cell proliferation.

Screening in Mice with Intraperitoneal P388 Tumour

Female B6D2F1 hybrid mice weighing 19-23 grams were inoculated with the tumour cell line P388 ($10^6$ cells in 0.2 mL) intraperitoneally (IP). Inoculation of tumour cells was performed on a Friday and treatment with compounds at a dose of 64 µmol/kg/day started on Day 3 (Monday). The compounds were given as a single daily IP dose for five consecutive days. Compounds were dissolved in DMSO, at a concentration corresponding to 50 µL injection volume per treatment. Treatments were given at the same hour of the day (within one hour). Five mice in each group were treated with compounds, and with each series of experiments, control groups (not treated, and DMSO-treated) were included. Moribund mice were euthanised, and the day of death was recorded. Log-rank analysis of the survival data was performed using the statistical software SAS v8.1 (SAS Institute, Cary, N.C., USA).

Biological Data

IC50 (or percent activity) data for several compounds of the present invention, as determined using the assays described above are summarised in Table 1 and Table 2, below.

The results of in vivo studies of mice with intraperitoneal P388 tumour for several compounds of the present invention, using the methods described above, are summarised in Table 3.

TABLE 1

Biochemical Assay Data

| Compound | | HDAC Inhibition (IC50 unless otherwise specified) | | |
|---|---|---|---|---|
| No. | Ref. | HeLa | HDAC1 | HDAC2 |
| 1 | TSA | 5 nM | 15 nM | 17 nM |
| 2 | SAHA | 189 nM | — | — |
| 3 | PX117403 | 28% @ 500 nM | — | — |
| 4 | PX117404 | 35% @ 500 nM | — | — |
| 5 | PX117764 | 785 nM | — | — |
| 6 | PX117768 | 175 nM | — | — |
| 7 | PX118490 | 59% @ 100 nM | — | — |
| 8 | PX118491 | 47% @ 100 nM | — | — |
| 9 | PX118807 | 60% @ 100 nM | — | — |
| 10 | PX118810 | 46 nM | — | — |
| 11 | PX118811 | 42 nM | — | — |
| 12 | PX118812 | 26 nM | — | — |
| 13 | PX118791 | 36 nM | — | — |
| 14 | PX118792 | 34 nM | — | — |

TABLE 1-continued

Biochemical Assay Data

| Compound | | HDAC Inhibition (IC50 unless otherwise specified) | | |
|---|---|---|---|---|
| No. | Ref. | HeLa | HDAC1 | HDAC2 |
| 15 | PX118793 | 188 nM | — | — |
| 16 | PX118794 | 74 nM | — | — |
| 17 | PX118830 | 133 nM | — | — |
| 18 | PX118831 | 194 nM | — | — |
| 19 | PX118832 | 212 nM | — | — |
| 20 | PX118844 | 286 nM | — | — |
| 21 | PX118846 | 3.4 nM | — | — |
| 22 | PX118847 | 31 nM | — | — |
| 23 | PX118848 | 44% @ 100 nM | — | — |
| 24 | PX118849 | 26 nM | — | — |
| 25 | PX118850 | 70 nM | — | — |

TABLE 2

Cell-Based Antiproliferation Assay Data

| Compound | | Cell Proliferation Inhibition WST-1 IC50 unless otherwise specified) | | | |
|---|---|---|---|---|---|
| No. | Ref. | HeLa | K11 | NHEK-AD | Jurkat |
|  | TSA | 350 nM | 0.38 μM | 0.2 μM | 42 nM |
|  | Oxamflatin | — | 4.82 μM | 3.53 μM | 170 nM |
|  | MS-275 | — | 9.16 μM | 3.1 μM | 365 nM |
|  | SAHA | — | 6.82 μM | 5.37 μM | 750 nM |
| 1 | PX117403 | — | — | — | — |
| 2 | PX117404 | — | — | — | — |
| 3 | PX117764 | 29.2 μM | 9.45 μM | — | 2.68 μM |
| 4 | PX117768 | 3.30 μM | 8.67 μM | — | 1.04 μM |
| 5 | PX118490 | 1.00 μM | 2.49 μM | — | 460 nM |
| 6 | PX118491 | 18 μM | 8.24 μM | — | 3.21 μM |

TABLE 3

In Vivo Studies of Mice with Intraperitoneal P388 Tumour

| Compound | Log rank statistic | Wilcoxon statistic | No. of mice |
|---|---|---|---|
| — | 6.8173 | 1556.0 | 25 |
| DMSO | 6.4056 | 1290.0 | 20 |
| PX118490 | −3.3797 | −654.0 | 5 |
| PX118807 | −4.6177 | −750.0 | 5 |
| PX118871 | −3.4210 | −605.0 | 5 |
| PX118875 | −3.0949 | −525.0 | 5 |
| PX118882 | −4.9869 | −613.0 | 5 |
| PX118893 | −3.5651 | −725.0 | 5 |
| PX118905 | −4.0610 | −565.0 | 5 |
| PX118907 | −4.1247 | −817.0 | 5 |
| PX118910 | −9.6221 | −869.0 | 5 |

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention as set out in the appended claims.

REFERENCES

A number of patents and publications are cited herein in order to more fully describe and disclose the invention and the state of the art to which the invention pertains. Full citations for these references are provided herein. Each of these references is incorporated herein by reference in its entirety into the present disclosure.

Alpegiani et al., 1999, "Preparation of succinyl piperidinamides, morpholinamides, piperazinamides, and analogs as matrix metalloprotease inhibitors," published international (PCT) patent application number WO 99/02510, published 21 Jan. 1999.

Andrews et al., 2000, *Int. J. Parasitol.*, Vol. 30, No. 6, pp. 761-768.

Bair et al., 2002, "Deacetylase Inhibitors," published international (PCT) patent application number WO 02/22577, published 21 Mar. 2002.

Barlaam et al., 2000, "Preparation of arylpiperazines as metalloproteinase inhibiting agents (MMP)," published international (PCT) patent application number WO 00/12478, published 9 Mar. 2000.

Barlaam et al., 2001, "Preparation of arylpiperazines and arylpiperidines as metalloproteinase inhibiting agents," published international (PCT) patent application number WO 01/62751, published 30 Aug. 2001.

Barta et al., 2000, "Synthesis and activity of selective MMP inhibitors with an aryl backbone," *Bioorg. Med. Chem. Lett.*, Vol. 10, No. 24, pp. 2815-2817.

Baxter et al, 2000, "Preparation of hydroxamic acid derivatives as inhibitors of matrix metalloproteinses," published international (PCT) patent application number WO 00/69839, published 23 Nov. 2000.

Baxter et al., 1999, "Hydroxamic and carboxylic acid derivatives having MMP and TNF inhibitory activity," published international (PCT) patent application number WO 99/24399, published 20 May 1999.

Bedell et al., 2000, "Preparation of hydroxamic acid derivatives as matrix metalloprotease inhibitors," published international (PCT) patent application number WO 00/69819, published 23 Nov. 2000.

Bedell et al., 2001, "Preparation of sulfonyl aryl or heteroaryl hydroxamic acid compounds as inhibitors of matrix metalloproteinase," published international (PCT) patent application number WO 01/85680, published 15 Nov. 2001.

Bernhard, D. et al., 1999, "Apoptosis induced by the histone deacetylase inhibitor sodium butyrate in human leukemic lymphoblasts," *FASEB J.*, Vol. 13, No. 14, pp. 1991-2001.

Bernstein et al., 2000, *Proc. Natl. Acad. Sci. USA*, Vol. 97, No. 25, pp. 13708-13713.

Billedeau et al., 2000, "Preparation of amino acid sulfonamide hydroxamates as inhibitors of procollagen C-proteinase," published international (PCT) patent application number WO 00/37436, published 29 Jun. 2000.

Billedeau R J et al (2000) "Preparation of amino acid sulfonamide hydroxamates as inhibitors of procollagen C-proteinase." U.S. Pat. No. 6,492,394.

Brehm, A., et al., 1998, "Retinoblastoma protein recruits histone deacetylase to repress transcription," *Nature*, 1998, Vol. 391, pp. 597-601.

Broadhurst et al., 1993, "Preparation of oxoheterocyclyl-substituted hydroxamic acid derivatives as collagenase inhibitors," published European patent application number EP 574 758, published 22 Dec. 1993.

Broadhurst et al., 1995, "Hydroxamic acid derivatives with tricyclic substitution, useful as collagenase inhibitors," published European patent application number EP 684 240 published 29 Nov. 1995.

Buchwald, S. L., et al., 2000a, *J. Org. Chem.*, Vol. 65, p. 1144; Buchwald, S. L., et al., 2000b, *J. Org. Chem.*, Vol. 65, p. 1158; Buchwald, S. L., et al., 2001, *J. Org. Chem.*, Vol. 66, p. 3820;

Chang et al., 2000, *Nucleic Acids Res.*, Vol. 28, No. 20, pp. 3918-3925.

Chong L et al (2002) "Preparation of hydroxamic acid peptide deformylase inhibitors as antibacterial agents." Published PCT application WO0228829

Corneil et al., 1998, published Japanese patent application, publication number JP 10114681 A2.

Dangond et al., 1998, *Biochem. Biophys. Res. Commun.*, Vol. 242, No. 3, pp. 648-652.

David, G., et al., 1998, *Oncogene*, Vol. 16(19), pp. 2549-2556.

Davie, J. R., 1998, "Covalent modifications of histones: expression from chromatic templates," *Curr. Opin. Genet. Dev.*, Vol. 8, pp. 173-178.

De Crescenzo et al., 2000, "Preparation of sulfamato hydroxamic acid metalloprotease inhibitors," published international (PCT) patent application number WO 00/46221, published 10 Aug. 2000.

Desai et al., 1999, *Proc. AACR*, Vol. 40, abstract #2396.

Emiliani, S., et al., 1998, "Characterization of a human RPD3 ortholog, HDAC3," *Proc. Natl. Acad. Sci. USA*, Vol. 95, p. 2795-2800.

Finnin et al., 1999, *Nature*, Vol. 401, pp. 188-193.

Fort, Y. et al., 2001, *Tetrahedron*, Vol. 57, p. 7657.

Furukawa et al., 1998, U.S. Pat. No. 5,834,249, "Process for production of protein," 10 Nov. 1998.

Geerts et al., 1998, European patent publication no. EP 0 827 742 A1, published 11 Mar. 1998.

Grozinger et al., 1999, *Proc. Natl. Acad. Sci. USA*, Vol. 96, pp. 4868-4873.

Hannah et al., 2001, "Preparation of hydroxamic acid derivatives," published international (PCT) patent application number WO 01/87870, published 22 Nov. 2001.

Hartwig, J. F., et al., 1999, *J. Org. Chem.*, Vol. 64, p. 5575.

Hoshikawa, Y., et al., 1994, *Exp. Cell. Res.*, Vol. 214(1), pp. 189-197.

Hou et al., 2001, "Binding affinities for a series of selective inhibitors of gelatinase-A using molecular dynamics with a linear interaction energy approach," *J. Phys. Chem. B*, Vol. 105, No. 22, pp. 5304-5315.

Howe, L., et al., 1999, *Crit. Rev. Eukarvot. Gene Expr.*, Vol. 9(3-4), pp. 231-243.

Iavarone et al., 1999, *Mol. Cell. Biol.*, Vol. 19, No. 1, pp. 916-922.

Kao et al., 2000, *Genes & Dev.*, Vol. 14, p. 55-66.

Kijima et al., 1993, *J. Biol. Chem.*, Vol. 268, pp. 22429-22435.

Kim et al., 1999, *Oncogene*, Vol. 18(15), pp. 2461-2470.

Kim et al., 2001, *Nature Medicine*, Vol. 7, No. 4, pp. 437-443.

Kim, M. S., et al., 2001 "Histone deacetylases induce angiogenesis by negative regulation of tumour suppressor genes," *Nature Medicine*, Vol 7. No. 4 pp. 437-443.

Kimura et al., 1994, *Biol. Pharm. Bull.*, Vol. 17, No. 3, pp. 399-402.

Kitamura, K., et al., 2000, *Br. J. Haematol.*, Vol. 108(4), pp. 696-702.

Kouzarides, T., 1999, "Histone acetylases and deacetylases in cell proliferation," *Curr. Opin. Genet. Dev.*, Vol. 9, No. 1, pp. 40-48.

Kuusisto et al., 2001, *Biochem. Biophys. Res. Commun.*, Vol. 280, No. 1, pp. 223-228.

Kwon et al., 1998, *Proc. Natl. Acad. Sci. USA*, Vol. 95, pp. 3356-3361.

Laherty, C. D., et al., 1997, *Cell*, Vol. 89(3), pp. 349-356.

Lea and Tulsyan, 1995; *Anticancer Res.*, Vol. 15, pp. 879-883.

Lea et al., 1999, *Int. J. Oncol.*, Vol. 2, pp. 347-352.

Lin, R. J., et al., 1998, *Nature*, Vol. 391(6669), pp. 811-814.

Martin et al., 2000, "Preparation of hydroxamic acid derivatives as proteinase inhibitors," published international (PCT) patent application number WO 00/12477, published 9 Mar. 2000.

McCaffrey et al., 1997, *Blood*, Vol. 90, No. 5, pp. 2075-2083.

Mielnicki, L. M., et al., 1999, *Exp. Cell. Res.*, Vol. 249(1), pp. 161-176.

Ng, H. H. and Bird, A., 2000, *Trends Biochem. Sci.*, Vol. 25(3), pp. 121-126.

Niki et al., 1999, *Hepatology*, Vol. 29, No. 3, pp. 858-867.

Nokajima et al., 1998, *Exp. Cell Res.*, Vol. 241, pp. 126-133.

Onishi et al., 1996, *Science*, Vol. 274, pp. 939-940.

Owen et al., 2000, "Preparation of hydroxamic acid carboxylic acid derivatives for treating conditions associated with matrix metalloproteinase, ADAM or ADAM-TS enzymes," published international (PCT) patent application number WO 00/56704, published 28 Nov. 2000.

Owen et al., 2001, "Preparation of hydroxamic acid derivatives as matrix metalloprotease (MM P) inhibitors," published international (PCT) patent application number WO 01/44189, published 21 Jun. 2001.

Pazin, M. J., et al., 1997, "What's up and down with histone deacetylation and transcription?," *Cell*, Vol. 89, No. 3, pp. 325-328.

Pratt et al., 2001, "Preparation of hydroxamic acid and N-formyl hydroxylamine derivatives as antibacterial agents," published international (PCT) patent application number WO 01/10834, published 15 Feb. 2001.

Richon et al, 1996, *Proc. Natl. Acad. Sci. USA*, Vol. 93, pp. 5705-5708.

Richon et al., 1998, "A class of hybrid poler inducers of transformed cell differentiation inhibits histone deacetylases," *Proc. Natl. Acad. Sci. USA*, Vol. 95, pp. 3003-3007.

Saito et al., 1999, *Proc. Natl. Acad. Sci. USA*, Vol. 96, pp. 4592-4597.

Saunders, N. et al, 1999 "Histone deacetylase inhibitors as potential anti-skin cancer agents," *Cancer Res.*, Vol. 59, No. 2 pp. 399-404.

Sonoda, H. et al., 1996, *Oncogene*, Vol. 13, pp. 143-149.

Spencer, V. A. and Davie, J. R., 1999, *Gene*, Vol. 240(1), pp. 1-12.

Suzuki et al., 1999, "Synthesis and histone deacetylase inhibitory activity of new benzamide derivatives," *J. Med. Chem.*, Vol. 42, pp. 3001-3003.

Takahashi et al., 1996, *J. Antibiot. (Tokyo)*, Vol. 49, No. 5, pp. 453-457.

Takahashi, I., et al, 1996, "Selective inhibition of IL-2 gene expression by trichostatin A, a potent inhibitor of mammalian histone deacetylase," *J. Antibiot. (Tokyo)*, Vol. 49, No. 5, pp. 453-457.

Tauton, J., et al., 1996, "A mammalian histone deacetylase related to the yeast transcriptional regulator Rpd3p," *Science*, Vol. 272, pp. 408-411.

Tsuji et al., 1976, *J. Antibiot. (Tokyo)*, Vol. 29, No. 1, pp. 1-6.

Ueda, H., et al., 1994, *J. Antibiot. (Tokyo)*, Vol. 47(3), pp. 315-323.

Van den Wyngaert et al., 2000, *FEBS*, Vol. 478, pp. 77-83.

Vigushin et al., 2001, *Clin. Cancer Res.*, Vol. 7, No. 4, pp. 971-976.

Warrell et al., 1998, *J. Natl. Cancer Inst.*, Vol. 90, pp. 1621-1625.

Watkins, C., et al., 2002a, "Carbamic acid compounds comprising a sulfonamide linkage as HDAC inhibitors," published international (PCT) patent application number WO 02/30879(PCT/GB01/04326) published 27 Sep. 2002.

Watkins, C., et al., 2002b, "Carbamic acid compounds comprising an ether linkage as HDAC inhibitors," published international (PCT) patent application number WO 02/26703(PCT/GB01/04327) published 27 Sep. 2002.

Watkins, C., et al., 2002c, "Carbamic acid compounds comprising an amide linkage as HDAC inhibitors," published international (PCT) patent application number WO 02/26696 (PCT/GB01/04329) published 27 Sep. 2002.

Wong, J., et al., 1998, *EMBO J.*, Vol. 17(2), pp. 520-534.

Yang, W. M., et al., 1996, "Transcriptional repression of YY1 is mediated by interaction with a mammalian homolog of the yeast global regulator RPD3," *Proc. Natl. Acad. Sci. USA*, Vol. 93, pp. 12845-12850.

Yang, W. M., et al., 1997, "Isolation and characterization of cDNAs corresponding to an additional member of the human histone deacetylase gene family," *J. Biol. Chem.*, Vol 272, pp. 28001-28007.

Yoshida et al., 1995, *Bioessays*, Vol. 17, pp. 423-430.

Yoshida, M. and Horinouchi, S., 1999, *Ann. N.Y. Acad. Sci.*, Vol. 886, pp. 23-36.

Yoshida, M., Beppu, T., 1988, "Reversible arrest of proliferation of rat 3Y1 fibroblasts in both G1 and G2 phases by trichostatin A," *Exp. Cell. Res.*, Vol. 177, pp. 122-131.

Yoshida, M., et al., 1990a, *J. Biol. Chem.*, Vol. 265(28), pp. 17174-17179.

Yoshida, M., et al., 1990b, *J. Antibiot. (Tokyo)*, Vol. 43(9), pp. 1101-1106.

The invention claimed is:

1. A method for the treatment of a condition selected from melanoma or leukemia or cervical cancer
comprising administering a therapeutically-effective amount of a compound of the following formula or a pharmaceutically acceptable salt thereof:

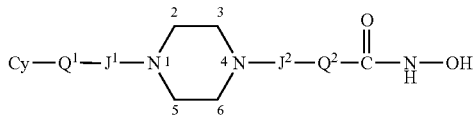

wherein:
the piperazin-1,4-diyl group is optionally substituted at one or more the 2-, 3-, 5-, and 6-positions with $C_{1-4}$alkyl;
$Q^1$ is a covalent bond; saturated $C_{1-3}$alkylene optionally substituted with -Ph;
partially unsaturated $C_{2-3}$alkylene; or —O—$C_{1-3}$alkylene;
either: $J^1$ is a covalent bond or —C(=O)— and $J^2$ is —C(=O)—;
or: $J^1$ is a covalent bond and $J^2$ is —S(=O)$_2$—;
$Q^2$ is —(CH$_2$)$_5$—, —(CH$_2$)$_{8-3}$—(CH$_2$)$_{7-3}$—(CH$_2$)$_8$—, or phenylene-ethenylene;
Cy is phenyl, pyridinyl, furanyl, indolyl, pyrrolyl, imidazolyl, pyrazinyl, pyridizinyl, naphthyl, quinolinyl, indolyl, benzimidazolyl, benzothiofuranyl, fluorenyl, acridinyl, or carbazolyl; and is optionally substituted.

2. A method according to claim 1, wherein:
$J^1$ is a covalent bond or —C(=O)—;
$J^2$ is —C(=O)—; and
$Q^2$ is —(CH$_2$)$_5$—, —(CH$_2$)$_8$—, —(CH$_2$)$_7$—, or —(CH$_2$)$_8$—.

3. A method according to claim 1, wherein:
$J^1$ is a covalent bond;
$J^2$ is —S(=O)$_2$—; and
$Q^2$ is phenylene-ethenylene.

4. A method according to claim 2, wherein $Q^1$ is a covalent bond.

5. A method according to claim 3, wherein $Q^1$ is a covalent bond.

6. A method according to claim 2, wherein $Q^1$ is —CH$_2$—, —CH(Ph)-, —CH$_2$CH$_2$—, —CH(Ph)CH$_2$—, —CH$_2$CH$_2$CH$_2$—, —CH=CHCH$_2$—, —O—CH$_2$—, or —O—CH$_2$CH$_2$—.

7. A method according to claim 3, wherein $Q^1$ is —CH$_2$—, —CH(Ph)-, —CH$_2$CH$_2$—, —CH(Ph)CH$_2$—, —CH$_2$CH$_2$CH$_2$—, —CH=CHCH$_2$—, —O—CH$_2$—, or —O—CH$_2$CH$_2$—.

8. A method according to claim 2, wherein Cy is phenyl, and is optionally substituted with one or more groups selected from: —F, —Cl, —Br, —I, -Me, -Et, -nPr, -iPr, -nBu, -iBu, -sBu, -tBu, —CF$_3$, —OH, —OMe, —OEt, —O(iPr), —O(tBu), —OCF$_3$, —NMe$_2$, —NEt$_2$, morpholino, —NO$_2$, and —CN.

9. A method according to claim 3, wherein Cy is phenyl, and is optionally substituted with one or more groups selected from: —F, —Cl, —Br, —I, -Me, -Et, -nPr, -iPr, -nBu, -iBu, -sBu, -tBu, —CF$_3$, —OH, —OMe, —OEt, —O(iPr), —O(tBu), —OCF$_3$, —NMe$_2$, —NEt$_2$, morpholino, —NO$_2$, and —CN.

10. A method according to claim 4, wherein Cy is phenyl, and is optionally substituted with one or more groups selected from: —F, —Cl, —Br, —I, -Me, -Et, -nPr, -iPr, -nBu, -iBu, -sBu, -tBu, —CF$_3$, —OH, —OMe, —OEt, —O(iPr), —O(tBu), —OCF$_3$, —NMe$_2$, —NEt$_2$, morpholino, —NO$_2$, and —CN.

11. A method according to claim 5, wherein Cy is phenyl, and is optionally substituted with one or more groups selected from: —F, —Cl, —Br, —I, -Me, -Et, -nPr, -iPr, -nBu, -iBu, -sBu, -tBu, —CF$_3$, —OH, —OMe, —OEt, —O(iPr), —O(tBu), —OCF$_3$, —NMe$_2$, —NEt$_2$, morpholino, —NO$_2$, and —CN.

12. A method according to claim 6, wherein Cy is phenyl, and is optionally substituted with one or more groups selected from: —F, —Cl, —Br, —I, -Me, -Et, -nPr, -iPr, -nBu, -iBu, -sBu, -tBu, —CF$_3$, —OH, —OMe, —OEt, —O(iPr), —O(tBu), —OCF$_3$, —NMe$_2$, —NEt$_2$, morpholino, —NO$_2$, and —CN.

13. A method according to claim 7, wherein Cy is phenyl, and is optionally substituted with one or more groups selected from: —F, —Cl, —Br, —I, -Me, -Et, -nPr, -iPr, -nBu, -iBu, -sBu, -tBu, —CF$_3$, —OH, —OMe, —OEt, —O(iPr), —O(tBu), —OCF$_3$, —NMe$_2$, —NEt$_2$, morpholino, —NO$_2$, and —CN.

14. A method according to claim 1, wherein the compound is selected from the following compounds and pharmaceutically acceptable salts thereof:

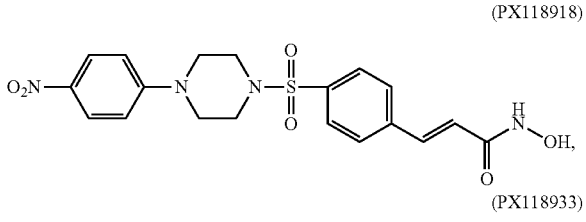

(PX118918)

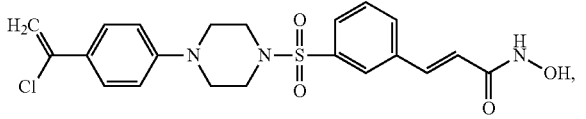

(PX118933)

(PX118937)
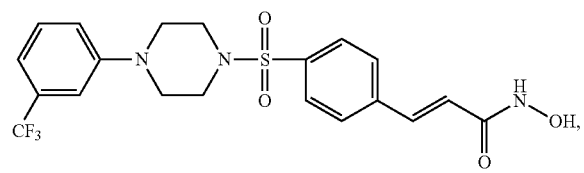
(PX118971)
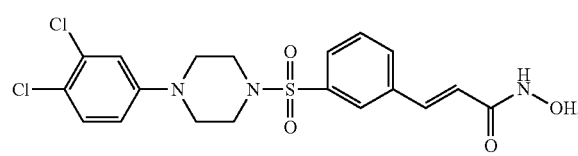
(PX118972)
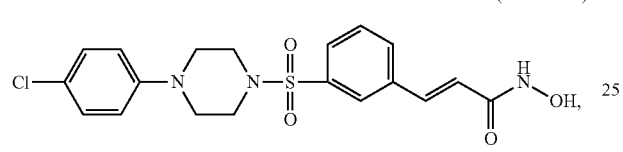
(PX118490)
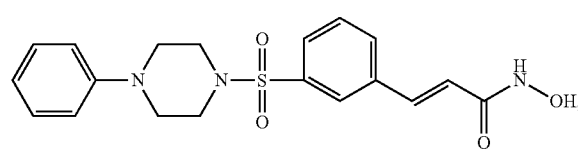
(PX118807)
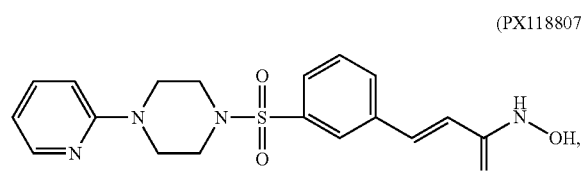
(PX11810)
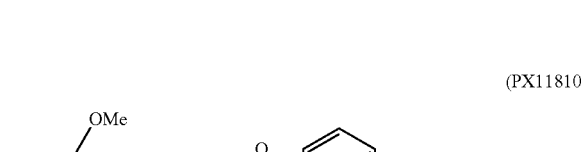
(PX118811)
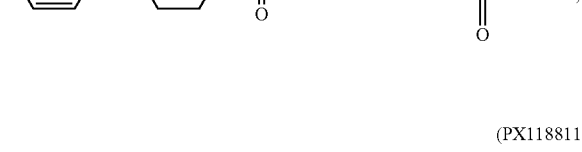
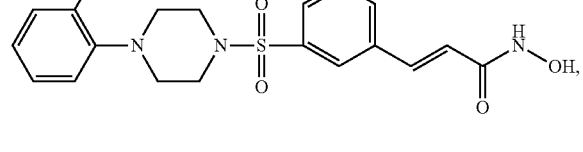
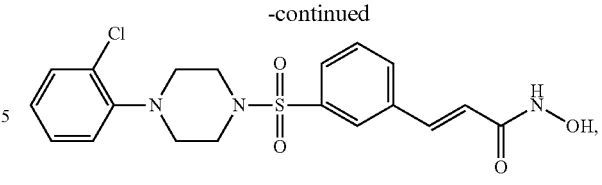
(PX118812)
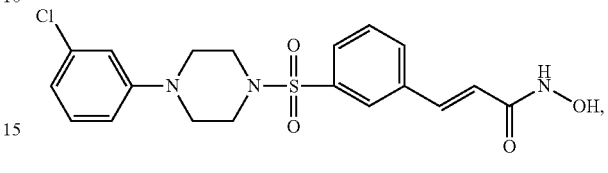
(PX118871)
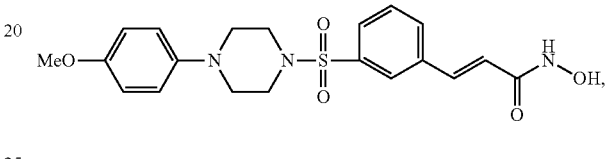
(PX118872)
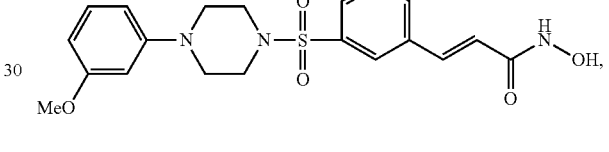
(PX118876)
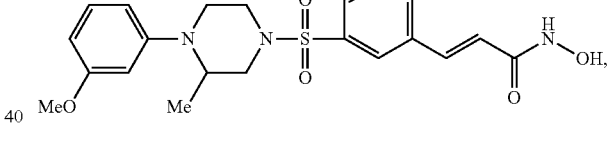
(PX118877)
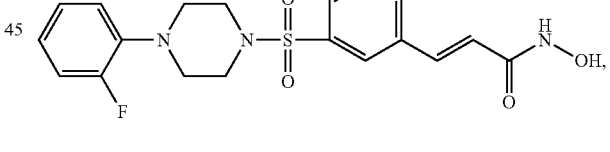
(PX118878)
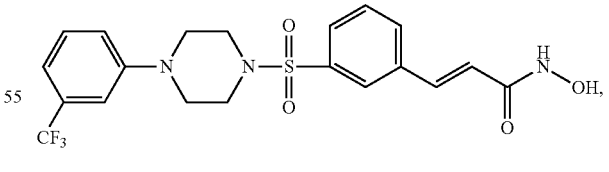
(PX118891)
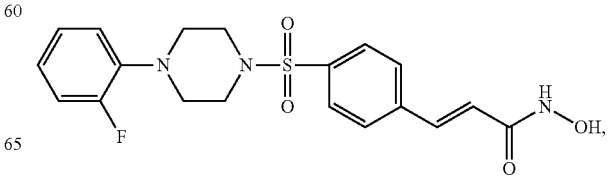

-continued
(PX118892)
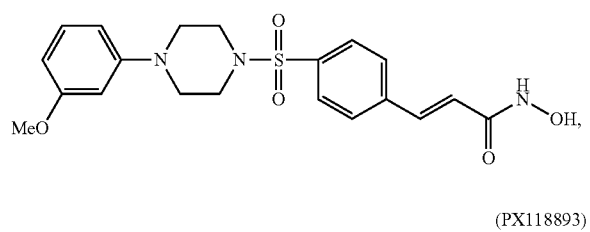
(PX118893)
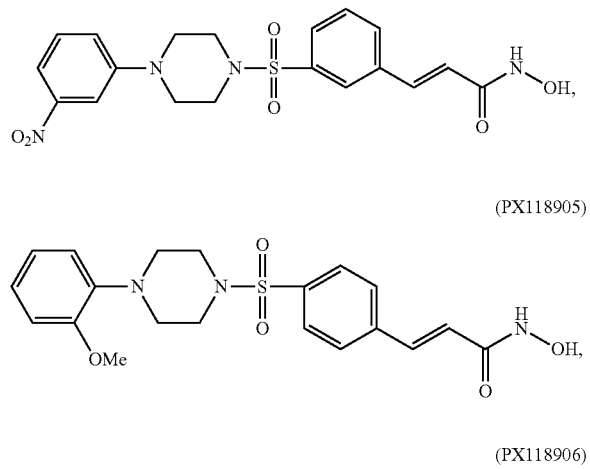
(PX118905)
(PX118906)
(PX118911)
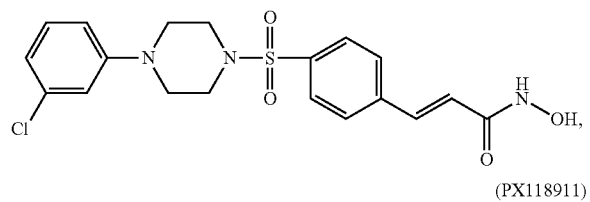
(PX118873)
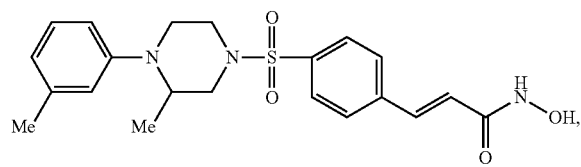
(PX118874)
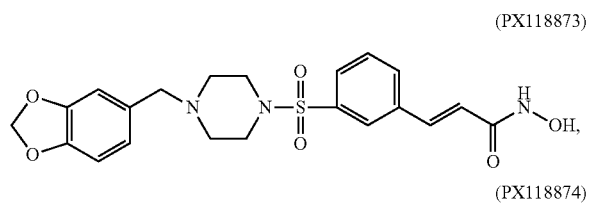
(PX118882)
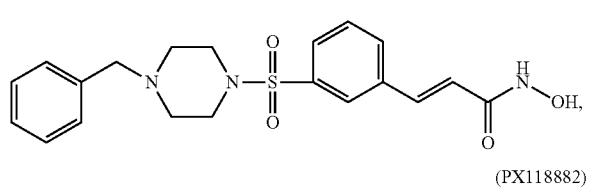
(PX118491)
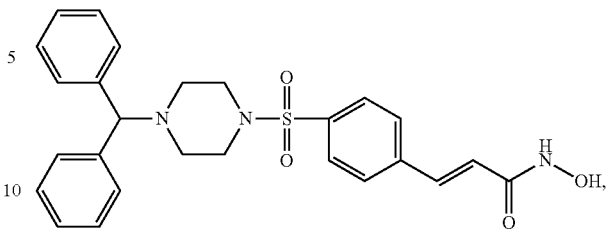
(PX118910)
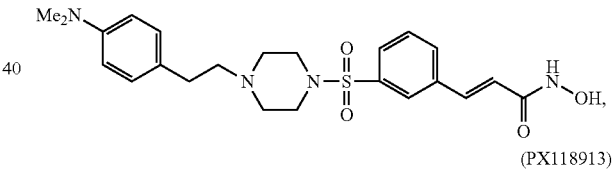
(PX118914)
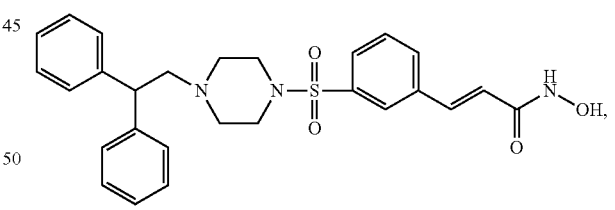
(PX118870)
(PX118951)
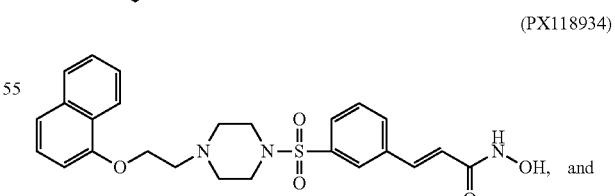
(PX118913)
(PX118934)
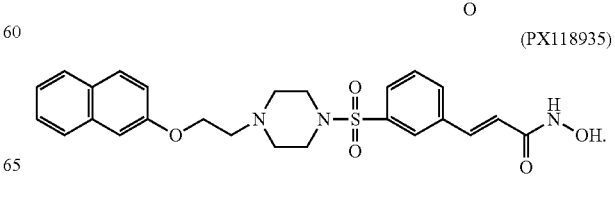
(PX118935)
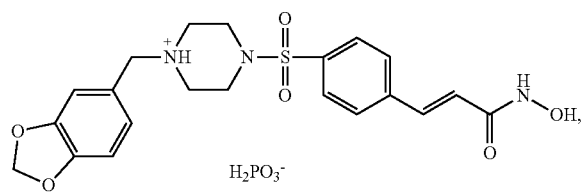
and 15. A method according to claim 1, wherein the compound is selected from the following compounds and pharmaceutically acceptable salts thereof:
(PX117402)
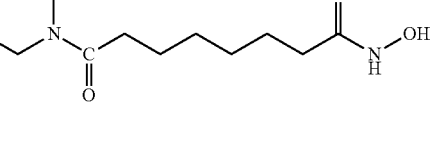
(PX117404)
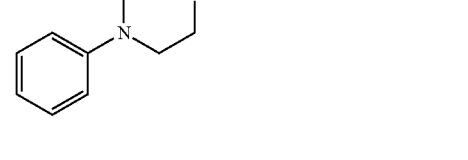
(PX117768)
(PX118791)
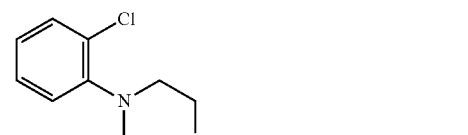
(PX118792)
(PX118793)
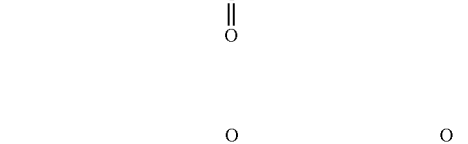
(PX118794)
(PX118845)
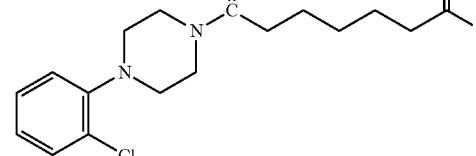
(PX118846)
(PX118847)
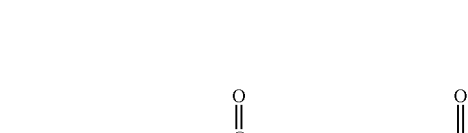
(PX118849)
(PX118859)
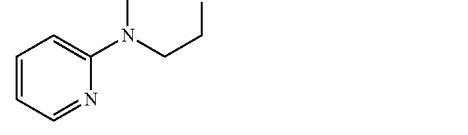

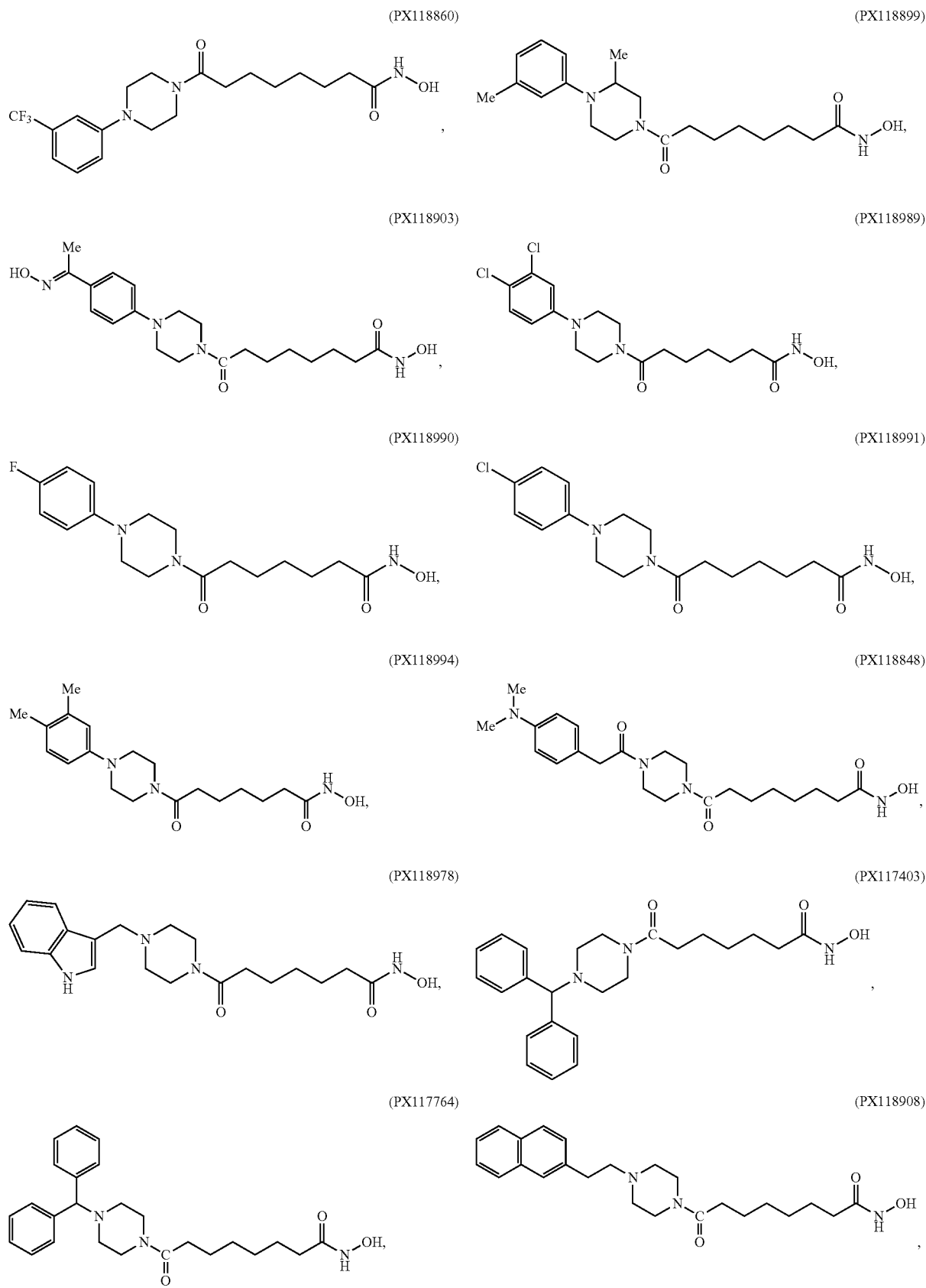

-continued
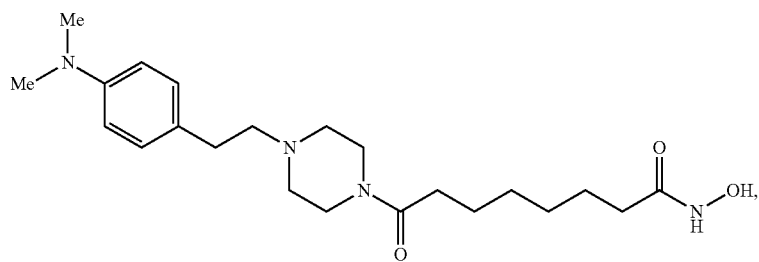
(PX118928)
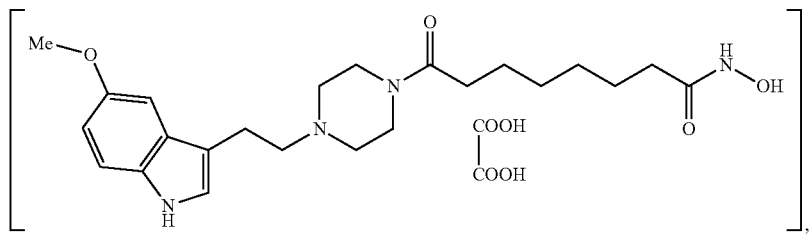
(PX118932)
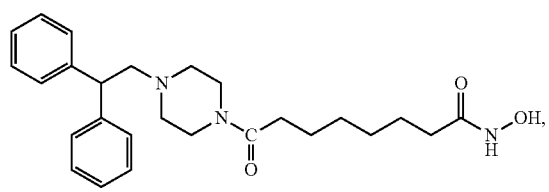
(PX118909)
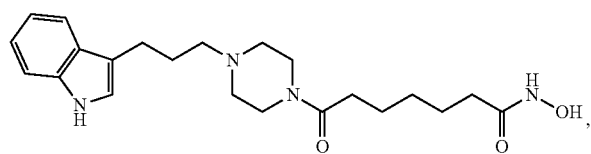
(PX118970)
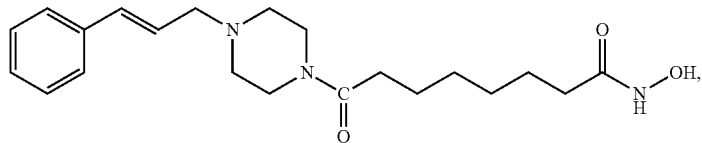
(PX118904)
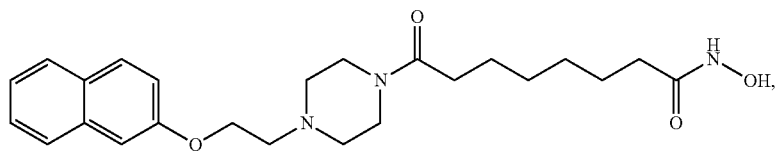
(PX118930)
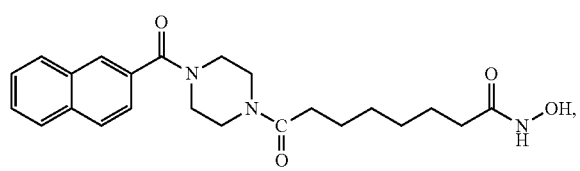
(PX118830)
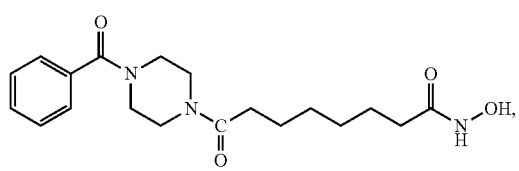
(PX118831)
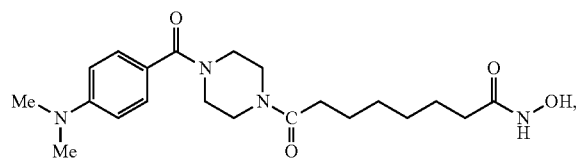
(PX118832)
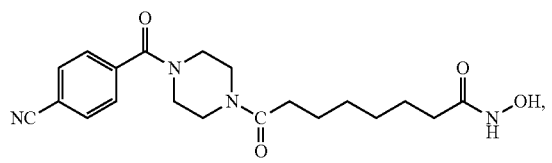
(PX118844)
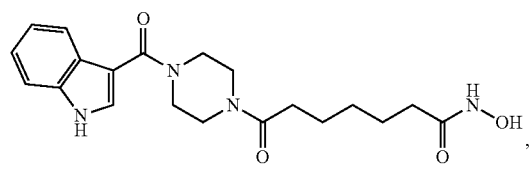
(PX118969)
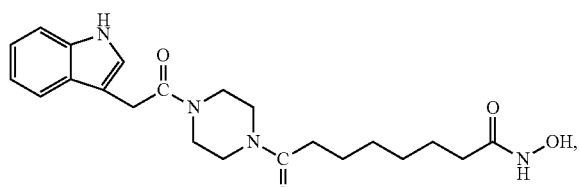
(PX118900)

-continued (PX118902)
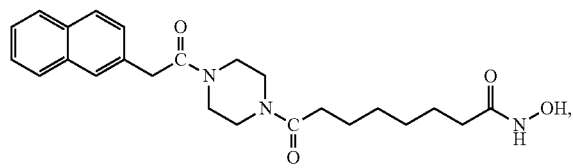

(PX118927)
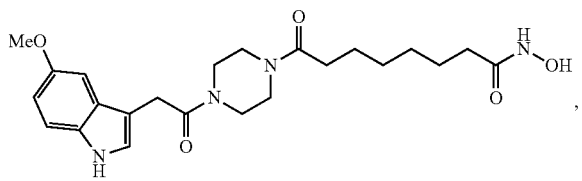

(PX118967)
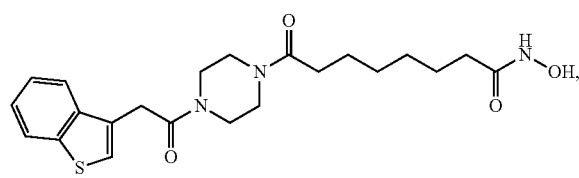

(PX118901)
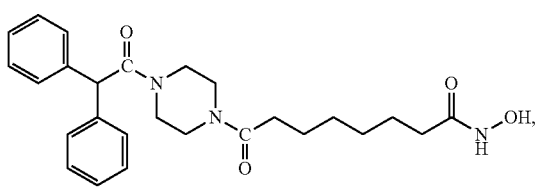

(PX118968)
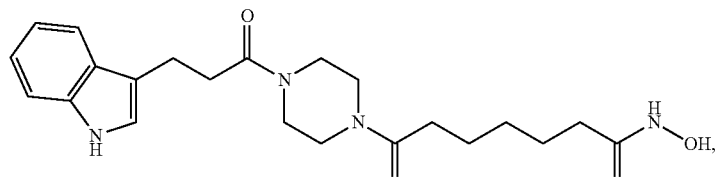

(PX118929)
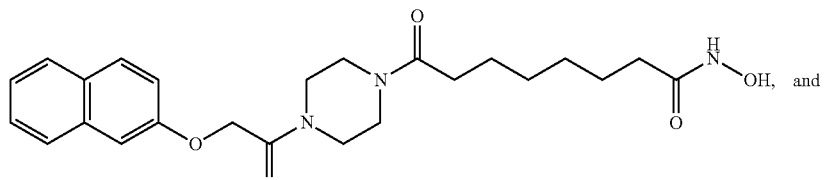

(PX118931)
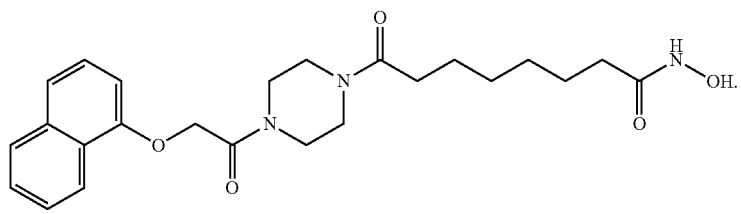

16. A method according to claim 1, comprising administering a therapeutically-effective amount of the following compound or a pharmaceutically acceptable salt thereof:

(PX118490)
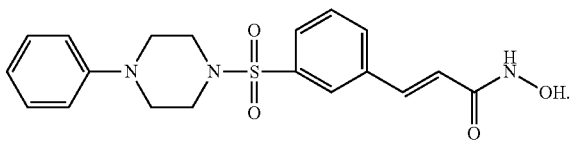

17. A method according to claim 1, wherein the condition is melanoma.
18. A method according to claim 2, wherein the condition is melanoma.
19. A method according to claim 3, wherein the condition is melanoma.
20. A method according to claim 4, wherein the condition is melanoma.
21. A method according to claim 5, wherein the condition is melanoma.
22. A method according to claim 6, wherein the condition is melanoma.
23. A method according to claim 7, wherein the condition is melanoma.
24. A method according to claim 8, wherein the condition is melanoma.
25. A method according to claim 9, wherein the condition is melanoma.
26. A method according to claim 10, wherein the condition is melanoma.
27. A method according to claim 11, wherein the condition is melanoma.
28. A method according to claim 12, wherein the condition is melanoma.
29. A method according to claim 13, wherein the condition is melanoma.
30. A method according to claim 14, wherein the condition is melanoma.
31. A method according to claim 15, wherein the condition is melanoma.

32. A method according to claim 16, wherein the condition is melanoma.
33. A method according to claim 1, wherein the condition is leukemia.
34. A method according to claim 2, wherein the condition is leukemia.
35. A method according to claim 3, wherein the condition is leukemia.
36. A method according to claim 4, wherein the condition is leukemia.
37. A method according to claim 5, wherein the condition is leukemia.
38. A method according to claim 6, wherein the condition is leukemia.
39. A method according to claim 7, wherein the condition is leukemia.
40. A method according to claim 8, wherein the condition is leukemia.
41. A method according to claim 9, wherein the condition is leukemia.
42. A method according to claim 10, wherein the condition is leukemia.
43. A method according to claim 11, wherein the condition is leukemia.
44. A method according to claim 12, wherein the condition is leukemia.
45. A method according to claim 13, wherein the condition is leukemia.
46. A method according to claim 14, wherein the condition is leukemia.
47. A method according to claim 15, wherein the condition is leukemia.
48. A method according to claim 16, wherein the condition is leukemia.
49. A method according to claim 1, wherein the condition is cervical cancer.
50. A method according to claim 2, wherein the condition is cervical cancer.
51. A method according to claim 3, wherein the condition is cervical cancer.
52. A method according to claim 4, wherein the condition is cervical cancer.
53. A method according to claim 5, wherein the condition is cervical cancer.
54. A method according to claim 6, wherein the condition is cervical cancer.
55. A method according to claim 7, wherein the condition is cervical cancer.
56. A method according to claim 8, wherein the condition is cervical cancer.
57. A method according to claim 9, wherein the condition is cervical cancer.
58. A method according to claim 10, wherein the condition is cervical cancer.
59. A method according to claim 11, wherein the condition is cervical cancer.
60. A method according to claim 12, wherein the condition is cervical cancer.
61. A method according to claim 13, wherein the condition is cervical cancer.
62. A method according to claim 14, wherein the condition is cervical cancer.
63. A method according to claim 15, wherein the condition is cervical cancer.
64. A method according to claim 16, wherein the condition is cervical cancer.

* * * * *